(12) United States Patent
Fujiwara et al.

(10) Patent No.: US 7,312,347 B2
(45) Date of Patent: Dec. 25, 2007

(54) SUBSTITUTED OPTICALLY ACTIVE DISPHOSPHINE COMPOUND

(75) Inventors: Takahiro Fujiwara, Kanagawa (JP); Tohru Yokozawa, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 11/526,252

(22) Filed: Sep. 22, 2006

(65) Prior Publication Data
US 2007/0073065 A1 Mar. 29, 2007

(30) Foreign Application Priority Data
Sep. 22, 2005 (JP) ............................. 2005-275455

(51) Int. Cl.
*C07F 15/00* (2006.01)
*C07F 9/02* (2006.01)
(52) U.S. Cl. ...................................................... 556/21
(58) Field of Classification Search ...................... None
See application file for complete search history.

(56) References Cited

FOREIGN PATENT DOCUMENTS

| | | |
|---|---|---|
| JP | 10-182678 | 7/1998 |
| WO | WO-02/40491 A1 | 5/2002 |
| WO | WO-02/40492 A1 | 5/2002 |

OTHER PUBLICATIONS

Leroux et al., Synthesis, 3:326-328 (2004).
Sun et al., Tetrahedron: Asymmetry, 15:2185-2188 (2004).

*Primary Examiner*—Yvonne Eyler
*Assistant Examiner*—Kellette Gale

(74) *Attorney, Agent, or Firm*—Peter F. Corless; Christine C. O'Day; Edwards Angell Palmer & Dodge, LLP

(57) ABSTRACT

Provided is a method for producing an optically active compound, in more detail, for producing an optically active compound by asymmetric hydrogenation in a high yield and asymmetric yield. The present invention also provides a catalyst for asymmetric synthesis for the above production method, especially a catalyst for asymmetric hydrogenation, containing a transition metal complex. Further, the present invention provides a new diphosphine compound useful as a ligand of the above transition metal complex and a new transition metal complex containing the above diphosphine compound.

The present invention relates to a diphosphine compound represented by the following formula (1):

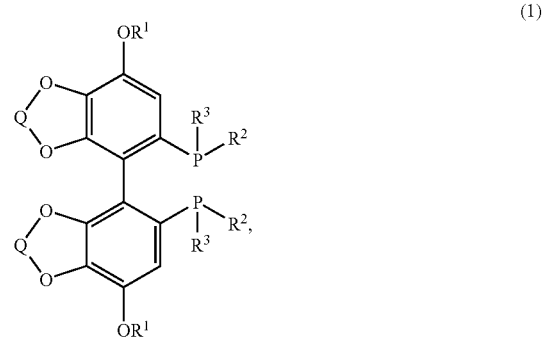

(1)

a transition metal complex using the compound, a catalyst for asymmetric synthesis comprising the above transition metal complex and a method for producing an optically active compound using the above catalyst for asymmetric synthesis.

25 Claims, No Drawings

SUBSTITUTED OPTICALLY ACTIVE DISPHOSPHINE COMPOUND

BACKGROUND OF THE INVENTION

1. Field of the Invention

The present invention relates to a novel diphosphine compound characterized by introducing an oxygen-containing functional group bonded via an oxygen atom such as an alkoxy group to the benzene rings of an optically active diphosphine compound having two benzene rings of a biphenyl skeleton at the 4- and 4'-positions thereof, a transition metal complex containing said diphosphine compound, a catalyst for an asymmetric synthesis comprising said transition metal complex, and a method for producing an optically active compound characterized by subjecting an unsaturated compound to an asymmetric reduction in the presence of said transition metal complex.

2. Description of the Related Art

Recently, an asymmetric synthesis using a transition metal complex containing a diphosphine ligand has been desired a formulation of various diphosphine ligands so as to improve the performance of the reaction. Patent literature 1, for example, discloses various diphosphine ligands having a ((5,6),(5',6')-bis(methylenedioxy)biphenyl-2,2'-diyl) group, specifically ((5,6),(5',6')-bis(methylenedioxy)biphenyl-2,2'-diyl)bis(diphenylphosphine) (hereinafter referred to as SEG-PHOS).

Patent literature 2 describes an asymmetric diphosphine compound introducing a methoxy group to a benzene ring that is different from methylenedioxybenzene, however, it does not describe an example of synthesis of the asymmetric diphosphine compound introducing a methoxy group, nor an example of synthesis of a symmetric diphosphine compound introducing a methoxy group, nor a reaction example of an asymmetric hydrogenation using the diphosphine compound as a ligand.

Non-patent literature 1 describes synthesis of a SEG-PHOS derivative formed by substituting a methylene proton of methylenedioxybenzene with fluorine and its application to asymmetric hydrogenation as a ruthenium complex, but does not show any practical data thereof. Non-patent literature 2 describes synthesis of a SEGPHOS derivative formed by substituting a methylene proton of methylenedioxybenzene with an alkyl group and its application to asymmetric hydrogenation as a ruthenium complex, but hardly contributes to improvement of asymmetric recognition.

Patent literature 3 describes a ligand substituting at the 3- and 3'-positions, and patent literature 2 describes a ligand having different modes of substitution in two benzene rings, however, both ligands have a complicated synthesis route and are difficult to use industrially due to an insufficient substrate/catalyst ratio of about 100 in the symmetric hydrogenation.

Patent literature 1: JP-A-10-182678
Patent literature 2: WO 02/40492 pamphlet
Patent literature 3: WO 02/40491 pamphlet
Non-patent literature 1: Synthesis, 2004, 326
Non-patent literature 2: Tetrahedron: Asymmetry, 2004, 15, 2185

DISCLOSURE OF THE PRESENT INVENTION

The present invention has been made considering the above-mentioned situations, and an object of the present invention is to provide a method for producing an optically active compound, in more detail, a method for producing an optically active compound by an asymmetric hydrogenation in a high yield and high asymmetry yield. The present invention also provides a catalyst for asymmetric synthesis, especially a catalyst for asymmetric hydrogenation containing a transition metal complex used in said production method. Further, the present invention provides a new diphosphine compound useful as a ligand for the above transition metal complex and a new transition metal complex containing said diphosphine compound.

The present inventors have made eager researches to solve the above-mentioned problems, so as to find out that a catalyst containing a transition metal complex of which the ligand is a diphosphine compound introducing an oxygen-containing functional group such as an alkoxy group to the 4- and 4'-positions of two methylenedioxybenzene groups of SEGPHOS has a higher yield, a higher optical purity and better operability and is more economical compared with conventional ones, and has excellent properties as a catalyst for asymmetric synthesis, especially as a catalyst for asymmetric hydrogenation, and thus completed the present invention.

In other words, the present invention relates to a diphosphine compound represented by the following formula (1)

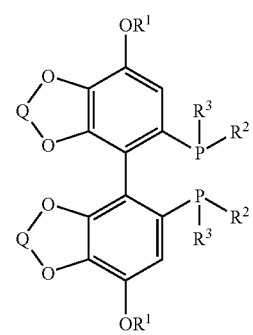

(1)

wherein, two $R^1$s are the same or different, and represent an optionally substituted hydrocarbon group or an optionally substituted heterocyclic group; two $R^2$s and $R^3$s each represent independently an optionally substituted hydrocarbon group or an optionally substituted heterocyclic group; and two Qs are the same or different, and represent a spacer. The diphosphine compound of the present invention represented by the formula (1) is a compound of axial asymmetry due to hindered rotation of two benzene rings, and may be either a racemic form or an optically active compound, but the latter is preferable as a ligand in a catalyst for asymmetric synthesis.

Further, the present inventors have found that the catalyst containing the diphosphine oxide compound which is the derivative of the above mentioned diphosphine compound has a higher yield, a higher optical purity and better operability and is more economical compared with conventional ones, and has excellent properties as a catalyst for asymmetric synthesis, especially as a catalyst for asymmetric hydrogenation.

In other words, the present invention further relates to a diphenylphosphine oxide compound represented by the following formula (6)

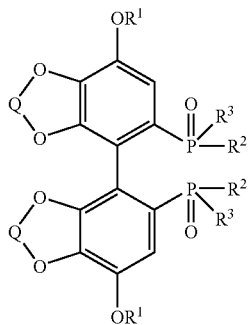

(6)

(wherein, two R¹s are the same or different, and represent an optionally substituted hydrocarbon group or an optionally substituted heterocyclic group; two R²s and R³s each represent independently an optionally substituted hydrocarbon group or an optionally substituted heterocyclic group; and two Qs are the same or different, and represent a spacer).

The present invention relates to a transition metal complex containing a diphosphine compound represented by the above formula (1) as a ligand thereof. The present invention relates to use of a diphosphine compound represented by the above formula (1) as a ligand of a transition metal complex.

Further, the present invention relates to a catalyst for asymmetric synthesis, preferably a catalyst for asymmetric reduction or a catalyst for asymmetric hydrogenation that contains the above transition metal complex. The present invention relates to use of the above transition metal complex as a catalyst for asymmetric synthesis, preferably a catalyst for asymmetric reduction or a catalyst for asymmetric hydrogenation.

The present invention relates to a method for producing a chiral compound by reacting a compound having a prochiral center in the presence of the above catalyst for asymmetric synthesis of the present invention. In detail, the present invention relates to a method for producing a chiral compound by reducing a compound having a prochiral center in the presence of the above catalyst for asymmetric reduction of the present invention. In more detail, the present invention relates to a method for producing a chiral compound by hydrogenating a compound having a prochiral center in the presence of the above catalyst for asymmetric hydrogenation of the present invention.

The present invention is described in more detail as follows (1) a diphosphine compound represented by the above formula (1) (wherein, two R¹s are the same or different, and represent an optionally substituted hydrocarbon group or an optionally substituted heterocyclic group; two R²s and R³s each represent independently an optionally substituted hydrocarbon group or an optionally substituted heterocyclic group; and two Qs are the same or different, and represent a spacer)

(2) the diphosphine compound according to the above item (1), wherein the diphosphine compound represented by the above formula (1) is an optically active diphosphine compound (3) a diphenylphosphine oxide compound represented by the above formula (6) (wherein, two R¹s are the same or different, and represent an optionally substituted hydrocarbon group or an optionally substituted heterocyclic group; two R²s and R³s each represent independently an optionally substituted hydrocarbon group or an optionally substituted heterocyclic group; and two Qs are the same or different, and represent a spacer)

(4) the diphenylphosphine oxide compound according to the above item (3), wherein the diphenylphosphine oxide compound represented by the above formula (6) is an optically active diphenylphosphine oxide compound (5) a chiral ligand, which comprises the optically active diphosphine compound described in the above item (2)

(6) a chiral catalyst, which comprises the diphosphine compound described in the above item (2) or the optically active diphenylphosphine oxide compound described in the above item (4)

(7) a transition metal complex containing the diphosphine compound described in the above item (1) or (2)

(8) a transition metal complex obtained by reacting the diphosphine compound described in the above item (1) or (2) and a transition metal complex precursor (9) the transition metal complex according to the above item (7) or (8), wherein the transition metal complex is an optically active transition metal complex

(10) a chiral catalyst, which comprises the transition metal complex described in the above item (9)

(11) a chiral catalyst containing the diphosphine compound described in the above item (2) and a transition metal complex precursor

(12) the chiral catalyst according to the above item (10) or (11), wherein said catalyst is a catalyst for asymmetric synthesis described in the above item (10) or (11)

(13) the catalyst for asymmetric synthesis according to the above item (12), wherein the catalyst for asymmetric synthesis is a catalyst for asymmetric reduction

(14) a method for producing an optically active compound, which comprises reacting a compound having a prochiral center in the presence of the catalyst for asymmetric synthesis described in the above item (10) or (11)

(15) use of the optically active diphosphine compound described in the above item (2) as a chiral ligand

(16) the transition metal complex according to the above item (7), wherein the transition metal complex according to the above item (7) is a transition metal complex represented by the following formula (11) or (12):

$$M_m L_n X_p Y_q \qquad (11)$$

$$[M_m L_n X_p Y_q]Z_s \qquad (12)$$

(wherein, L represents an optically active substance of a diphosphine compound represented by the above formula (1); M represents a transition metal; X represents a halogen atom, a carboxylate group, an allyl group, 1,5-cyclooctadiene or norbornadiene; Y represents a ligand; Z represents an anion or a cation; n represents an integer of 1 to 5; and m, p, q and s represent an integer of 0 to 5)

The ligand of the present invention is characterized by introducing an oxygen-containing functional group bonded via an oxygen atom such as an alkoxy group at the 4- and 4'-positions of the benzene rings of an optically active diphosphine compound having two benzene rings in a biphenyl skeleton. The two benzene rings of the diphosphine compound of the present invention represented by the formula (1) have axial asymmetry due to hindered rotation. It is known that change of the dihedral angle between two benzene rings in a biphenyl skeleton of a diphosphine compound contributes to stereoselectivity in asymmetric hydrogenation.

The present inventors confirmed by chemical calculation that the dihedral angle between two benzene rings in a biphenyl skeleton of a diphosphine compound changed by introducing an oxygen-containing functional group bonded via an oxygen atom such as an alkoxy group at the 4- and 4'-positions of the benzene rings of an optically active diphosphine compound having two benzene rings in a biphenyl skeleton. It is considered that due to this structural change, an optically active compound can be produced in a high yield and a high asymmetric yield by using a catalyst for asymmetric synthesis comprising a transition metal complex containing as a ligand a diphosphine compound of the present invention represented by the formula (1). The optically active diphosphine compound of the present invention can be easily and selectively subjected to halogenation and coupling reaction by means of substituting in advance an unnecessary reaction site for synthesis, and can be easily treated in reaction and purification after reaction by increasing lipid solubility, and thus an objective optically active diphosphine compound can be produced efficiently.

The diphosphine compound of the present invention represented by the above formula (1) is explained below.

In the formula (1), two $R^1$s represent an optionally substituted hydrocarbon group or an optionally substituted heterocyclic group, and may be the same or different, but preferably the same. Two $R^2$s and $R^3$s each independently represent an optionally substituted hydrocarbon group or an optionally substituted heterocyclic group.

The optionally substituted hydrocarbon groups represented by $R^1$ to $R^3$ include a hydrocarbon group and a substituted hydrocarbon group.

The hydrocarbon group includes, for example, an alkyl group, an alkenyl group, an alkynyl group, an alkadienyl group, an aryl group, an aralkyl group and the like.

The alkyl group may be linear, branched or cyclic, and includes, for example, a linear or branched alkyl group having 1 to 20, preferably 1 to 15, more preferably 1 to 10 carbon atom(s), or a monocyclic, polycyclic, fused-cyclic or a cross-linked cycloalkyl group having 3 to 20, preferably 3 to 15, more preferably 3 to 10 carbon atoms. Specific examples thereof include methyl, ethyl, n-propyl, 2-propyl, n-butyl, 1-methylpropyl, isobutyl, tert-butyl, n-pentyl, 1-methylbutyl, tert-pentyl, 2-methylbutyl, 3-methylbutyl, 2,2-dimethylpropyl, n-hexyl, 1-methylpentyl, 1-ethylbutyl, tert-hexyl, 2-methylpentyl, 3-methylpentyl, 4-methylpentyl, 2-methylpentane-3-yl, heptyl, octyl, nonyl, decyl, lauryl, stearyl, cyclopropyl, cyclobutyl, cyclopentyl, cyclohexyl and the like.

The alkenyl group may be linear or branched, and includes, for example, an alkenyl group having 2 to 20, preferably 2 to 15, more preferably 2 to 10 carbon atoms. Specific examples thereof include vinyl, propenyl, butenyl, pentenyl, hexenyl, heptenyl, octenyl, nonenyl, decenyl and the like.

The alkynyl group may be linear or branched, and includes, for example, an alkynyl group having 2 to 20, preferably 2 to 15, more preferably 2 to 10 carbon atoms. Specific examples thereof include ethynyl, propynyl, butynyl, pentynyl, hexynyl and the like.

The alkadienyl group may be linear, branched or cyclic, and includes, for example, an alkadienyl group of 4 or more, preferably 4 to 20, more preferably 4 to 15, and still more preferably 4 to 10 carbon atoms that has two double bonds in the chain of the above alkyl group. Specific examples thereof include 1,3-butadienyl, 2,3-dimethyl-1,3-butadienyl and the like.

The aryl group includes, for example, a monocyclic, polycyclic or fused aryl group having 6 to 20, preferably 6 to 15 carbon atoms. Specific examples thereof include phenyl, naphthyl, anthryl, biphenyl and the like.

The aralkyl group includes, for example, an aralkyl group having 7 to 20, preferably 7 to 15 carbon atoms wherein at least one hydrogen atom of the above alkyl group is substituted with the above aryl group. Specific examples thereof include benzyl, 1-phenylethyl, 2-phenylethyl, 1-phenylpropyl, 3-naphthylpropyl and the like.

The substituted hydrocarbon group (hydrocarbon group having a substituent) includes a hydrocarbon group wherein at least one hydrogen atom of the above hydrocarbon group is substituted with a substituent, and example thereof includes a substituted alkyl group, a substituted alkenyl group, a substituted alkynyl group, a substituted alkadienyl group, a substituted aryl group, a substituted aralkyl group and the like. The substituent is described later.

Among the substituted hydrocarbon group, the substituted alkyl group include methoxymethyl, ethoxyethyl and the like. The substituted aryl group include tolyl (for example, 4-methylphenyl), xylyl (for example, 3,5-dimethylphenyl), 4-methoxy-3,5-dimethylphenyl, 4-methoxy-3,5-di-tert-butylphenyl and the like.

The optionally substituted heterocyclic group includes a heterocyclic group and a substituted heterocyclic group. The heterocyclic group includes an aliphatic heterocyclic group and an aromatic heterocyclic group.

The aliphatic heterocyclic group includes, for example, a 3- to 8-membered, preferably 5- or 6-membered monocyclic, polycyclic or fused-cyclic heterocyclic group having 2 to 14 carbon atoms and contains at least 1, preferably 1 to 3 heteroatom(s) such as a nitrogen atom, an oxygen atom and/or a sulfur atom. Specific examples thereof include pyrrolidyl-2-one, pyperidino, piperazinyl, morpholino, morpholinyl, tetrahydrofuryl, tetrahydropyranyl, thiolanyl and the like.

The aromatic heterocyclic group includes, for example, a 5- to 8-membered, preferably 5- or 6-membered monocyclic, polycyclic or fused hetero aryl group having 2 to 15 carbon atoms and contains at least 1, preferably 1 to 3 heteroatom(s) such as a nitrogen atom, an oxygen atom and/or a sulfur atom. Specific examples thereof include furyl, thienyl, pyridyl, pyrimidyl, pyrazyl, pyridazinyl, pyrazolyl, imidazolyl, oxazolyl, thiazolyl, benzofuryl, benzothienyl, quinolyl, isoquinolyl, quinoxalinyl, phthalazinyl, quinazolinyl, naphthyridinyl, cinnolinyl, benzoimidazolyl, benzooxazolyl, benzothiazolyl, acridinyl and the like.

The substituted heterocyclic group (heterocyclic group having a substituent) includes the above heterocyclic group of which at least one hydrogen atom is substituted with a substituent, and examples thereof include a substituted aliphatic heterocyclic group and a substituted aromatic heterocyclic group.

The substituent in the above hydrocarbon group and heterocyclic group includes, for example, an optionally substituted hydrocarbon group, an optionally substituted heterocyclic group, a halogen atom, a halogenated hydrocarbon group, an optionally substituted alkoxy group, an optionally substituted aryl group, an optionally substituted aralkyloxy group, an optionally substituted heteroaryloxy group, an optionally substituted alkylthio group, an optionally substituted arylthio group, an optionally substituted aralkylthio group, an optionally substituted heteroarylthio group, an optionally substituted acyl group, an optionally substituted acyloxy group, an optionally substituted alkoxycarbonyl group, an optionally substituted aryloxycarbonyl group, an optionally substituted aralkyloxycarbonyl group, an optionally substituted alkylenedioxy group, a nitro group, an amino group, a substituted amino group, a cyano group, a sulfo group, a substituted silyl group, a hydroxy group, a carboxy group, an optionally substituted alkoxythiocarbonyl group, an optionally substituted aryloxythiocarbonyl group, an optionally substituted aralkyloxythiocarbonyl group, an optionally substituted alkylthiocarbonyl group, an optionally substituted arylthiocarbonyl group, an optionally substituted aralkylthiocarbonyl group, an optionally substituted carbamoyl group, a substituted phosphino group, an aminosulfonyl group, an alkoxysulfonyl group, an oxo group and the like. The optionally substituted hydrocarbon group and optionally substituted heterocyclic group used here for explanation are the same as the groups described above. These substituents other than the optionally substituted hydrocarbon group and the optionally substituted heterocyclic group are the same as each group which will be explained in a method for producing an optically active compound mentioned below, provided that the acyl group represents a group where a carbonyl group is bonded to the above described hydrocarbon group and the alkylene group represents a divalent group where one hydrogen atom is removed from the above described alkyl group.

Two Qs represent a spacer, and may be the same or different, but preferably the same. The spacer includes a divalent organic group such as alkylene group, arylene group and heteroarylene group, that may have a substituent (i.e., an optionally substituted divalent organic group). The alkylene group is the same as the alkylene group described above, and the arylene group represents a divalent group where one hydrogen atom is removed from the above described aryl group. The heteroarylene group represents a divalent group where one hydrogen atom is removed from the above described aromatic heterocyclic group. The above divalent organic group may have at least one heteroatom or heteroatom group such as an oxygen atom, a carbonyl group, a sulfur atom, an imino group, a substituted imino group and the like inserted at an optional position in the carbon chain of the organic group. Further, the above divalent organic group may have a substituent. The above substituent and the substituent in the substituted imino group are the same as the above described substituent. Preferably, the above spacer is an alkylene group.

The alkylene group in the spacer Q is preferably, for example, linear or branched alkylene group having 1 to 10 carbon atom(s). Specific examples thereof include methylene, ethylene, trimethylene, tetramethylene, pentamethylene, hexamethylene, heptamethylene, octamethylene, nonamethylene, decamethylene, propylene, dimethylmethylene and the like.

Specific examples of the above alkylene group having a substituent include difluoromethylene and the like.

Specific examples of the diphosphine compound represented by the above formula (1) of the present invention include, for example, [4,4'-bi(7-methoxy-1,3-benzodioxol)]-5,5'-diyl-bis(diphenylphosphine), [4,4'-bi(7-ethoxy-1,3-benzodioxol)]-5,5'-diyl-bis(diphenylphosphine), [4,4'-bi(7-n-propoxy-1,3-benzodioxol)]-5,5'-diyl-bis(diphenylphosphine), [4,4'-bi(7-n-butoxy-1,3-benzodioxol)]-5,5'-diyl-bis(diphenylphosphine), [4,4'-bi(7-phenoxy-1,3-benzodioxol)]-5,5'-diyl-bis(diphenylphosphine), [4,4'-bi(7-methoxy-1,3-benzodioxol)]-5,5'-diyl-bis[di(4-methylphenyl)phosphine], [4,4'-bi(7-methoxy-1,3-benzodioxol)]-5,5'-diyl-bis[di(3,5-dimethylphenyl)phosphine], [4,4'-bi(7-methoxy-1,3-benzodioxol)]-5,5'-diyl-bis[di(4-methoxy-3,5-dimethylphenyl)phosphine], [4,4'-bi(7-methoxy-1,3-benzodioxol)]-5,5'-diyl-bis[di(4-methoxy-3,5-di-tert-butylphenyl)phosphine] and the like. The 1,3-benzodioxol in this description represents 1,2-methylenedioxybenzene, and the numbering begins with an oxygen atom. The chemical formulae of these diphosphine compounds are shown below:

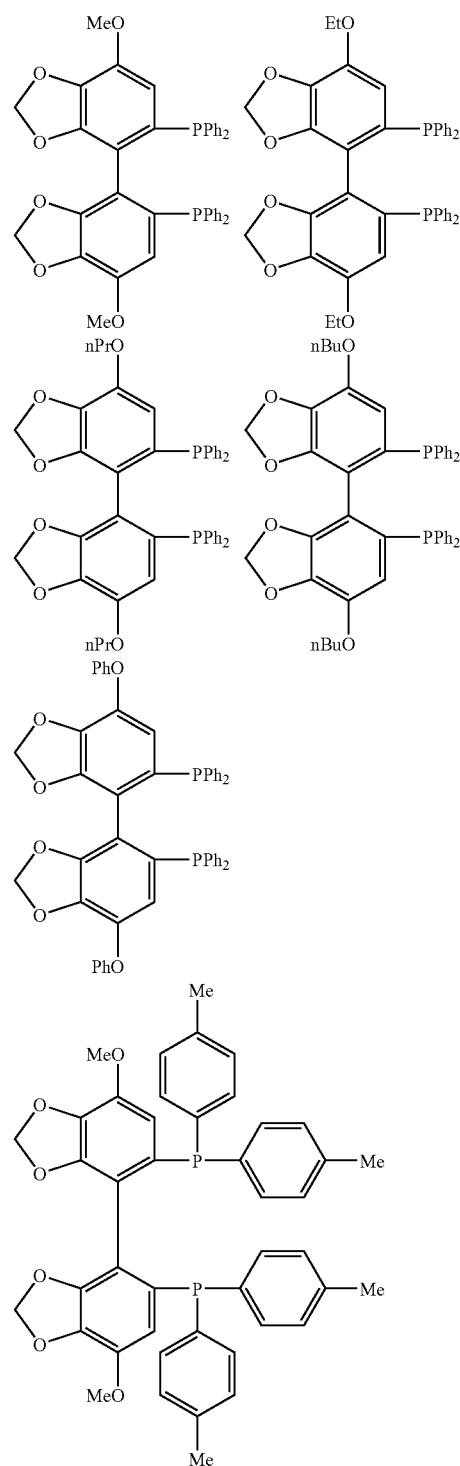

-continued
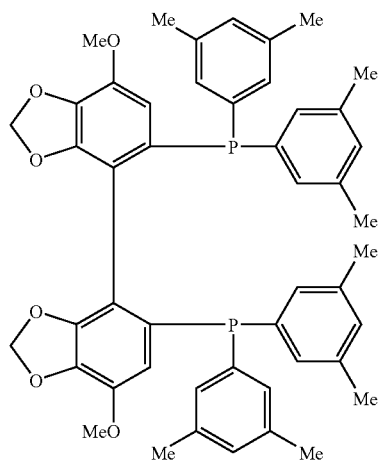
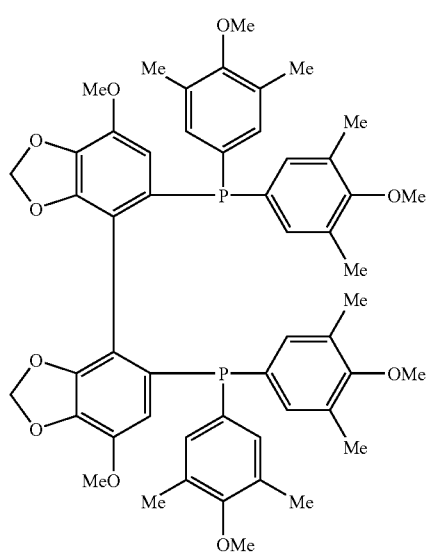
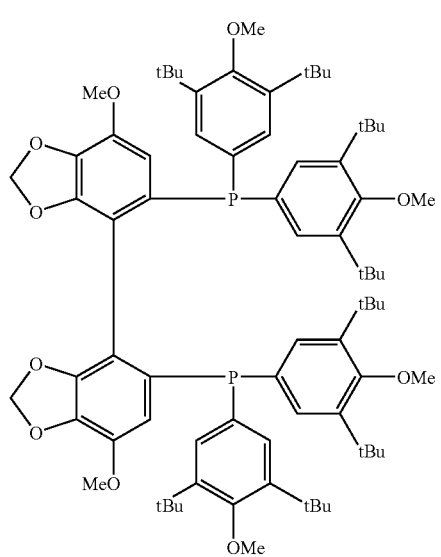
The diphosphine compound of the present invention also includes the following diphosphine compounds:
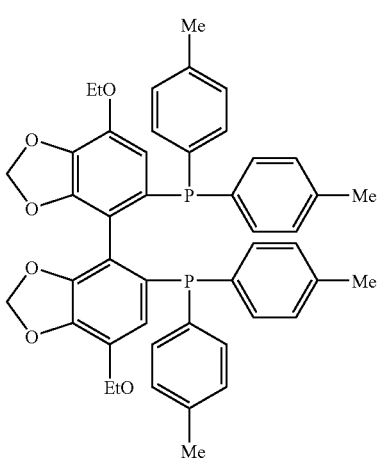
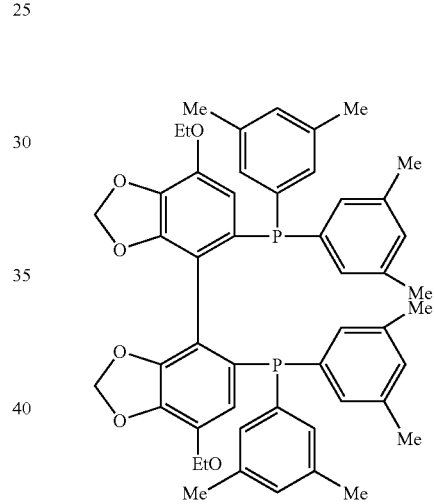
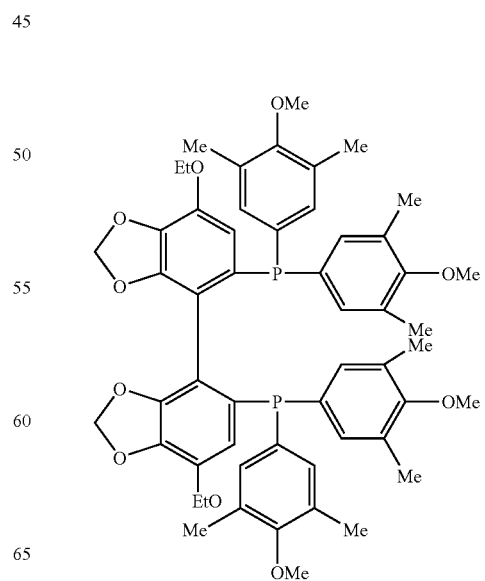

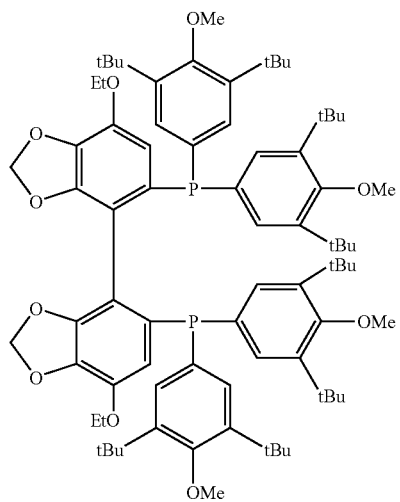
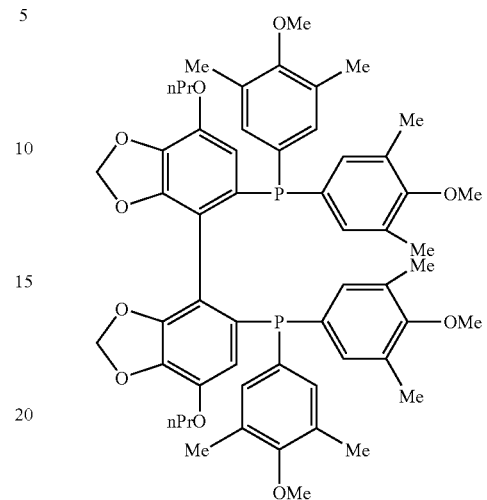
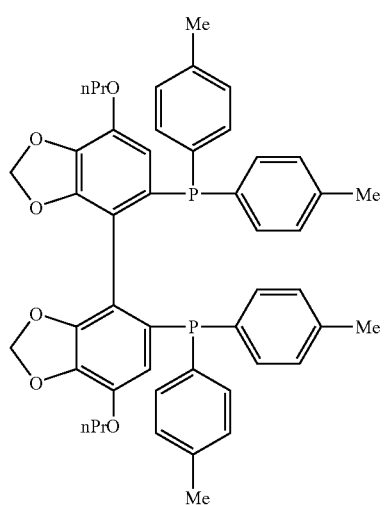
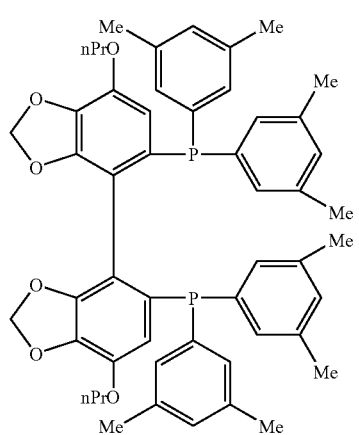

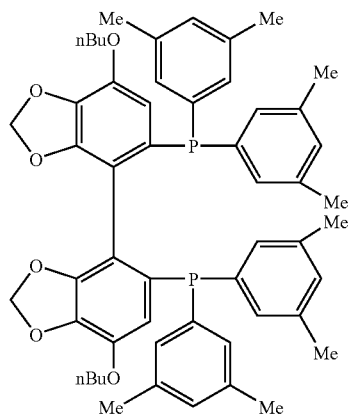
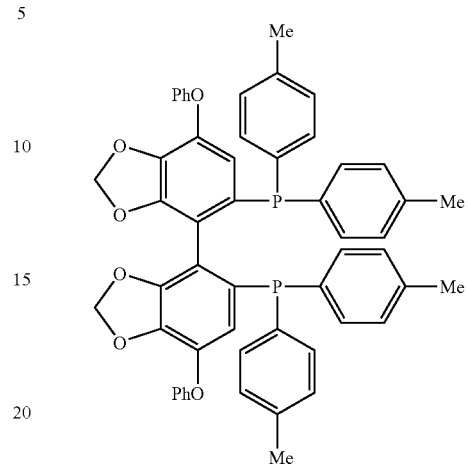
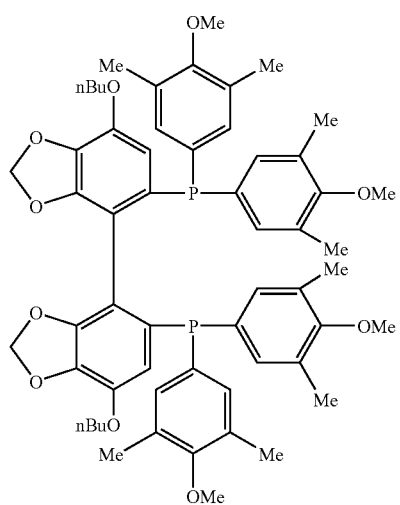
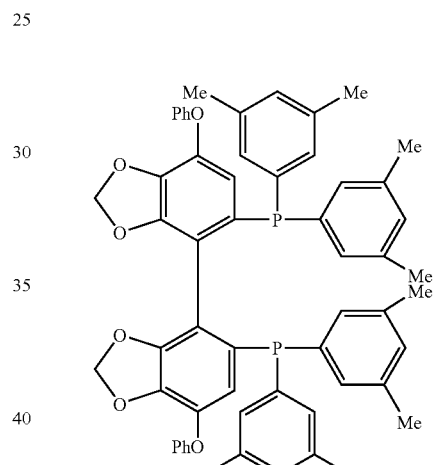
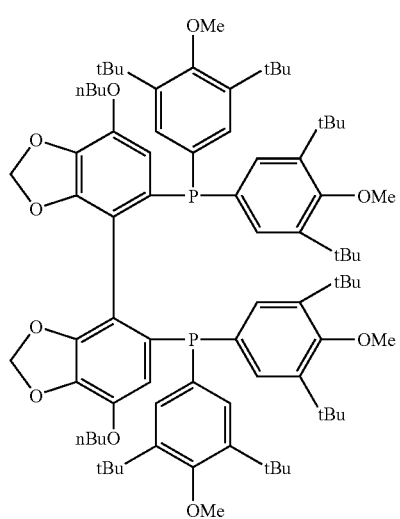
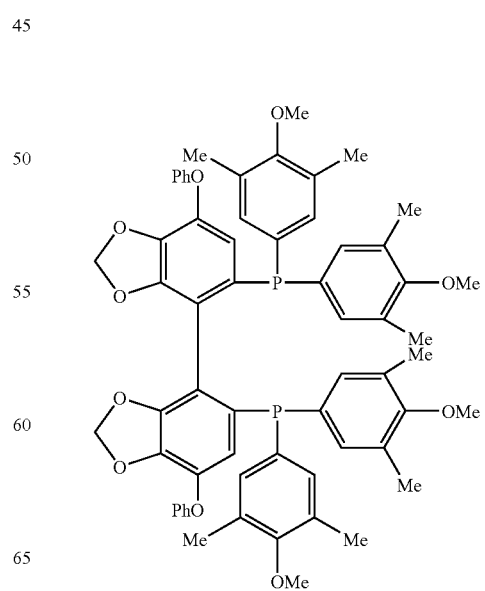

-continued
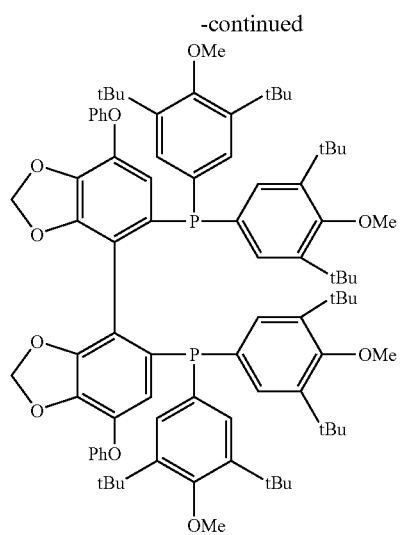
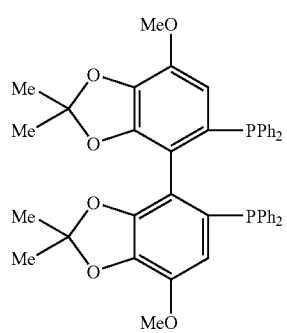
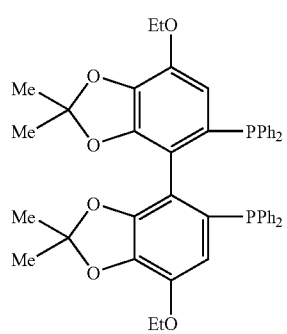
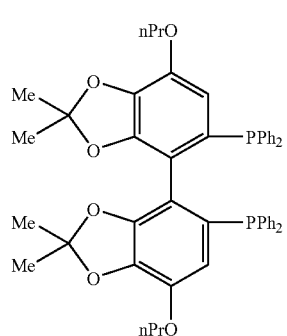
-continued
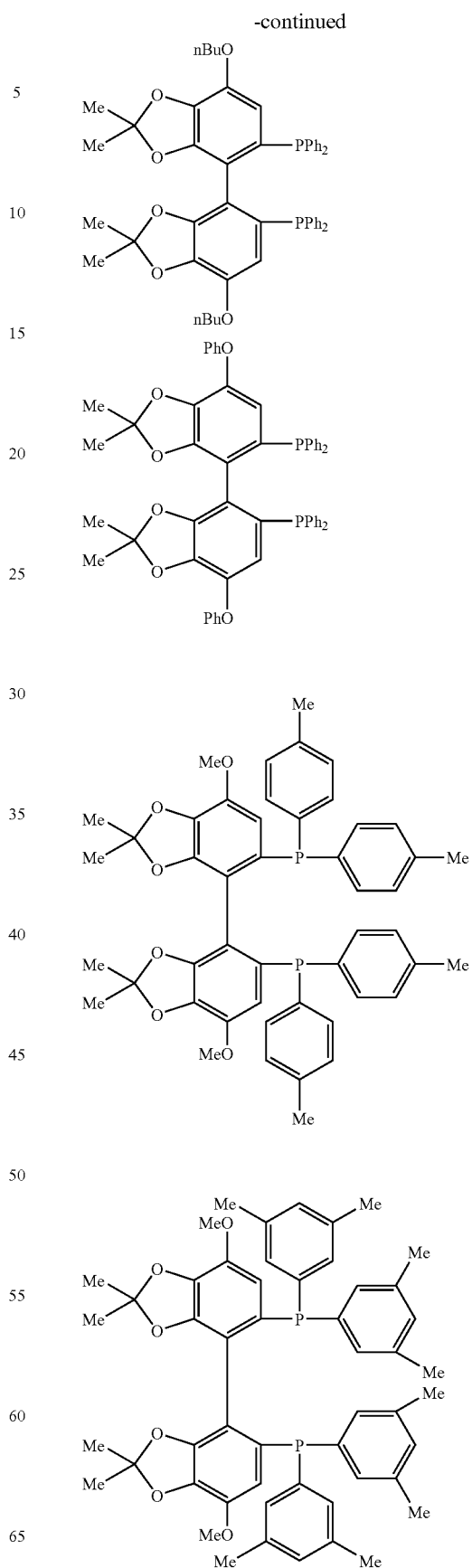

-continued
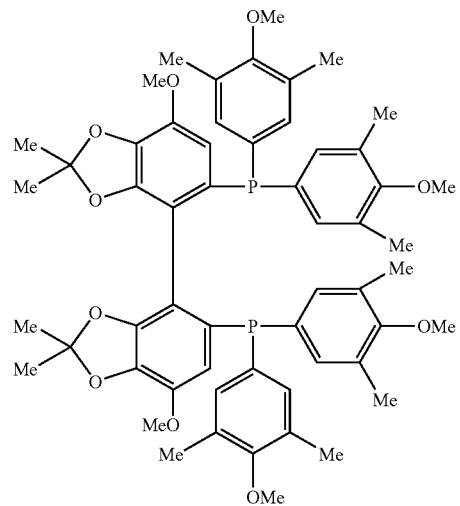
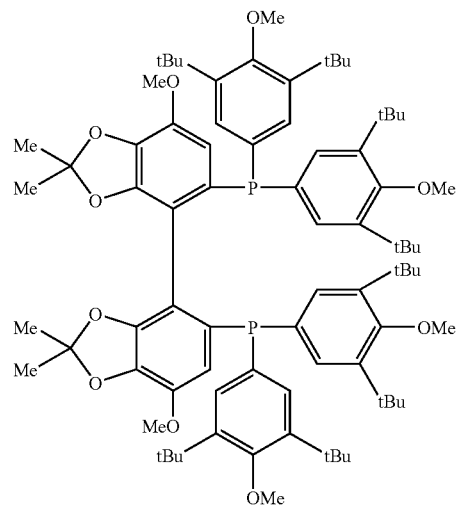
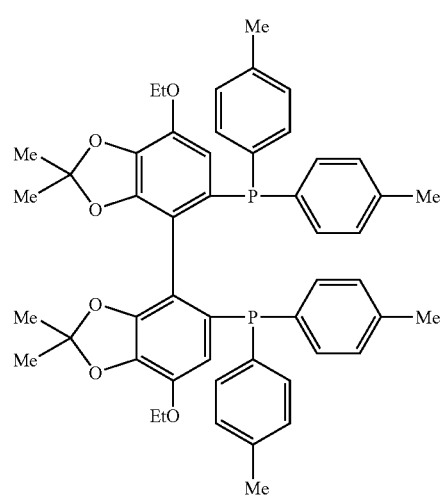
-continued
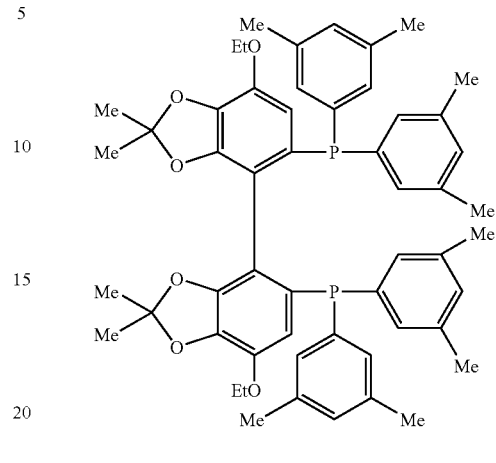
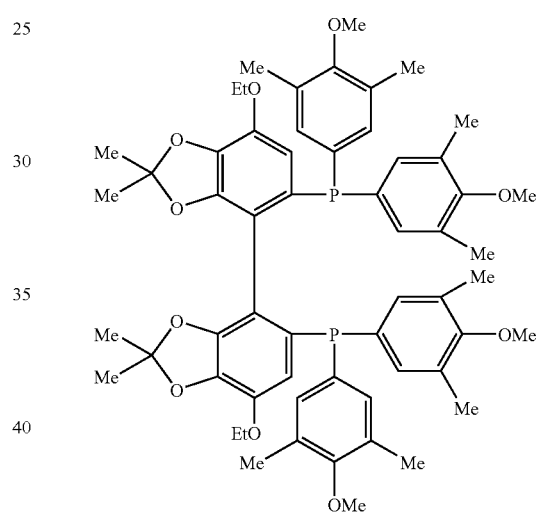
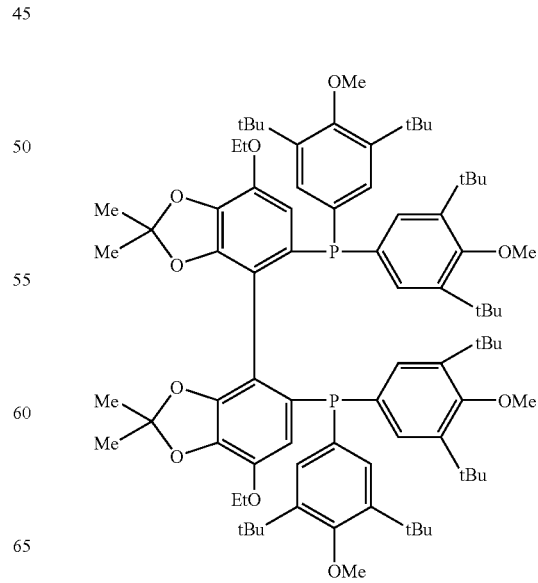

-continued
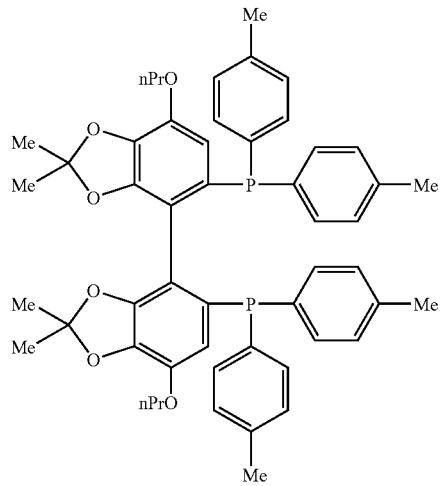
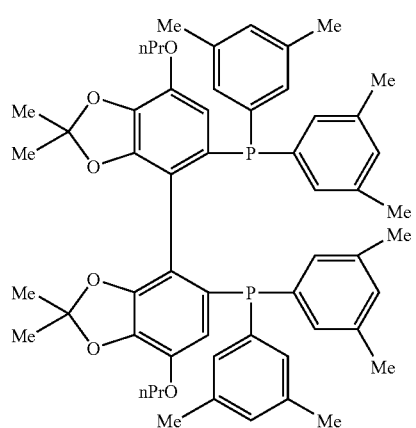
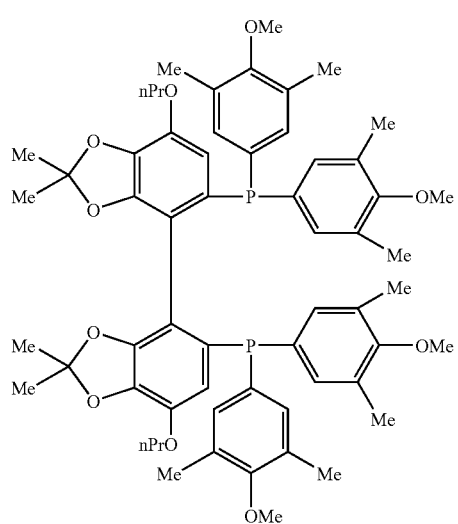
-continued
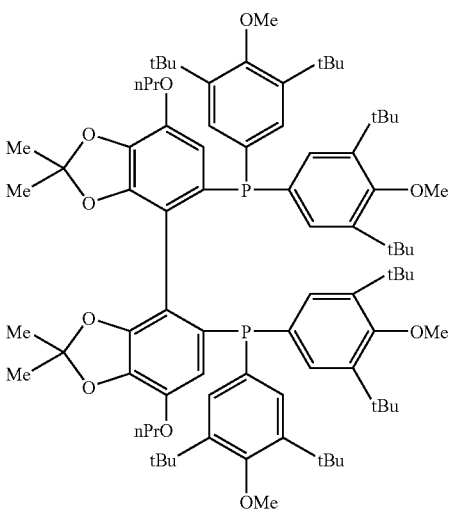
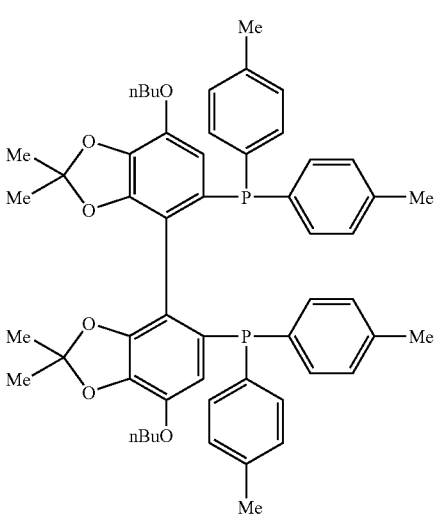
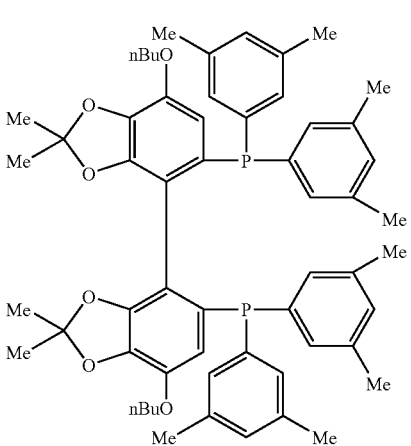

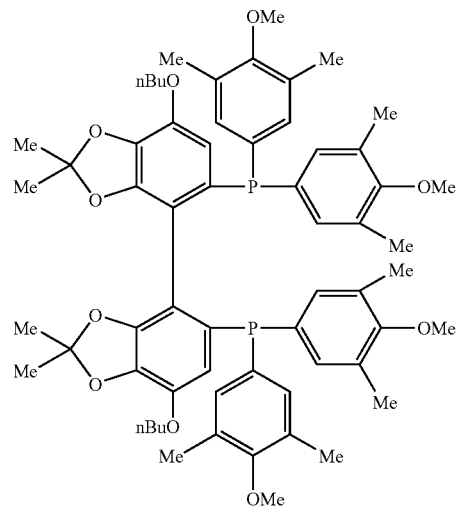
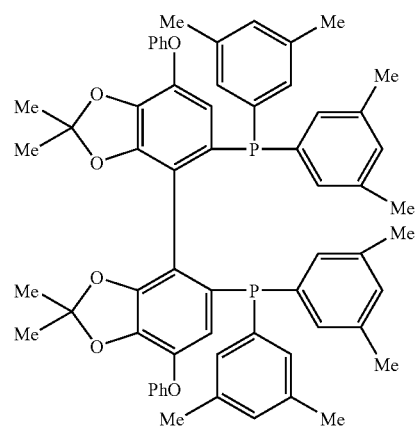
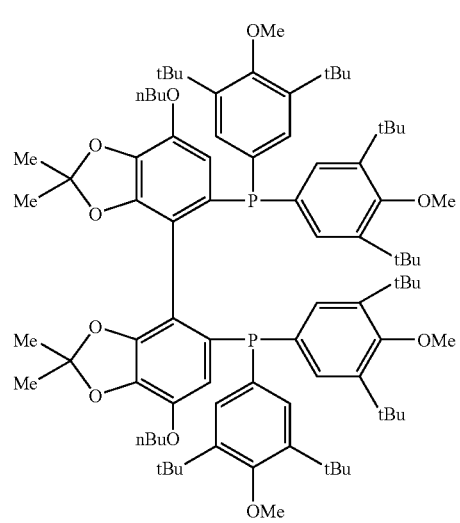
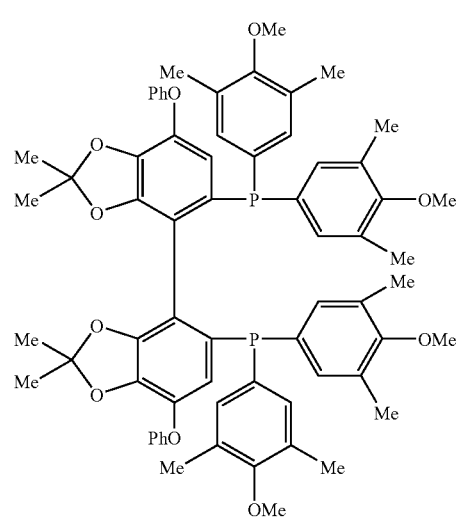
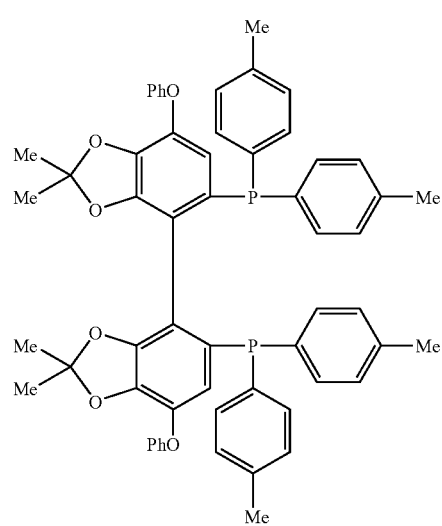
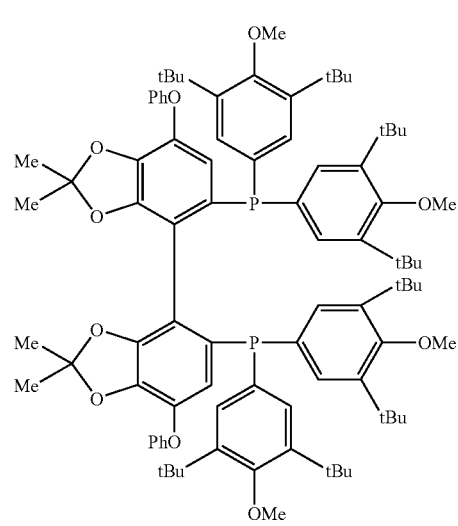

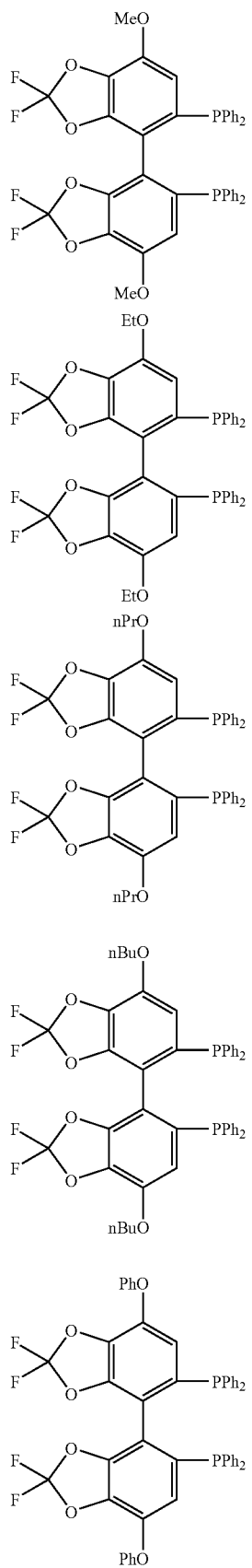
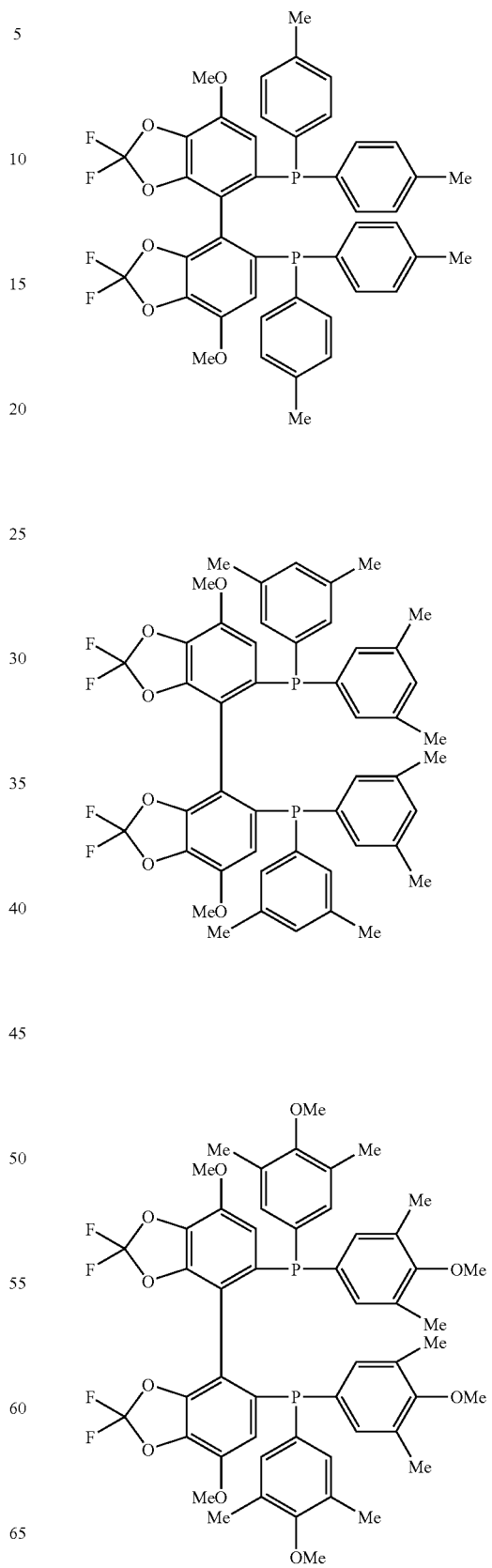

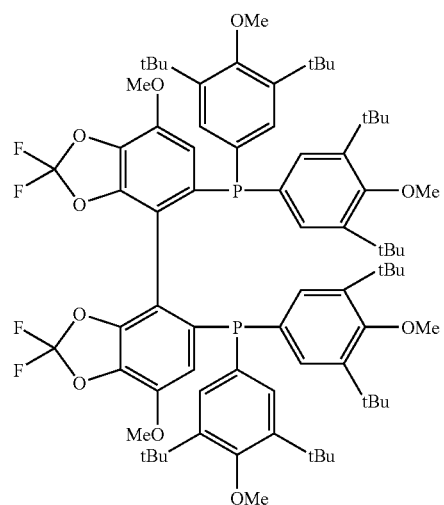
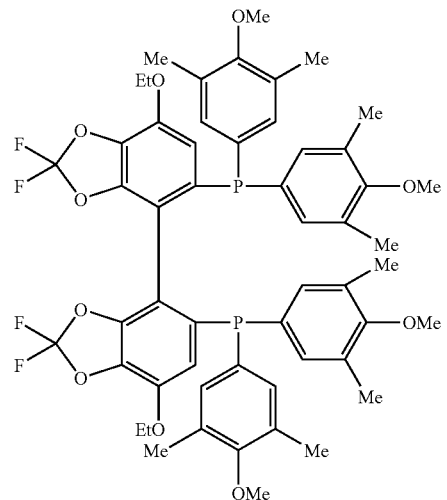
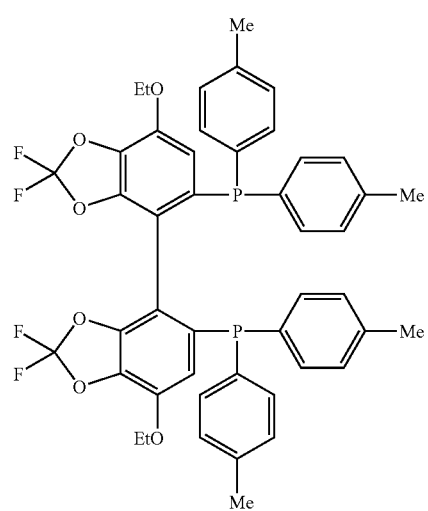
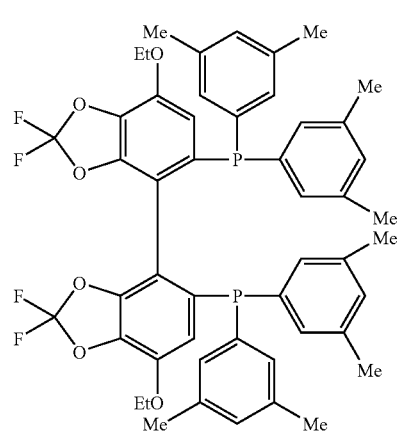

-continued
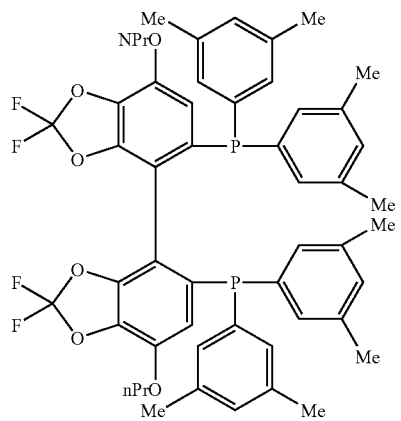
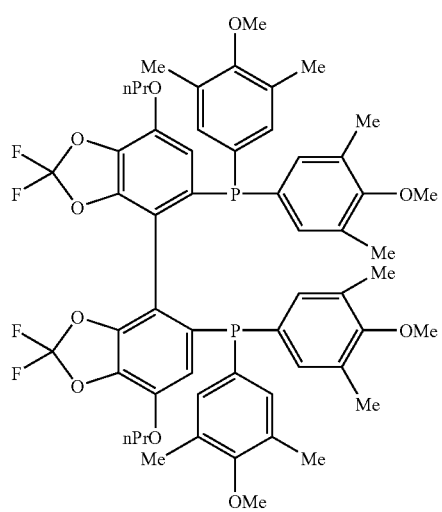
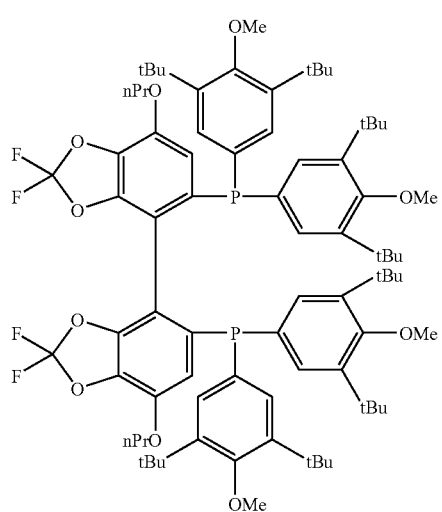
-continued
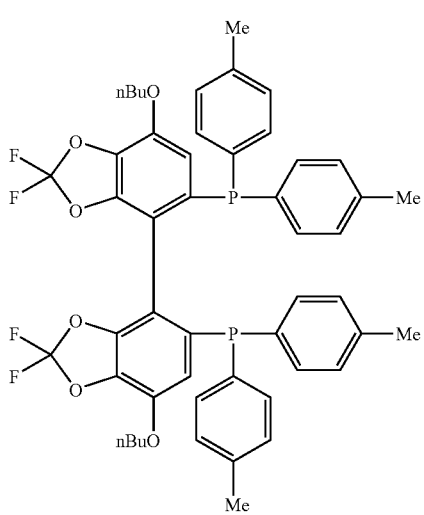
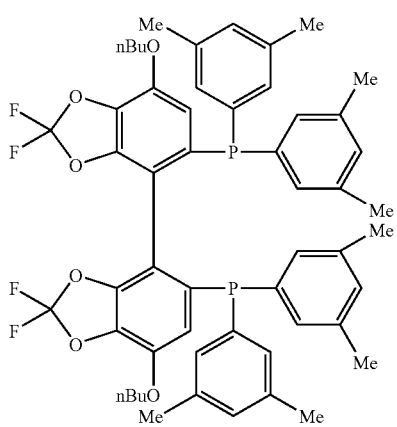
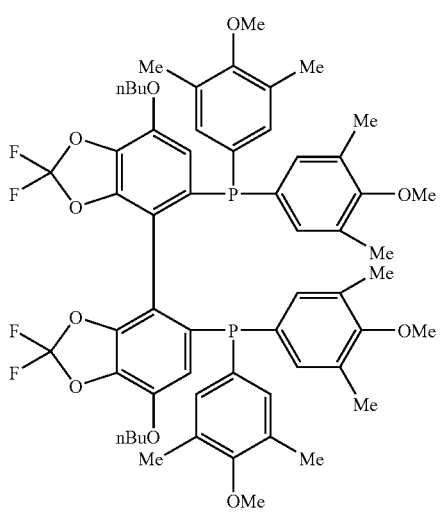

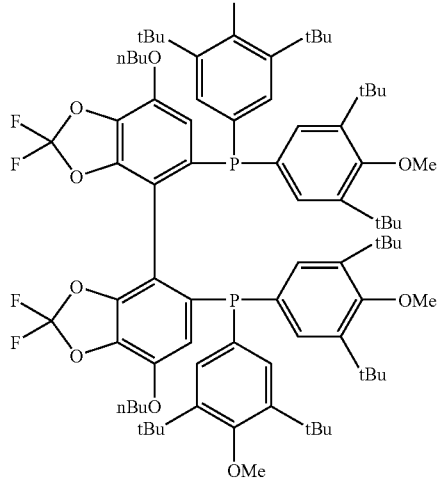

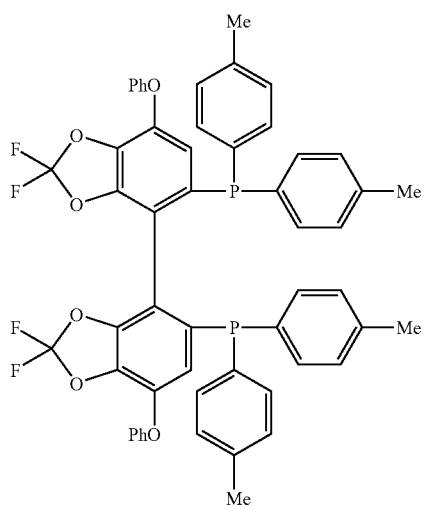

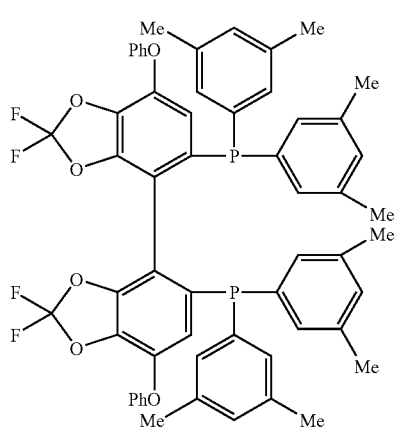

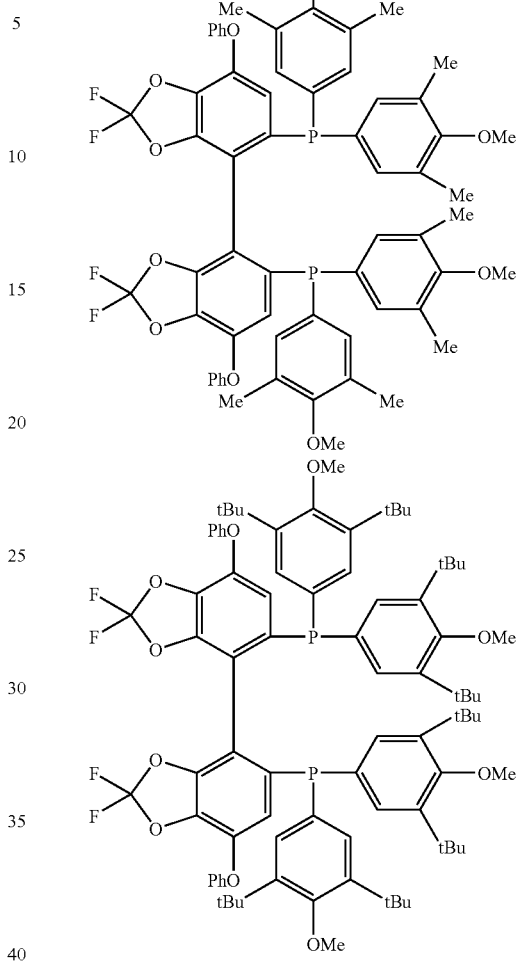

In order to use a diphosphine compound represented by the above formula (1) of the present invention as a chiral ligand, an optically active substance thereof is used. Specific examples of the optically active that is, the optically active diphosphine compound represented by the formula (1) include, for example, the (+)-compounds such as (+)-[4,4'-bi(7-methoxy-1,3-benzodioxol)]-5,5'-diyl-bis(diphenylphosphine), (+)-[4,4'-bi(7-ethoxy-1,3-benzodioxol)]-5,5'-diyl-bis(diphenylphosphine), (+)-[4,4'-bi(7-n-propoxy-1,3-benzodioxol)]-5,5'-diyl-bis(diphenylphosphine), (+)-[4,4'-bi(7-n-butoxy-1,3-benzodioxol)]-5,5'-diyl-bis(diphenylphosphine), (+)-[4,4'-bi(7-phenoxy-1,3-benzodioxol)]-5,5'-diyl-bis(diphenylphosphine), (+)-[4,4'-bi(7-methoxy-1,3-benzodioxol)]-5,5'-diyl-bis[di(4-methylphenyl)phosphine], (+)-[4,4'-bi(7-methoxy-1,3-benzodioxol)]-5,5'-diyl-bis[di(3,5-dimethylphenyl)phosphine], (+)-[4,4'-bi(7-methoxy-1,3-benzodioxol)]-5,5'-diyl-bis[di(4-methoxy-3,5-dimethylphenyl)phosphine], (+)-[4,4'-bi(7-methoxy-1,3-benzodioxol)]-5,5'-diyl-bis[di(4-methoxy-3,5-di-tert-butylphenyl)phosphine] and the like.

The chemical formulae of these diphosphine compounds are shown below:

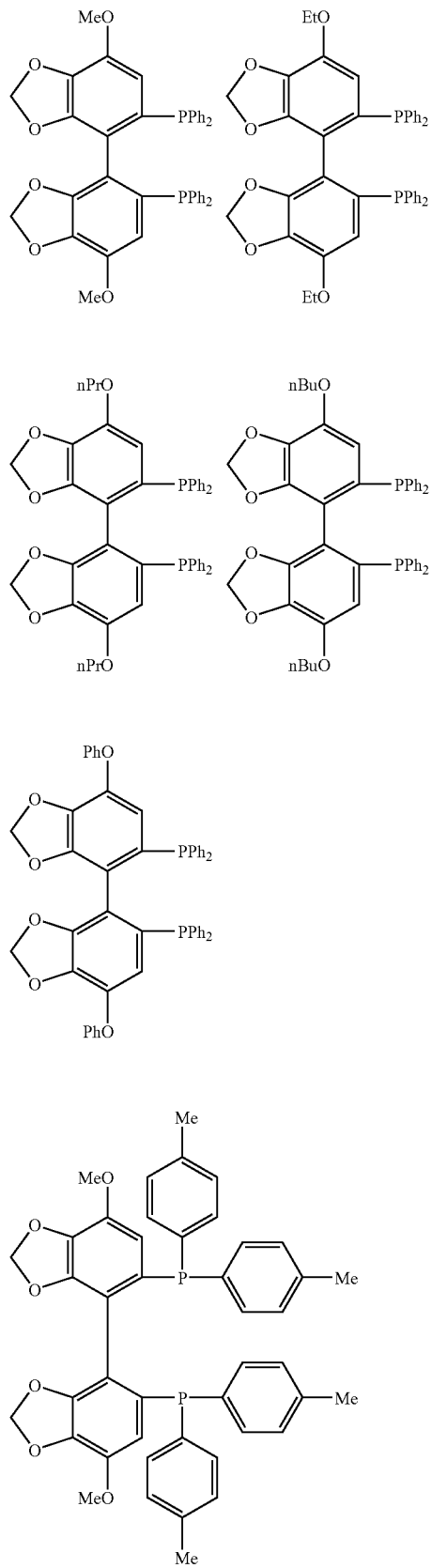
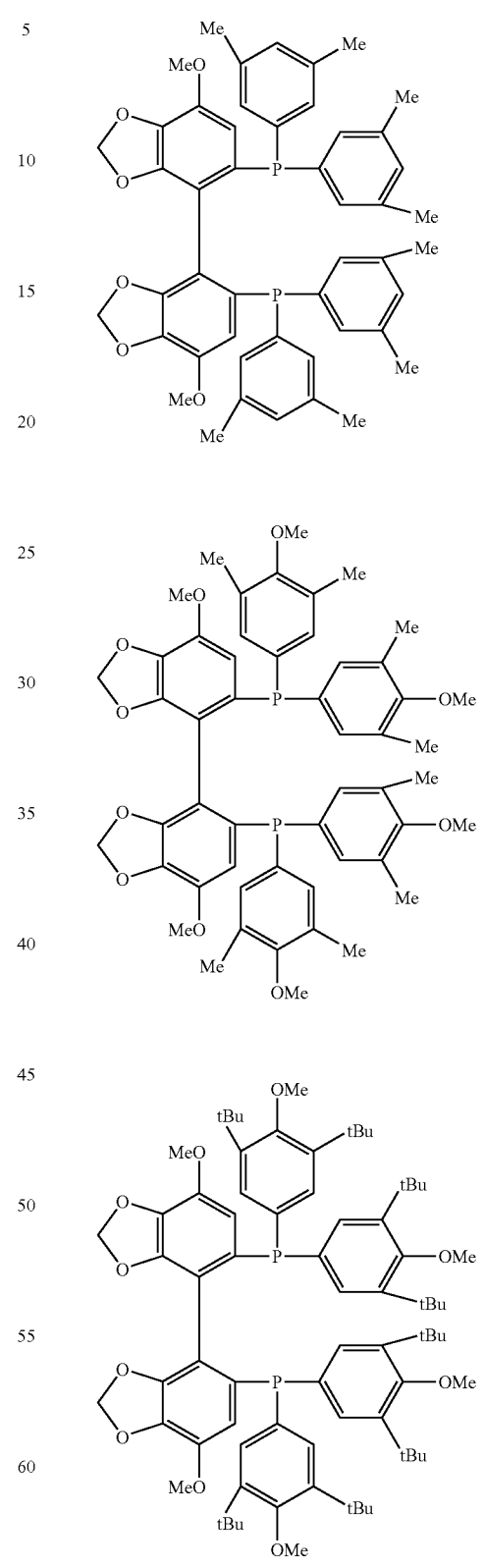
Another example of the (+)-compounds includes the following diphosphine compounds:

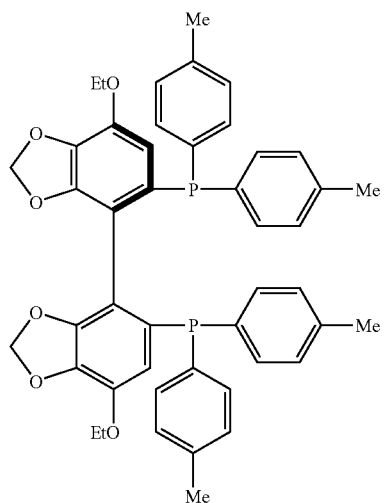
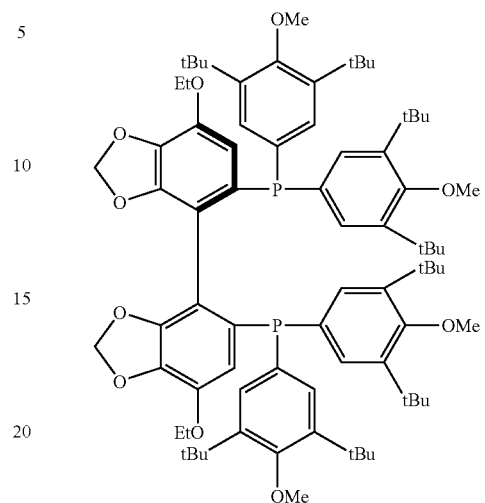
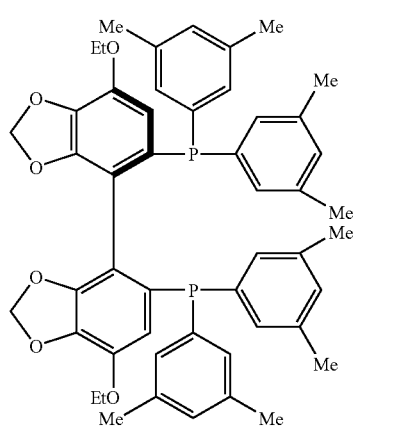
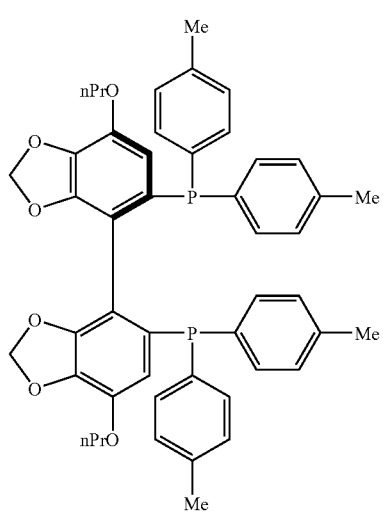
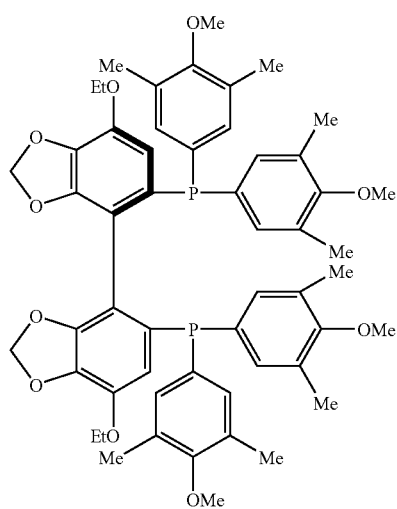
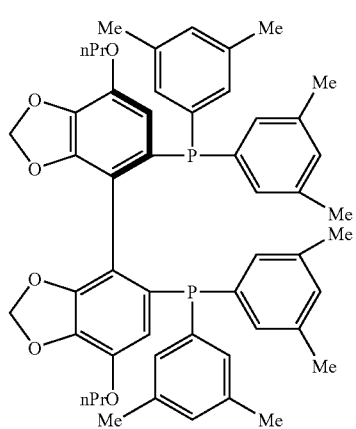

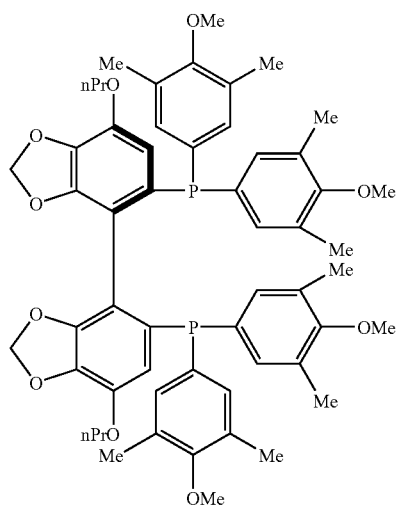
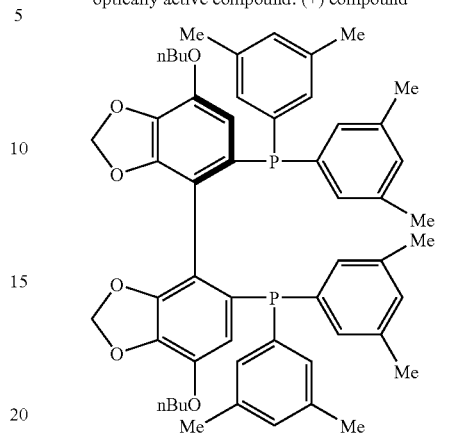
optically active compound: (+) compound
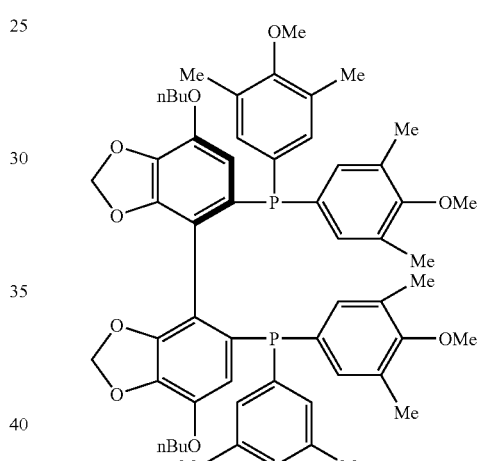
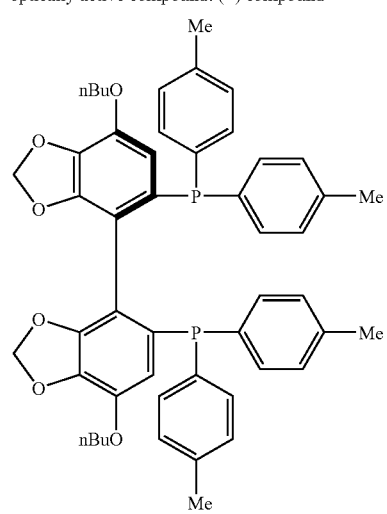
optically active compound: (+) compound
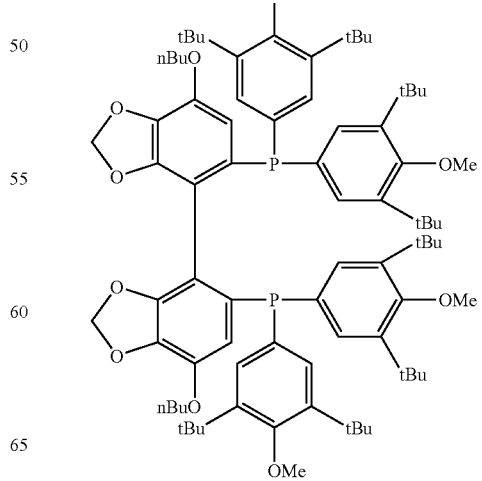

-continued
optically active compound: (+) compound
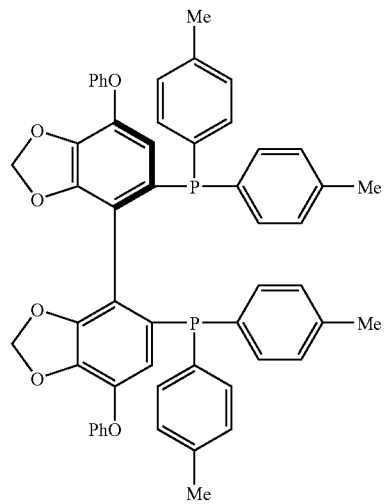
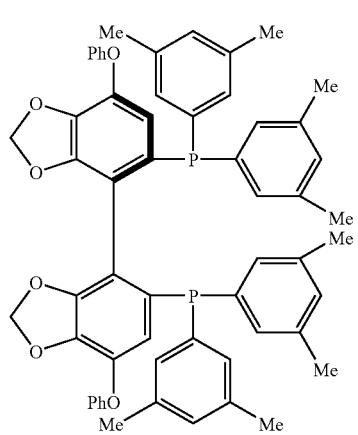
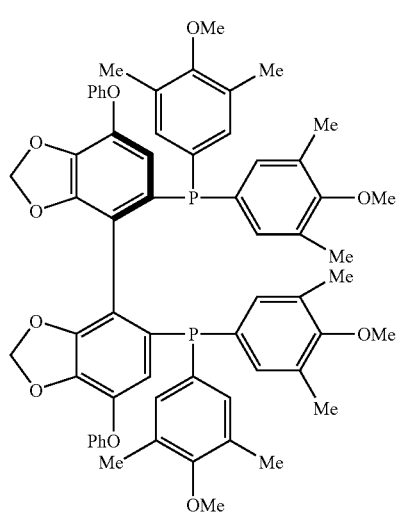
-continued
optically active compound: (+) compound
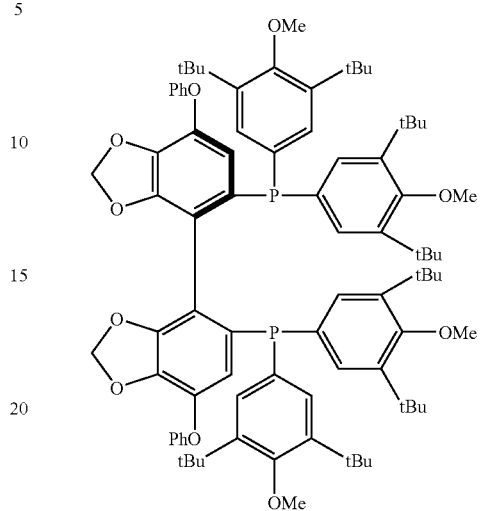
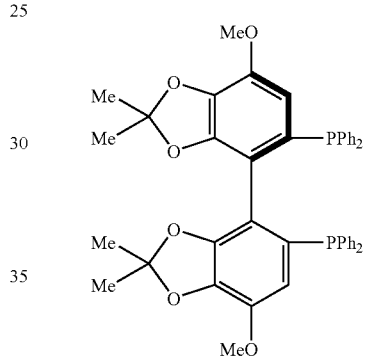
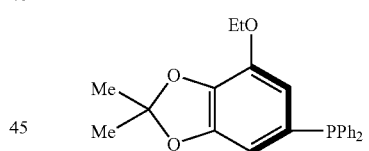
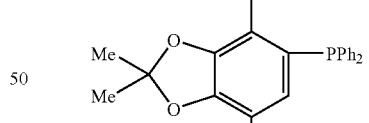
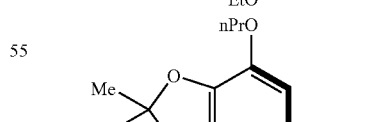
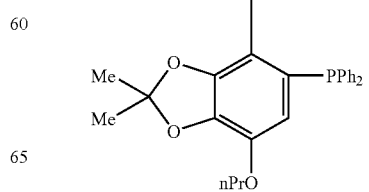

-continued
optically active compound: (+) compound
-continued
optically active compound: (+) compound
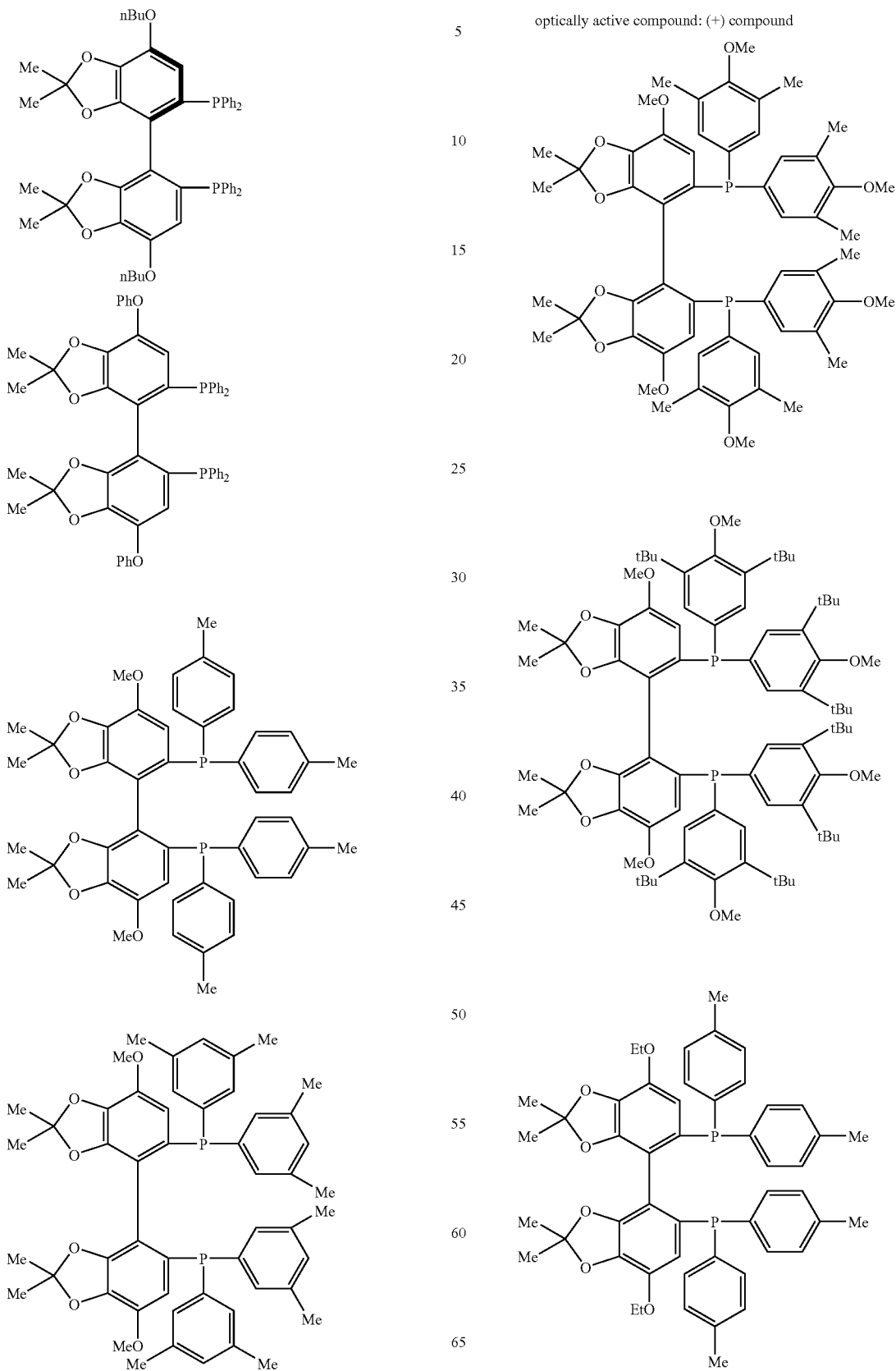

-continued
optically active compound: (+) compound
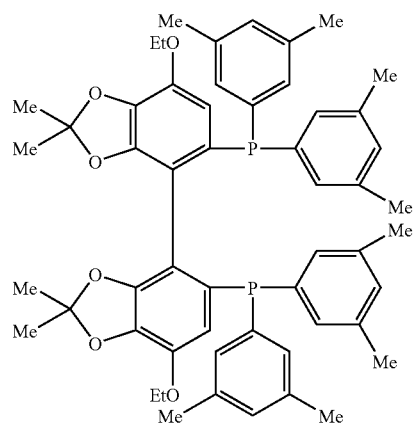
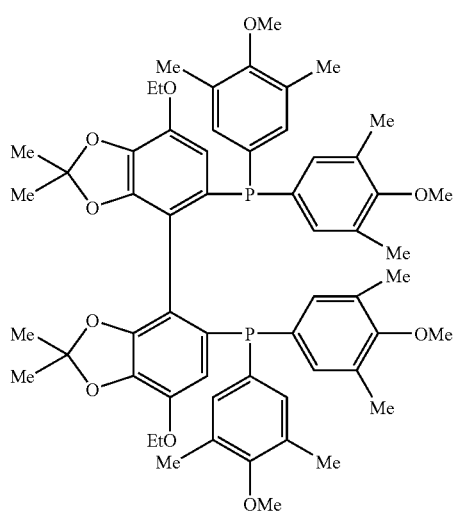
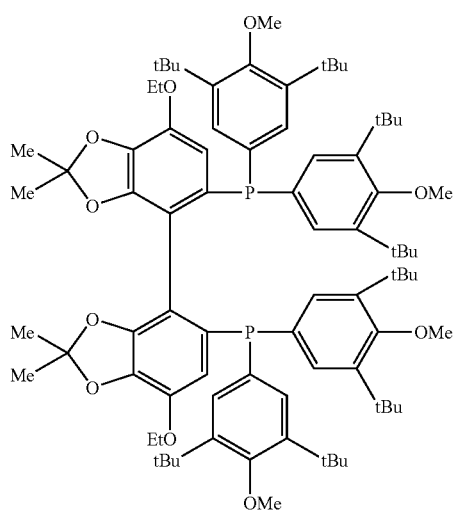
-continued
optically active compound: (+) compound
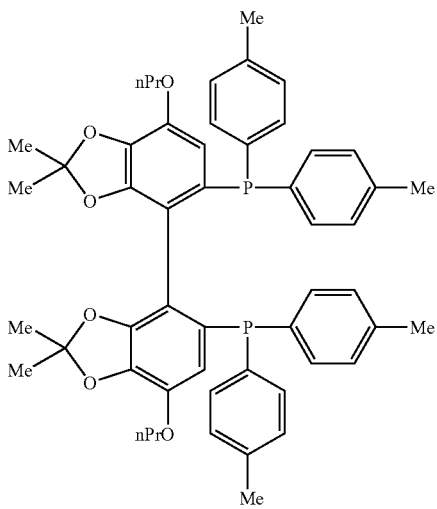
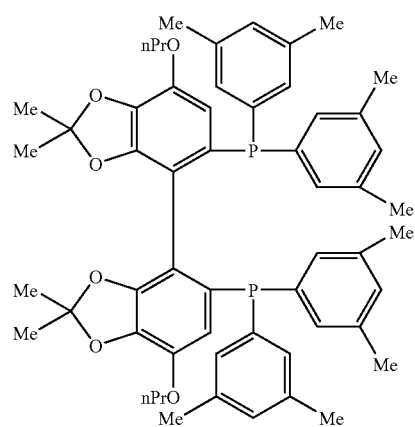
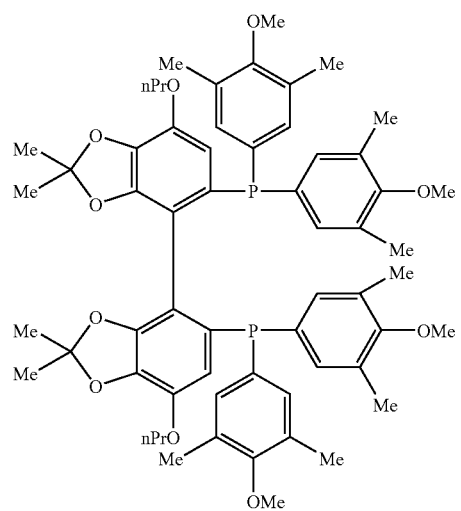

optically active compound: (+) compound
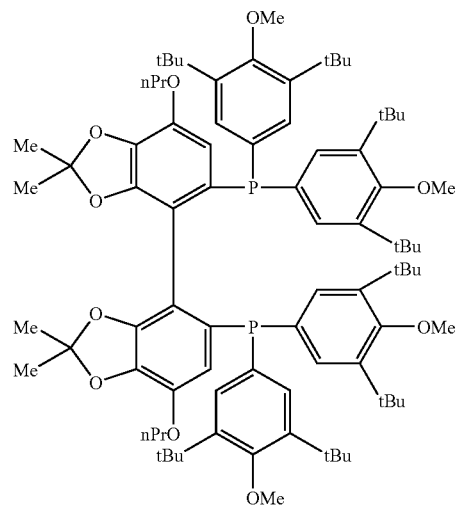
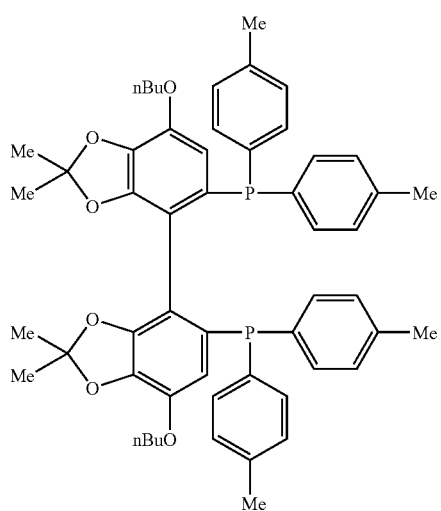
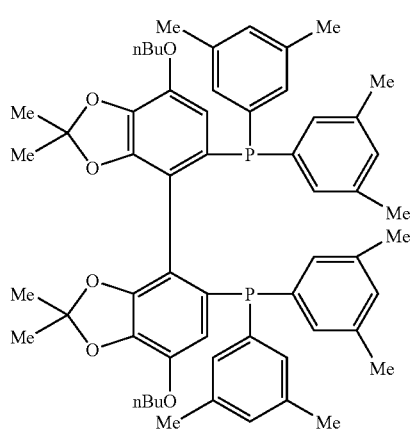
optically active compound: (+) compound
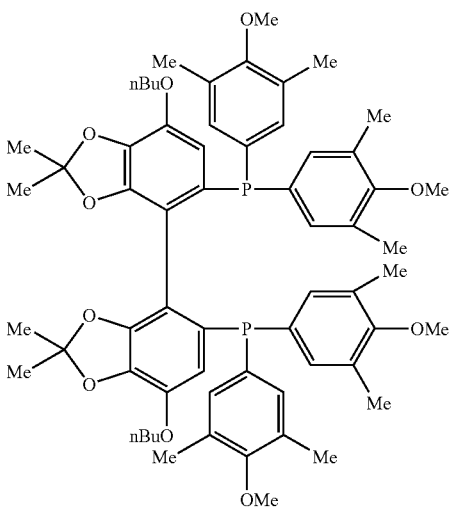
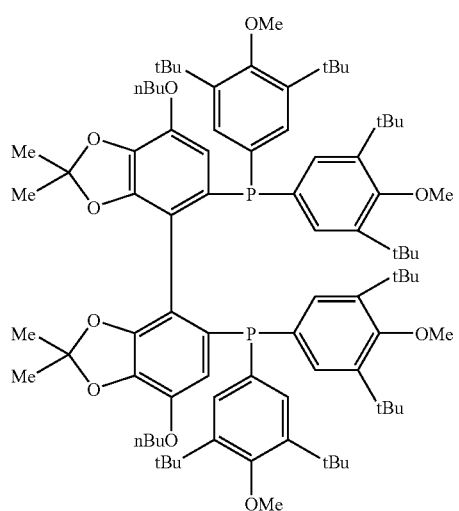
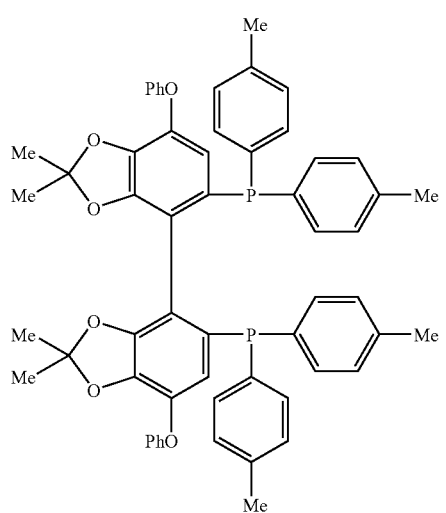

optically active compound: (+) compound
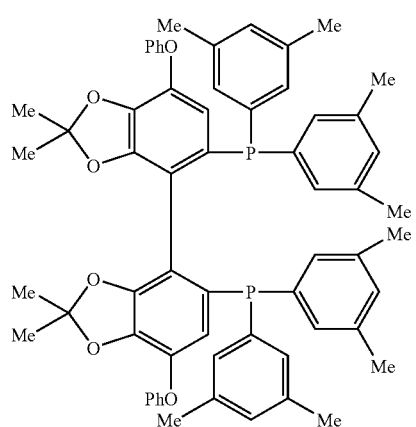
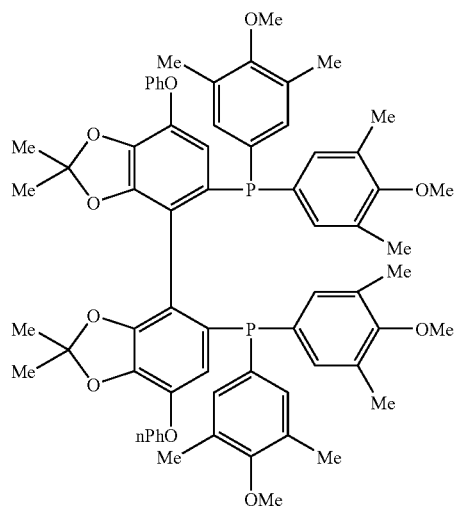
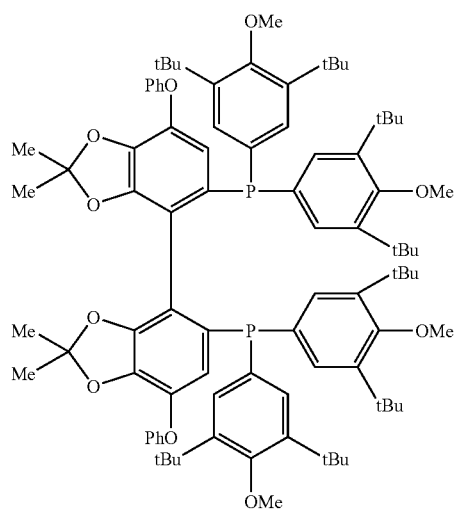
optically active compound: (+) compound
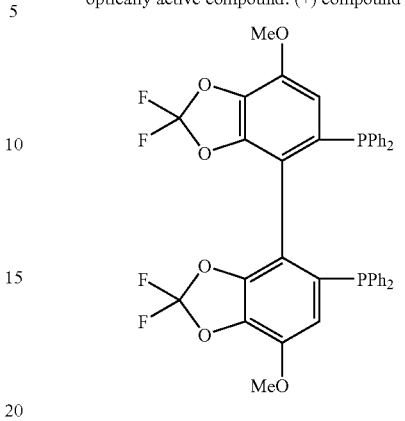
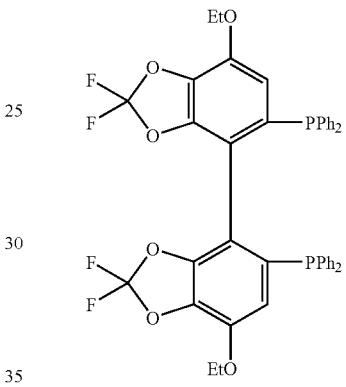
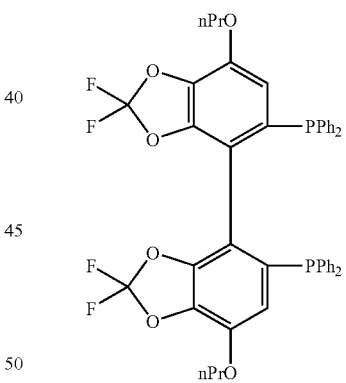
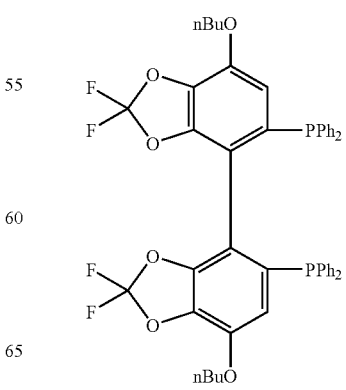

optically active compound: (+) compound
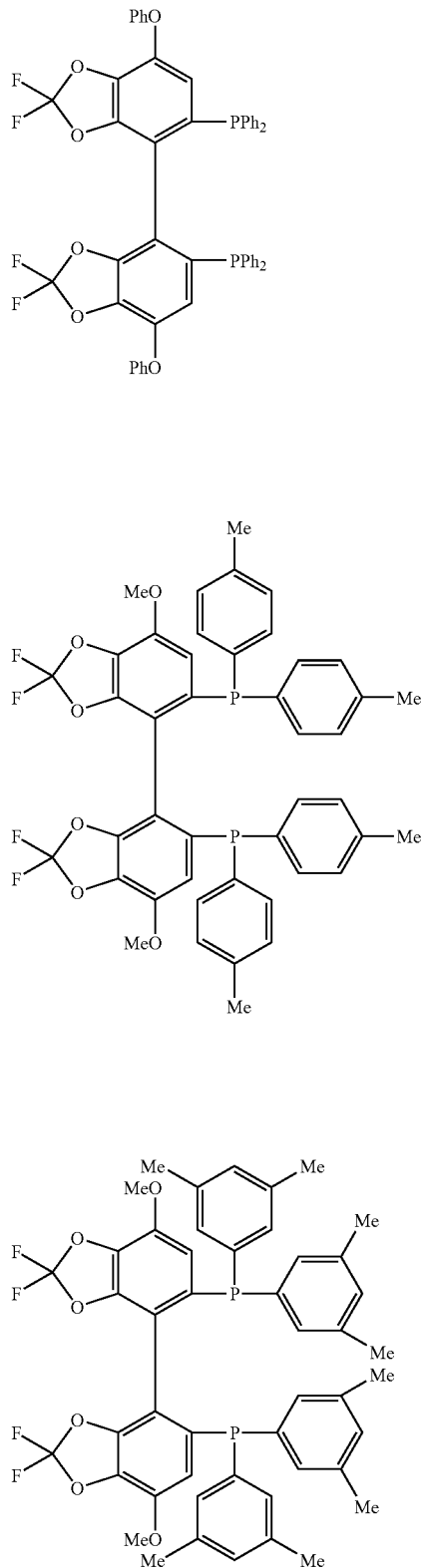
optically active compound: (+) compound
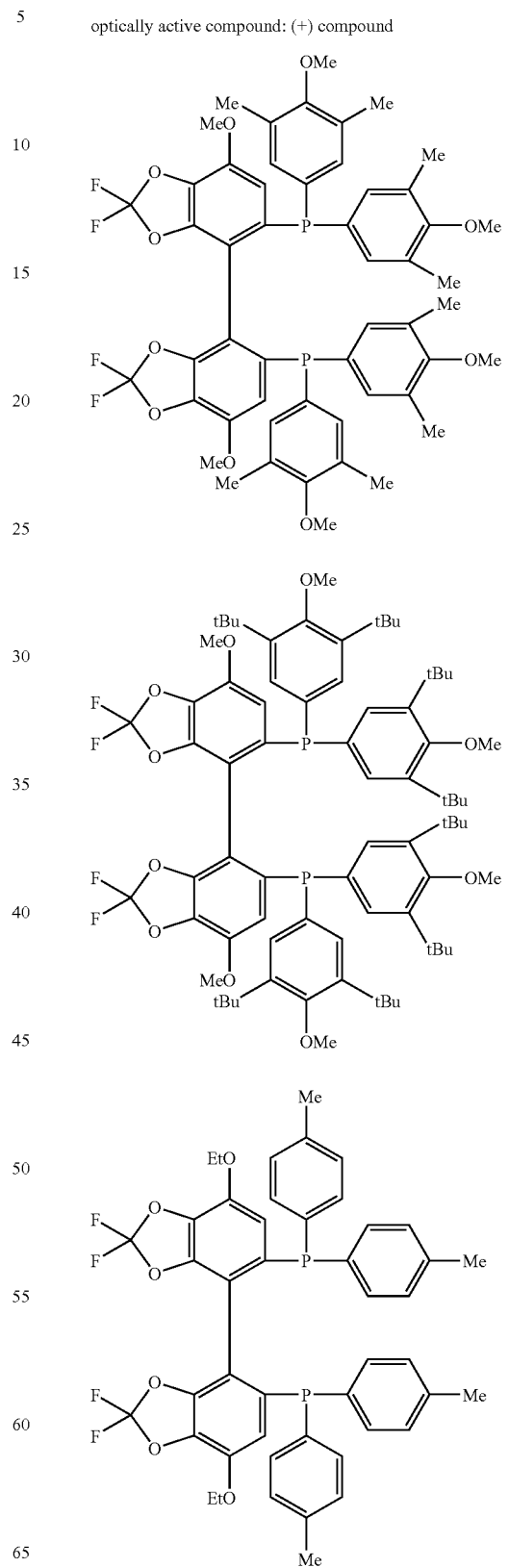

optically active compound: (+) compound
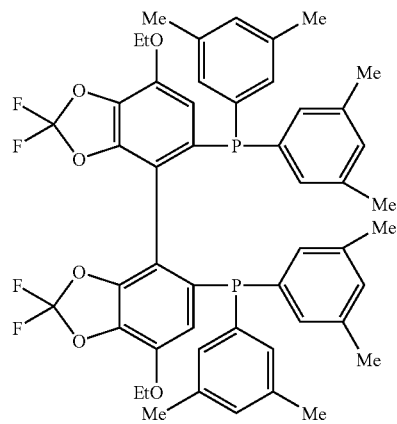
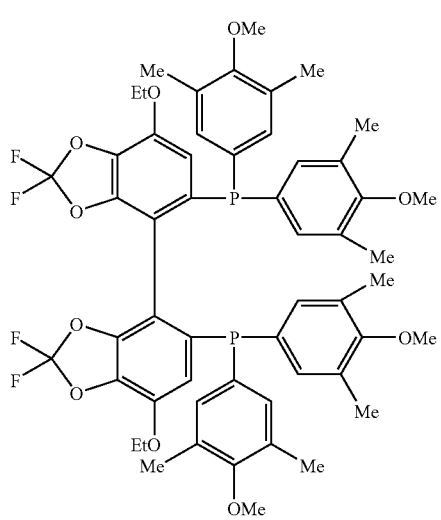
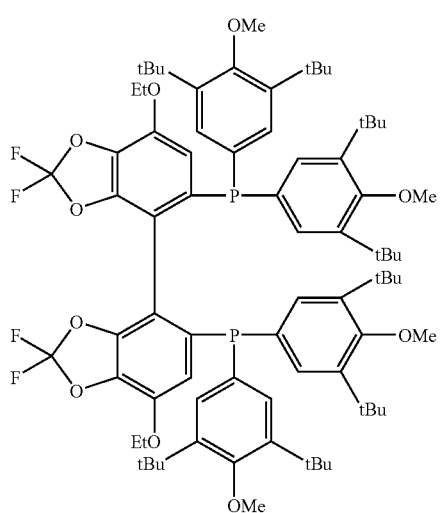
optically active compound: (+) compound
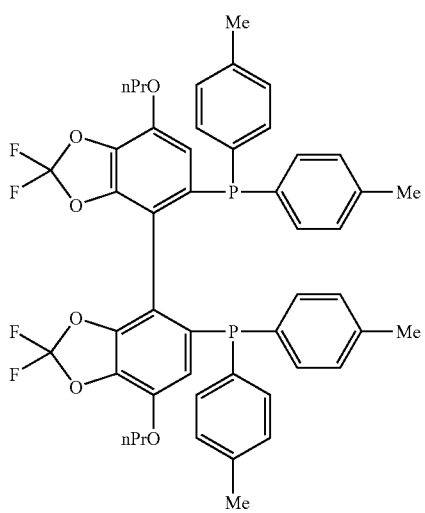
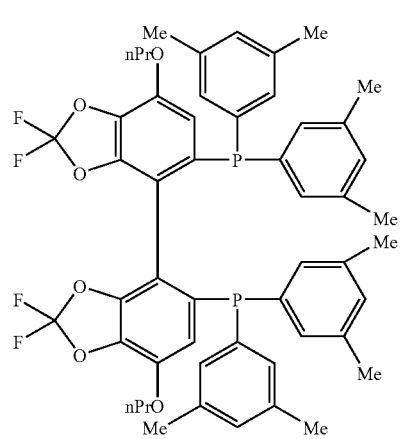
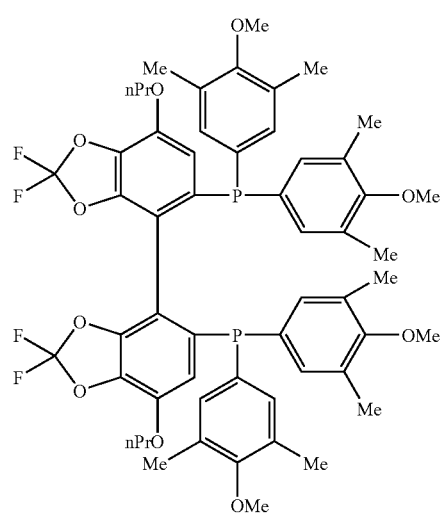

optically active compound: (+) compound
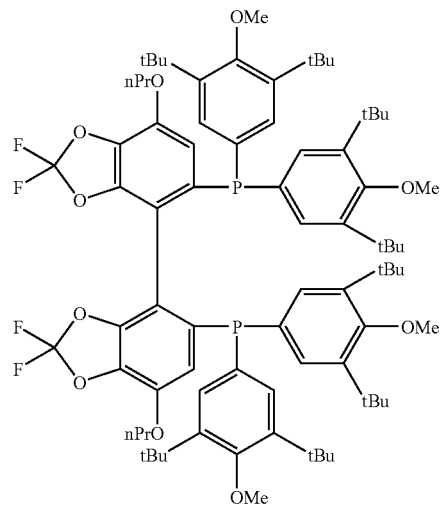
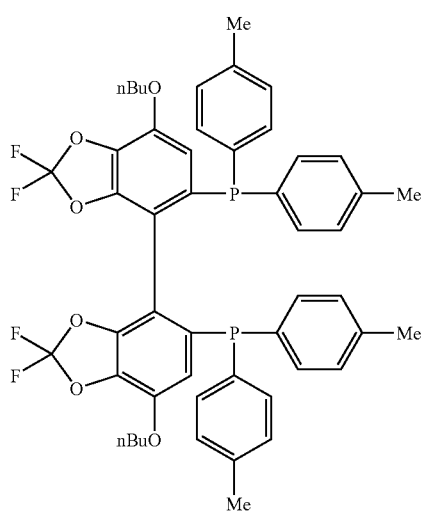
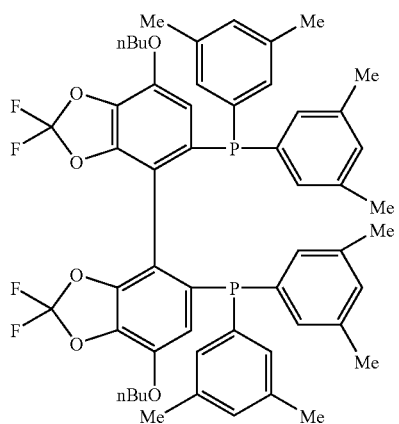
optically active compound: (+) compound
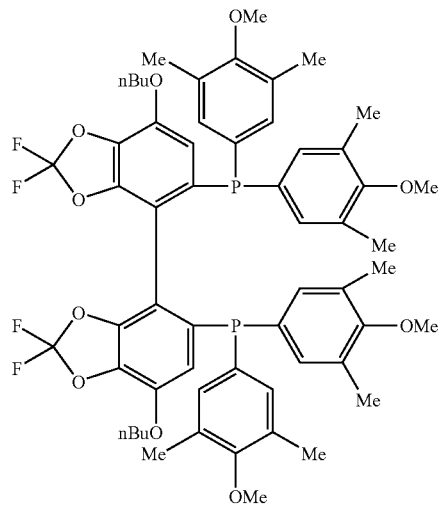
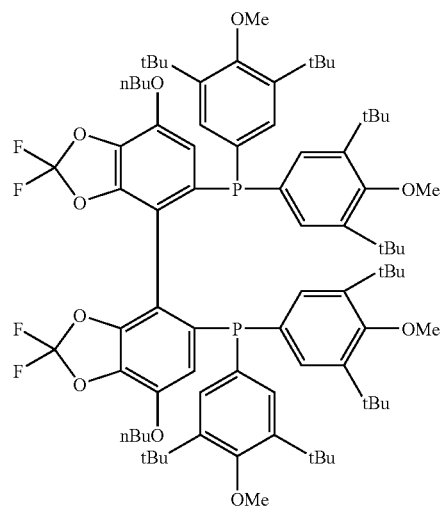
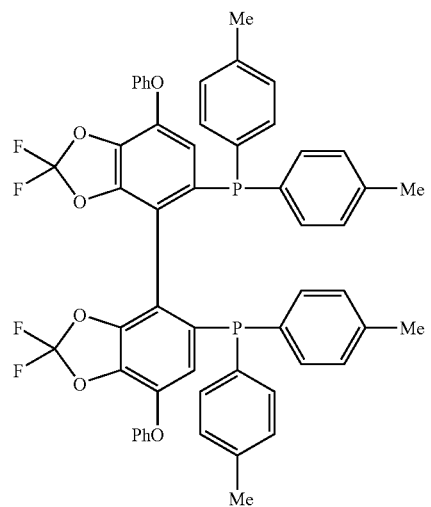

-continued optically active compound: (+) compound

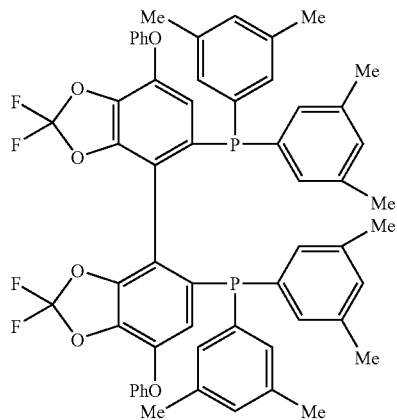

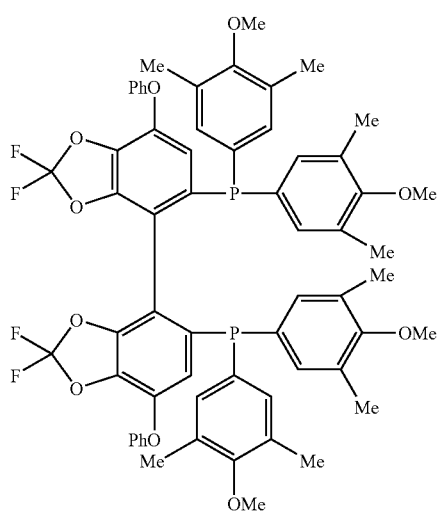

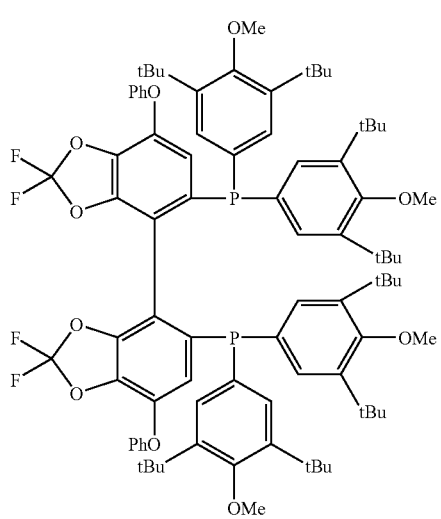

Similar to the above (+) compounds, the (−) compounds of the diphosphine compound include, for example, (−)-[4,4'-bi(7-methoxy-1,3-benzodioxol)]-5,5',-diyl-bis(diphenylphosphine), (−)-[4,4'-bi(7-ethoxy-1,3-benzodioxol)]-5,5'-diyl-bis(diphenylphosphine), (−)[4,4'-bi(7-n-propoxy-1,3-benzodioxol)]-5,5'-diyl-bis(diphenylphosphine), (−)-[4,4'-bi(7-n-butoxy-1,3-benzodioxol)]-5,5'-di yl-bis(diphenylphosphine), (−)-[4,4'-bi(7-phenoxy-1,3-benzodioxol)]-5,5'-diyl-bis(diphenylphosphine), (−)-[4,4'-bi(7-methoxy-1,3-benzodioxol)]-5,5'-diyl-bis[di(4-methylphenyl)phosphine], (−)-[4,4'-bi(7-methoxy-1,3-benzodioxol)]-5,5'-diyl-bis[di(3,5-dimethylphenyl)phosphine], (−)-[4,4'-bi(7-methoxy-1,3-benzodioxol)]-5,5'-diyl-bis[di(4-methoxy-3,5-dimethylphenyl)phosphine], (−)-[4,4'-bi(7-methoxy-1,3-benzodioxol)]-5,5'-diyl-bis[di(4-methoxy-3,5-di-tert-butylphenyl)phosphine] and the like. The chemical formulae of these (−)-diphosphine compounds are shown below:

optically active compound: (−) compound

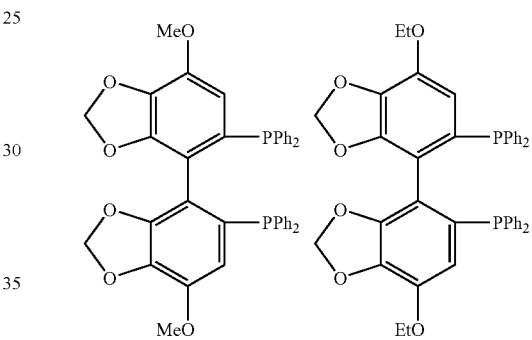

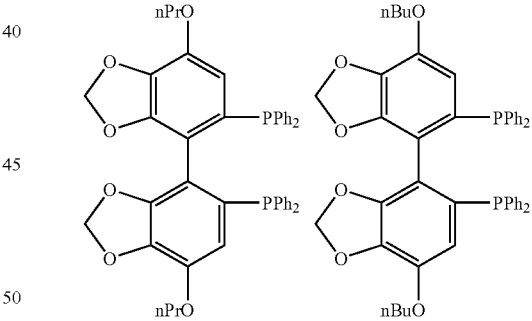

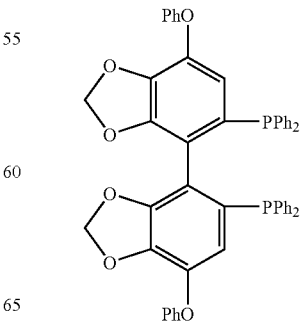

-continued
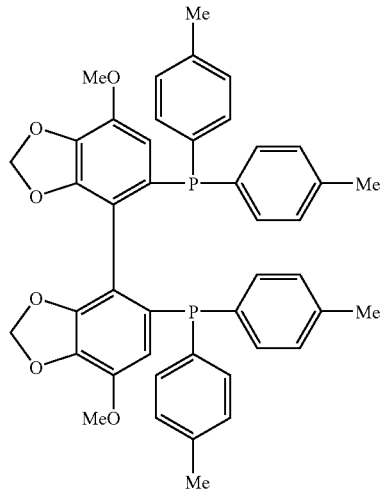
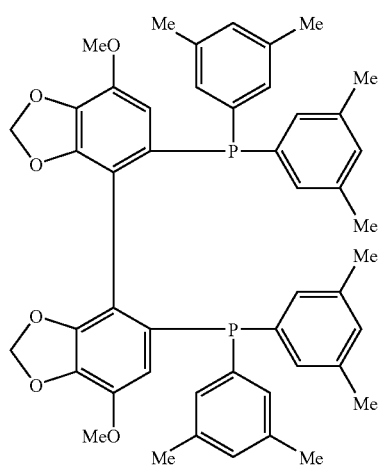
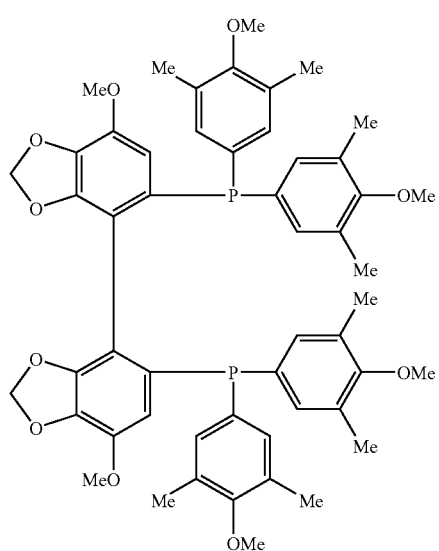
-continued
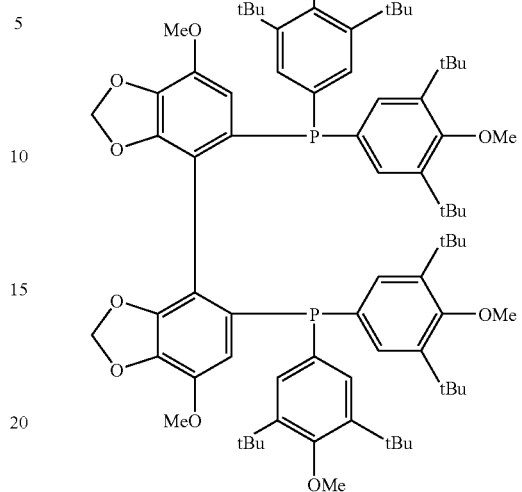
Another example of the (−)-compounds includes the following compounds:
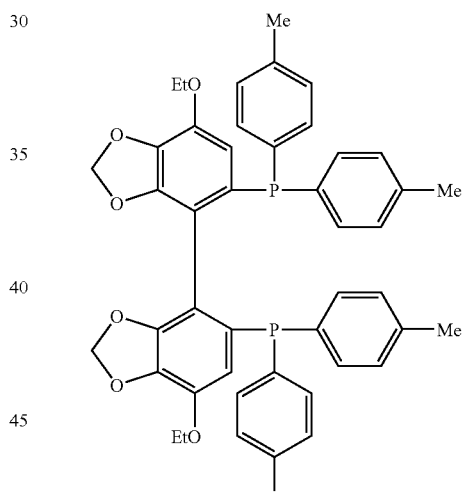
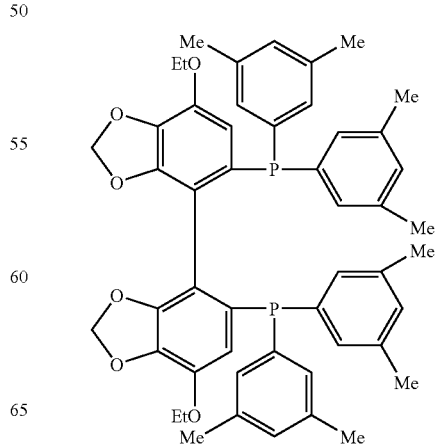

-continued
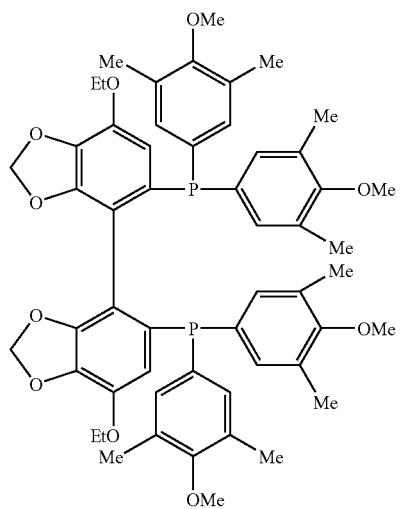
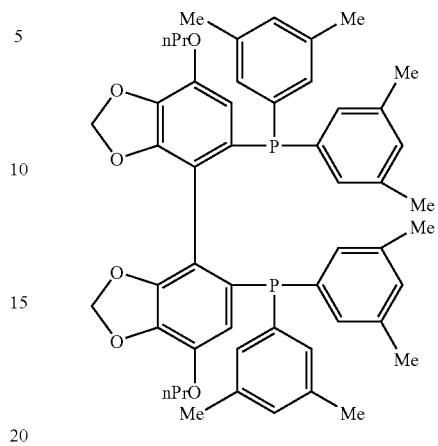
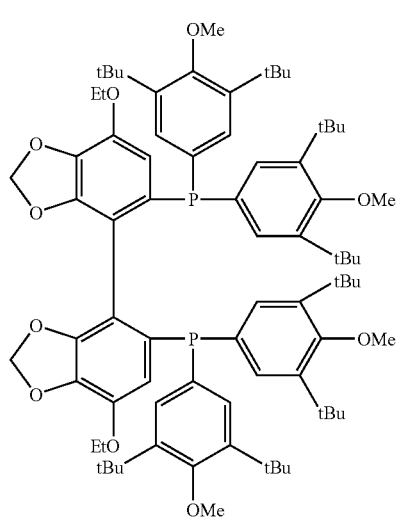
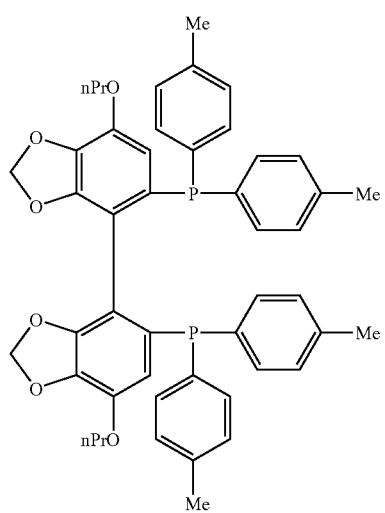

-continued
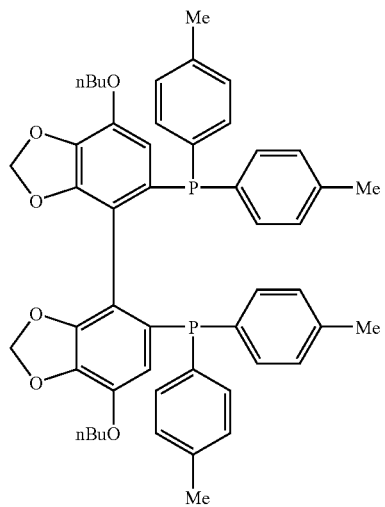
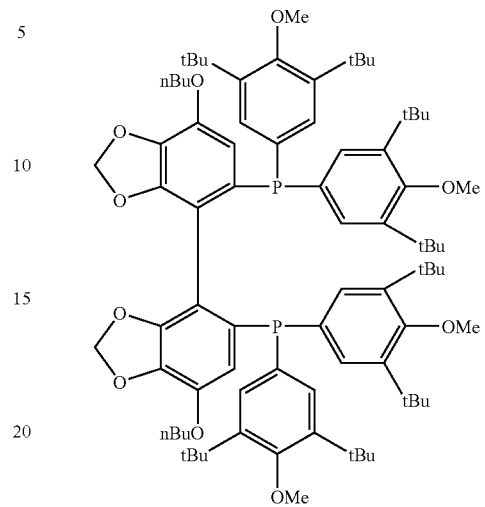
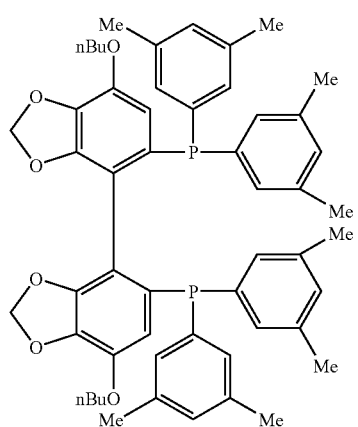
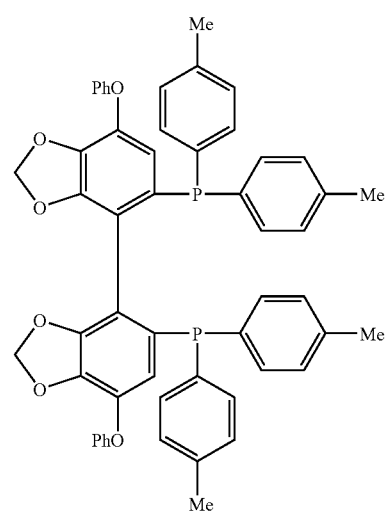
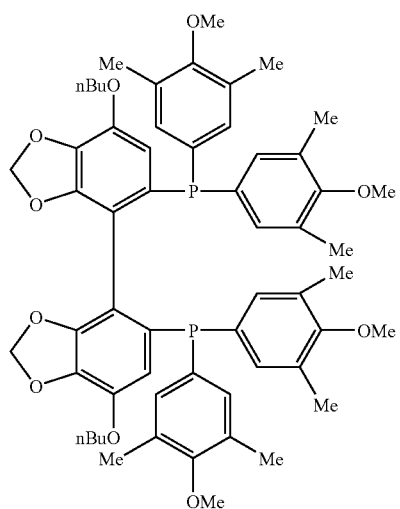
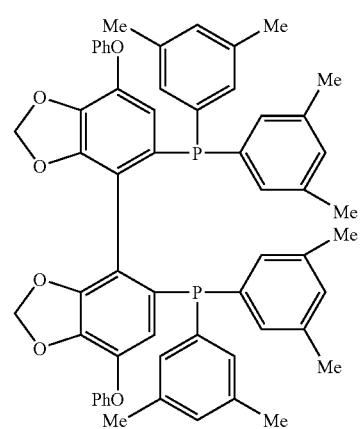

-continued
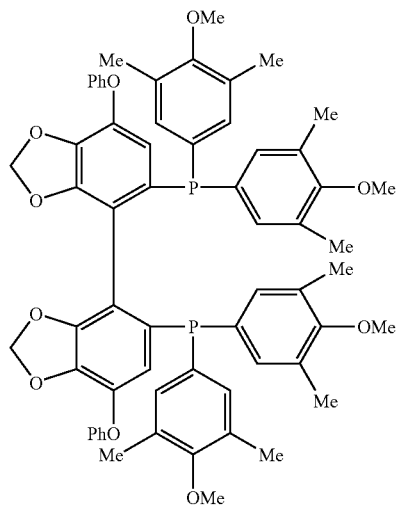
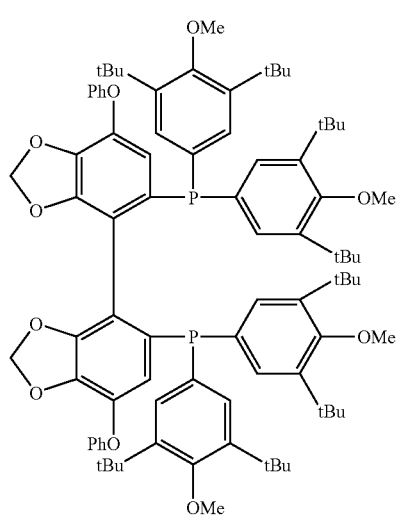
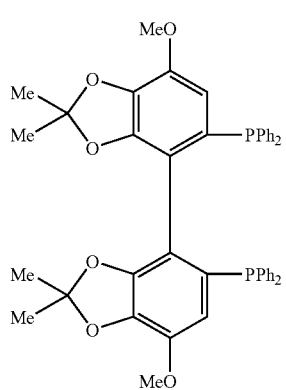
-continued
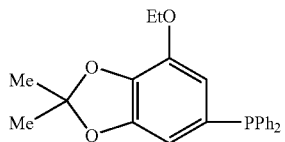
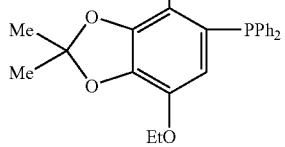
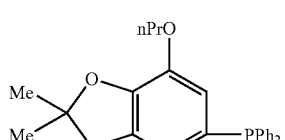
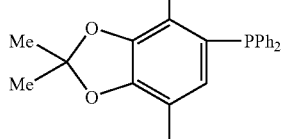
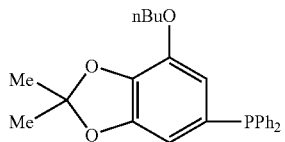
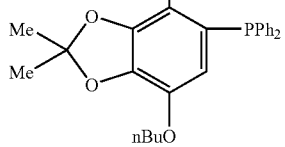
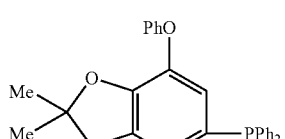
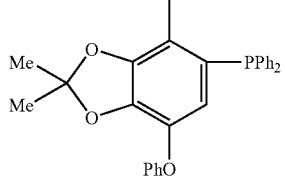

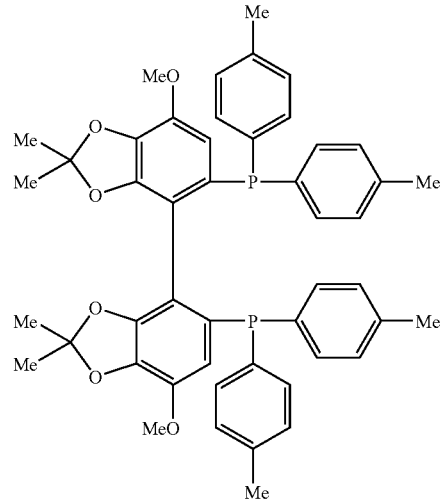
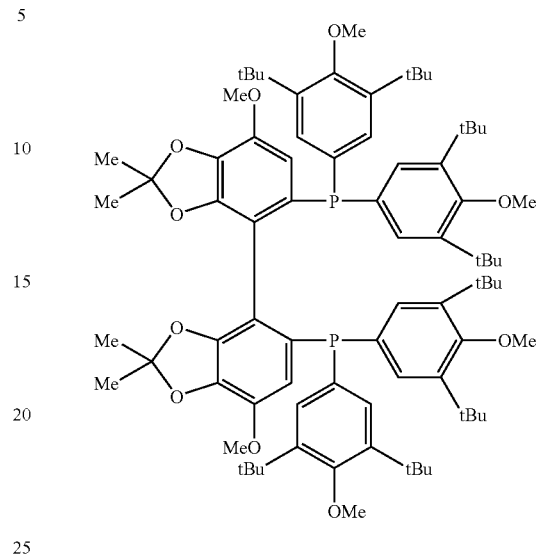
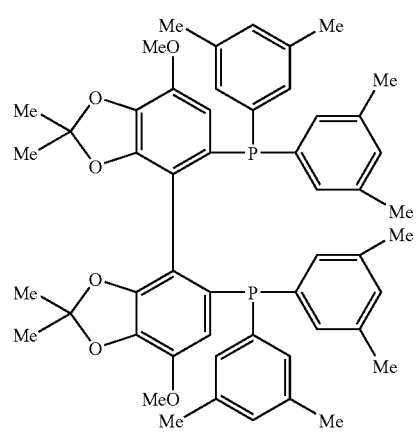
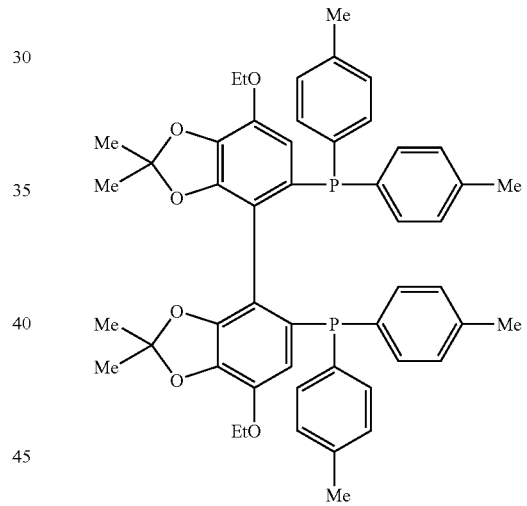
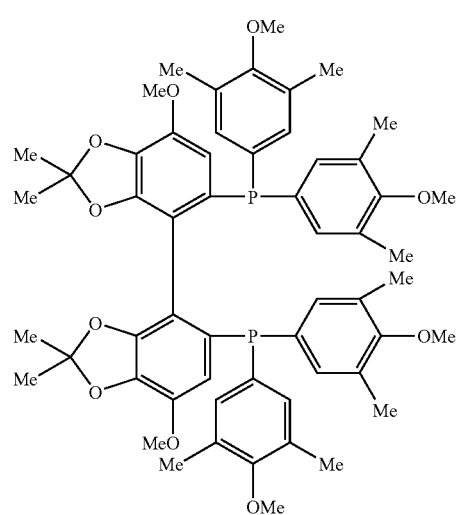
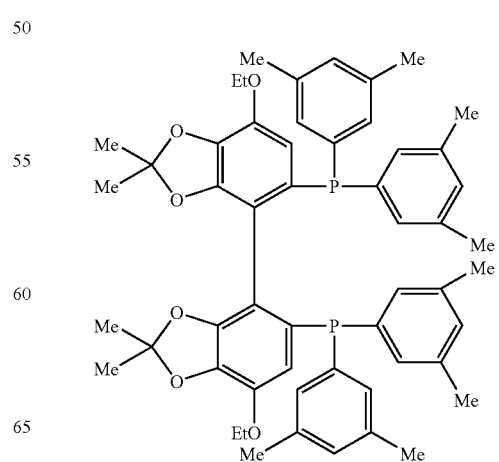

-continued
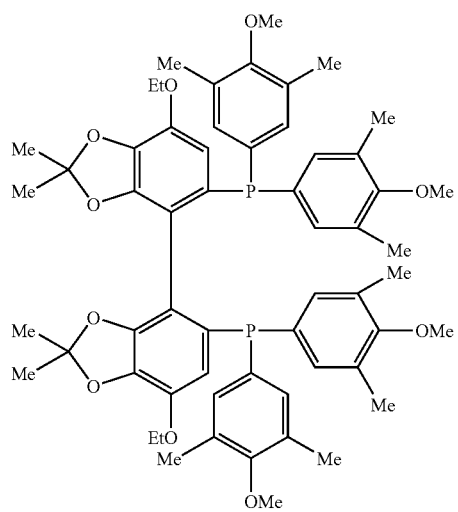
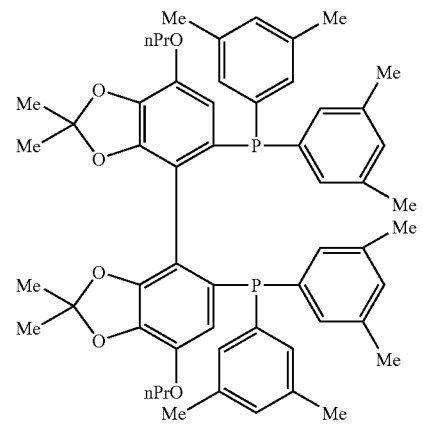
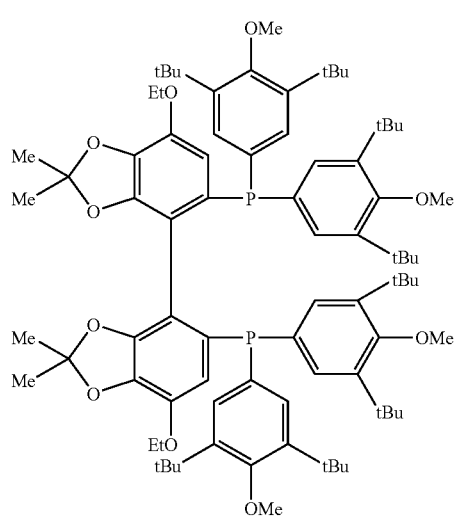
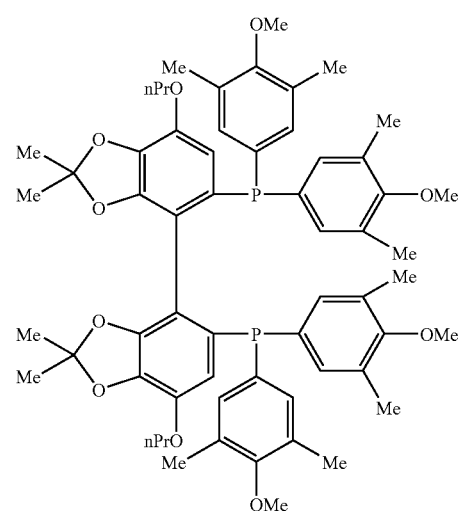
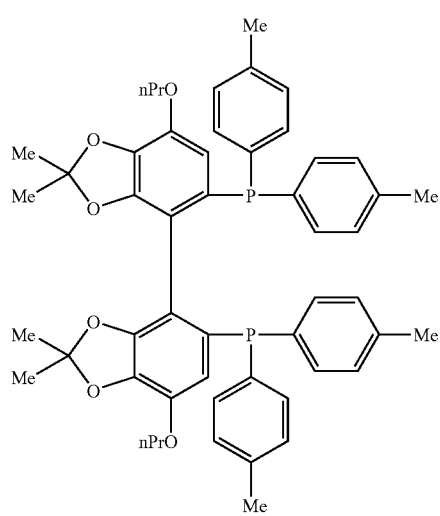
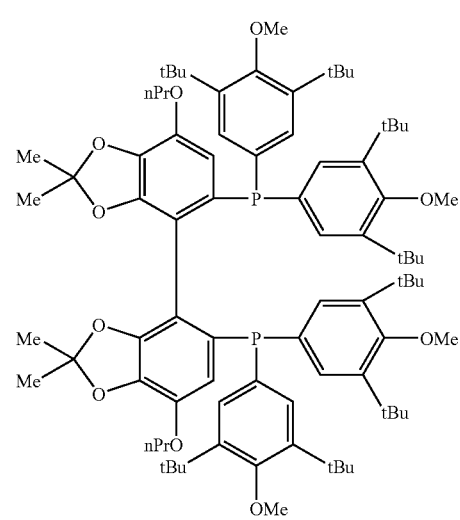

-continued
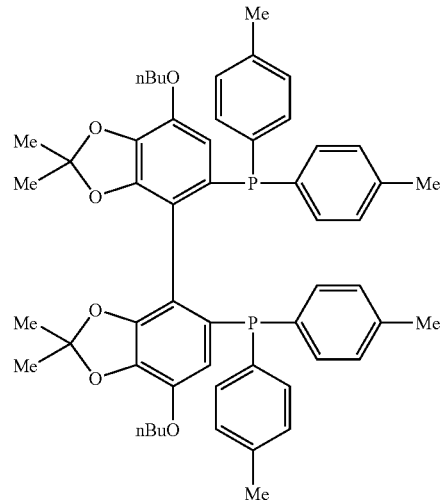
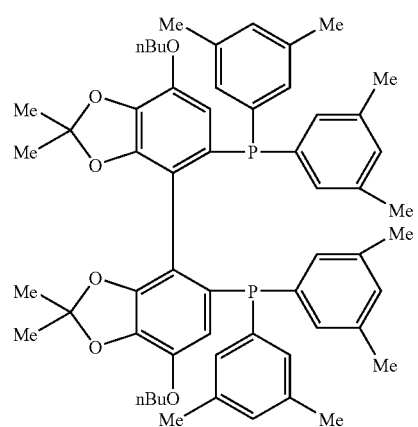
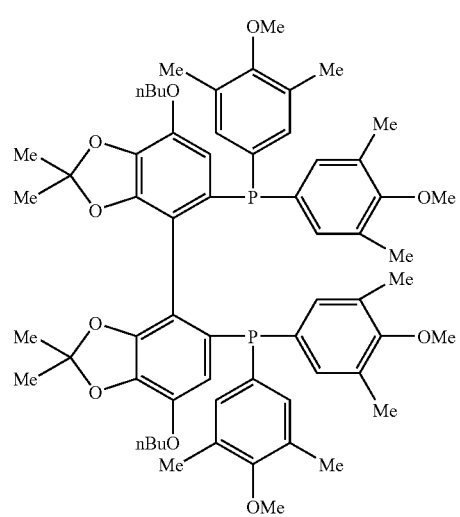
-continued
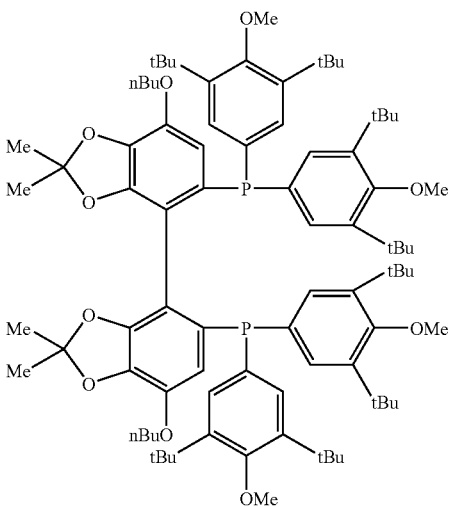
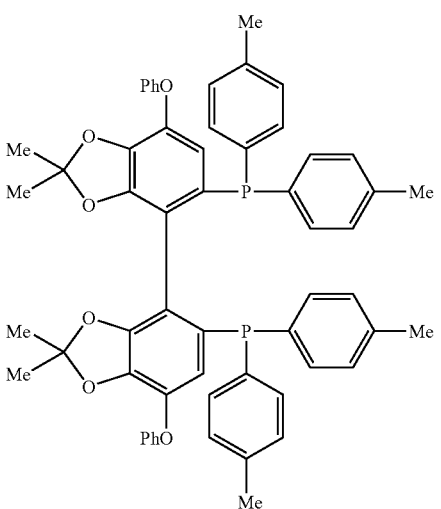
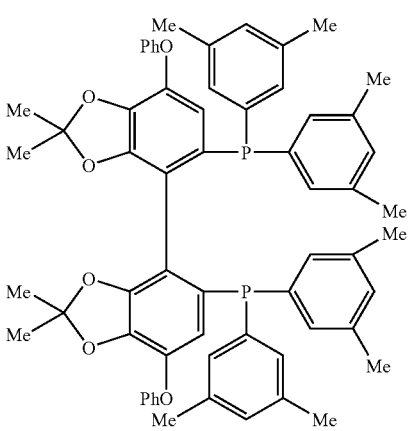

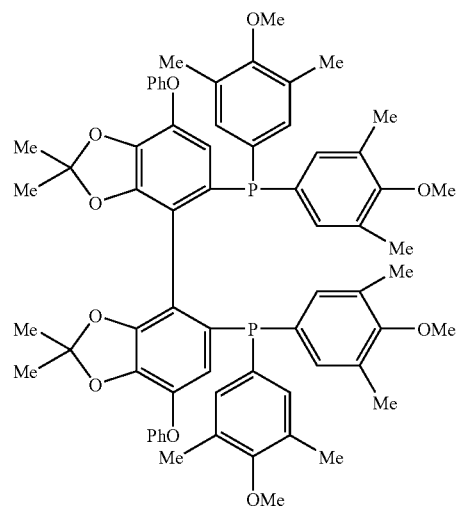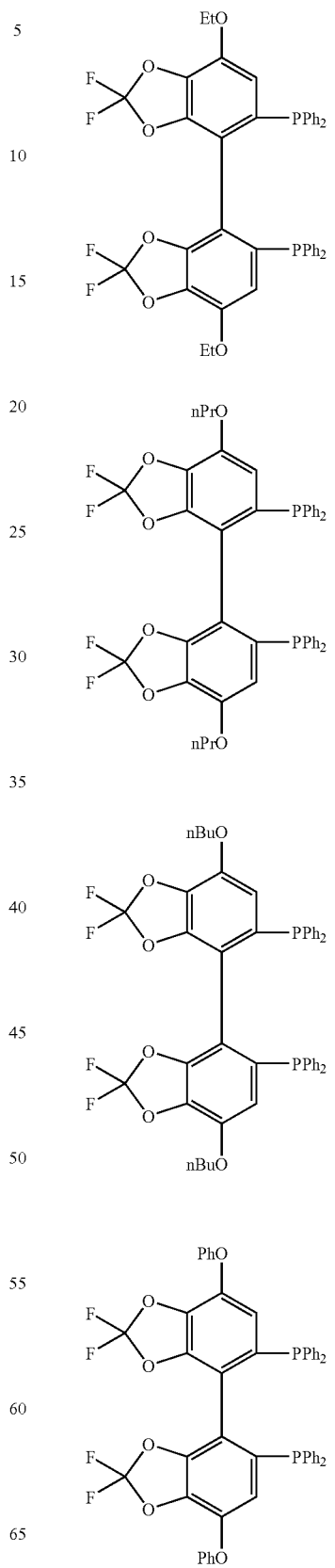

-continued
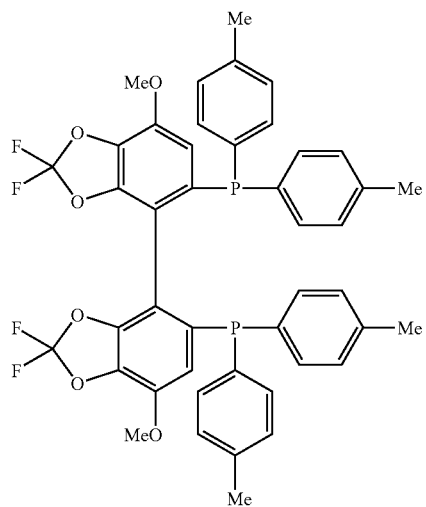
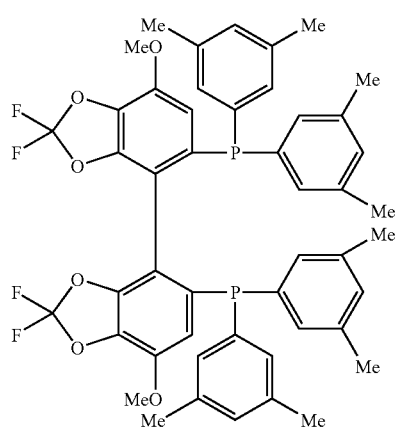
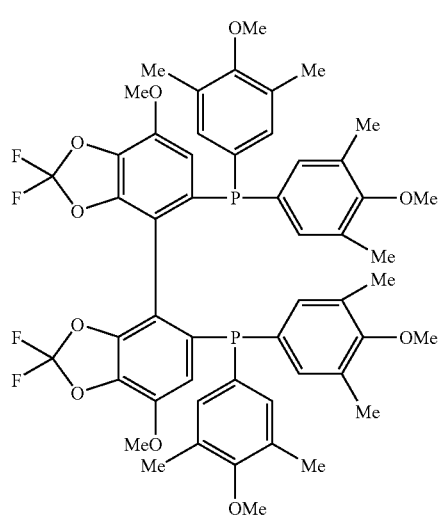
-continued
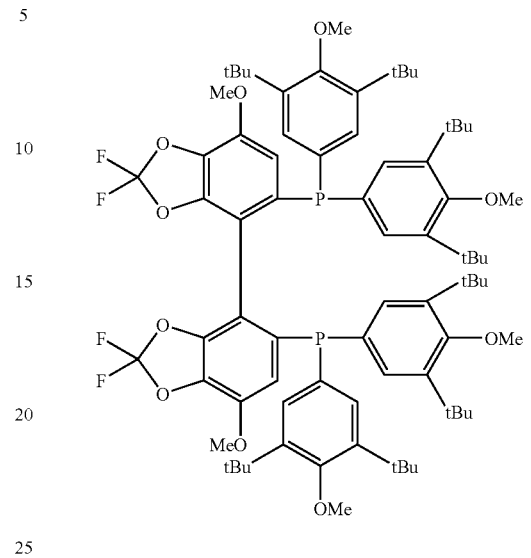

-continued
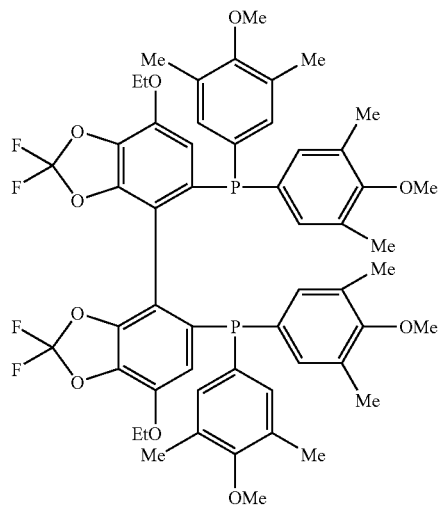
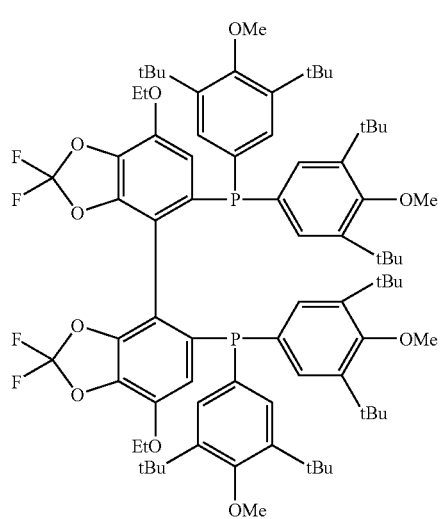
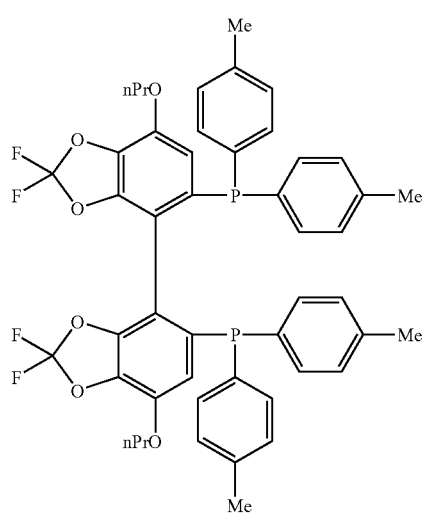
-continued
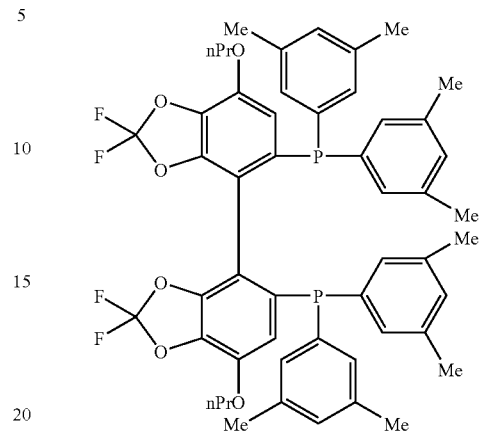
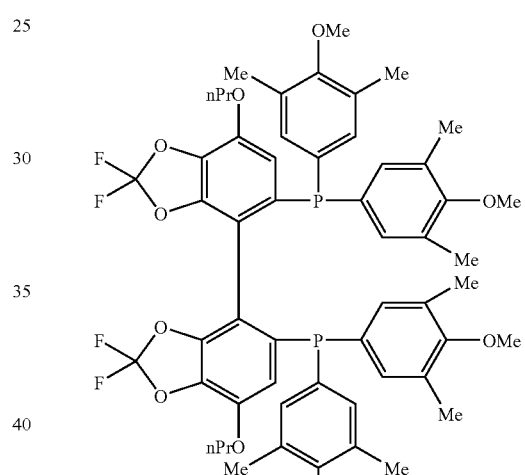
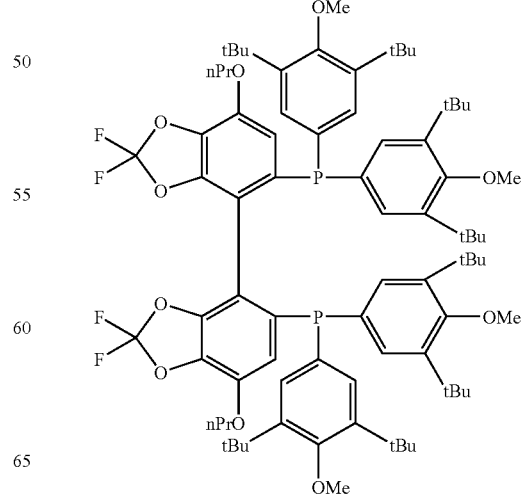

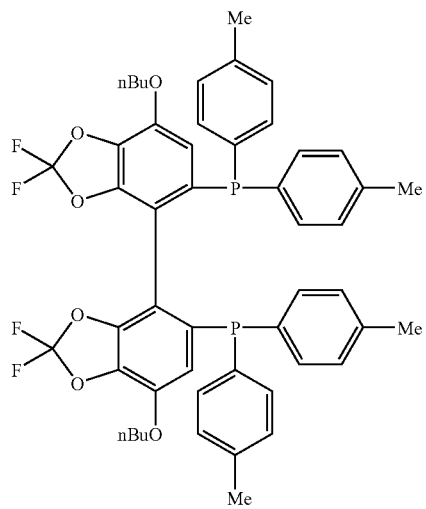
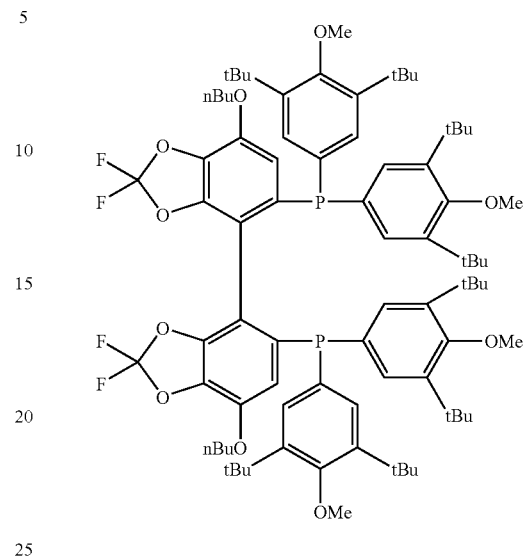
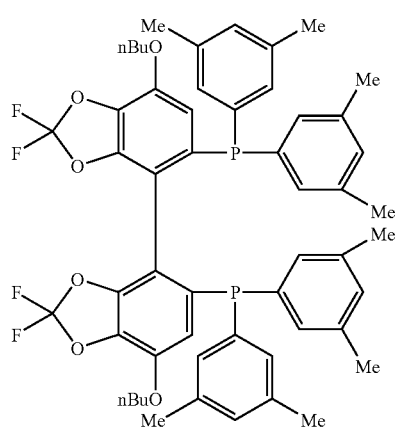
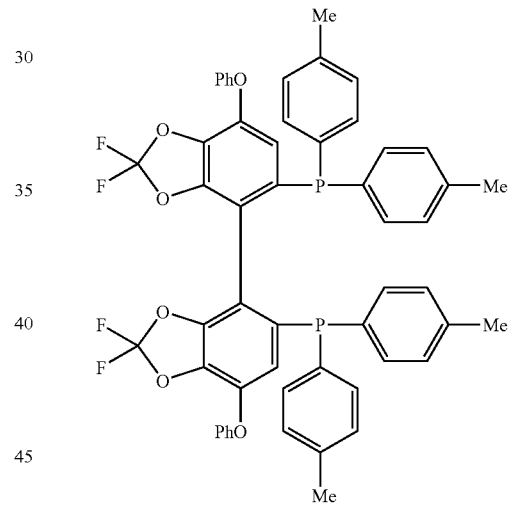
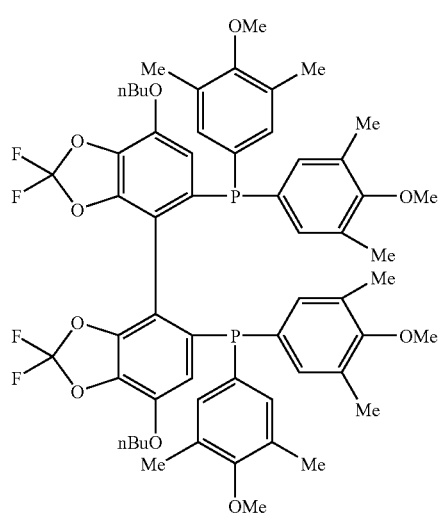
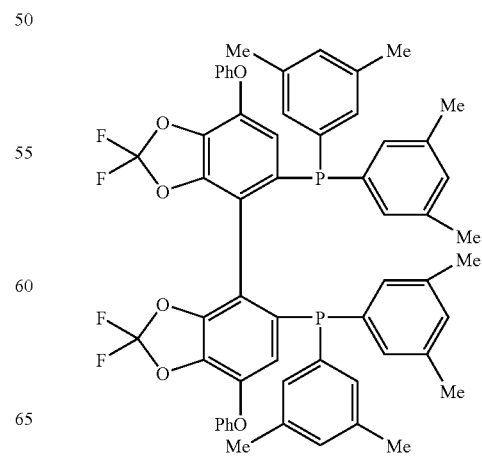

-continued

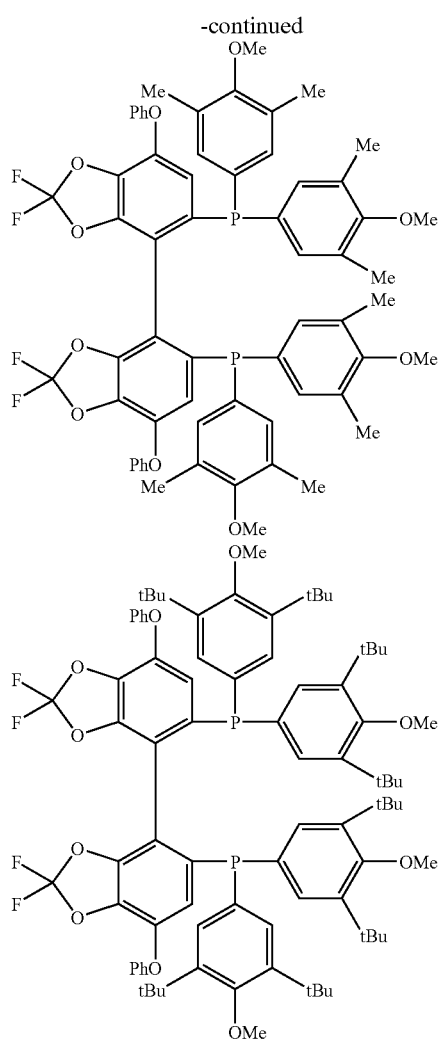

The diphosphine compound represented by the above formula (1) of the present invention can be produced by an ordinary method, a method described in the following step 1 to step 4, and the like.

(1) Step 1

A compound represented by the following formula (2):

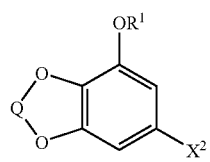
(2)

(wherein, $X^2$ represents a halogen atom; $R^1$ and Q are the same as described above) and a phosphonic halide represented by the following formula (3):

$$PR^2R^3(=O)X^3 \quad (3)$$

(wherein, $X^3$ represents a halogen atom; $R^2$ and $R^3$ are the same as described above) are reacted in an appropriate solvent in the presence of magnesium to produce a phosphine oxide compound represented by the following formula (4):

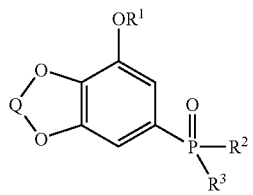
(4)

(wherein, $R^1$ to $R^3$ and Q are the same as described above).

(2) Step 2

The phosphine oxide compound represented by the formula (4) obtained in the above step (1) is reacted with a lithium compound and a halogenating agent, in a solvent if necessary, in the presence of a base if necessary, to produce a 4-halogenophosphine oxide compound represented by the following formula (5):

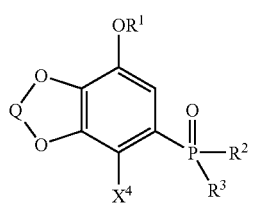
(5)

(wherein, $X^4$ represents a halogen atom; $R^1$ to $R^3$ and Q are the same as described above).

(3) Step 3

The 4-halogenophosphine oxide compound represented by the formula (5) obtained in the above step (2) is subjected to coupling reaction in an appropriate solvent to produce a diphenylphosphine oxide compound represented by the following formula (6):

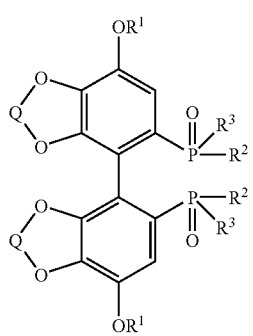
(6)

(wherein, $R^1$ to $R^3$ and Q are the same as described above).

(4) Step 4

The diphenylphosphine oxide compound represented by the formula (6) obtained in the above step (3) is reduced in an appropriate solvent to produce an objective diphosphine compound represented by the formula (1).

The halogen atom represented by X² in the above formula (2) and the halogen atom represented by X³ in the above formula (3) include each independently fluorine, chlorine, bromine, iodine and the like.

Specific examples of the compound represented by the formula (2) include, for example, 6-bromo-4-methoxy-1,3-benzodioxol, 6-bromo-4-ethoxy-1,3-benzodioxol, 6-bromo-4-n-propoxy-1,3-benzodioxol, 6-bromo-4-n-butoxy-1,3-benzodioxol, 6-bromo-4-phenoxy-1,3-benzodioxol and the like, of which the chemical formulae are shown below together with those of other compounds.

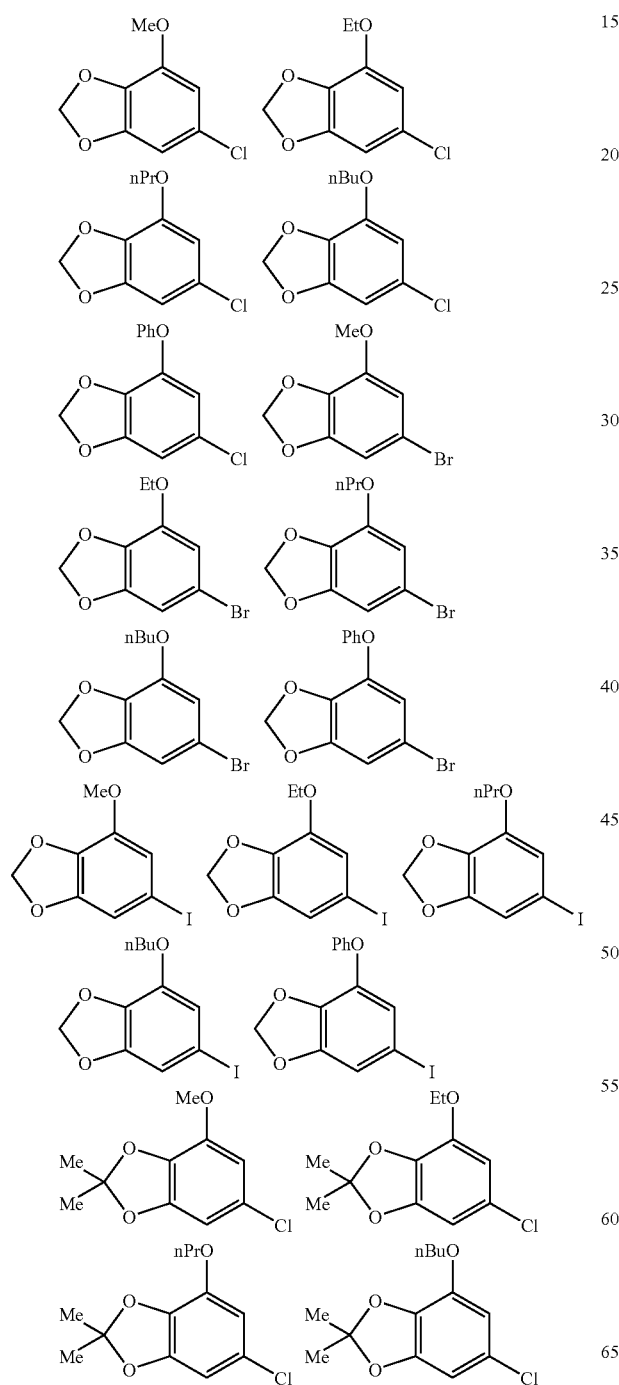

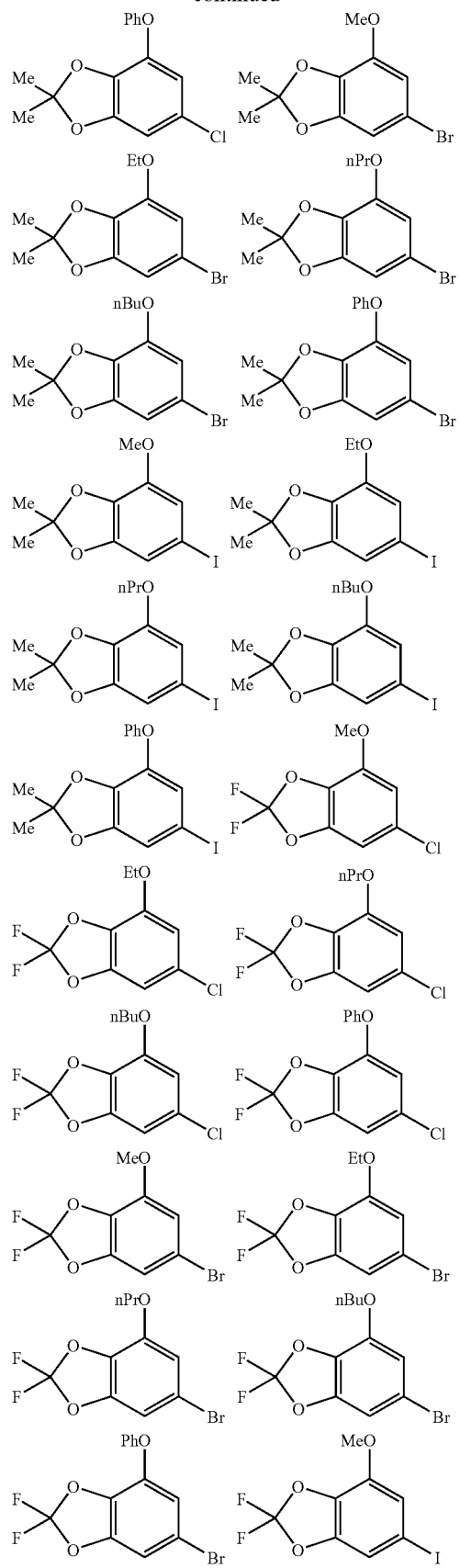

-continued

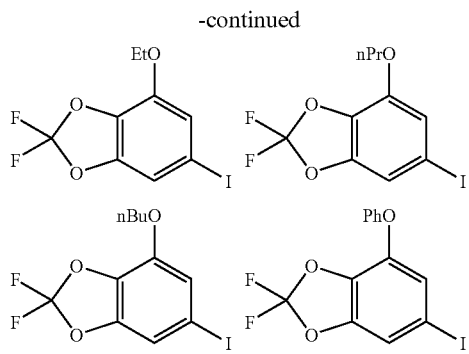

Specific examples of the phosphonic halide represented by the above formula (3) include, for example, diphenyl phosphonic chloride, di(4-methylphenyl)phosphonic chloride, di(3,5-dimethylphenyl)phosphonic chloride, di(4-methoxy-3,5-dimethylphenyl)phosphonic chloride, di(4-methoxy-3,5-di-tert-butylphenyl)phosphonic chloride and the like, of which the chemical formulae are shown below together with those of other compounds.

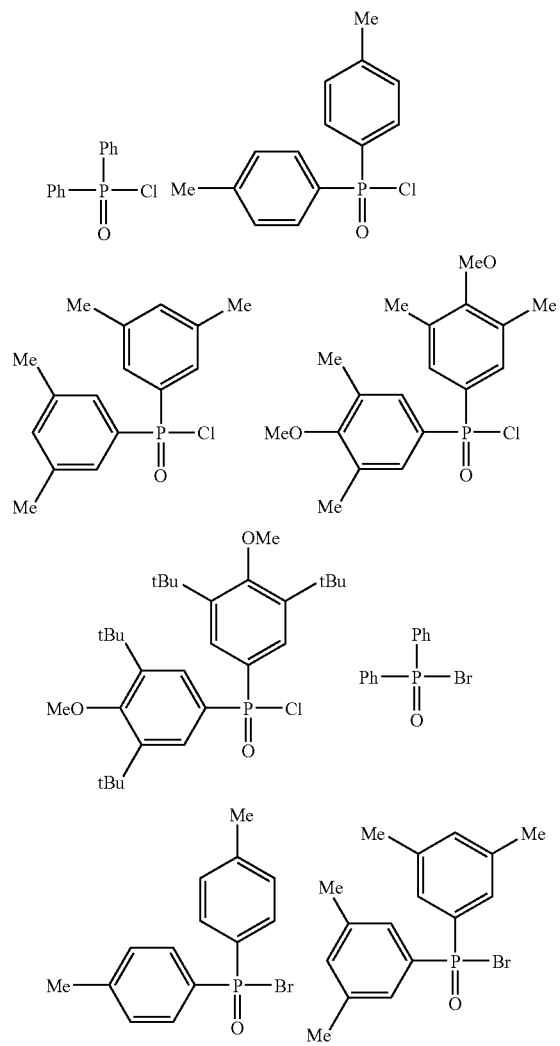

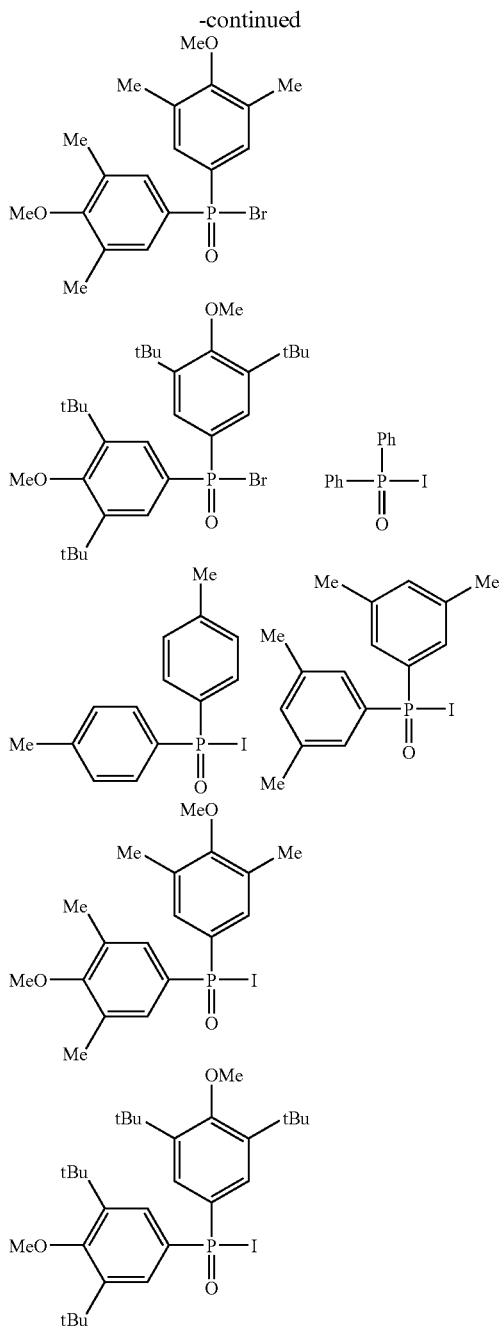

Specific examples of the phosphine oxide compound represented by the formula (4) that can be produced in the above step (1) include, for example, (4-methoxy-1,3-benzodioxol)-6-yl-diphenylphosphine oxide, (4-ethoxy-1,3-benzodioxol)-6-yl-diphenylphosphine oxide, (4-n-propoxy-1,3-benzodioxol)-6-yl-diphenylphosphine oxide, (4-n-butoxy-1,3-benzodioxol)-6-yl-diphenylphosphine oxide, (4-phenoxy-1,3-benzodioxol)-6-yl-diphenylphosphine oxide, (4-methoxy-1,3-benzodioxol)-6-yl-di(4-methylphenyl)phosphine oxide, (4-methoxy-1,3-benzodioxol)-6-yl-di(3,5-dimethylphenyl)phosphine oxide, (4-methoxy-1,3-benzodioxol)-6-yl-di(4-methoxy-3,5-dimethylphenyl)phosphine oxide and the like, of which the chemical formulae are shown below together with those of other compounds.

-continued
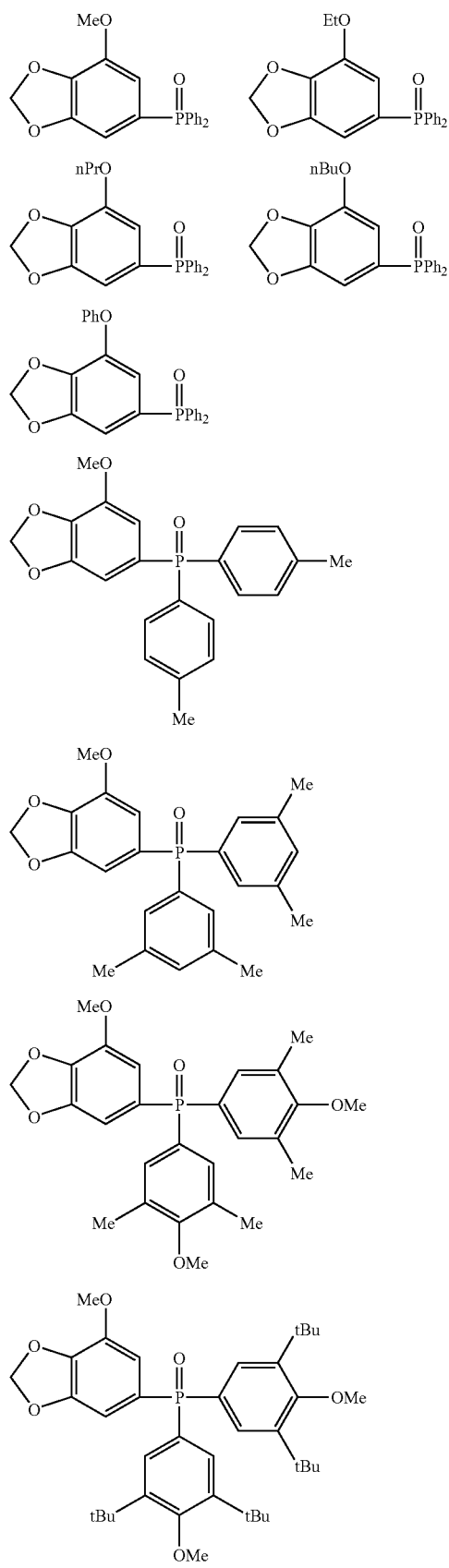
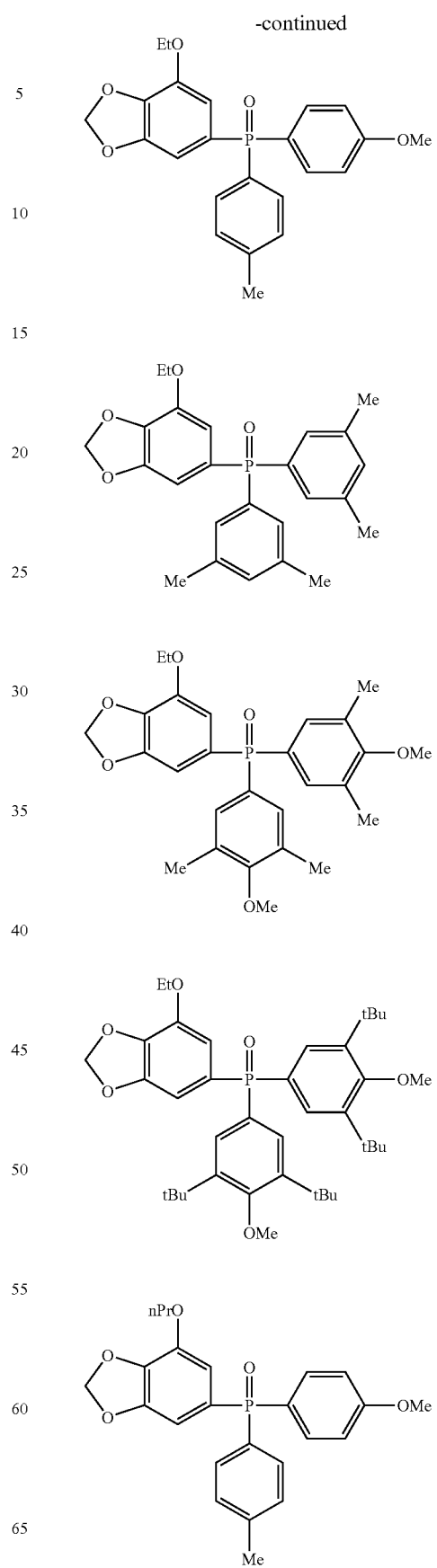

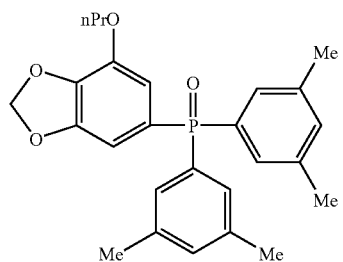
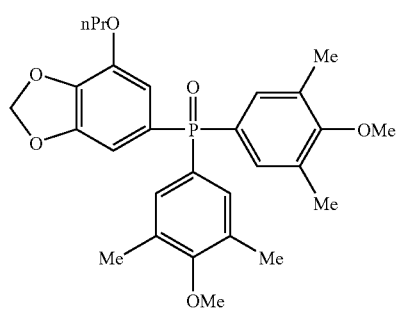
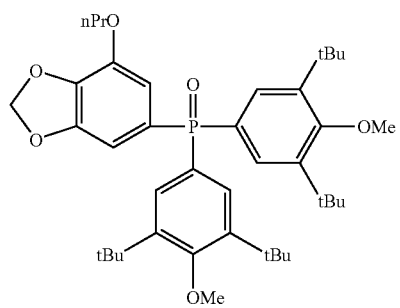
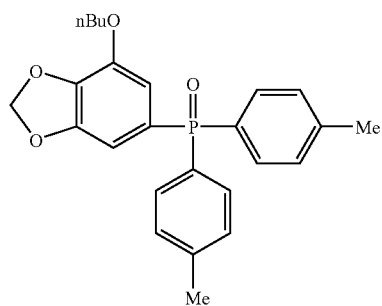
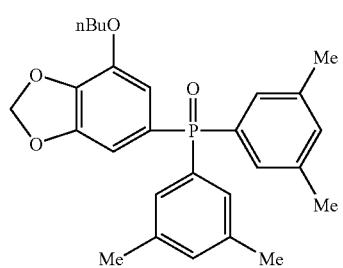
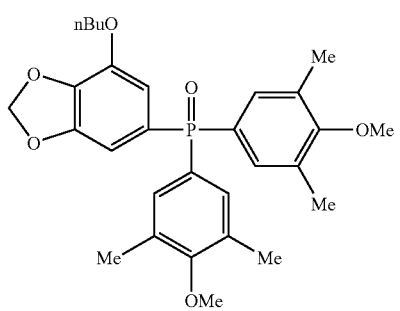
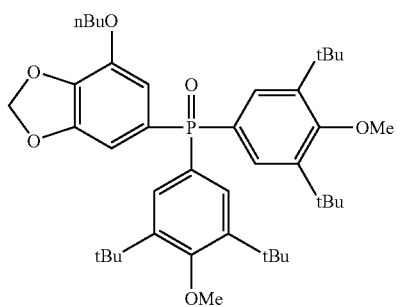
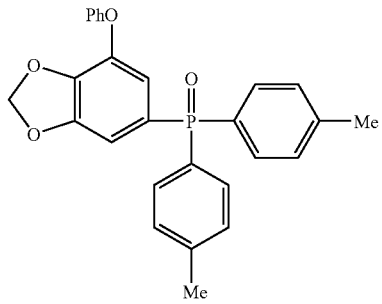
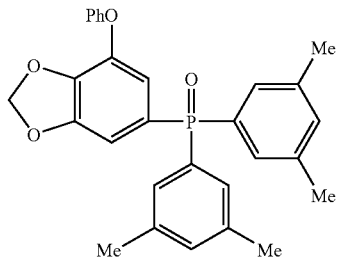
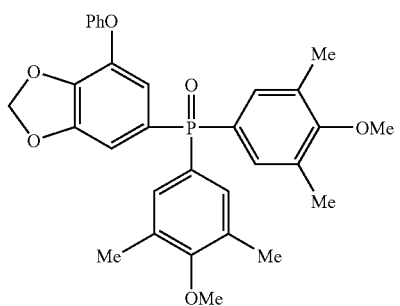

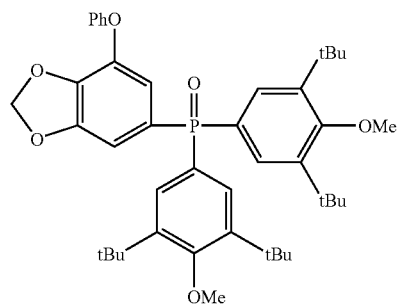
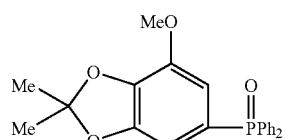
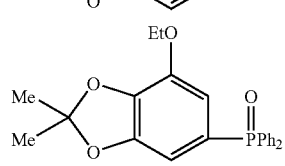
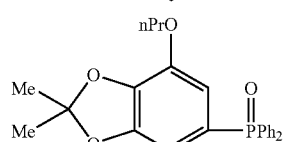
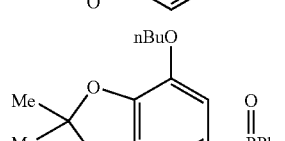
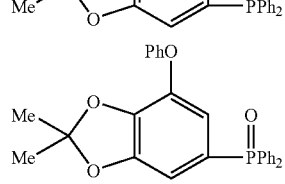
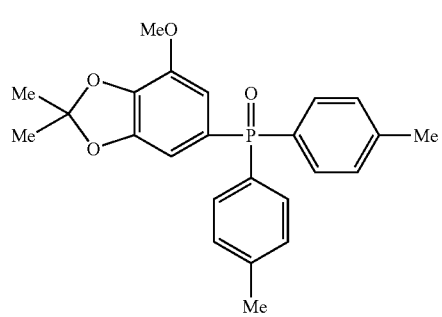
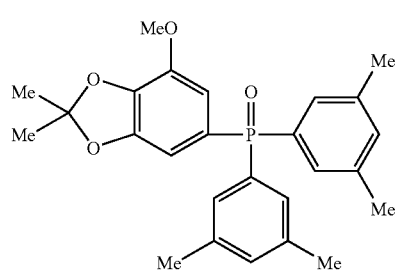
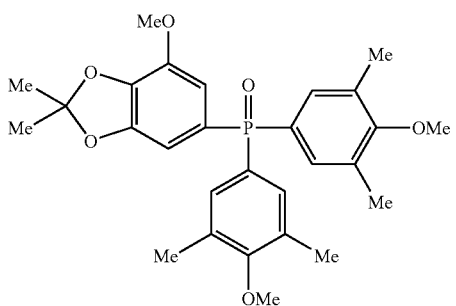
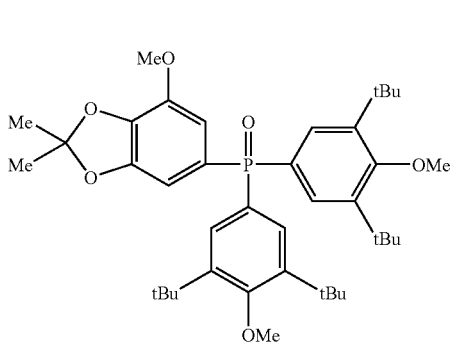
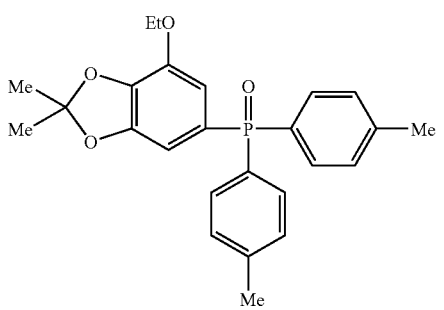
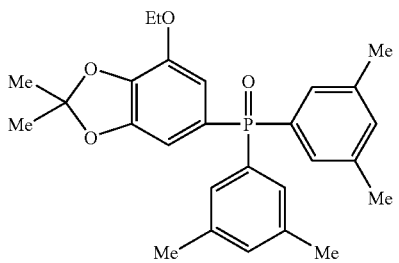
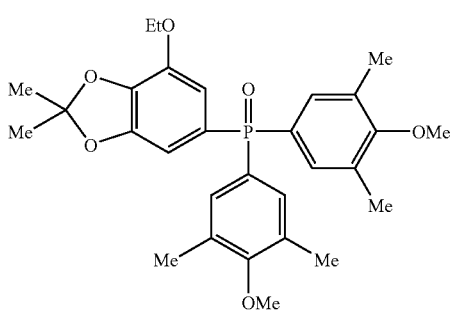

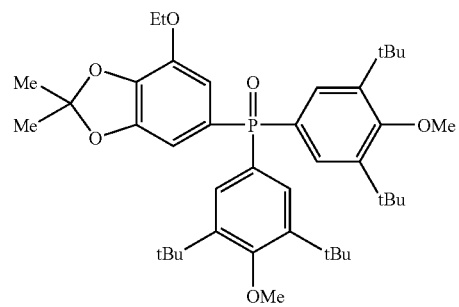
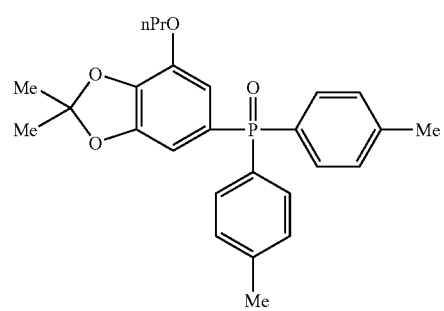
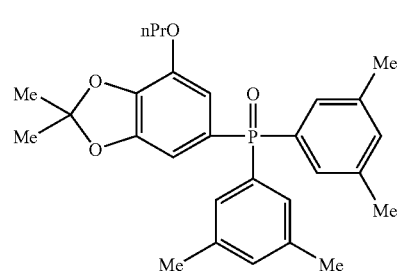
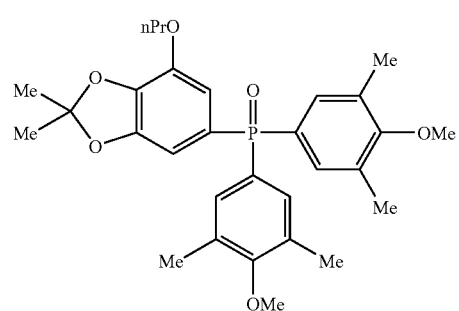
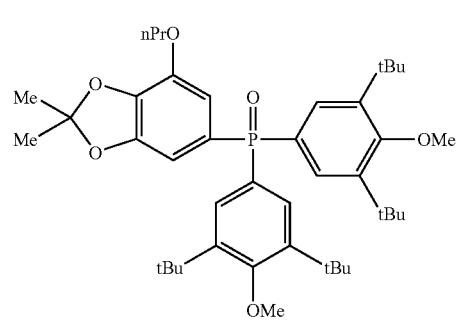
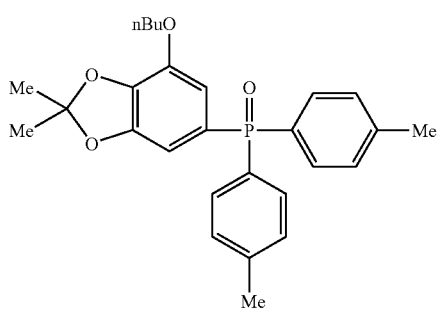
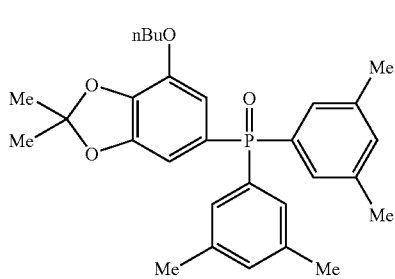
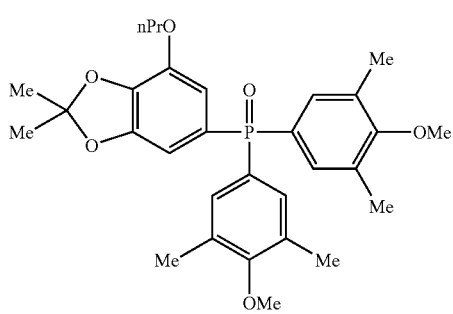
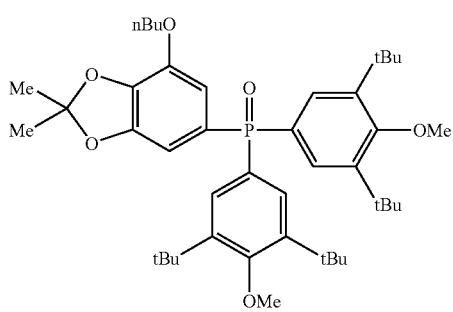
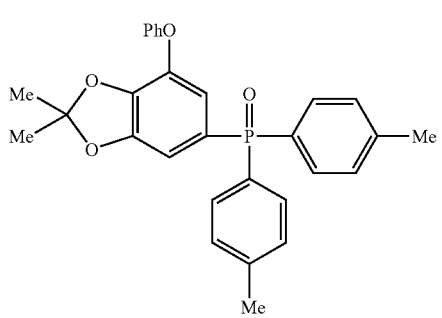

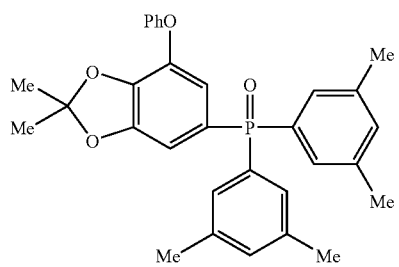
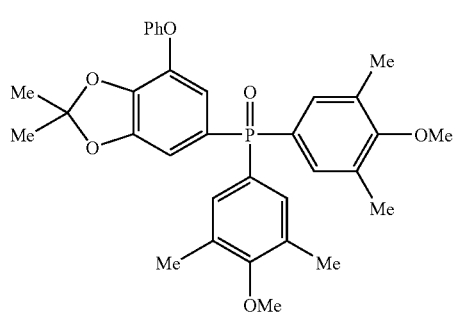
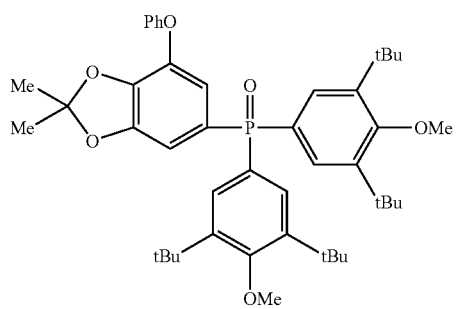
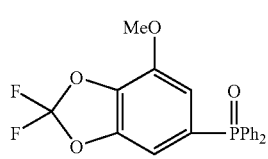
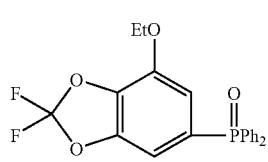
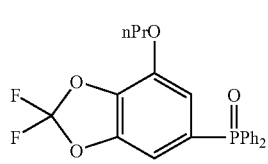
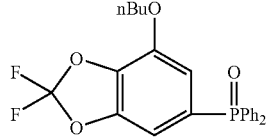
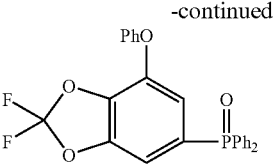
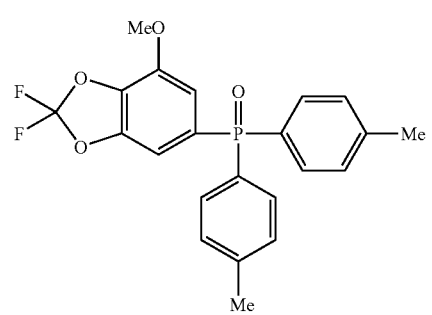
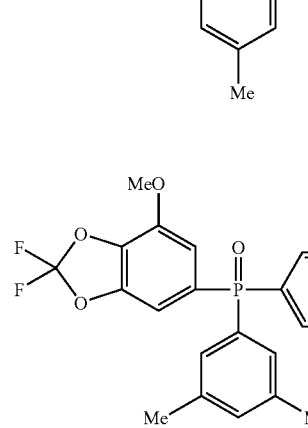
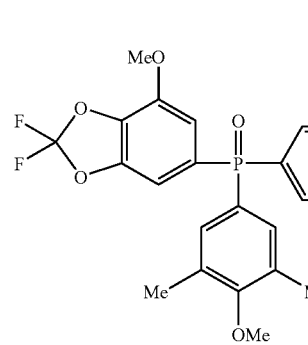
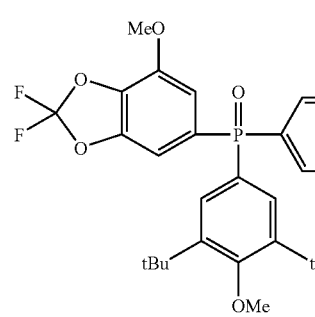

-continued
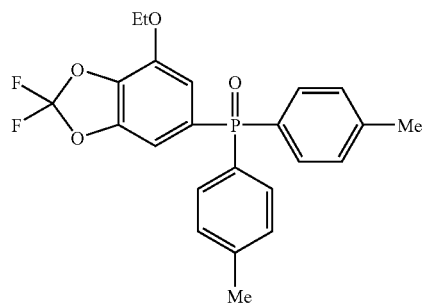
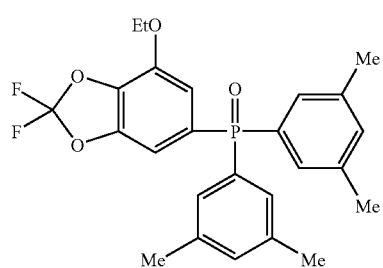
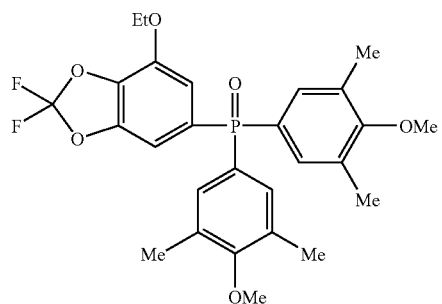
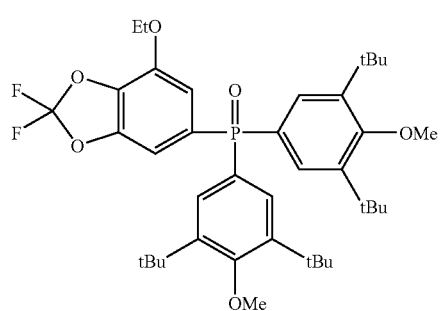
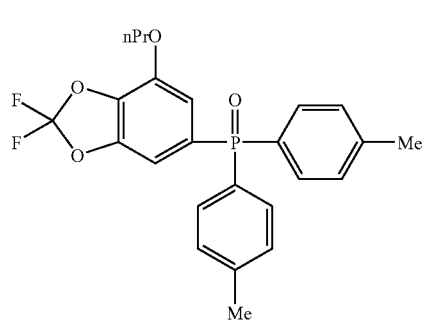
-continued
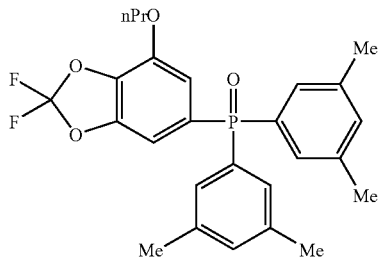
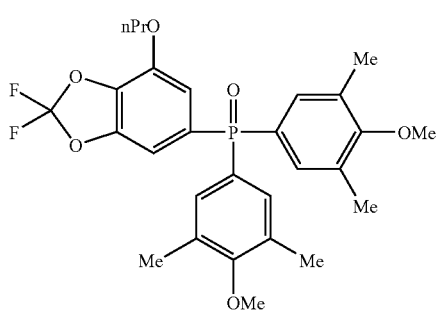
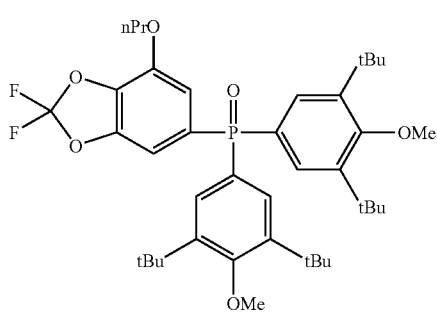
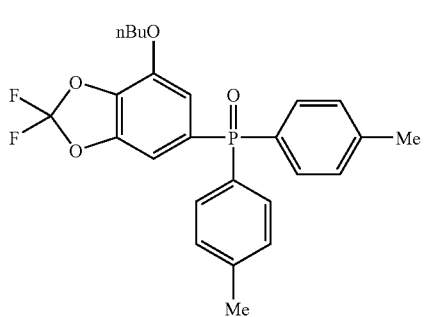
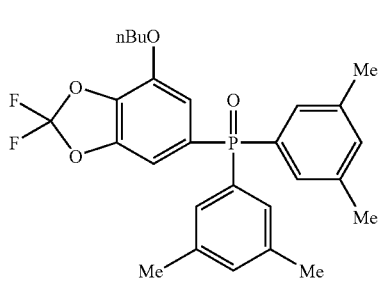

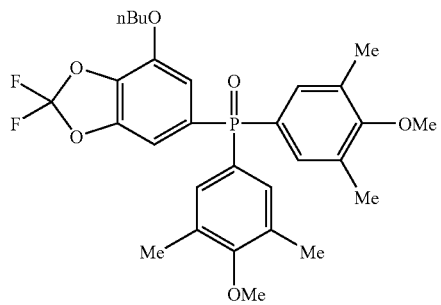

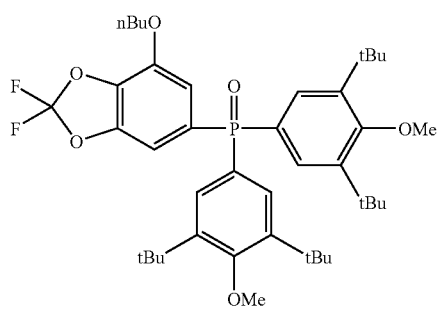

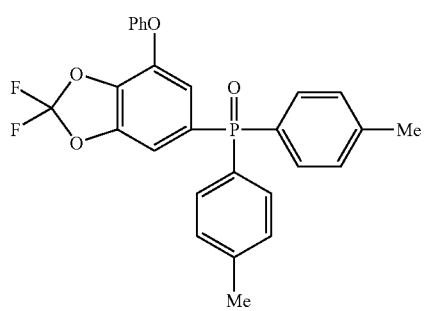

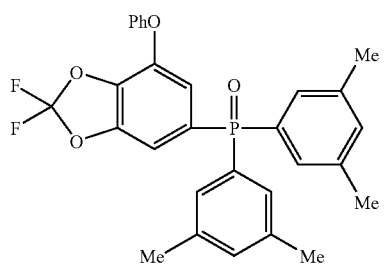

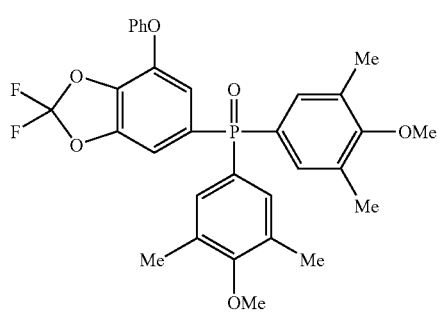

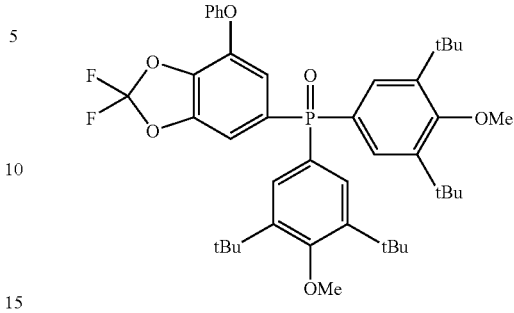

In the step (1), with regard to the amount of, the compound represented by the above formula (2) and the phosphonic halide represented by the formula (3) used, the phosphonic halide represented by the formula (3) is appropriately selected usually in the range of 1 to 5 equivalents, preferably 1 to 3 equivalents based on that of the compound represented by the above formula (2).

The amount of magnesium used is appropriately selected usually in the range of 1 to 5 equivalents, preferably 1 to 3 equivalents based on that of the compound represented by the above formula (2).

The solvent includes, for example, aliphatic hydrocarbons such as pentane, hexane, heptane, octane, decane and cyclohexane; aromatic hydrocarbons such as benzene, toluene and xylene; halogenated hydrocarbons such as dichloromethane, 1,2-dichloroethane, chloroform, carbon tetrachloride and o-dichlorobenzene; ethers such as diethyl ether, diisopropyl ether, tert-butyl methyl ether, dimethoxyethane, ethylene glycol diethyl ether, tetrahydrofuran, 1,4-dioxane, 1,3-dioxolane, 2-methyltetrahydrofuran and cyclopentyl methyl ether; sulfoxides such as dimethyl sulfoxide; N-methylpyrrolidone; and the like. These solvents may be used alone or in an appropriate combination of two or more thereof.

The amount of the solvent used is appropriately selected usually in the range of 1 to 20 times by volume, preferably 2 to 10 times by volume based on that of the compound represented by the above formula (2).

The reaction temperature is appropriately selected usually in the range of 0° C. to a reflux temperature of the solvent used, preferably 15 to 40° C., depending on the kinds of the raw material and the solvent used.

The reaction time is appropriately selected usually in the range of 0.1 to 24 hours, preferably 5 to 12 hours.

The phosphine oxide compound represented by the above formula (4) that is produced in step (1) may be used as it is, or may be used after post-treatment, purification, isolation and the like as needed. Specific method for post-treatment, purification and isolation includes a known method, for example, solvent extraction, salting out, crystallization, recrystallization and various kinds of chromatography.

The compound represented by the formula (2) and the phosphonic halide represented by the formula (3) may be available commercially or produced as appropriate.

In the step (2), the phosphine oxide compound represented by the above formula (4) that is produced in step (1) can be reacted with a halogenating agent and lithium compound, in a solvent if necessary, in the presence of a base if necessary, to produce the 4-halogenophosphine oxide compound represented by the above formula (5).

The halogen atom represented by $X^4$ in the above formula (5) includes a chlorine atom, a bromine atom, an iodine atom and the like.

Specific examples of the 4-halogenophosphine oxide compound represented by the formula (5) include, for example, (4-iodo-7-methoxy-1,3-benzodioxol)-5-yl-diphenylphosphine oxide, (4-iodo-7-ethoxy-1,3-benzodioxol)-5-yl-diphenylphosphine oxide, (4-iodo-7-n-propoxy-1,3-benzodioxol)-5-yl-diphenylphosphine oxide, (4-iodo-7-n-butoxy-1,3-benzodioxol)-5-yl-diphenylphosphine oxide, (4-iodo-7-phenoxy-1,3-benzodioxol)-5-yl-diphenylphosphine oxide, (4-iodo-7-methoxy-1,3-benzodioxol)-5-yl-di(4-methylphenyl)phosphine oxide, (4-iodo-7-methoxy-1,3-benzodioxol)-5-yl-di(3,5-dimethylphenyl)phosphine oxide, (4-iodo-7-methoxy-1,3-benzodioxol)-5-yl-di(4-methoxy-3,5-dimethylphenyl)phosphine oxide, (4-iodo-7-methoxy-1,3-benzodioxol)-5-yl-di(4-methoxy-3,5-di-tert-butylphenyl)phosphine oxide and the like, of which the chemical formulae are shown below together with those of other compounds.

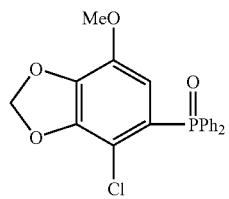
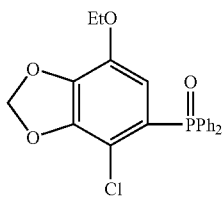
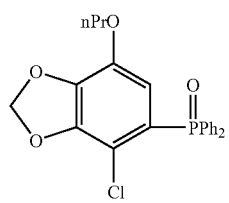
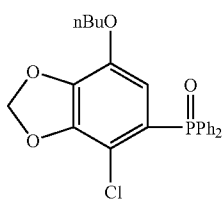
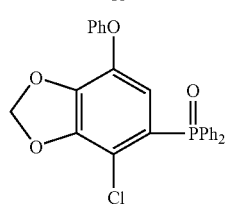
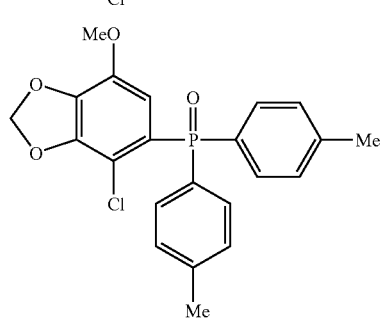

-continued

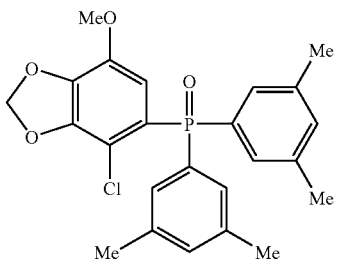
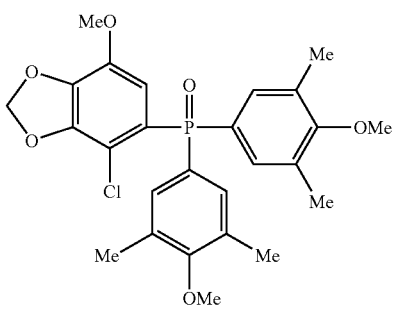
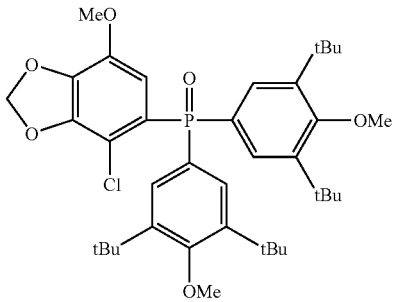
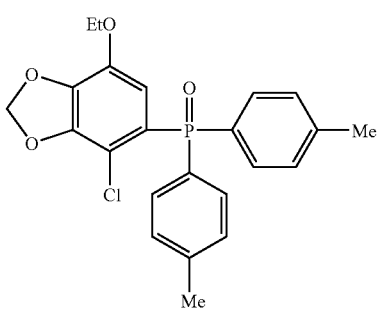
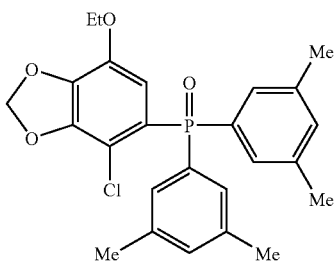

-continued
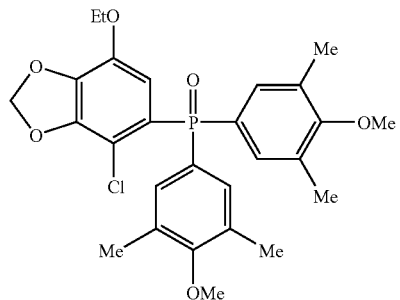
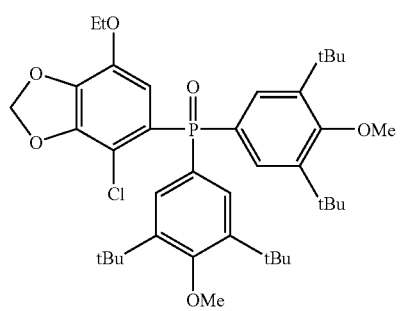
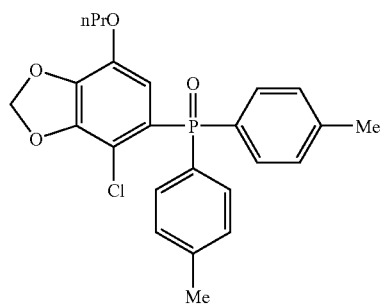
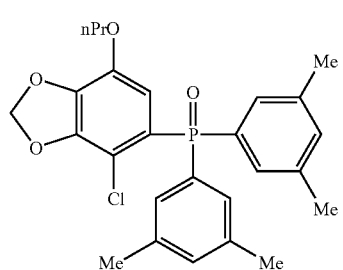
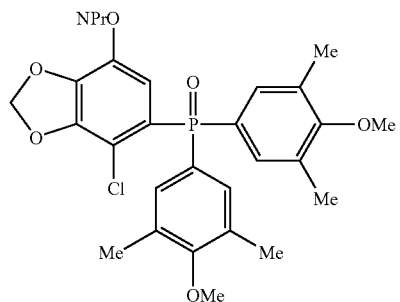
-continued
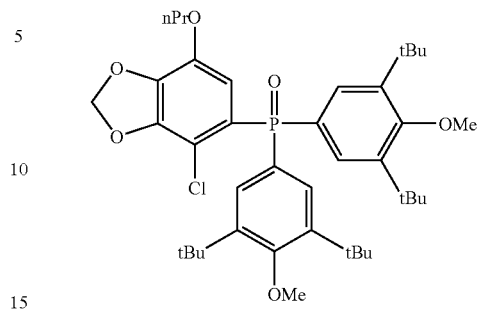
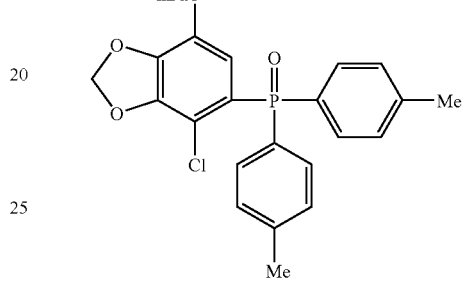
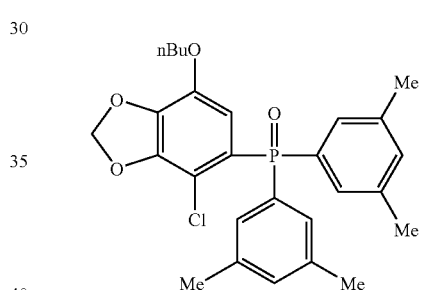
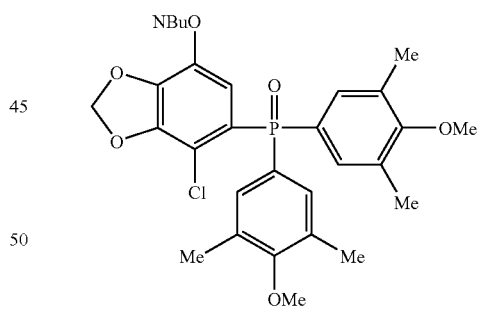
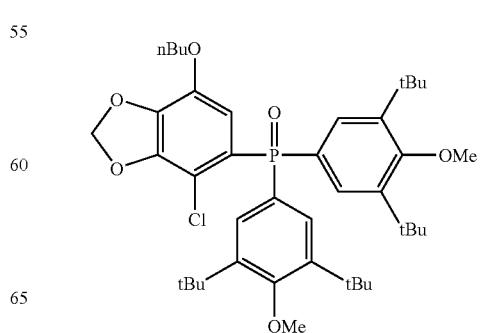

101
-continued
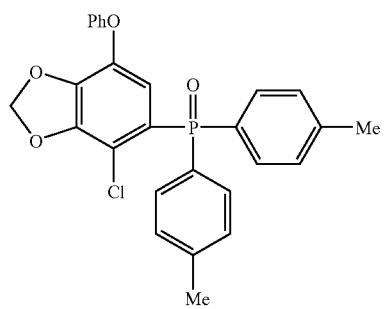
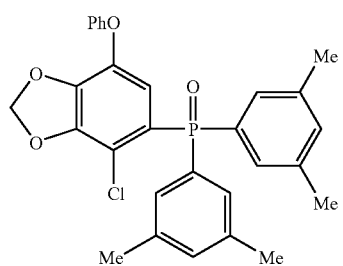
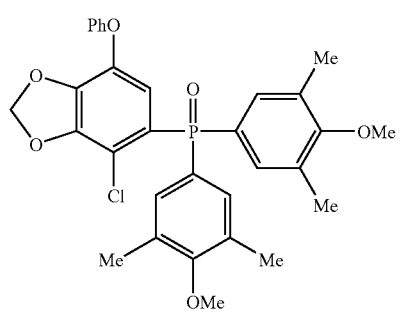
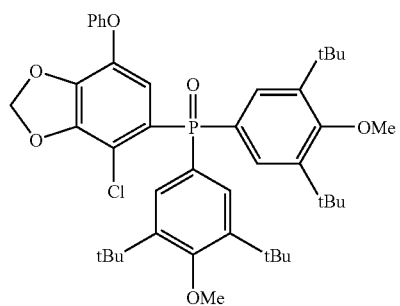
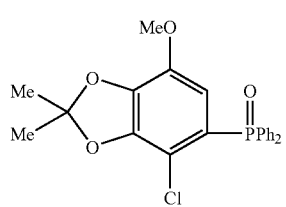
102
-continued
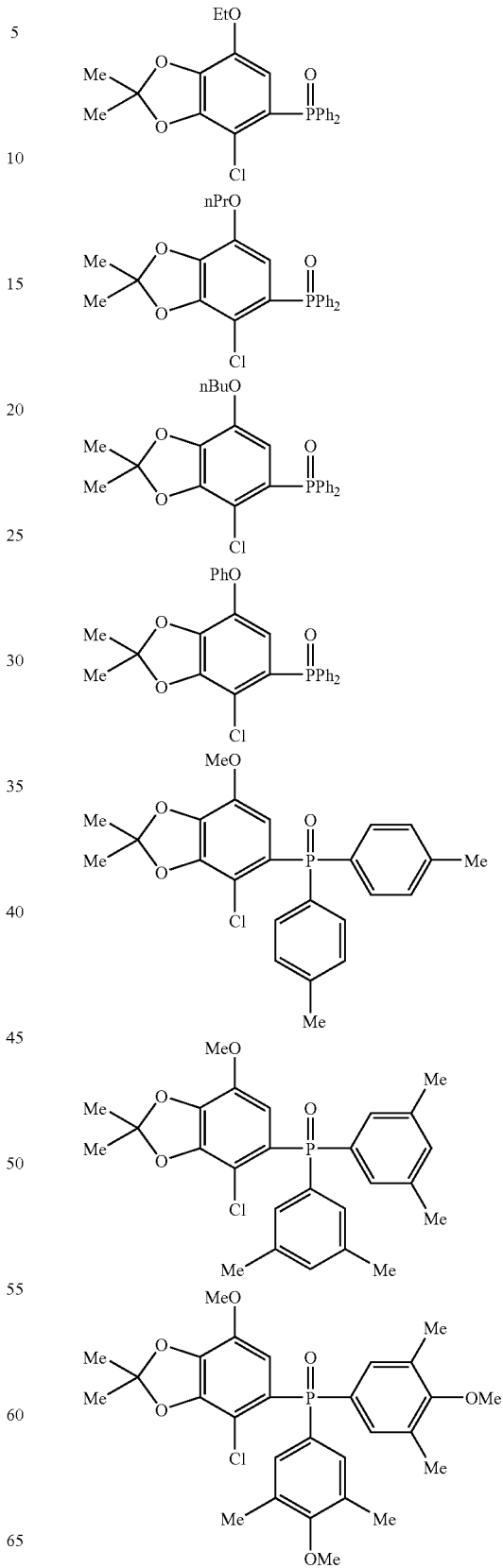

-continued
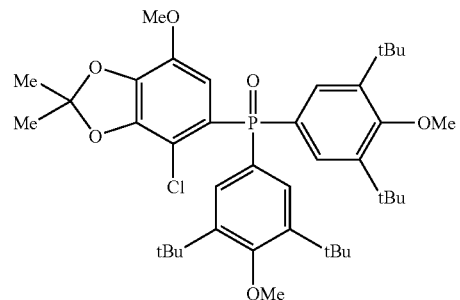
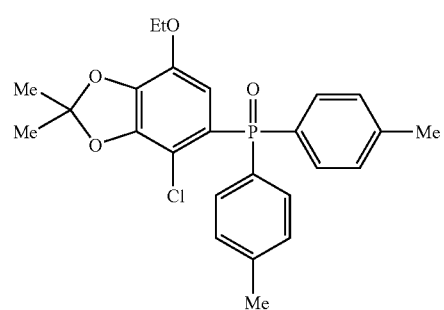
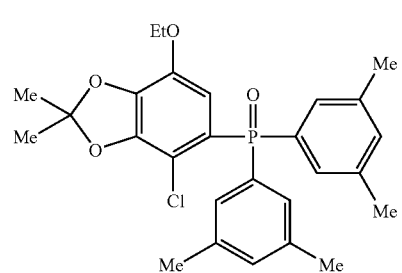
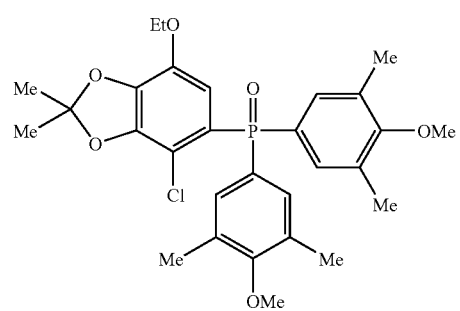
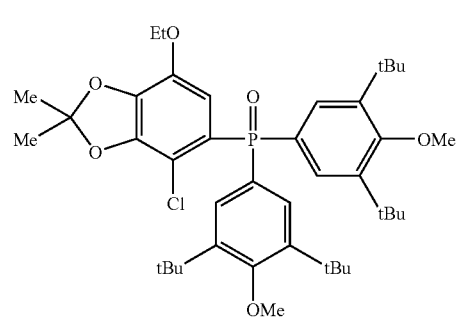
-continued
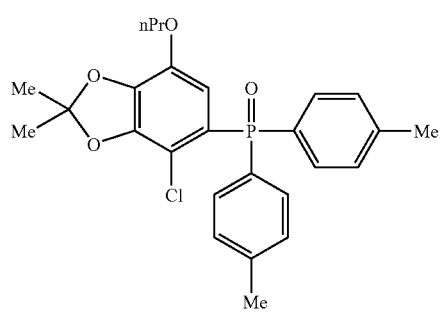
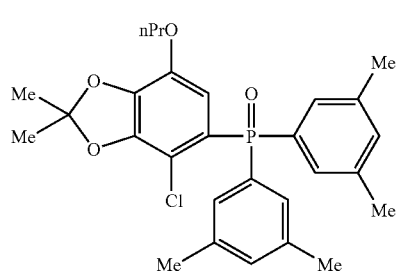
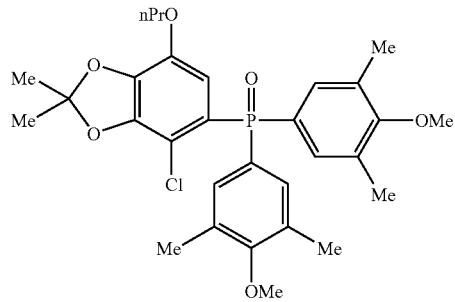
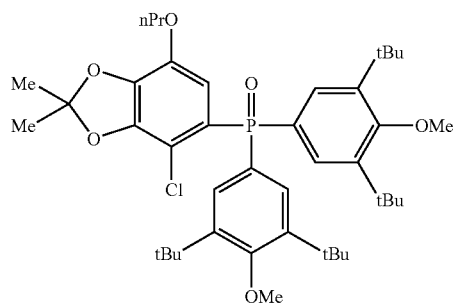
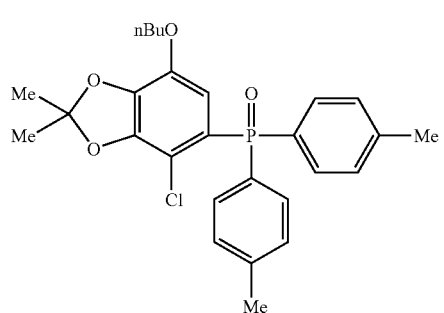

-continued
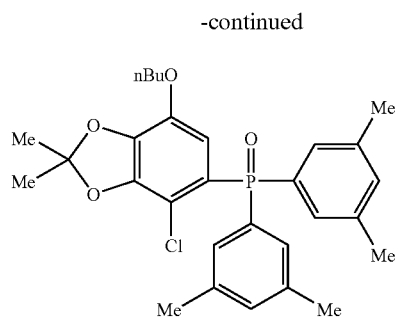
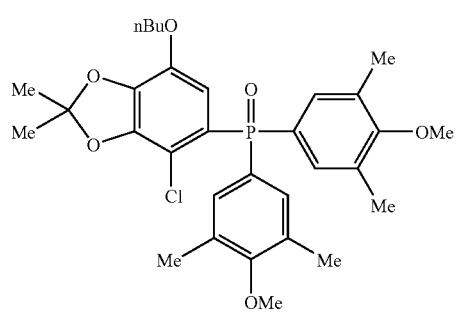
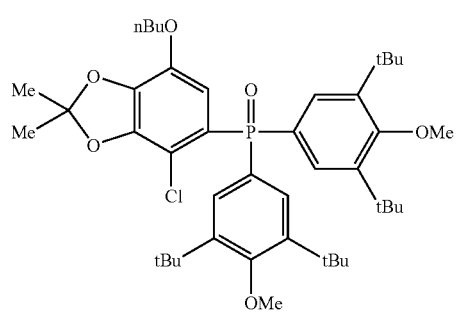
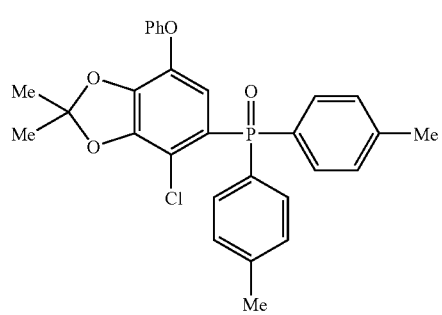
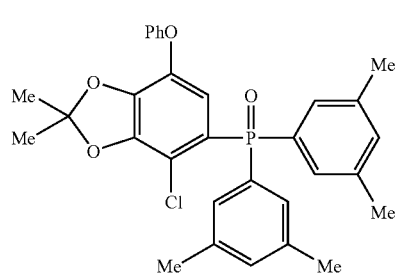
-continued
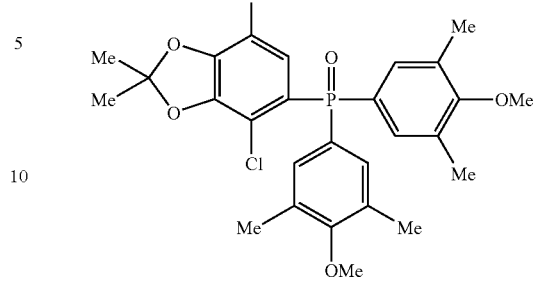
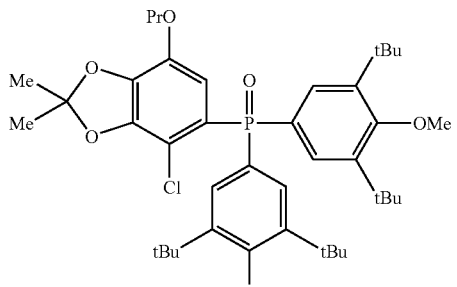
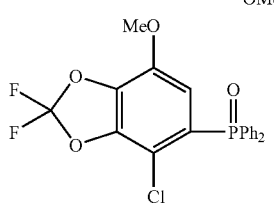
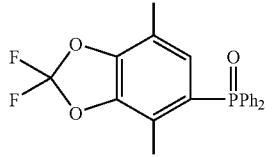
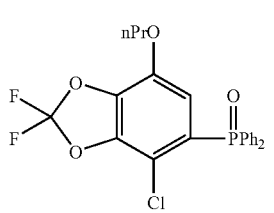
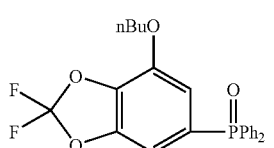
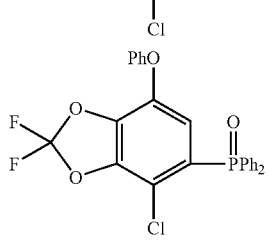

-continued
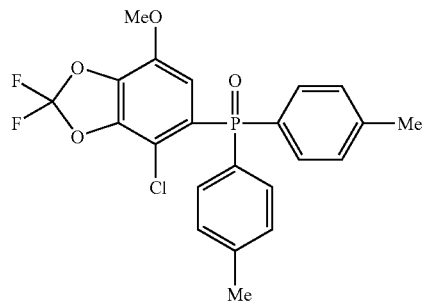
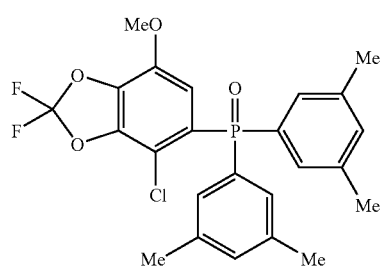
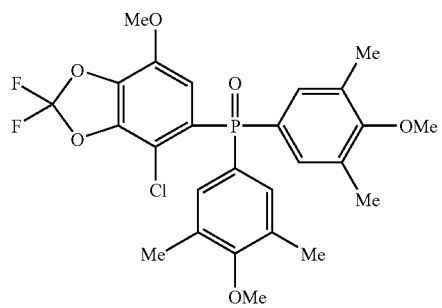
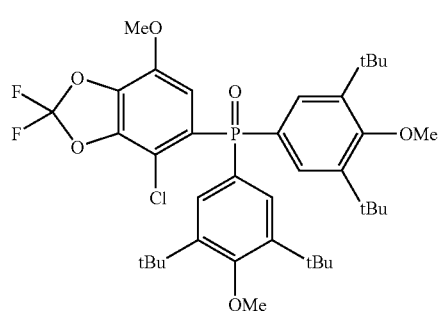
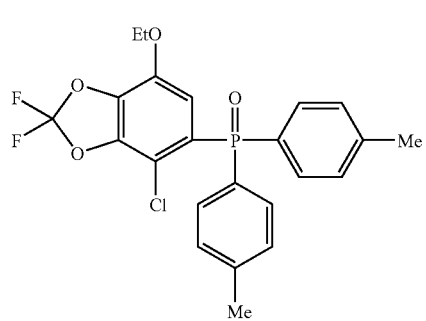
-continued
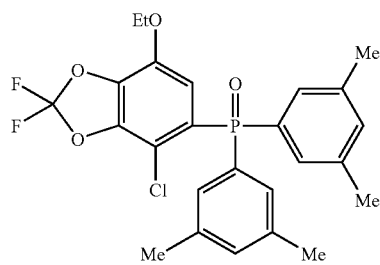
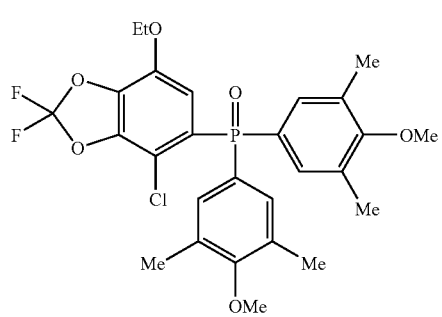
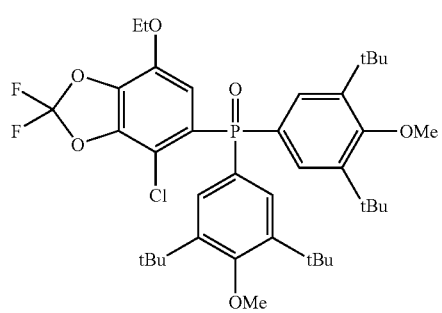
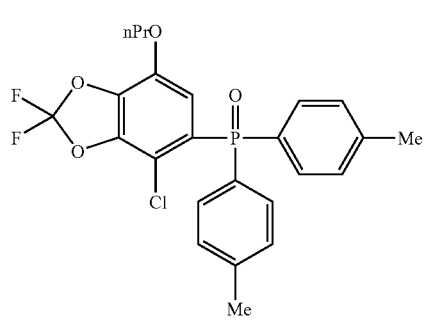
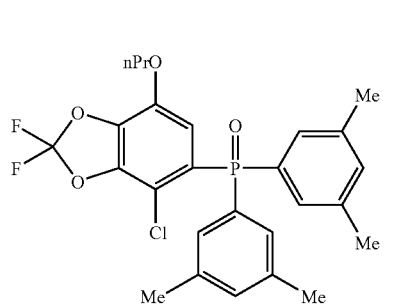

-continued
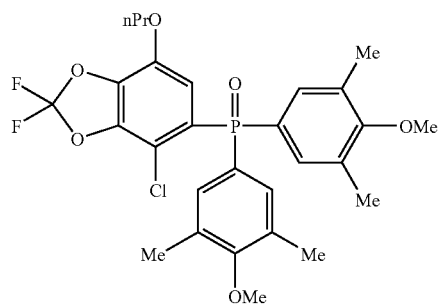
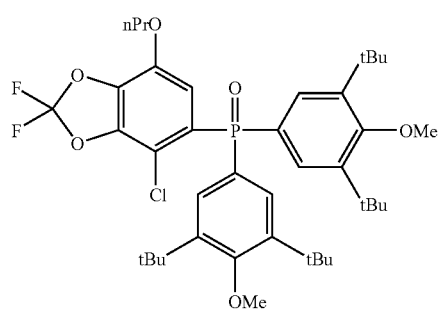
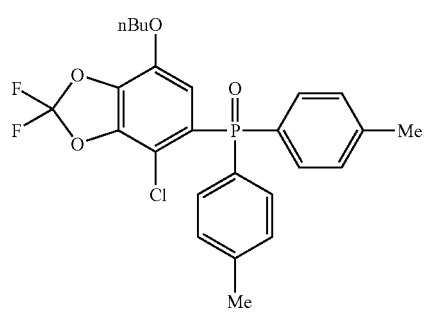
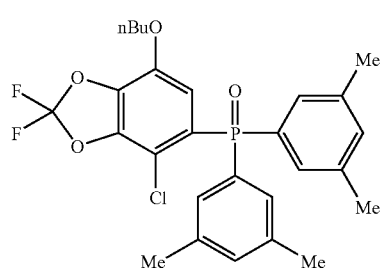
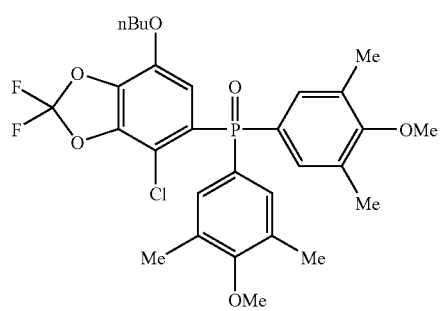
-continued
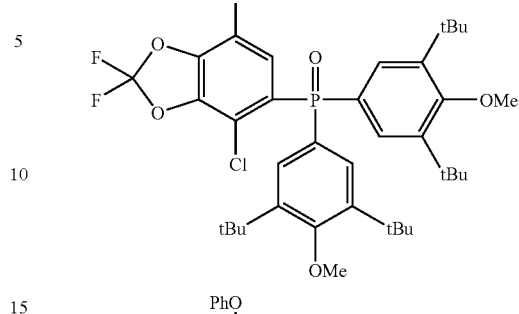
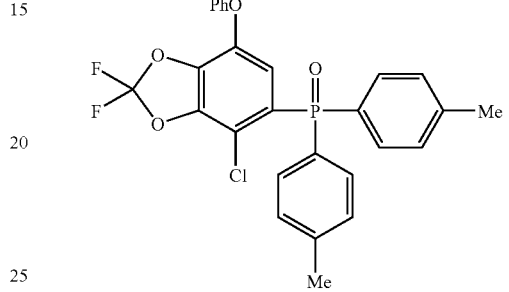
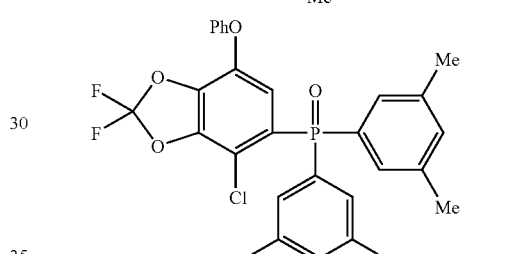
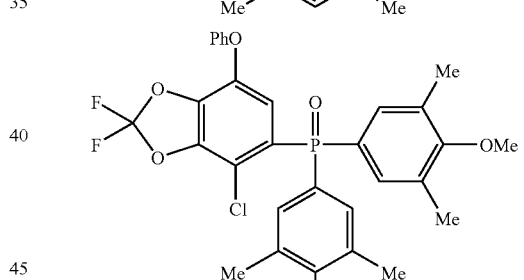
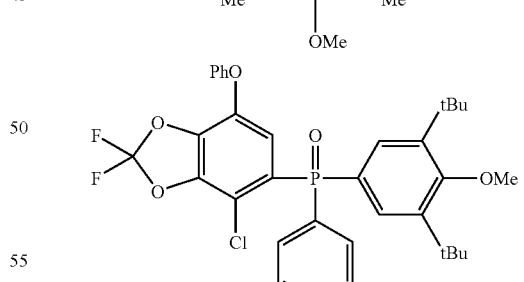
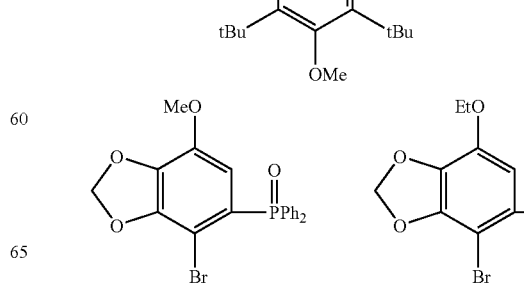

-continued
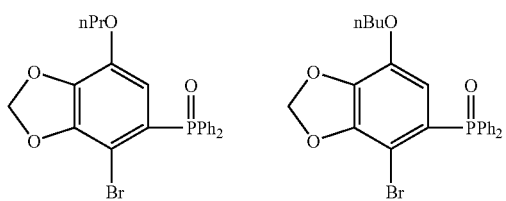
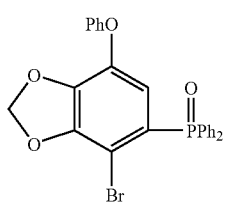
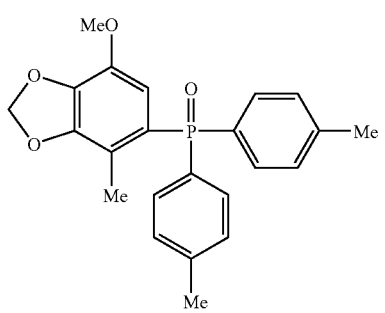
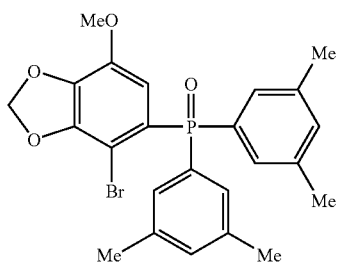
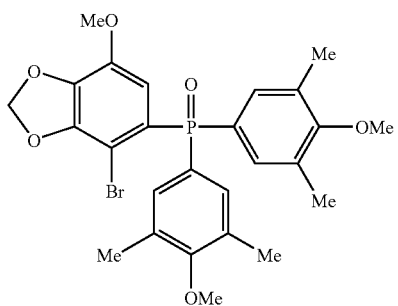
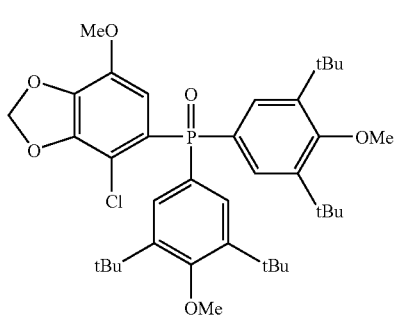
-continued
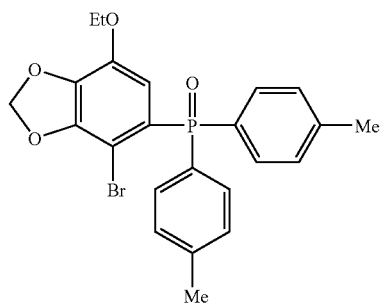
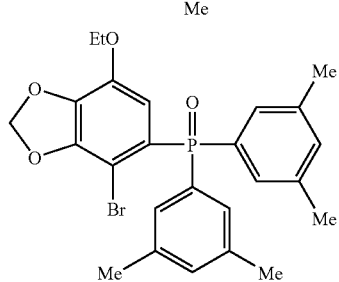
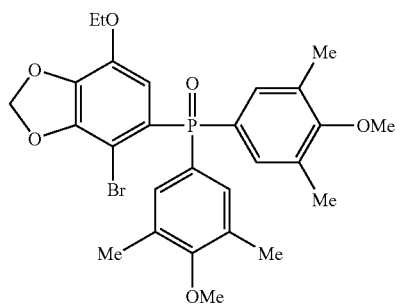
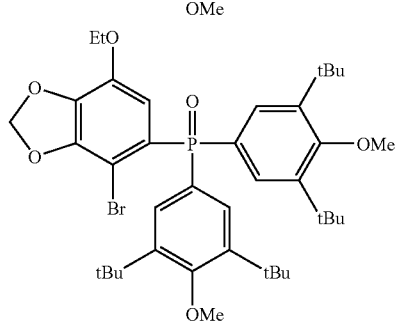
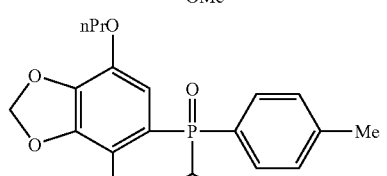
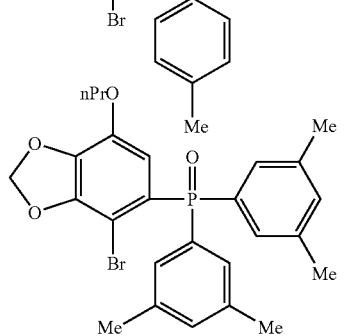

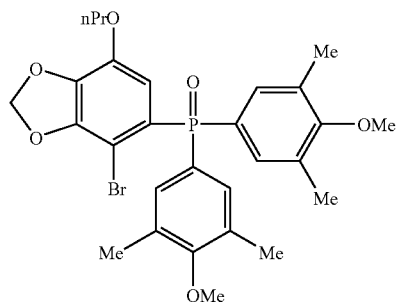
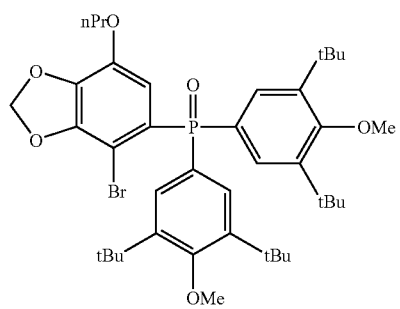
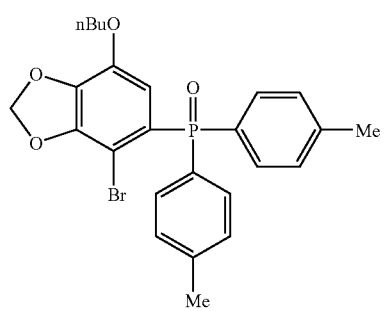
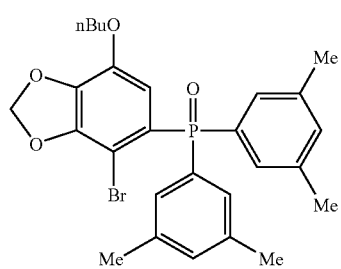
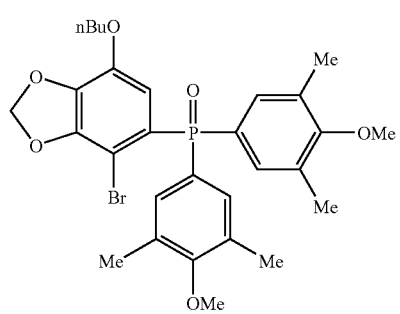
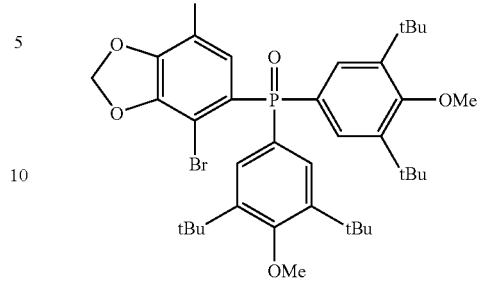
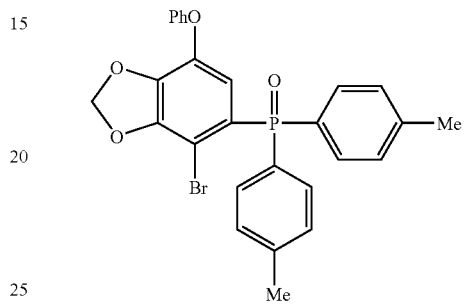
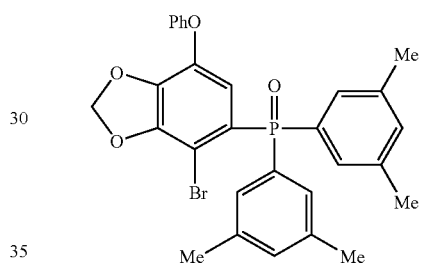
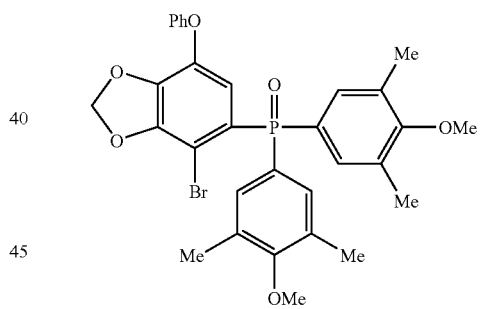
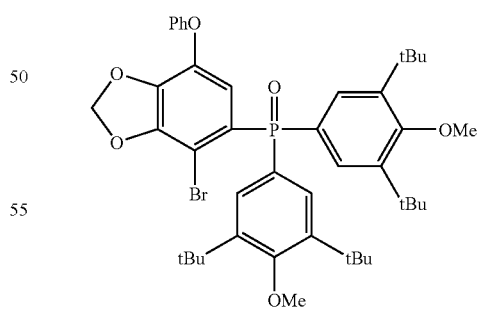
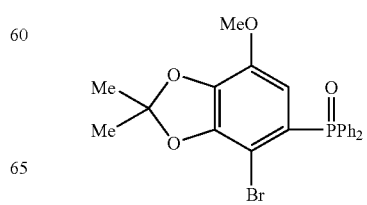

-continued
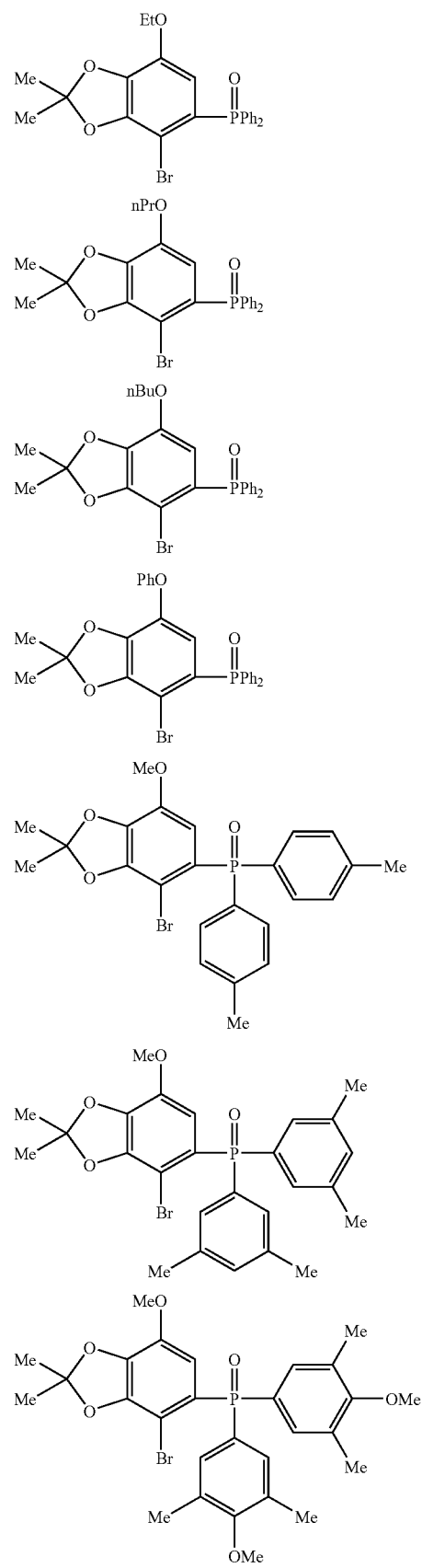
-continued
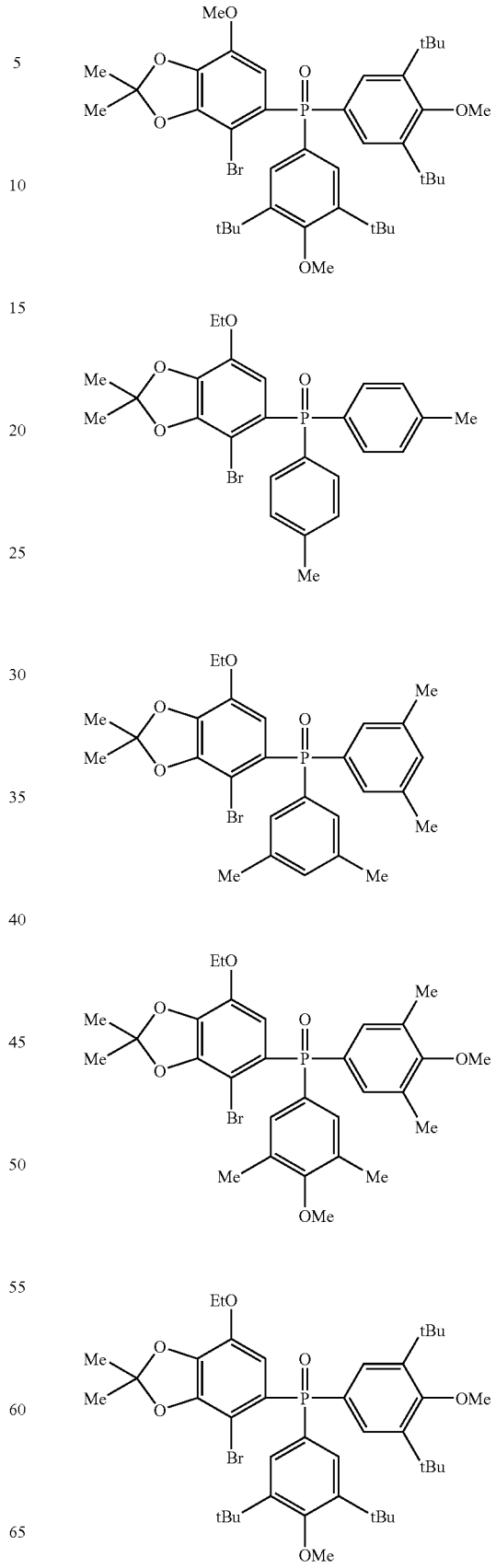

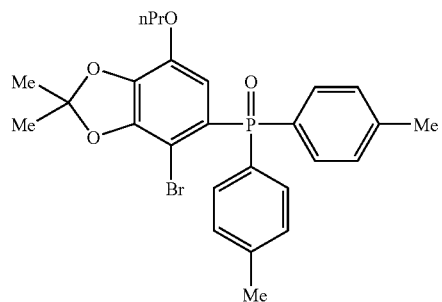
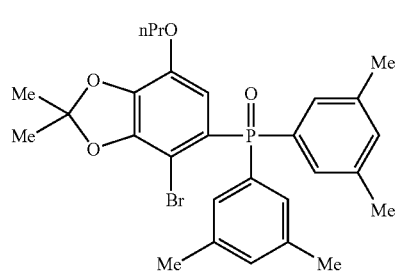
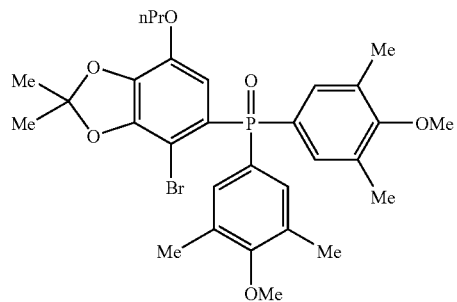
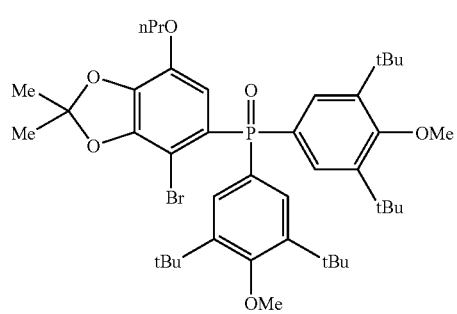
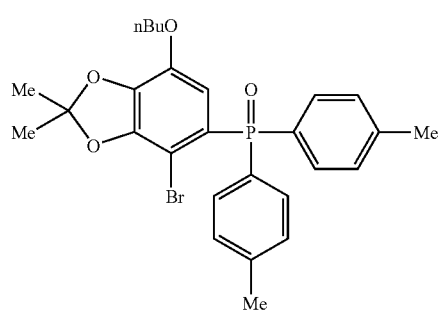
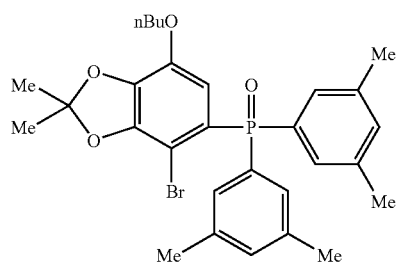
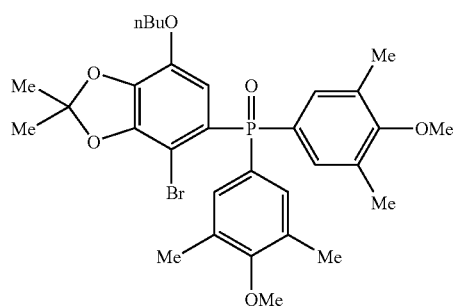
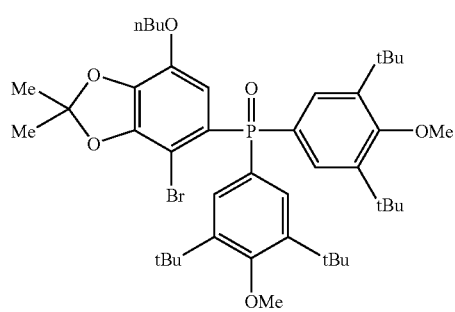
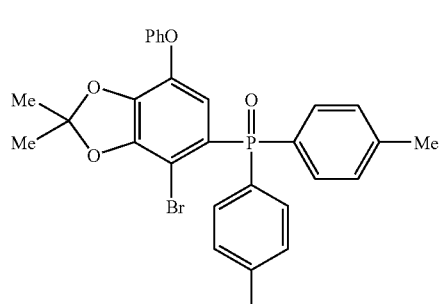
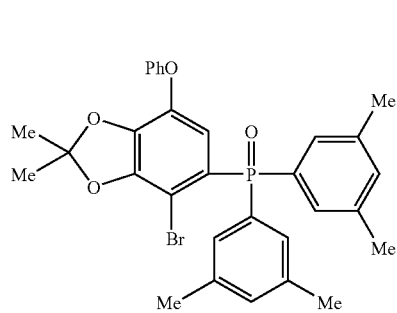

-continued
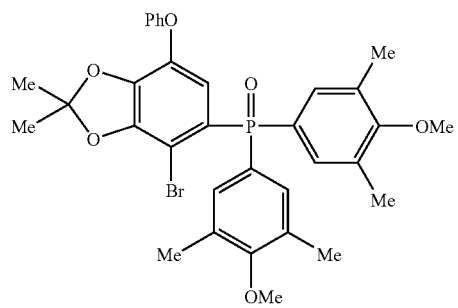
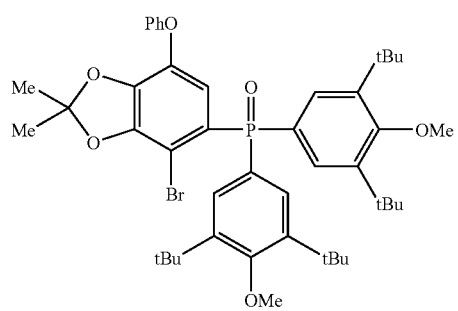
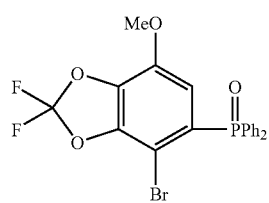
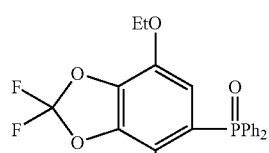
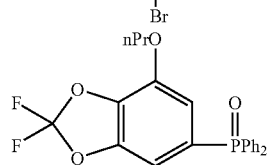
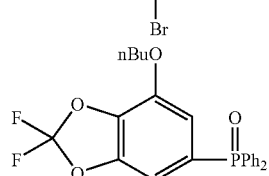
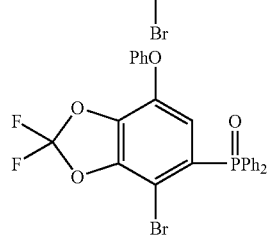
-continued
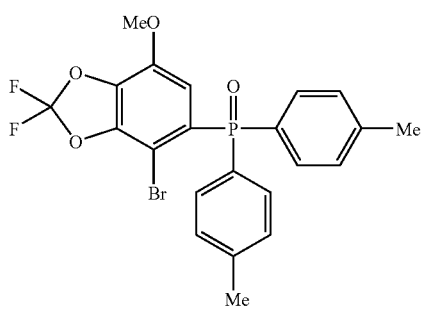
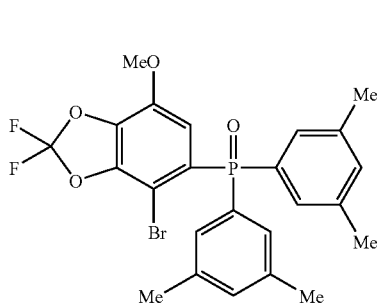
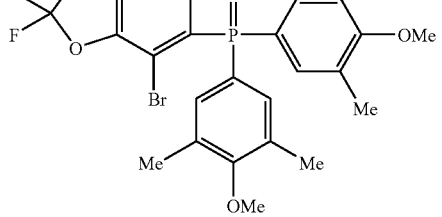
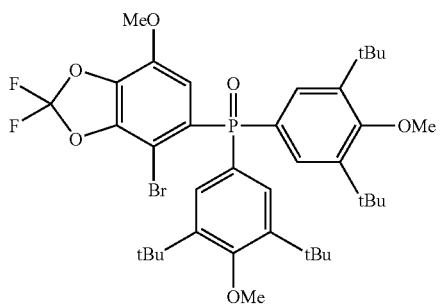
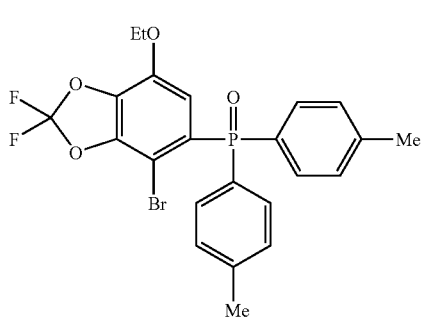

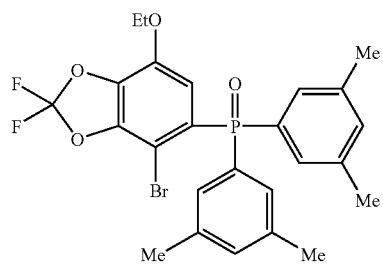
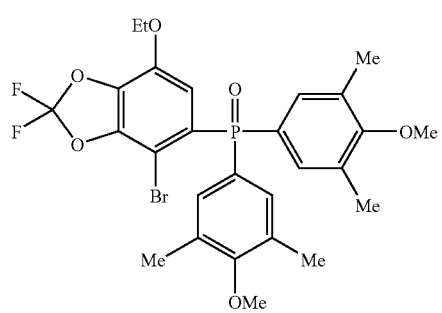
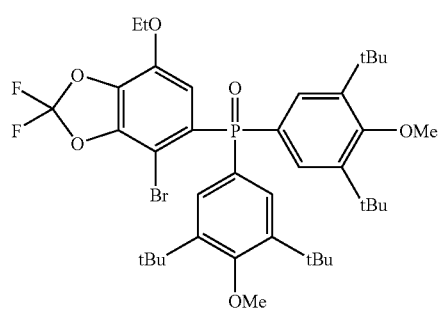
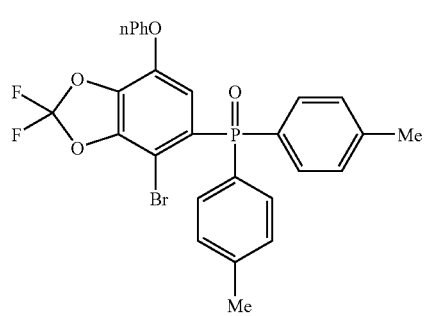
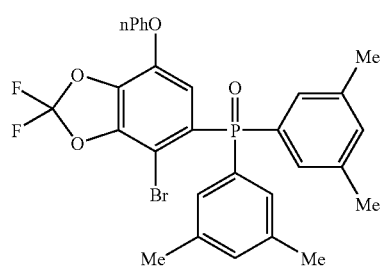
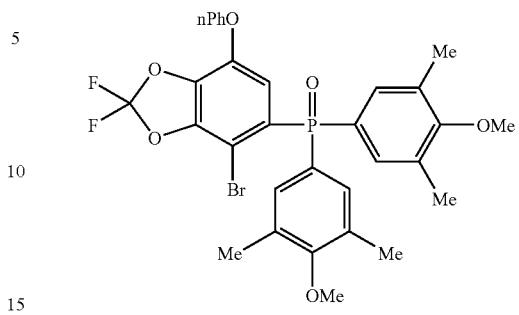
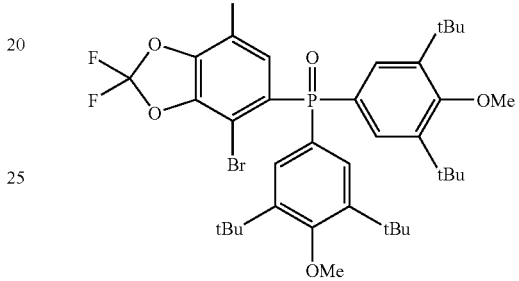
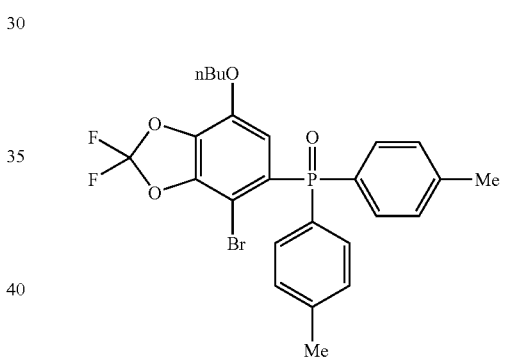
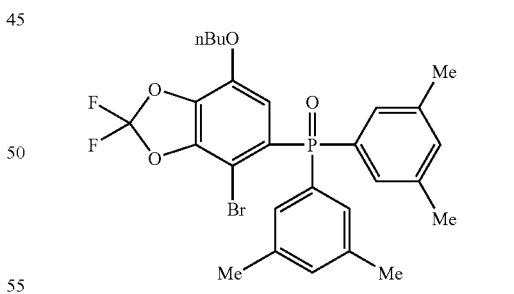
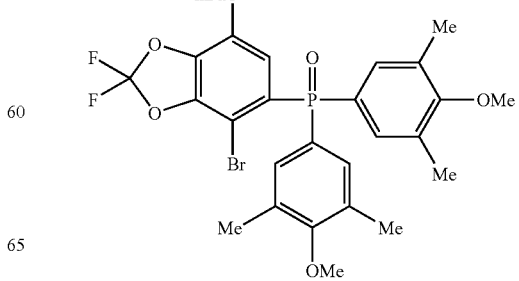

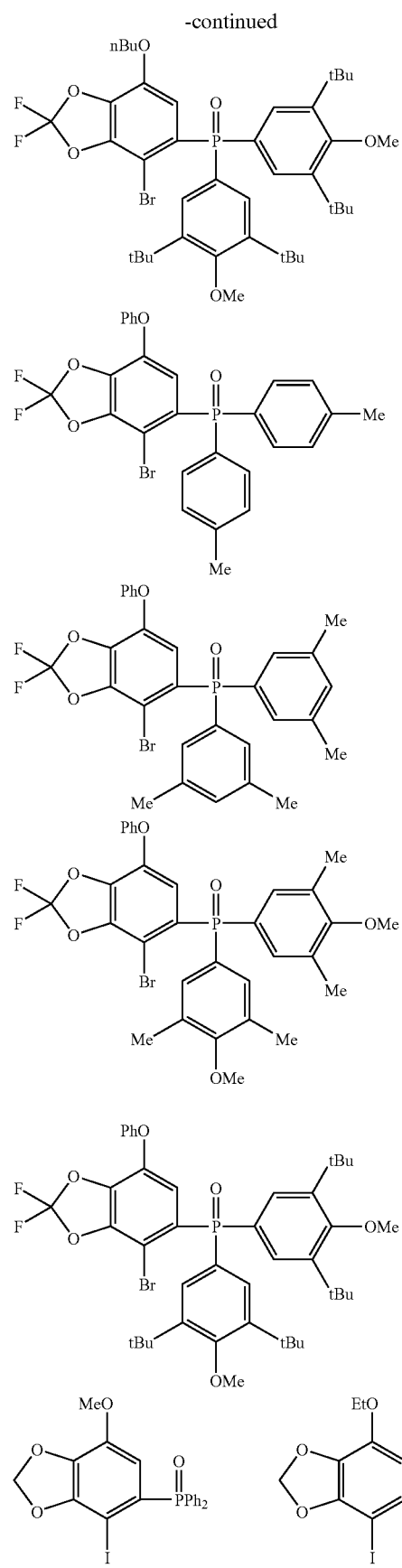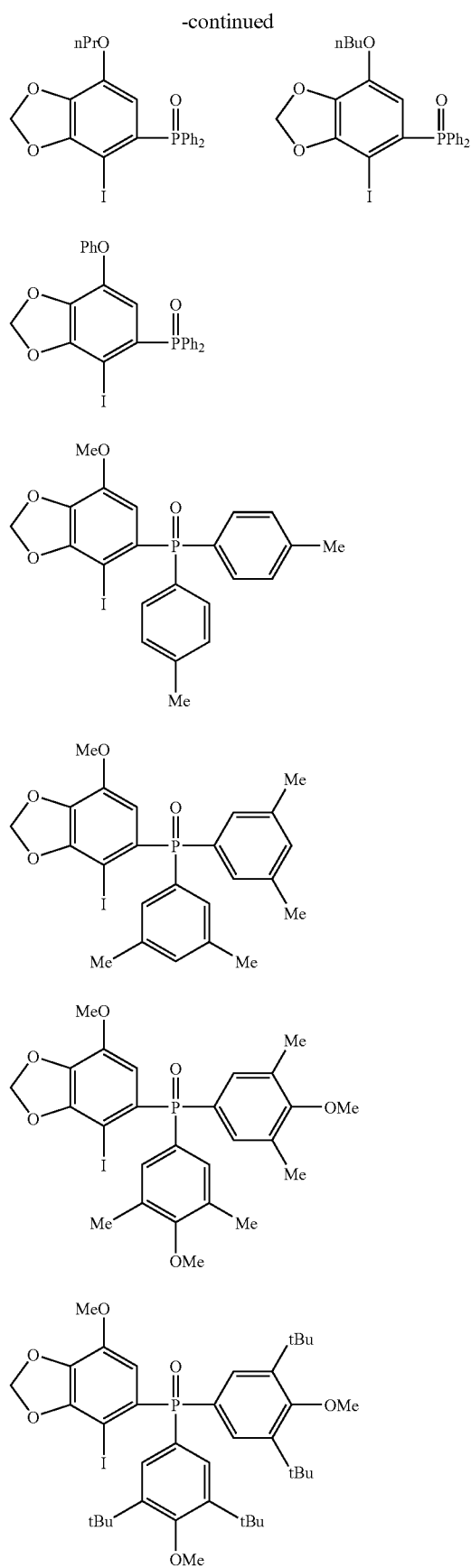

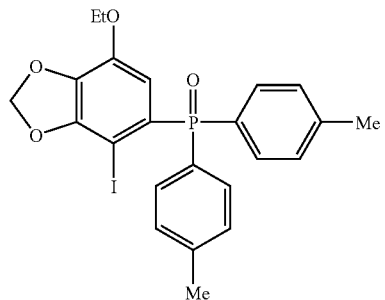
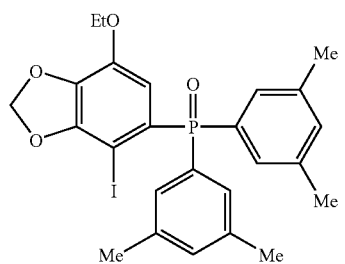
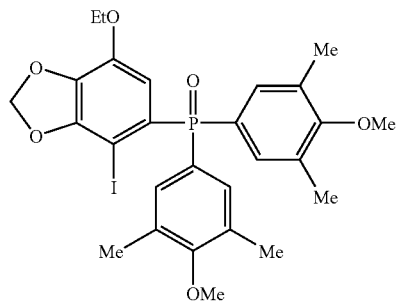
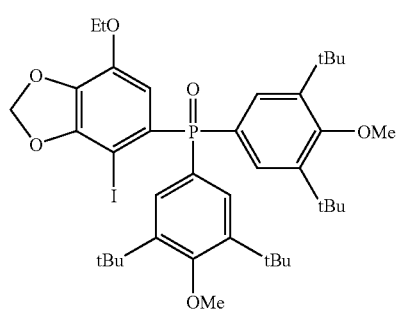
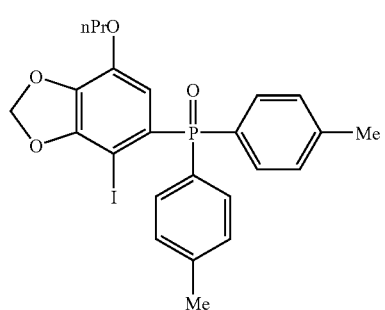
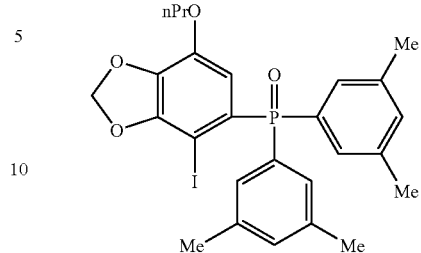
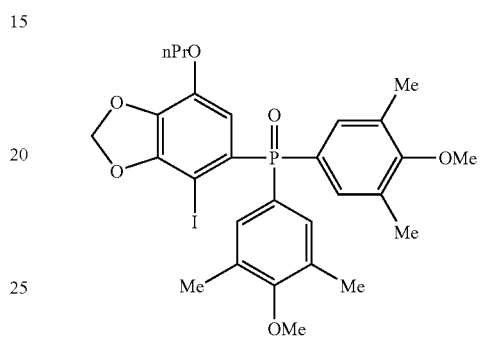
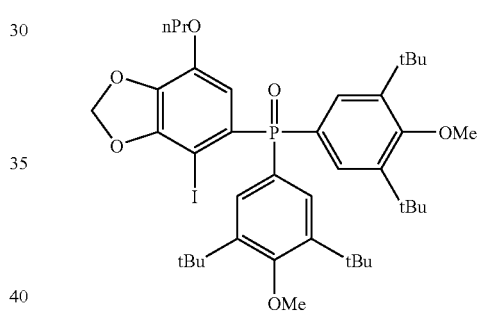
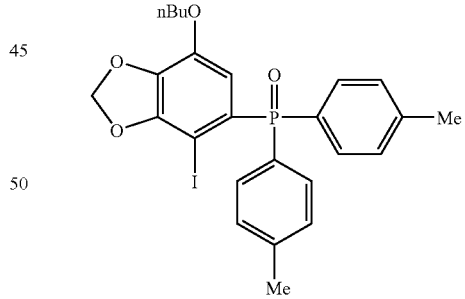
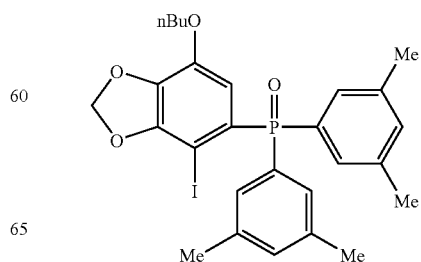

-continued
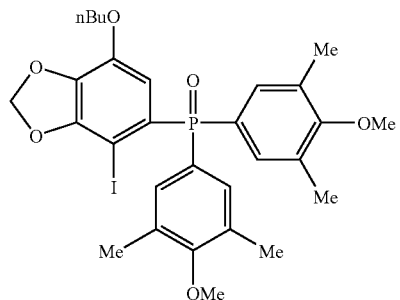
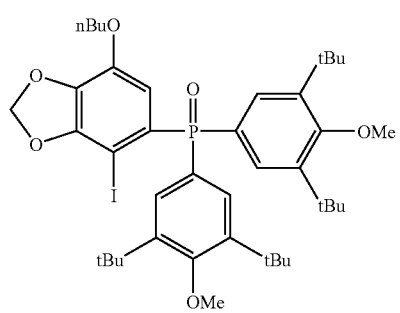
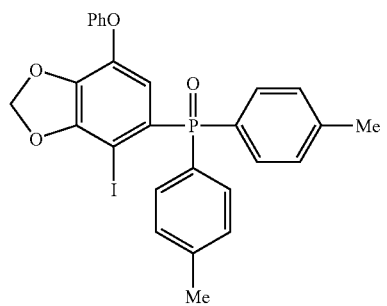
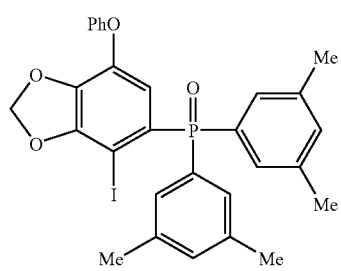
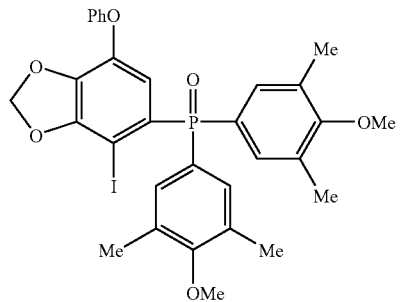
-continued
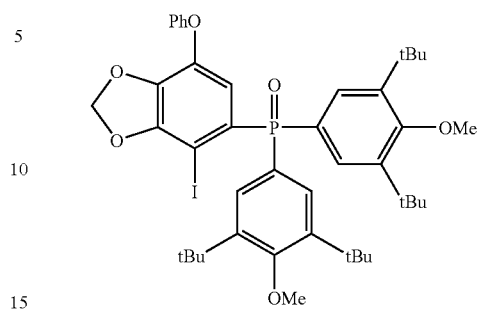
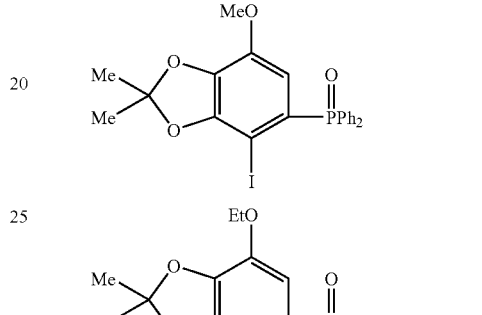
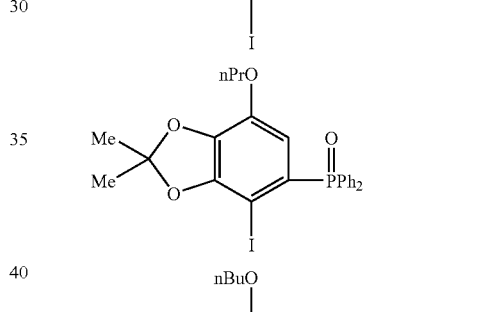
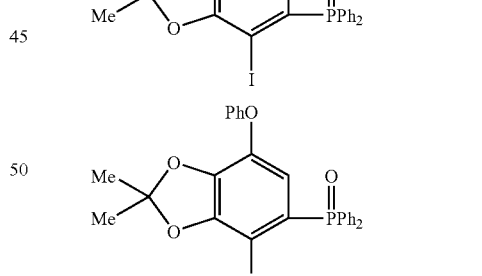
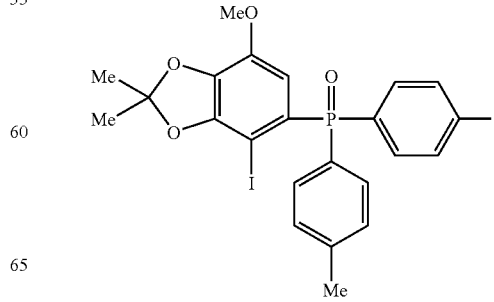

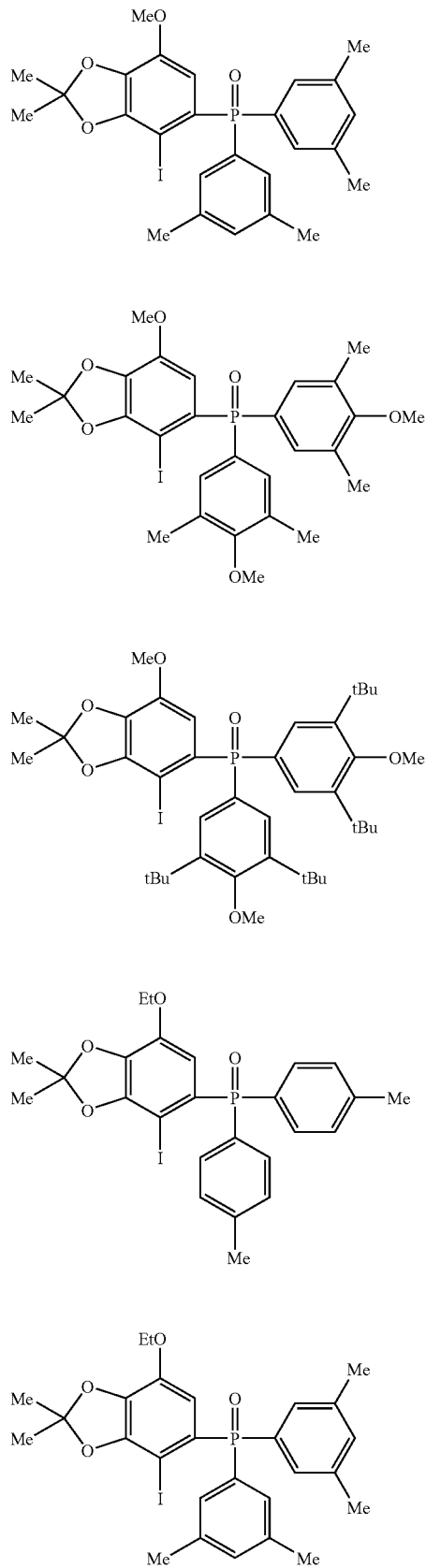

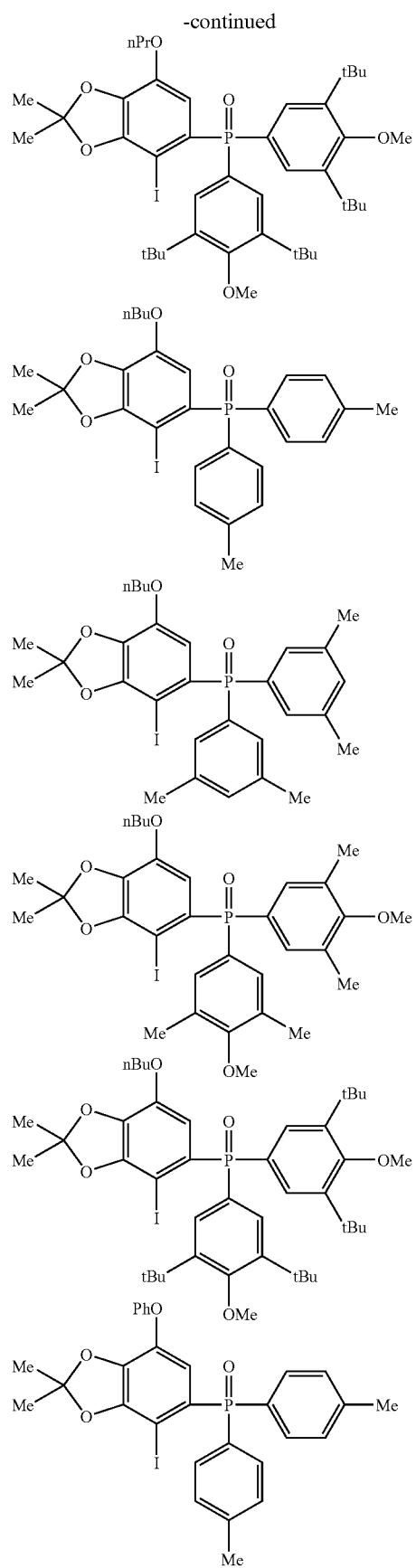
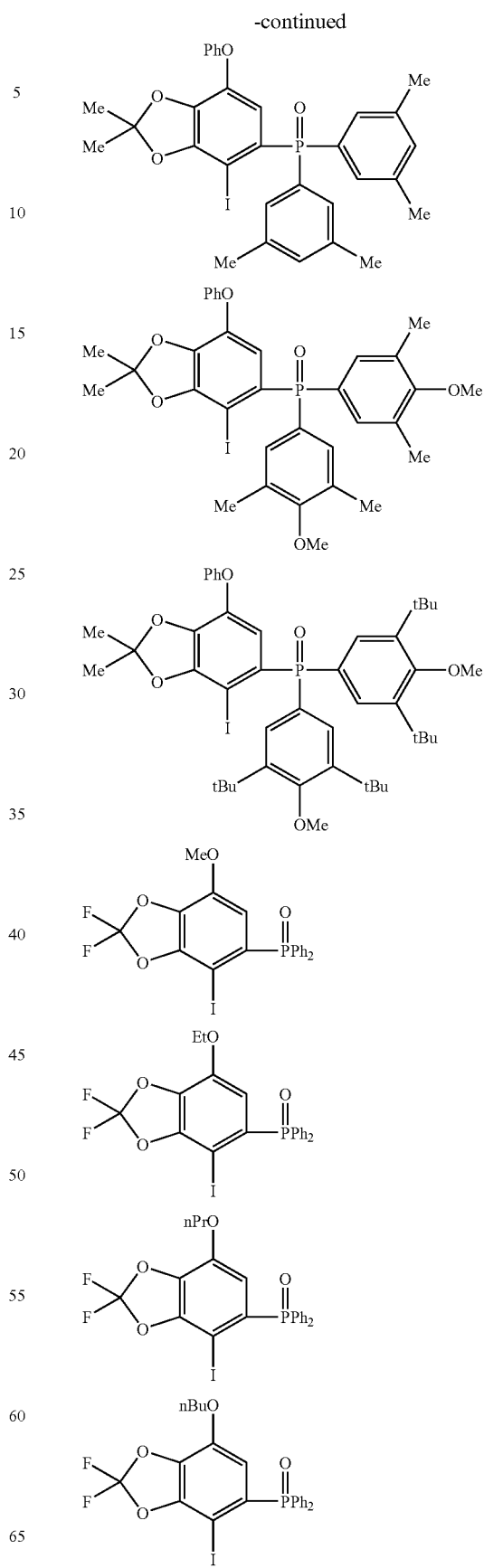

-continued
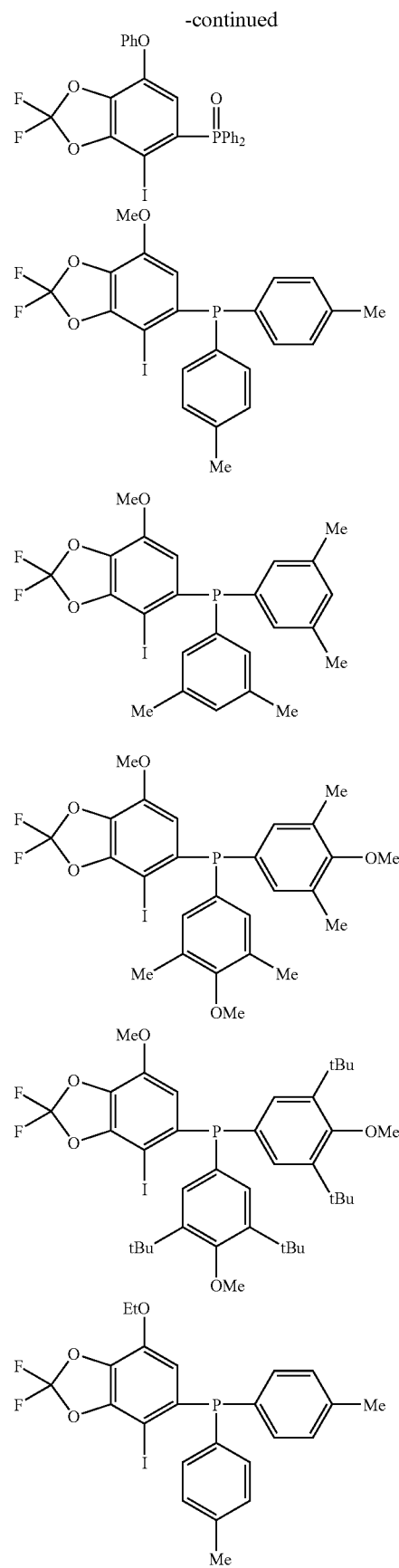
-continued
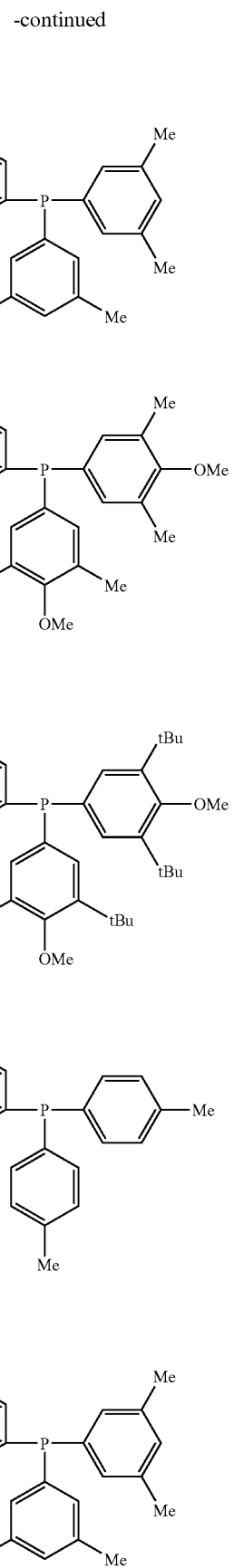

-continued
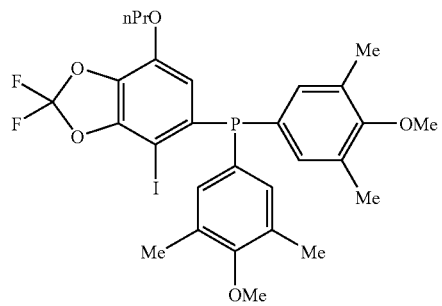
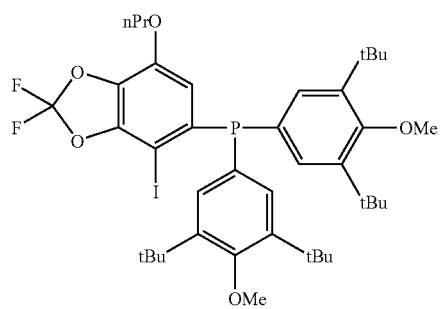
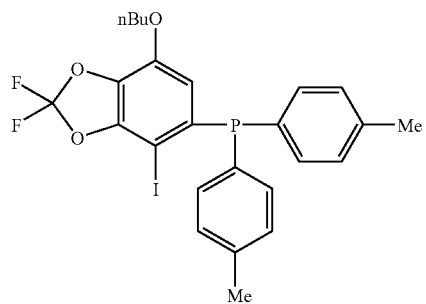
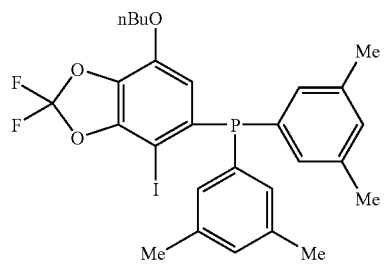
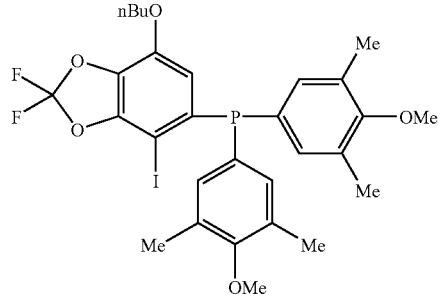
-continued
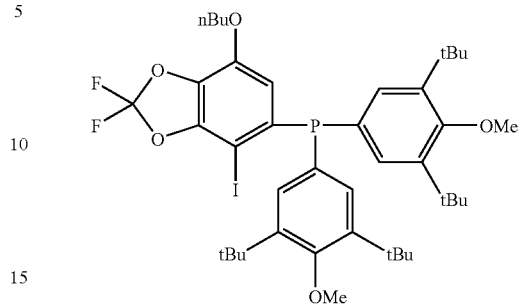
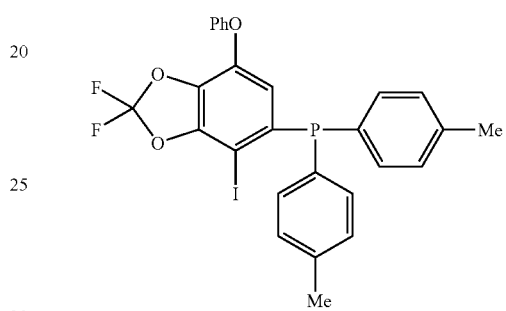
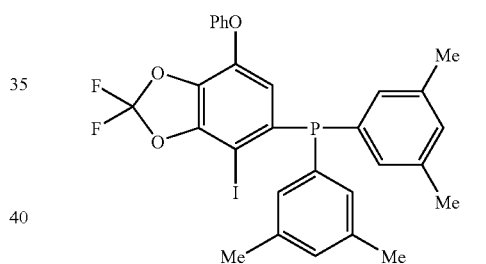
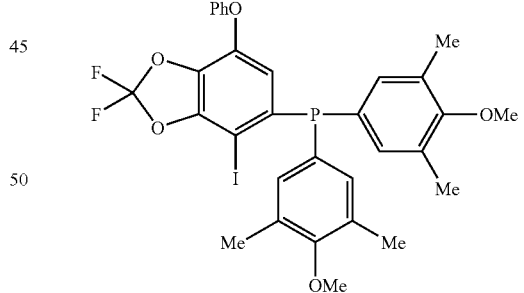
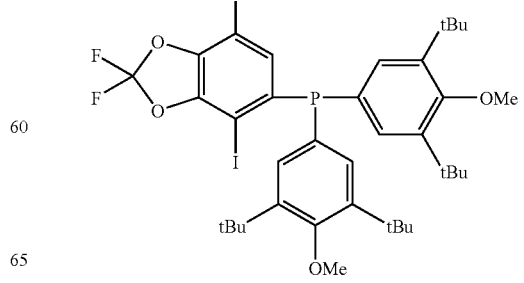

The lithium compound used in step (2) includes, for example, organic lithium compounds such as alkyllithium, aryllithium, aralkyllithium and the like. Among these, alkyllithium is preferable. Specific examples of the alkyllithium include methyllithium, ethyllithium, n-butyllithium, tert-butyllithium and the like.

The above lithium compound may be available commercially or produced as appropriate by, for example, reacting metallic lithium and an organic halide.

The amount of the lithium compound used is appropriately selected usually in the range of 1 to 5 equivalents, preferably 1 to 3 equivalents based on that of the phosphine oxide compound represented by the above formula (4).

The halogenating agent includes, for example, inorganic halogenating agents, organic halogenating agents and the like. The inorganic halogenating agents include, for example, metal halides such as alkaline metal halides such as lithium bromide, sodium bromide, potassium fluoride, potassium iodide and the like, and phosphorus halides such as phosphorus trichloride and phosphorus tribromide; halogens such as fluorine, chlorine, bromine and iodine; and the like. The organic halogenating agents include, for example, succinimides such as N-chlorosuccinimide and N-bromosuccinimide; and the like. Among these halogenating agent, halogens are preferable, and chlorine, bromine, iodine and the like are more preferable.

The amount of the halogenating agent used is appropriately selected usually in the range of 1 to 5 equivalents, preferably 1 to 3 equivalents based on that of the phosphine oxide compound represented by the above formula (4).

The base used as needed includes an inorganic base, an organic base and the like.

The inorganic base includes, for example, salts and hydroxides of alkaline metals or alkaline-earth metals such as potassium carbonate, potassium hydroxide, lithium hydroxide, sodium hydrogencarbonate, sodium carbonate, potassium hydrogencarbonate, sodium hydroxide, magnesium carbonate and calcium carbonate; metal hydrides such as sodium hydride, sodium borohydride and lithium aluminum hydride; and the like.

The organic base includes, for example, alkaline metal alkoxides such as potassium methoxide, sodium methoxide, lithium methoxide, sodium ethoxide, potassium isopropoxide and potassium tert-butoxide; potassium naphthalenide; organic acid salts of alkaline metals or alkaline-earth metals such as sodium acetate, potassium acetate, magnesium acetate and calcium acetate; organic amines such as diisopropylamine, triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine and N-methylmorpholine; quaternary ammonium salts; and the like. Among these bases, organic amines are preferred.

The amount of the base used is appropriately selected usually in the range of 1 to 5 equivalents, preferably 1 to 3 equivalents based on that of the phosphine oxide compound represented by the above formula (4).

The solvent used as needed includes, for example, aliphatic hydrocarbons such as pentane, hexane, heptane, octane, decane and cyclohexane; aromatic hydrocarbons such as benzene, toluene and xylene; halogenated hydrocarbons such as dichloromethane, 1,2-dichloroethane, chloroform, carbon tetrachloride and o-dichlorobenzene; ethers such as diethyl ether, diisopropyl ether, tert-butyl methyl ether, dimethoxyethane, ethylene glycol diethyl ether, tetrahydrofuran, 1,4-dioxane, 1,3-dioxolane, 2-methyltetrahydrofuran and cyclopentyl methyl ether; ketones such as acetone, methyl ethyl ketone, methyl isobutyl ketone and cyclohexanone; alcohols such as methanol, ethanol, 2-propanol, n-butanol, 2-ethoxyethanol and benzyl alcohol; polyhydric alcohols such as ethylene glycol, 1,2-propanediol, 1,3-propanediol and glycerin; esters such as methyl acetate, ethyl acetate, n-butyl acetate and methyl propionate; amides such as formamide, N,N-dimethylformamide and N,N-dimethylacetoamide; sulfoxides such as dimethyl sulfoxide and the like; cyano-containing organic compounds such as acetonitrile and the like; N-methylpyrrolidone; water; and the like. These solvents may be used alone or in an appropriate combination of two or more thereof.

The amount of the solvent used is appropriately selected usually in the range of 0.1 to 25 times by volume, preferably 5 to 15 times by volume, depending on the kinds of the raw material, the halogenating agent and the solvent used.

The reaction temperature is appropriately selected usually in the range of −78° C. to a reflux temperature of the solvent used, preferably −78 to 0° C., depending on the kinds of the halogenating agent and the solvent used.

The reaction time is appropriately selected usually in the range of 0.11 to 24 hours, preferably 2 to 10 hours.

The 4-halogenophosphine oxide compound represented by the above formula (5) that is produced in step (2) may be used for reaction as it is, or may be used after post-treatment, purification, isolation and the like as needed. Specific method for post-treatment, purification and isolation is the same as described above.

In the step (3), the 4-halogenophosphine oxide compound represented by the above formula (5) that is produced in step (2) can be subjected to coupling reaction in a suitable solvent to produce the diphenylphosphine oxide compound represented by the above formula (6).

Specific examples of the diphenylphosphine oxide compound represented by the formula (6) include, for example, [4,4'-bi(7-methoxy-1,3-benzodioxol)]-5,5'-diyl-bis(diphenylphosphine oxide), [4,4'-bi(7-ethoxy-1,3-benzodioxol)]-5,5'-diyl-bis(diphenylphosphine oxide), [4,4'-bi(7-n-propoxy-1,3-benzodioxol)]-5,5'-diyl-bis(diphenylphosphine oxide), [4,4'-bi(7-n-butoxy-1,3-benzodioxol)]-5,5'-diyl-bis(diphenylphosphine oxide), [4,4'-bi(7-phenoxy-1,3-benzodioxol)]-5,5'-diyl-bis(diphenylphosphine oxide), [4,4'-bi(7-methoxy-1,3-benzodioxol)]-5,5'-diyl-bis[di(4-methylphenyl) phosphine oxide], [4,4'-bi(7-methoxy-1,3-benzodioxol)]-5,5'-diyl-bis[di(3,5-dimethylphenyl)phosphine oxide], [4,4'-bi(7-methoxy-1,3-benzodioxol)]-5,5'-diyl-bis[di(4-methoxy-3,5-dimethylphenyl)phosphine oxide], [4,4'-bi(7-methoxy-1,3-benzodioxol)]-5,5'-diyl-bis[di(4-methoxy-3,5-di-tert-butylphenyl)phosphine oxide] and the like, of which the chemical formulae are shown below together with those of other compounds.

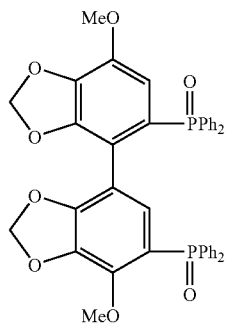
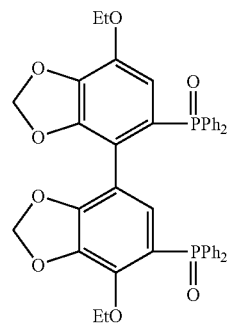

-continued
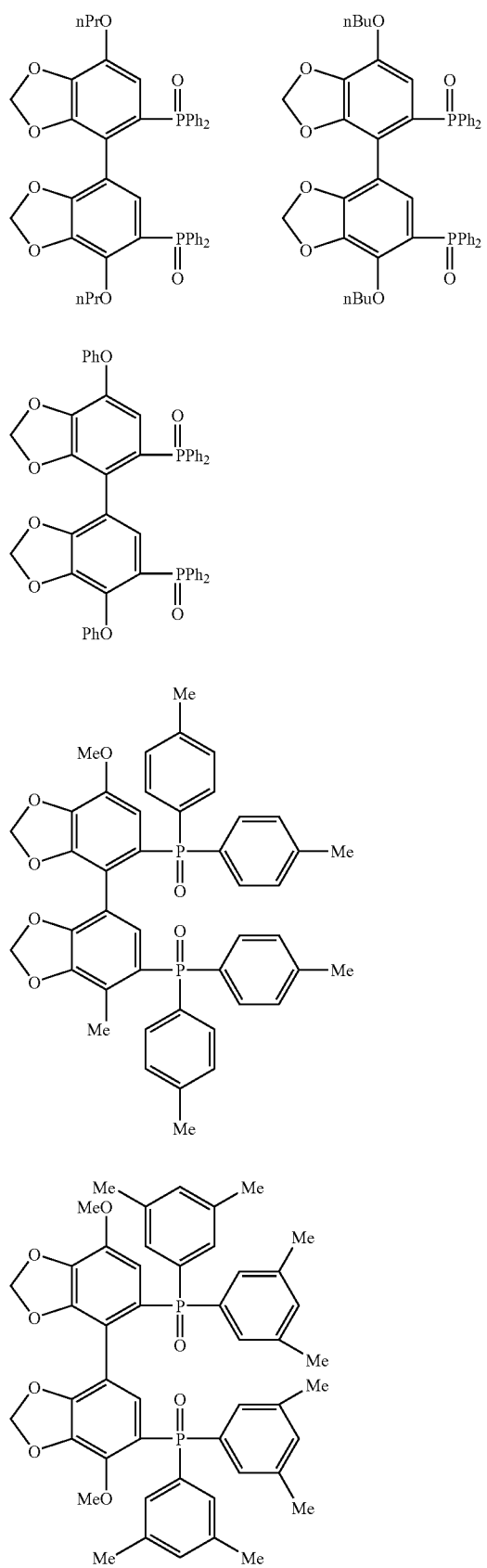
-continued
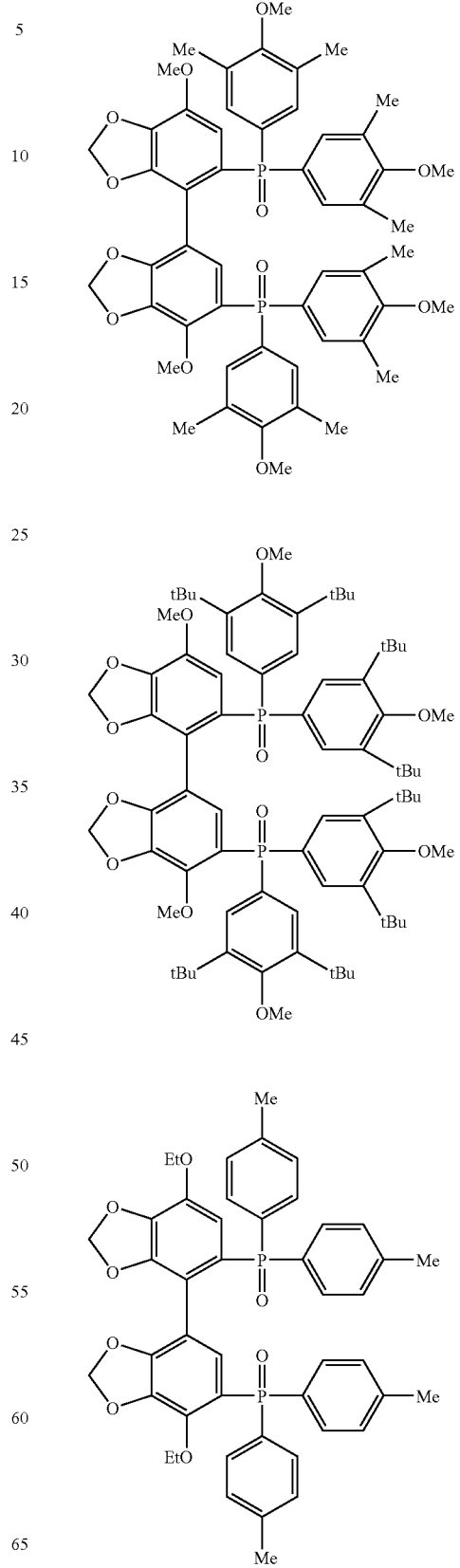

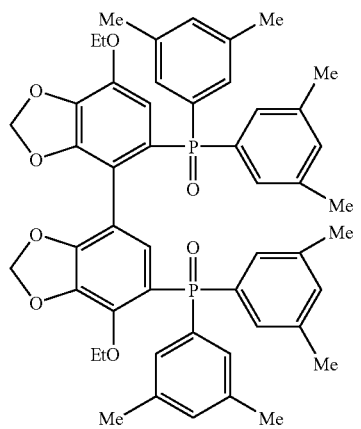
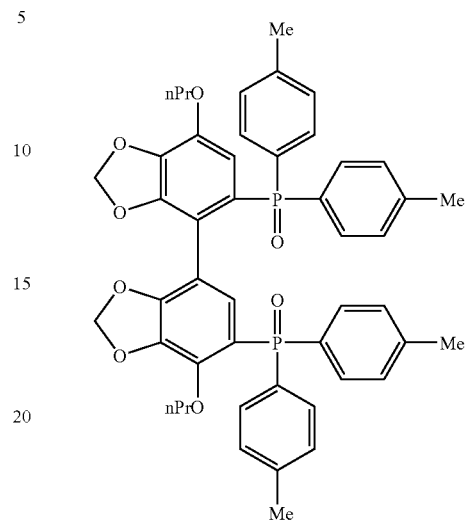
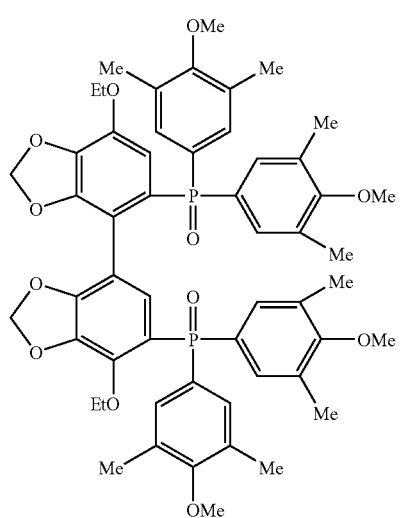
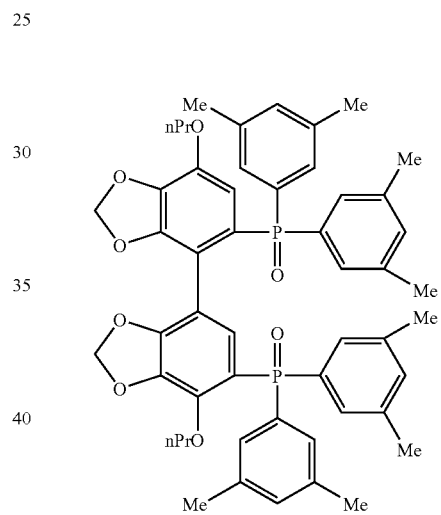
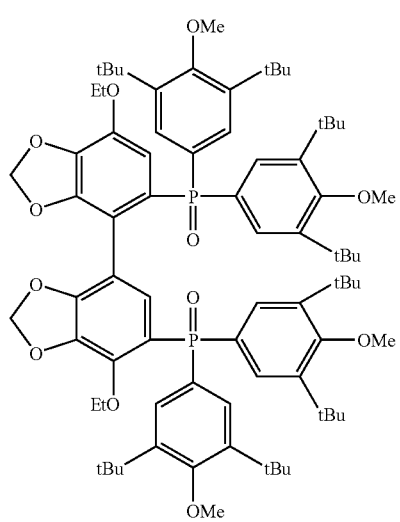
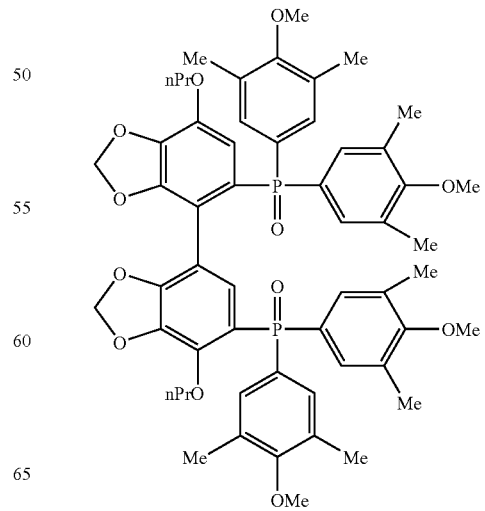

-continued
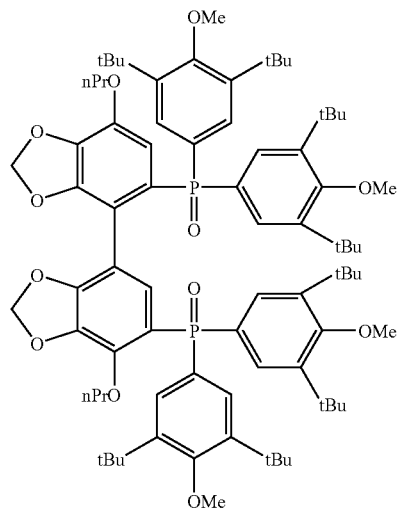
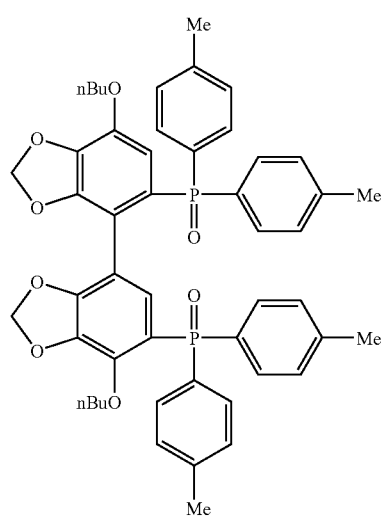
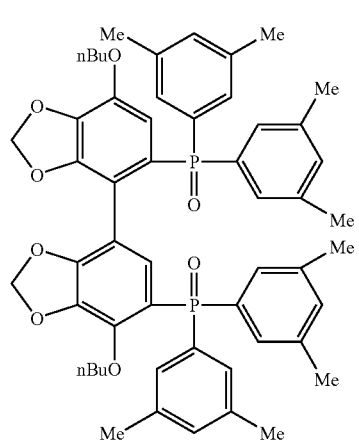
-continued
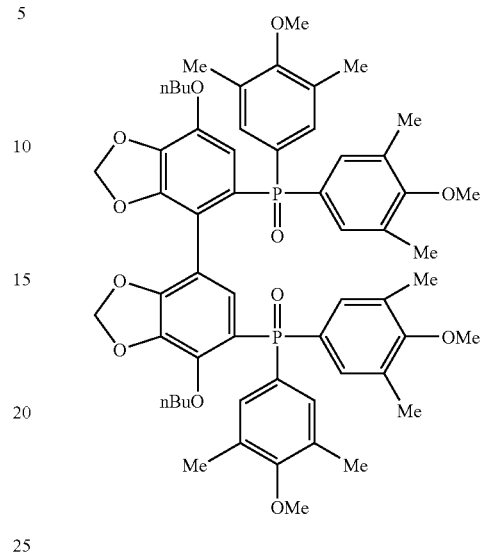
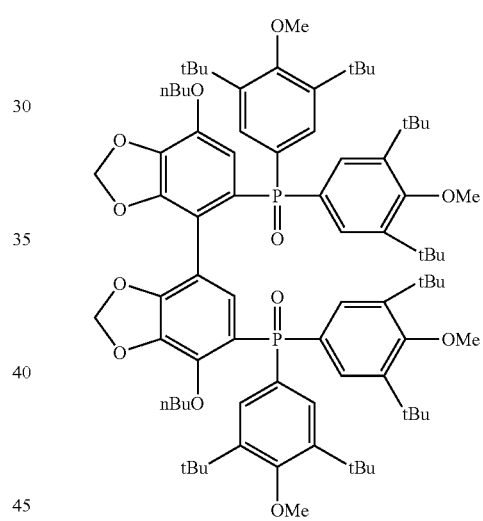
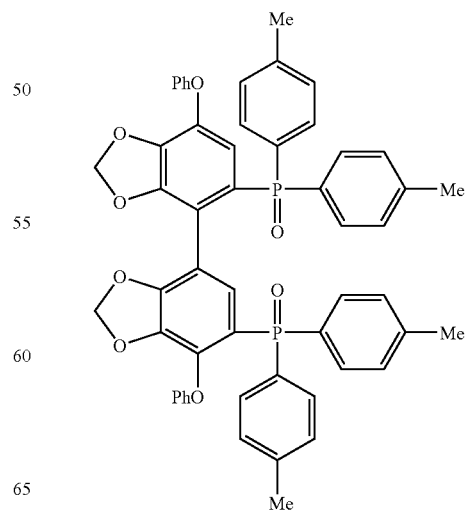

-continued
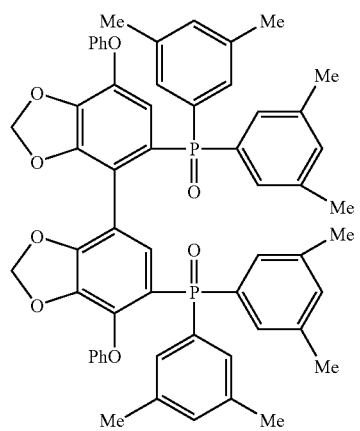
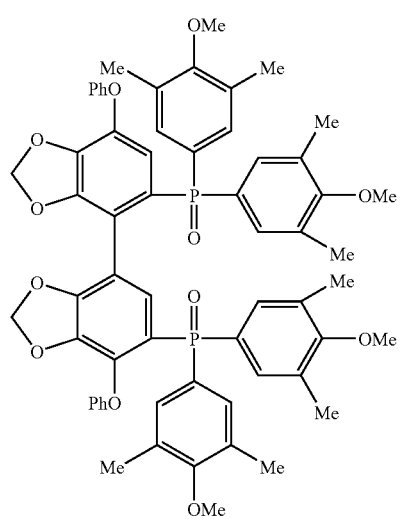
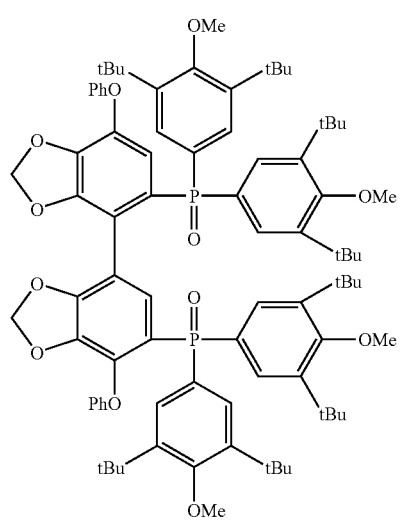
-continued
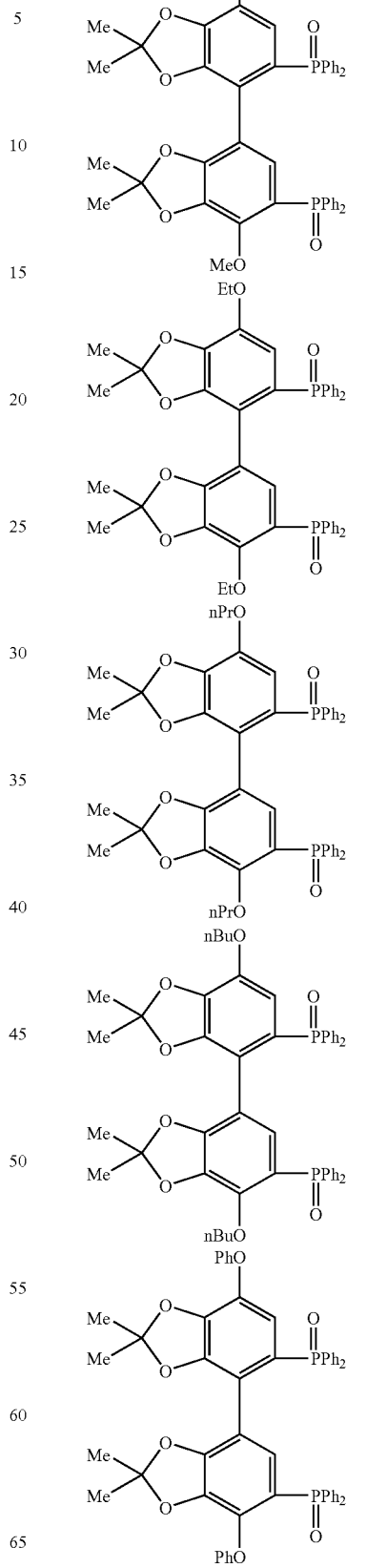

147
-continued
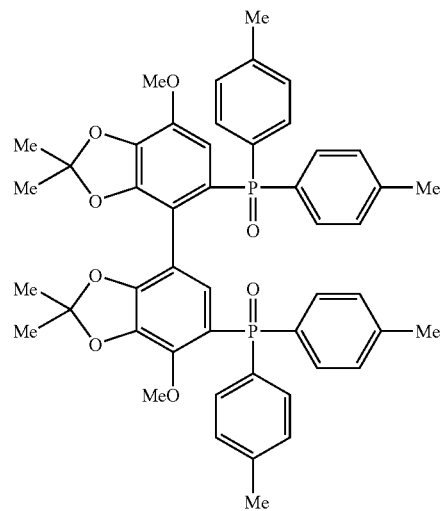
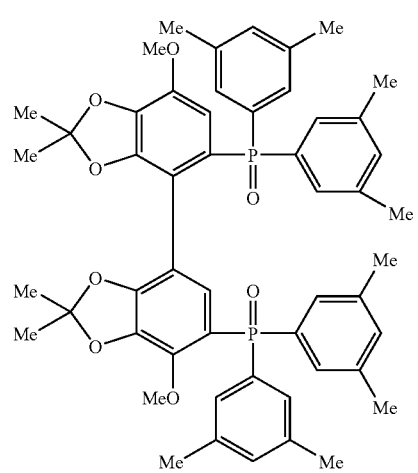
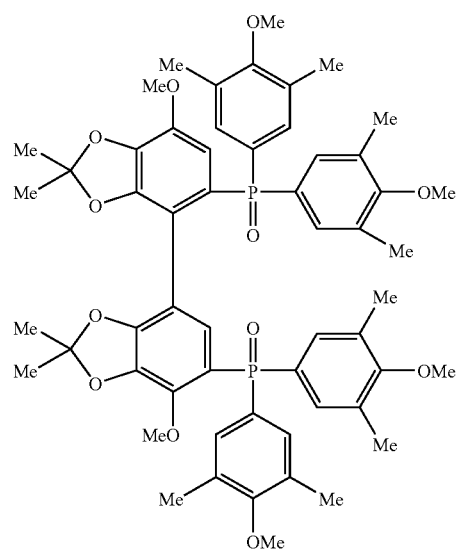
148
-continued
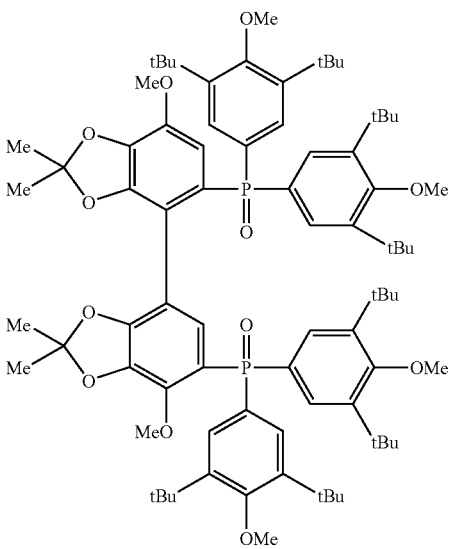
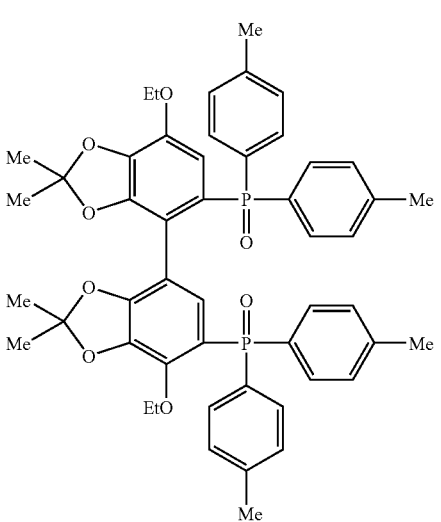
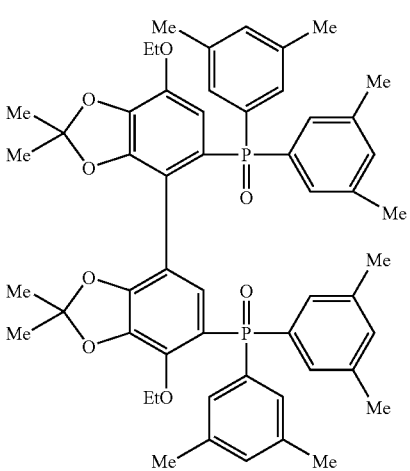

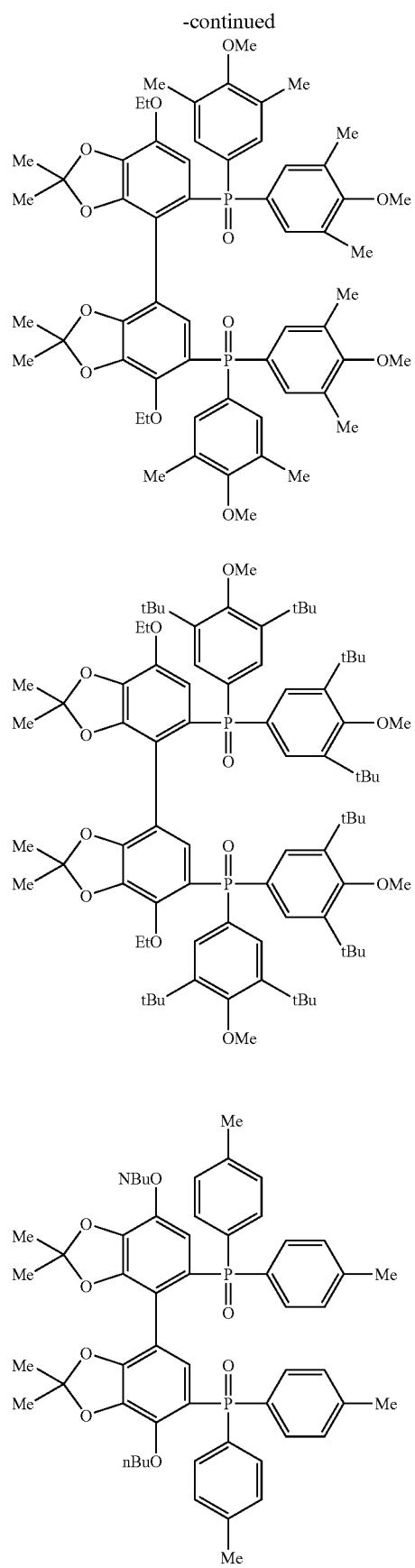
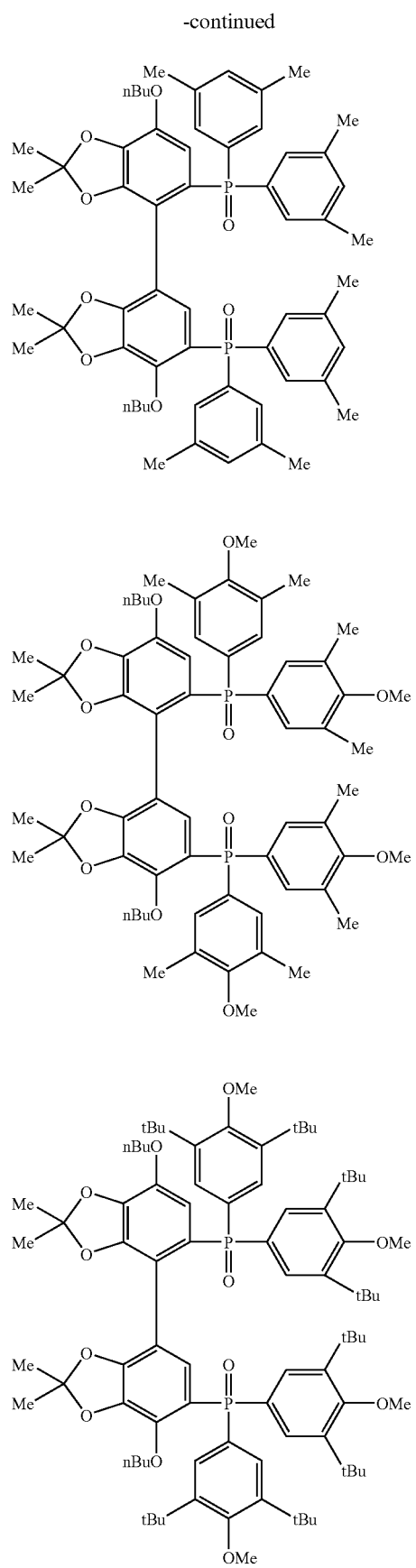

-continued
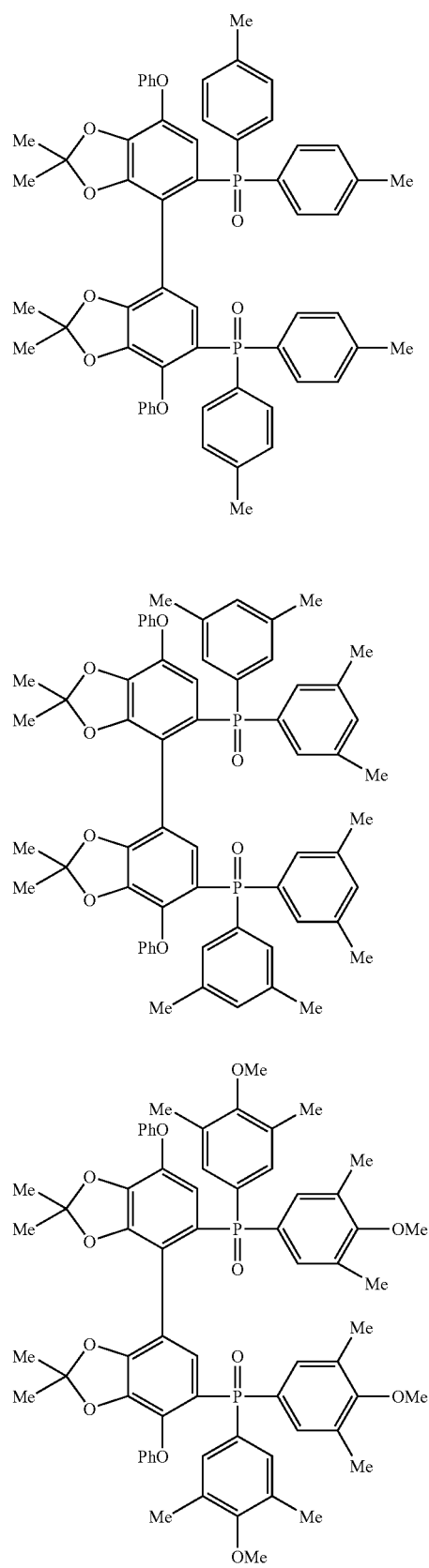
-continued
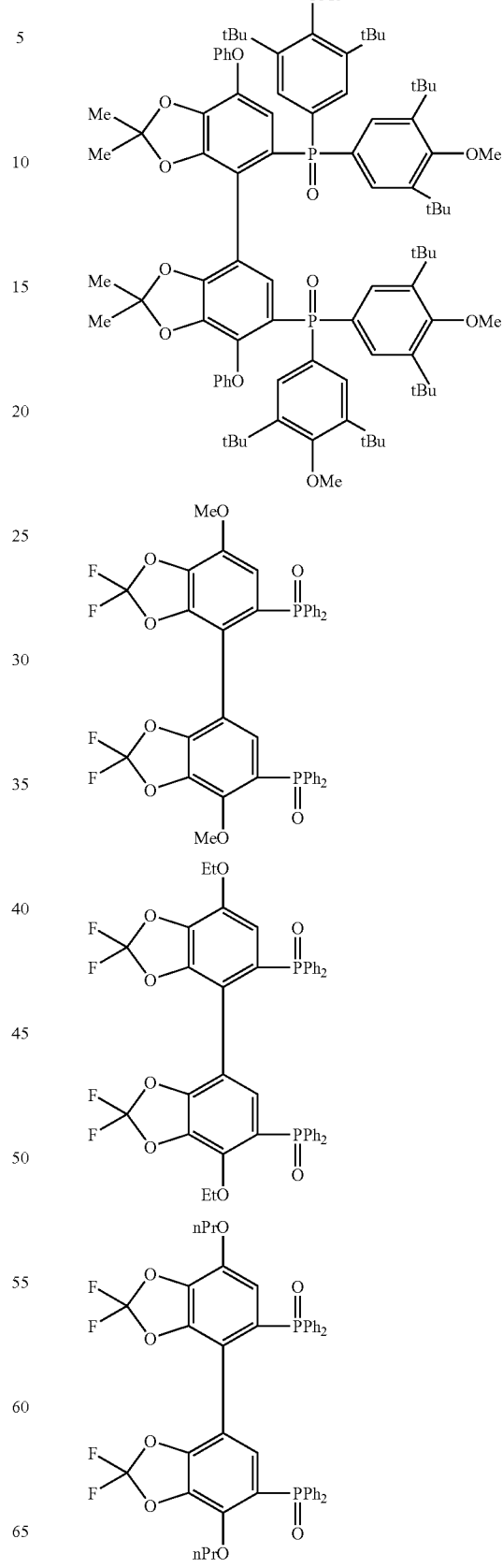

-continued
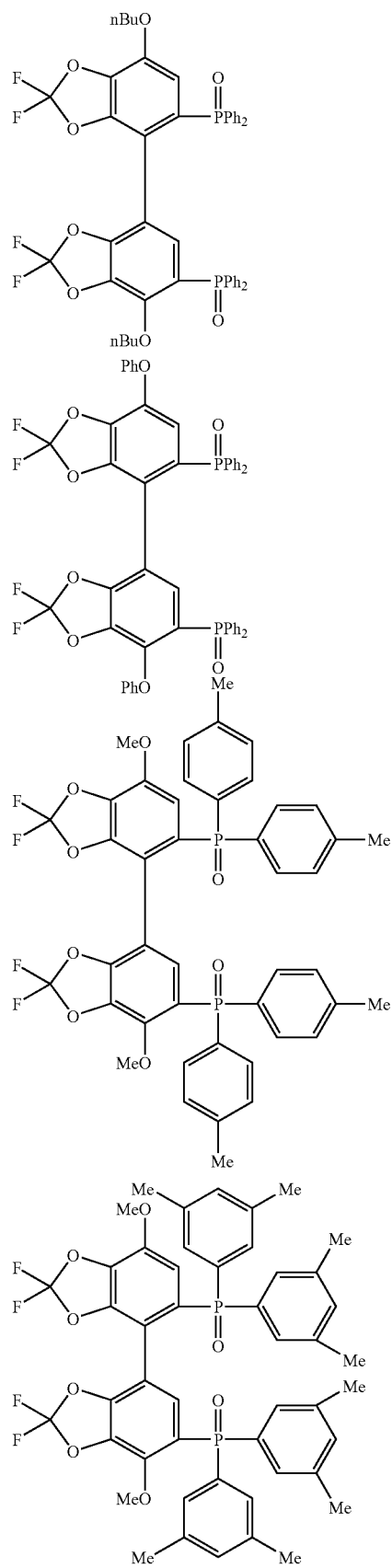
-continued
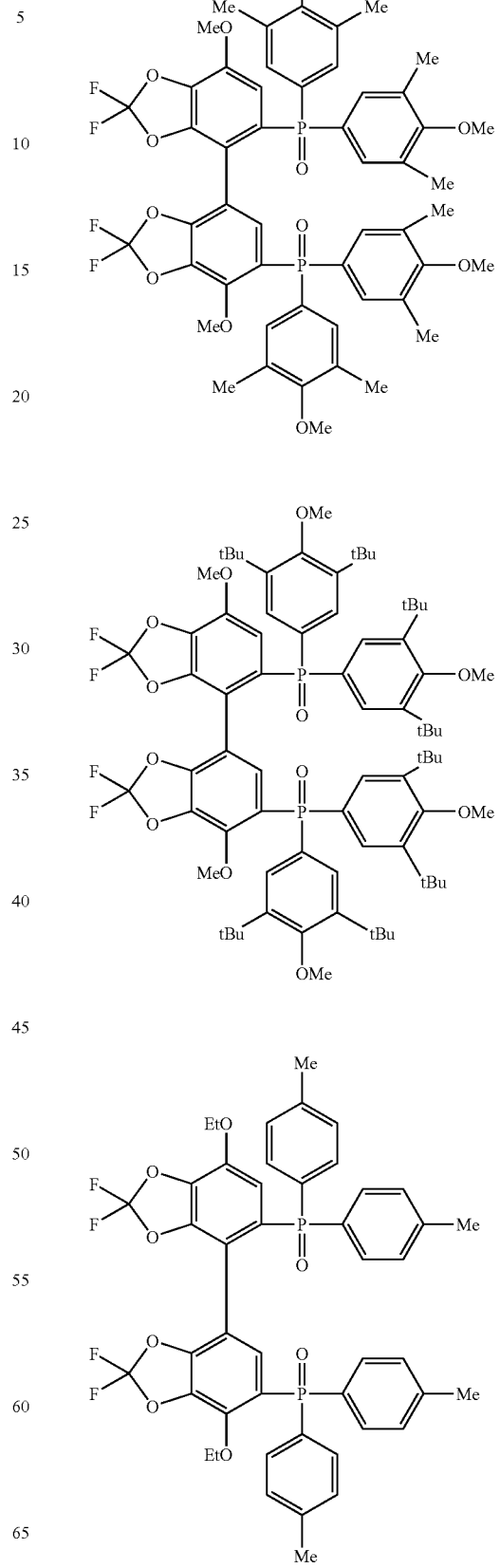

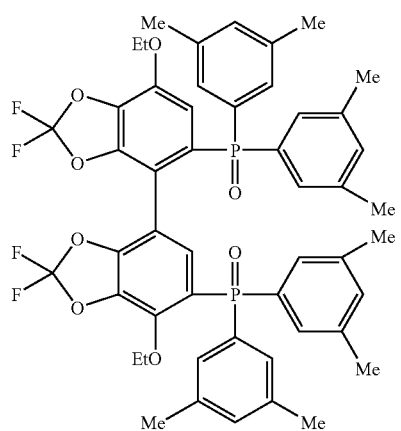
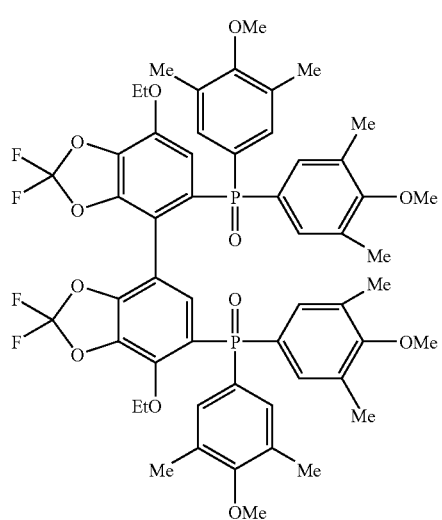
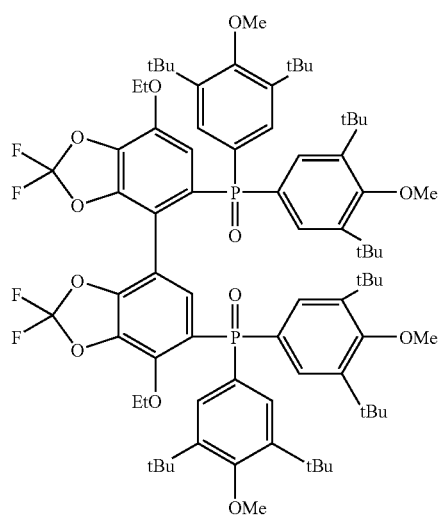
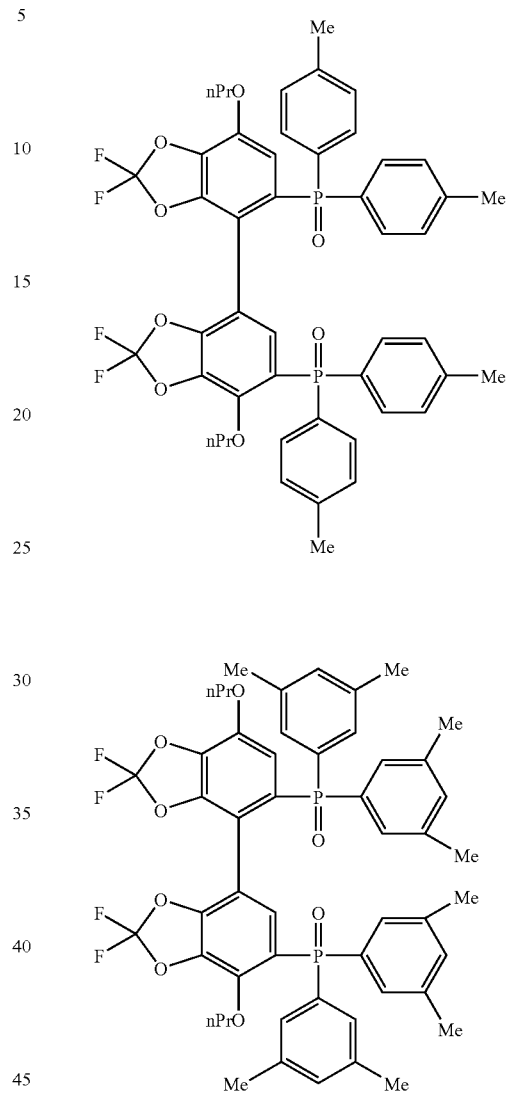
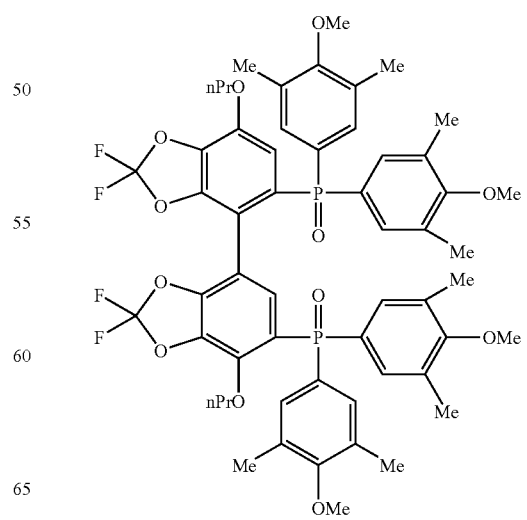

-continued
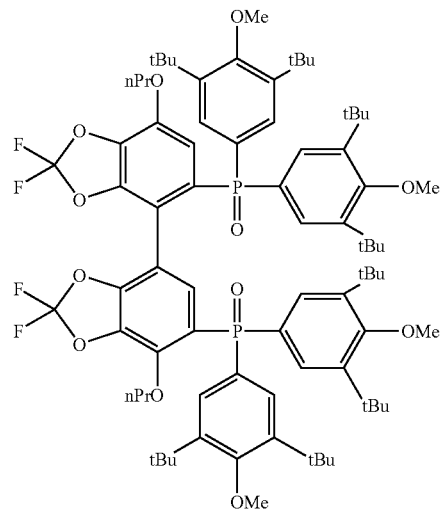
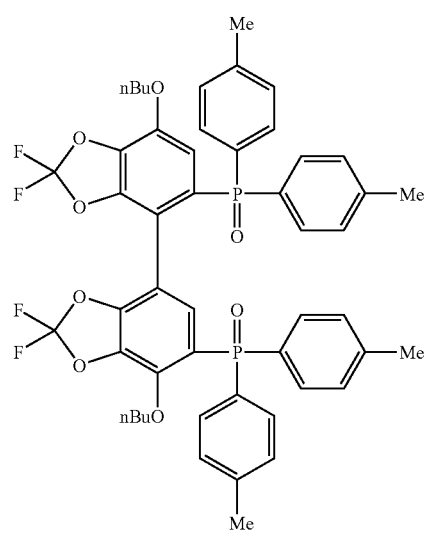
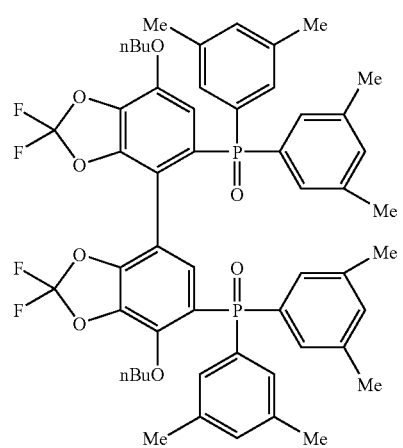
-continued
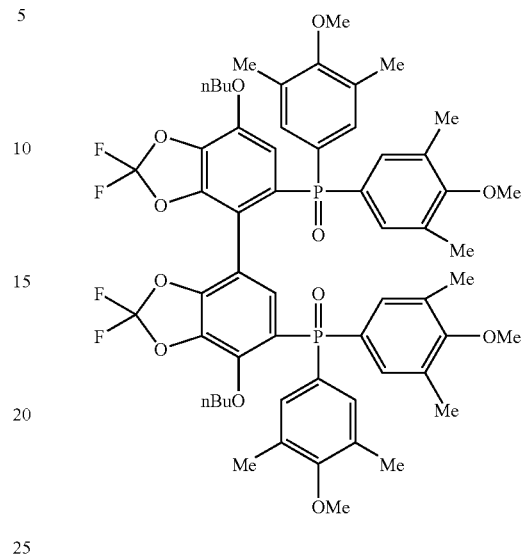
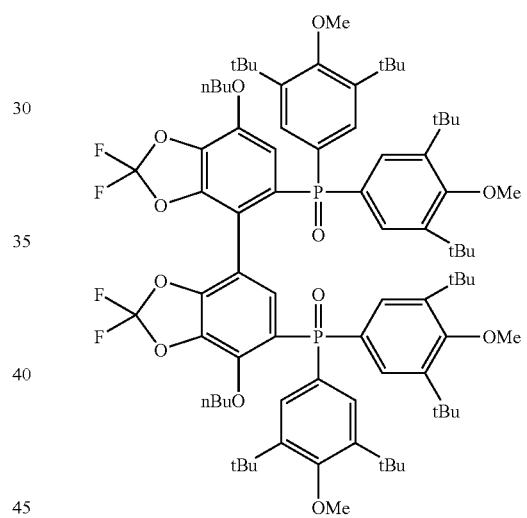
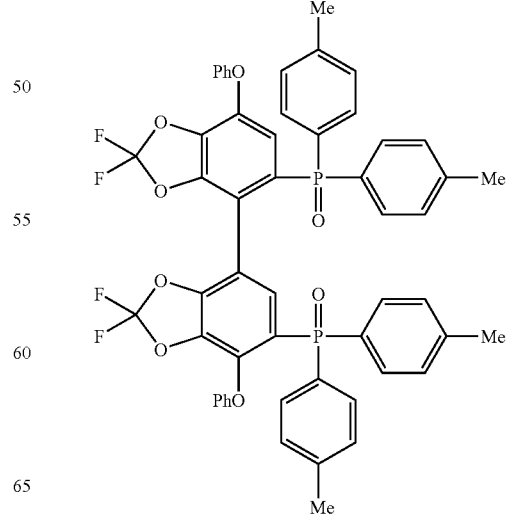

-continued

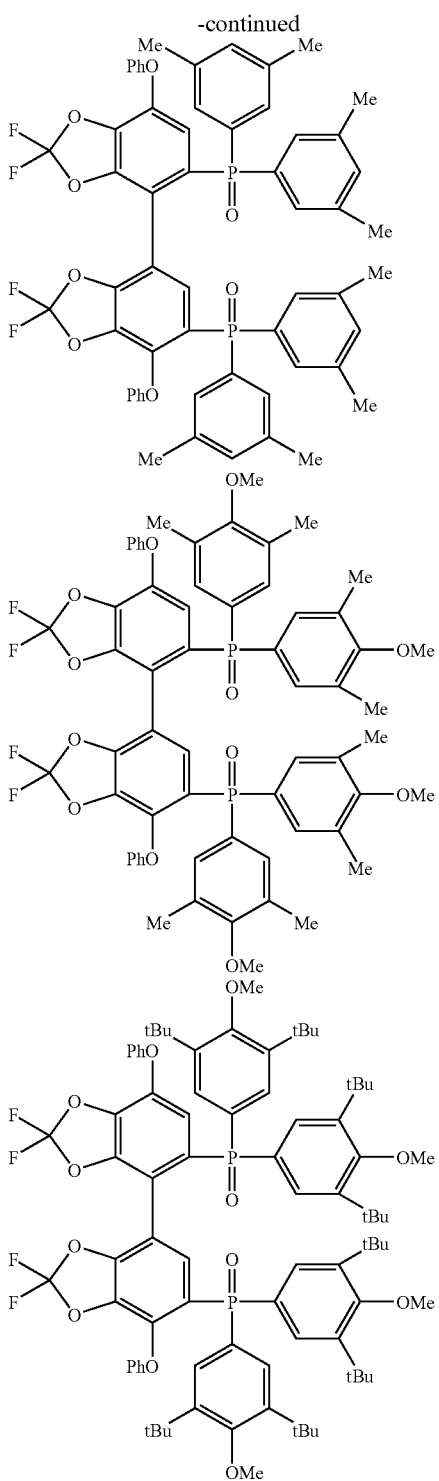

The coupling reaction of step (3) is preferably carried out in the presence of a coupling agent such as a metal and the like. The metal includes, for example, copper, zinc, magnesium and manganese, among which copper is preferable.

The amount of the coupling agent used is appropriately selected usually in the range of 1 to 10 equivalents, preferably 2 to 5 equivalents based on that of the 4-halogenophosphine oxide compound represented by the above formula (5).

The coupling reaction is preferably carried out in the presence of a solvent. The solvent includes, for example, aliphatic hydrocarbons such as pentane, hexane, heptane, octane, decane and cyclohexane; aromatic hydrocarbons such as benzene, toluene and xylene; halogenated hydrocarbons such as dichloromethane, 1,2-dichloroethane, chloroform, carbon tetrachloride and o-dichlorobenzene; ethers such as diethyl ether, diisopropyl ether, tert-butyl methyl ether, dimethoxyethane, ethylene glycol diethyl ether, tetrahydrofuran, 1,4-dioxane, 1,3-dioxolane, 2-methyltetrahydrofuran and cyclopentyl methyl ether; alcohols such as methanol, ethanol, 2-propanol, n-butanol, 2-ethoxyethanol and benzyl alcohol; ketones such as acetone, methyl ethyl ketone, methyl isobutyl ketone and cyclohexanone and the like; esters such as methyl acetate, ethyl acetate, n-butyl acetate and methyl propionate; amides such as formamide, N,N-dimethylformamide and N,N-dimethylacetoamide; sulfoxides such as dimethyl sulfoxide and the like; cyano-containing organic compounds such as acetonitrile and the like; N-methylpyrrolidone; water; and the like. These solvents may be used alone or in an appropriate combination of two or more of these solvents.

The amount of the solvent used is appropriately selected usually in the range of 1 to 15 times by volume, preferably 2 to 10 times by volume based on that of the 4-halogenophosphine oxide compound represented by the above formula (5).

The reaction temperature is appropriately selected usually in the range of 50 to 200° C., preferably 80 to 150° C., depending on the kinds of the metal and the solvent used.

The reaction time is appropriately selected usually in the range of 1 to 15 hours, preferably 2 to 10 hours.

The diphenylphosphine oxide compound represented by the above formula (6) that is produced in step (3) may be, if necessary, subjected to optical resolution as it is, or may be subjected to optical resolution after post-treatment, purification, isolation and the like as needed. Specific method for post-treatment, purification and isolation and the like is the same as described above.

An optically active substance of the diphenylphosphine oxide compound represented by the above formula (6) can be readily obtained by using a known optical resolution method. The known optical resolution method includes a method of using a high-performance liquid chromatography with an optically active column, a method of forming a diastereomer salt of an optically active acidic compound in a solvent, and the like. The solvent includes, for example, aliphatic hydrocarbons such as pentane, hexane, heptane, octane, decane and cyclohexane; aromatic hydrocarbons such as benzene, toluene and xylene; halogenated hydrocarbons such as dichloromethane, 1,2-dichloroethane, chloroform, carbon tetrachloride and o-dichlorobenzene; ethers such as diethyl ether, diisopropyl ether, tert-butyl methyl ether, dimethoxyethane, ethylene glycol diethyl ether, tetrahydrofuran, 1,4-dioxane, 1,3-dioxolane, 2-methyltetrahydrofuran and cyclopentyl methyl ether; alcohols such as methanol, ethanol, 2-propanol, n-butanol, 2-ethoxyethanol and benzyl alcohol; ketones such as acetone, methyl ethyl ketone, methyl isobutyl ketone and cyclohexanone; esters such as methyl acetate, ethyl acetate, n-butyl acetate and methyl propionate; amides such as formamide, N,N-dimethylformamide and N,N-dimethylacetoamide; sulfoxides such as dimethyl sulfoxide and the like; cyano-containing organic compounds such as acetonitrile and the like; N-methylpyrrolidone; water; and the like. These solvents may be used alone or in an appropriate combination of two or more thereof.

The optically active acidic compound includes, for example, (+) or (−)-tartaric acid, (+) or (−)-benzoyl tartaric acid, (+) or (−)-toluoyl tartaric acid, (+) or (−)-pyvaloyl tartaric acid, (+) or (−)-camphor sulfonic acid, (+) or (−)-mandelic acid, and the like.

In the case that the diphenylphosphine oxide compound represented by the formula (6) of the present invention is used as the catalyst for asymmetric synthesis itself, specific examples of the asymmetric synthesis include, for example, an aldol reaction and the like.

In the step (4), the diphenylphosphine oxide compound represented by the above formula (6) that is produced in step (3) can be subjected to reduction in a suitable solvent to produce the diphosphine compound represented by the formula (1) of the present invention.

The reduction of step (4) may be carried out in the presence of a reducing agent such as silane compounds. The silane compounds include trichlorosilane and the like.

The amount of the reducing agent used is appropriately selected usually in the range of 5 to 20 equivalents, preferably 5 to 15 equivalents based on that of the diphenylphosphine oxide compound represented by the above formula (6).

Reduction is preferably carried out in the presence of a base. The base may be the same as the base described in the above step (2).

The amount of the base used is appropriately selected usually in the range of 5 to 20 equivalents, preferably 5 to 15 equivalents based on that of the diphenylphosphine oxide compound represented by the above formula (6).

The solvent includes, for example, aliphatic hydrocarbons such as pentane, hexane, heptane, octane, decane and cyclohexane; aromatic hydrocarbons such as benzene, toluene and xylene; halogenated hydrocarbons such as dichloromethane, 1,2-dichloroethane, chloroform, carbon tetrachloride and o-dichlorobenzene; ethers such as diethyl ether, diisopropyl ether, tert-butyl methyl ether, dimethoxyethane, ethylene glycol diethyl ether, tetrahydrofuran, 1,4-dioxane, 1,3-dioxolane, 2-methyltetrahydrofuran and cyclopentyl methyl ether; alcohols such as methanol, ethanol, 2-propanol, n-butanol, 2-ethoxyethanol and benzyl alcohol; ketones such as acetone, methyl ethyl ketone, methyl isobutyl ketone and cyclohexanone; esters such as methyl acetate, ethyl acetate, n-butyl acetate and methyl propionate; amides such as formamide, N,N-dimethylformamide and N,N-dimethylacetoamide; sulfoxides such as dimethyl sulfoxide and the like; cyano-containing organic compounds such as acetonitrile and the like; N-methylpyrrolidone; water; and the like. These solvents may be used alone or in an appropriate combination of two or more thereof.

The amount of the solvent used is appropriately selected usually in the range of 0.12 to 25 times by volume, preferably 5 to 15 times by volume based on that of the diphenylphosphine oxide compound represented by the above formula (6).

The reaction temperature is appropriately selected usually in the range of room temperature to 200° C., preferably 100 to 150° C., depending on the kinds of the base and the solvent used.

The reaction time is appropriately selected usually in the range of 0.1 to 15 hours, preferably 2 to 10 hours.

The diphosphine compound represented by the formula (1) of the present invention that is produced in step (4) may be used as a chiral ligand as it is or after post-treatment, purification, isolation and the like as needed. Specific method for post-treatment, purification, isolation and the like is the same as described above.

Any of the above steps may be carried out in an atmosphere of an inert gas. The inert gas includes an argon gas, a nitrogen gas and the like.

The optically active diphosphine compound represented by the formula (1) of the present invention that is produced by such methods can give a desired optically active compound in a high yield and asymmetry yield, when used as a catalyst for asymmetric synthesis itself, a chiral ligand for asymmetric synthesis carried out in the presence of a transition metal complex and asymmetric synthesis carried out in situ, and the like, especially asymmetric reduction such as asymmetric hydrogenation.

In the case that the optically active diphosphine compound represented by the formula (1) of the present invention is used as the catalyst for asymmetric synthesis itself, specific examples of the asymmetric synthesis include, for example, a Baylis-Hillman reaction and the like.

The transition metal complex of the present invention includes, for example, a transition metal complex represented by the following formula (11) or (12):

$$M_m L_n X_p Y_q \quad (11)$$

$$[M_m L_n X_p Y_q] Z_s \quad (12)$$

(wherein, L represents the diphosphine compound represented by the above formula (1); M represents a transition metal; X represents a halogen atom, a carboxylate group, an allyl group, 1,5-cyclooctadiene or norbornadiene; Y represents a ligand; Z represents an anion or a cation; m and n each independently represents an integer of 1 to 5; and p, q and s each independently represent an integer of 0 to 5).

Here, in the above formulae (11) and (12), the diphosphine compound represented by the above formula (1) of L is preferably an optically active substance. In the case that L represents an optically active substance of the diphosphine compound represented by the above formula (1), the transition metal complex of the present invention is an optically active transition metal complex.

The transition metal represented by M in the formula (11) and (12) may be the same or different and includes, for example, a transition metal of the groups 8 to 10 of the periodic table. Specific examples thereof include, for example, ruthenium (Ru), rhodium (Rh), iridium (Ir), palladium (Pd), nickel (Ni) and the like.

The ligand represented by Y may be the same or different and includes a neutral ligand such as an aromatic compound, an olefin compound and the like; amines; and the like.

The aromatic compound includes benzene, p-cymene, 1,3,5-trimethylbenzene (mesitylene), hexamethylbenzene and the like. The olefin compound includes ethylene, 1,5-cyclooctadiene, cyclopentadiene, norbornadiene and the like. The other neutral ligand includes N,N-dimethylformamide (DMF), acetonitrile, benzonitrile, acetone, chloroform and the like.

The amines include diamines such as 1,2-diphenylethylenediamine (DPEN), 1,2-dicyclohexylethylenediamine, 1,2-diaminocyclohexane, ethylenediamine, 1,1-bis(4-methoxyphenyl)-2-isopropylethylenediamine (DAIPEN) and the like; aliphatic amines such as trialkylamine such as triethylamine and the like; aromatic amines such as pyridine and the like; and the like.

The halogen atom represented by X includes a chlorine atom, a bromine atom, an iodine atom and the like.

The anion represented by Z in the formula (12) includes $BF_4$, $ClO_4$, OTf, $NO_3$, $PF_6$, $SbF_6$, $AsF_6$, $BPh_4$, $BH_4$, $BF_4$, Cl, Br, I, $I_3$, a sulfonate and the like. Here, Tf represents a triflate group ($SO_2CF_3$).

The cation include, for example, a cation represented by the following formula (13):

$$[(R^{11})_2NH_2]^+ \quad (13)$$

(wherein, two of $R^{11}$ are the same or different and represent a hydrogen atom or a optionally substituted hydrocarbon group).

The optionally substituted hydrocarbon group represented by $R^{11}$ in the formula (13) is similar to the optionally substituted hydrocarbon group described above in the formula (1). The optionally substituted hydrocarbon group represented by the above $R^{11}$ is preferably an alkyl group of 1 to 5 carbon atom(s), a cycloalkyl group, an optionally substituted phenyl group, an optionally substituted benzyl group and the like.

Specific examples of such cation include, for example, $[Me_2NH_2]^+$, $[Et_2NH_2]^+$, and $[Pr_2NH_2]^+$ and the like.

Preferable embodiments of the above transition metal complex of the present invention are described below.

[1] formula (11):

$$M_mL_nX_pY_q \quad (11)$$

1) When M is Ir or Rh, then X is Cl, Br or I, and m=n=p=2, and q=0.

2) When M is Ru, (i) in the case that X is Cl, Br or I, and Y is a trialkylamino group, then m=n=2, p=4 and q=1.

(ii) In the case that X is Cl, Br or I, and Y is a pyridyl group or a pyridyl group having a substituent in the ring, then m=n=1, p=2 and q=2.

(iii) In the case that X is a carboxylate group, then m=n=1, P=2 and q=0.

(iv) In the case that X is Cl, Br or I, then m=n=p=2 and q=0.

3) When M is Pd, (i) in the case that X is Cl, Br or I, then m=n=1, p=2 and q=0.

(ii) In the case that X is an allyl group, m=n=p=2 and q=0.

4) When M is Ni, in the case that X is Cl, Br or I, then m=n=1, p=2 and q=0.

[2] formula (12):

$$[M_mL_nX_pY_q]Z_s \quad (12)$$

1) When M is Ir or Rh, then X is 1,5-cyclooctadiene or norbornadiene, and Z is $BF_4$, $ClO_4$, OTf, $PF_6$, $SbF_6$ or $BPh_4$, and m=n=p=s=1, q=0; m=s=1, n=2, p=q=0; or m=s=1, n=1, p=q=0.

2) When M is Ru, then (i) X is Cl, Br or I, Y is a neutral ligand such as an aromatic compound and an olefin compound, Z is Cl, Br, I, $I_3$ and a sulfonate, and m=n=p=s=q=1.

(ii) Z is $BF_4$, $ClO_4$, OTf, $PF_6$, $SbF_6$ or $BPh_4$, and m=n=1, p=q=0 and s=2.

(iii) In the case that Z is an ammonium ion, then m=n=2, p=5 and q=0.

3) When M is Pd and Ni, then Z is $BF_4$, $ClO_4$, OTf, $PF_6$, $SbF_6$ or $BPh_4$, and m=n=1, p=q=0 and s=2.

The above transition metal complex of the present invention can be obtained by, for example, reacting an optically active diphosphine compound represented by the above formula (1) and a transition metal complex precursor.

The phrase "a transition metal complex obtained by reacting" in the above statement is defined as, for example, a transition metal complex obtained by undergoing post-treatment as needed, a transition metal complex obtained by undergoing isolation and/or purification after post-treatment and a transition metal complex obtained by using a reaction mixture as it is without any post-treatment, isolation, purification and the like.

The above transition metal complex of the present invention can be obtained by reacting a diphosphine compound of the present invention or a diphosphine compound of the present invention and another chiral ligand with a transition metal complex precursor.

The transition metal complex precursor includes, for example, a transition metal complex precursor represented by the following formula (15) and the like:

$$[MX_pY_q]Z_s \quad (15)$$

(wherein, M, X, Y, Z, p, q and s are the same as described above).

Specific examples of the transition metal complex precursor represented by the above formula (15) used in the present invention wherein the case that a transition metal represented by M in the above formula (15) is ruthenium, rhodium and iridium include, for example, $[RuCl_2(benzene)]_2$, $[RuBr_2(benzene)]_2$, $[RuI_2(benzene)]_2$, $[RuCl_2(p-cymene)]_2$, $[RuBr_2(p-cymene)]_2$, $[RuI_2(p-cymene)]_2$, $[RuCl_2(hexamethylbenzene)]_2$, $[RuBr_2(hexamethylbenzene)]_2$, $[RuI_2(hexamethylbenzene)]_2$, $[RuCl_2(mesitylene)]_2$, $[RuBr_2(mesitylene)]_2$, $[RuI_2(mesitylene)]_2$, $[RuCl_2(pentamethylcyclopentadiene)]_2$, $[RuBr_2(pentamethylcyclopentadiene)]_2$, $[RuI_2(pentamethylcyclopentadiene)]_2$, $[RuCl_2(cod)]_n$, $[RuBr_2(cod)]_n$, $[RuI_2(cod)]_n$, $[RuCl_2(nbd)]_n$, $[RuBr_2(nbd)]_n$, $[RuI_2(nbd)]_n$, $RuCl_3$ hydrate, $RuBr_3$ hydrate, $RuI_3$ hydrate; $[RhCl_2(cyclopentadiene)]_2$, $[RhBr_2(cyclopentadiene)]_2$, $[RhI_2(cyclopentadiene)]_2$, $[RhCl_2(pentamethylcyclopentadiene)]_2$, $[RhBr_2(pentamethylcyclopentadiene)]_2$, $[RhI_2(pentamethylcyclopentadiene)]_2$, $[RhCl_2(cod)]_n$, $[RhBr_2(cod)]_n$, $[RhI_2(cod)]_n$, $[RhCl_2(nbd)]_n$, $[RhBr_2(nbd)]_n$, $[RhI_2(nbd)]_n$, $[Rh(cod)_2]SbF_6$, $RhCl_3$ hydrate, $RhBr_3$ hydrate, $RhI_3$ hydrate, $[IrCl_2(cyclopentadiene)]_2$, $[IrBr_2(cyclopentadiene)]_2$, $[IrI_2(cyclopentadiene)]_2$, $[IrCl_2(pentamethylcyclopentadiene)]_2$, $[IrBr_2(pentamethylcyclopentadiene)]_2$, $[IrI_2(pentamethylcyclopentadiene)]_2$, $[IrCl_2(cod)]_n$, $[IrBr_2(cod)]_n$, $[IrI_2(cod)]_n$, $[IrCl_2(nbd)]_n$, $[IrBr_2(nbd)]_n$, $[IrI_2(nbd)]_n$, $IrCl_3$ hydrate, $IrBr_3$ hydrate, $IrI_3$ hydrate and the like. In the above formulae, n represents a positive number. The 'cod' and 'nbd' represent 1,5-cyclooctadiene and norbornadiene, respectively (hereinafter is the same).

The method for producing a transition metal complex of the present invention is specifically described below.

With regard to symbols used in the following formulae of the transition metal complexes, L represents 1) an optically active diphosphine compound of the present invention or 2) an optically active diphosphine compound of the present invention and another chiral ligand, and Tf, Ph and Ac represent a triflate group ($SO_2CF_3$), a phenyl group and an acetyl group, respectively.

Specific examples where a bidentate ligand is used as achiral ligand are given to avoid complexity.

[1] Rhodium Complex:

The rhodium complex can be produced according to, for example, the method described in "Jikken Kagaku Kouza, 4th edition (The 4th series of Experimental Chemistry)" edited by The Chemical Society of Japan, vol. 18, Organic Metal Complex p. 339-344, 1991 (Maruzen) and the like. Specifically, it can be obtained by reacting bis(1,5-cyclooctadiene)rhodium(I) tetrafluoroborate with the diphosphine compound of the present invention or the diphosphine compound of the present invention and another chiral ligand.

Specific examples of the rhodium complex include the following complexes: $[Rh(L)Cl]_2$, $[Rh(L)Br]_2$, $[Rh(L)I]_2$,

[Rh(cod)(L)]BF$_4$, [Rh(cod)(L)]ClO$_4$, [Rh(cod)(L)]PF$_6$, [Rh(cod)(L)]BPh$_4$, [Rh(cod)(L)]OTf, [Rh(nbd)(L)]BF$_4$, [Rh(nbd)(L)]ClO$_4$, [Rh(nbd)(L)]PF$_6$, [Rh(nbd)(L)]BPh$_4$, [Rh(nbd)(L)]OTf, [Rh(L)$_2$]ClO$_4$, [Rh(L)$_2$]PF$_6$, [Rh(L)$_2$]OTf, [Rh(L)$_2$]BF$_4$, etc.

[2] Ruthenium Complex:

The ruthenium complex can be produced according to, for example, the method described in T. Ikariya et al., J. Chem. Soc., Chem. Commun., 922, 1985 and the like. Specifically, it can be obtained by heating and refluxing [Ru(cod)Cl$_2$]$_n$ and the diphosphine compound of the present invention or the diphosphine compound of the present invention and another chiral ligand in a toluene solvent in the presence of triethylamine. It can be also produced according to the method described in K. Mashima et al., J. Chem. Soc., Chem. Commun., 1208, 1989. Specifically, it can be obtained by heating with stirring [Ru(p-cymene)I$_2$]$_2$ and the diphosphine compound of the present invention or the diphosphine compound of the present invention and another chiral ligand in dichloromethane and ethanol.

Specific examples of the ruthenium complex include the following complexes: Ru(OAc)$_2$(L), Ru$_2$Cl$_4$(L)$_2$NEt$_3$, [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)]I, [Ru(L)](BF$_4$)$_2$, [Ru(L)](ClO$_4$)$_2$, [Ru(L)](PF$_6$)$_2$, [Ru(L)](BPh$_4$)$_2$, [Ru(L)](OTf)$_2$, Ru(OCOCF$_3$)$_2$(L), [{RuCl(L)$_2$}($\mu$-Cl)$_3$][Me$_2$NH$_2$], [{RuCl(L)}$_2$($\mu$-Cl)$_3$][Et$_2$NH$_2$], [{RuBr(L)$_2$}($\mu$-Cl)$_3$][Me$_2$NH$_2$], [{RuBr(L)$_2$}($\mu$-Cl)$_3$][Et$_2$NH$_2$], RuCl$_2$(L), RuBr$_2$(L), RuI$_2$(L), RuCl$_2$(L)(diamine), RuBr$_2$(L)(diamine), RuI$_2$(L)(diamine), [{RuI(L)}$_2$($\mu$-I)$_3$][Me$_2$NH$_2$], [{RuI(L)}$_2$($\mu$-I)$_3$][Et$_2$NH$_2$], RuCl$_2$(L)(pyridine), RuBr$_2$(L)(pyridine), RuI$_2$(L)(pyridine), etc.

[3] Iridium Complex:

The iridium complex can be produced according to, for example, the method described in K. Mashima et al., J. Organomet. Chem., 428, 213, 1992 and the like. Specifically, it can be obtained by reacting with stirring the diphosphine compound of the present invention or the diphosphine compound of the present invention and another chiral ligand with [Ir(cod)(CH$_3$CN)$_2$]BF$_4$ in tetrahydrofuran.

Specific examples of the iridium complex include the following complexes: [Ir(L)Cl]$_2$, [Ir(L)Br]$_2$, [Ir(L)I]$_2$, [Ir(cod)(L)]BF$_4$, [Ir(cod)(L)]ClO$_4$, [Ir(cod)(L)]PF$_6$, [Ir(cod)(L)]BPh$_4$, [Ir(cod)(L)]OTf, [Ir(nbd)(L)]BF$_4$, [Ir(nbd)(L)]ClO$_4$, [Ir(nbd)(L)]PF$_6$, [Ir(nbd)(L)]BPh$_4$, [Ir(nbd)(L)]OTf, etc.

[4] Palladium Complex:

The palladium complex can be produced according to, for example, the method described in Y. Uozumi et al., J. Am. Chem. Soc. 9887, 1991 and the like. Specifically, it can be obtained by reacting the diphosphine compound of the present invention or the diphosphine compound of the present invention and another chiral ligand with $\pi$-allylpalladium chloride.

Specific examples of the palladium complex include the following complexes: PdCl$_2$(L), ($\pi$-allyl)Pd(L), [Pd(L)]BF$_4$, [Pd(L)]ClO$_4$, [Pd(L)]PF$_6$, [Pd(L)]BPh$_4$, [Pd(L)]OTf, etc.

[5] Nickel Complex:

The nickel complex can be produced according to, for example, the method described in "Jikken Kagaku Kouza, 4th edition (The 4th series of Experimental Chemistry)" edited by The Chemical Society of Japan, vol. 18, Organic Metal Complex p. 376, 1991 (Maruzen) and the like. It can be obtained also by dissolving the diphosphine compound of the present invention or the diphosphine compound of the present invention and another chiral ligand, and nickel chloride in a mixed solvent of 2-propanol and methanol and heating with stirring the solution according to the method described in Y. Uozumi et al., J. Am. Chem. Soc., 113, 9887, 1991.

Specific examples of the nickel complex include the following complexes: NiCl$_2$(L), NiBr$_2$(L), NiI$_2$(L), etc.

The transition metal complex of the present invention also may be used as a catalyst for asymmetric synthesis, especially as a catalyst for asymmetric reduction as it is, after mixing with the optically active diphosphine compound represented by the above formula (1) and the transition metal complex precursor without being isolated or purified. This is so-called in situ asymmetric reduction.

The transition metal complex of the present invention is an optically active transition metal complex having the optically active diphosphine compound represented by the above formula (1) as a chiral ligand. Therefore, a desired optically active compound can be obtained in a high yield and a high asymmetry yield by using the above optically active transition metal complex of the present invention as a chiral catalyst such as a catalyst for asymmetric synthesis, especially as a catalyst for asymmetric reduction in asymmetric reduction of an unsaturated compound.

A catalyst for asymmetric synthesis containing the optically active diphosphine compound represented by the formula (1) of the present invention and the above transition metal complex precursor has the optically active diphosphine compound represented by the formula (1) as a chiral ligand, and thus can give a desired optically active compound in a high yield and a high asymmetry yield similarly to the above, especially when used as a catalyst for asymmetric reduction in asymmetric reduction of an unsaturated compound.

The method for producing an optically active compound of the present invention is carried out in the presence of a catalyst for asymmetric synthesis of the present invention. The method for producing an optically active compound of the present invention includes, for example, a method for producing an optically active compound by asymmetric reduction of an unsaturated compound. The method for producing an optically active compound of the present invention is described below, taking as an example a method for producing an optically active compound by asymmetric reduction of an unsaturated compound.

In the method for producing an optically active compound by asymmetric reduction of an unsaturated compound, said asymmetric reduction is carried out using the above catalyst for asymmetric synthesis as a catalyst for asymmetric reduction in the presence of the catalyst for asymmetric reduction. In this case, the asymmetric reduction is carried out by asymmetric hydrogenation, and the catalyst for the asymmetric reduction is used as a catalyst for the asymmetric hydrogenation.

The asymmetric reduction is carried out in the presence of a hydrogen source. The hydrogen source includes a hydrogen gas, a hydrogen donor and the like.

The preferable asymmetric reduction in the present invention includes asymmetric hydrogenation, which includes catalytic asymmetric hydrogenation carried out in the presence of the hydrogen gas and asymmetric transfer hydrogenation carried out in the presence of the hydrogen donor.

The method for producing the optically active compound of the present invention may be carried out, for example, as follows:

That is, an unsaturated compound can be subjected to asymmetric hydrogenation in the presence of the above catalyst for asymmetric hydrogenation and the above hydrogen source to obtain an optically active compound that is a hydride of the unsaturated compound. Further, the transition metal complex of the present invention, the catalyst for asymmetric hydrogenation of the present invention containing a mixture of the chiral ligand of the present invention and the transition metal complex precursor, the chiral ligand of the present invention and/or the transition metal complex precursor may be further added as needed into the above reaction system (into the reaction mixture).

The unsaturated compound used in the method of the present invention for producing an optically active compound is preferably prochiral compounds such as alkenes, ketones, imines, ketocarboxylic acids, ketoalkenes and the like.

The alkenes are preferably prochiral alkenes and include, for example, alkenes represented by the following formula (21).

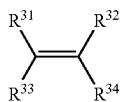

(21)

The ketones are preferably prochiral ketones and include, for example, ketones represented by the following formula (22).

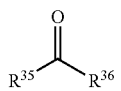

(22)

The imines are preferably prochiral imines and include, for example, imines represented by the following formula (23).

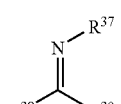

(23)

The ketocarboxylic acids are preferably prochiral ketocarboxylic acids and include, for example, ketocarboxylic acids represented by the following formula (24).

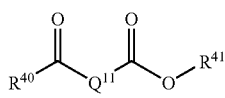

(24)

The ketoalkenes are preferably prochiral ketoalkenes and include, for example, ketoalkenes represented by the following formula (25).

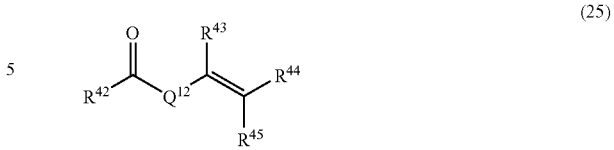

(25)

The groups represented by $R^{31}$ to $R^{45}$ in the above formulae (21) to (25) may be any group that has no adverse effect on the reaction and that the unsaturated compound is able to exist. Said groups includes, for example, a hydrogen atom, an optionally substituted hydrocarbon group, an optionally substituted heterocyclic group, a halogen atom, a halogenated hydrocarbon group, an optionally substituted alkoxy group, an optionally substituted aryloxy group, an optionally substituted aralkyloxy group, an optionally substituted heteroaryloxy group, an optionally substituted alkylthio group, an optionally substituted arylthio group, an optionally substituted aralkylthio group, an optionally substituted heteroarylthio group, an optionally substituted acyl group, an optionally substituted acyloxy group, an optionally substituted alkoxycarbonyl group, an optionally substituted aryloxycarbonyl group, an optionally substituted aralkyloxycarbonyl group, an optionally substituted alkylenedioxy group, a nitro group, an amino group, a substituted amino group, a cyano group, a sulfo group, a substituted silyl group, a substituted silyloxy group, a hydroxy group, a carboxy group, an optionally substituted alkoxythiocarbonyl group, an optionally substituted aryloxythiocarbonyl group, an optionally substituted aralkyloxythiocarbonyl group, an optionally substituted alkylthiocarbonyl group, an optionally substituted arylthiocarbonyl group, an optionally substituted aralkylthiocarbonyl group, an optionally substituted carbamoyl group, a substituted phosphino group, an aminosulfonyl group, an alkoxysulfonyl group and the like.

$Q^{11}$ and $Q^{12}$ in the formulae (24) and (25) represent a spacer or a direct link. The spacers represented by $Q^{11}$ and $Q^{12}$ may be the same as the spacer described in the above formula (1). The groups $R^{31}$ and $R^{32}$, $R^{31}$ and $R^{33}$, $R^{31}$ and $R^{34}$, $R^{32}$ and $R^{33}$, $R^{32}$ and $R^{34}$, $R^{33}$ and $R^{34}$, $R^{35}$ and $R^{36}$, $R^{38}$ and $R^{39}$, $R^{38}$ or $R^{39}$ and $R^{37}$, $R^{40}$ and $Q^{11}$, $R^{40}$ and $R^{41}$, $R^{41}$ and $Q^{11}$, $R^{41}$ and $Q^{12}$, $R^{44}$ and $Q^{12}$, $R^{42}$ and $R^{43}$, $R^{42}$ and $R^{44}$ or $R^{45}$, $R^{43}$ and $R^{44}$, $R^{43}$ and $R^{45}$, and $R^{44}$ and $R^{45}$ respectively, may be bonded to each other to form a ring. The formed ring includes, for example, a ring formed by combination of the alkylene group or the alkylenedioxy group. These formed rings may have a further substituent. The substituent is described later.

When the unsaturated compound is a prochiral compound, the groups represented by $R^{31}$ to $R^{45}$ in the above formulae (21) to (25) may be the groups that allow an obtained hydride of the above prochiral compound to become an optically active compound.

Each group in the above formulae is described, but a substituent is described later unless otherwise stated.

The optionally substituted hydrocarbon group includes a hydrocarbon group and a substituted hydrocarbon group.

The hydrocarbon group includes, for example, an alkyl group, an alkenyl group, an alkynyl group, an alkadienyl group, an aryl group, an aralkyl group and the like.

The alkyl group may be linear, branched or cyclic, and includes, for example, an alkyl group having 1 to 20 carbon atom(s), preferably 1 to 15 carbon atom(s), and more preferably 1 to 10 carbon atom(s). Specific examples thereof include methyl, ethyl, n-propyl, 2-propyl, n-butyl, 1-methylpropyl, isobutyl, tert-butyl, n-pentyl, 1-methylbutyl, tert-pentyl, 2-methylbutyl, 3-methylbutyl, 2,2-dimethylpropyl, n-hexyl, 1-methylpentyl, 1-ethylbutyl, tert-hexyl, 2-methylpentyl, 3-methylpentyl, 4-methylpentyl, 2-methylpentane-3-yl, heptyl, octyl, nonyl, decyl, lauryl, stearyl, cyclopropyl, cyclobutyl, cyclopentyl, cyclohexyl and the like.

The alkenyl group may be linear or branched, and includes, for example, an alkenyl group having 2 to 20 carbon atoms, preferably 2 to 15 carbon atoms, and more preferably 2 to 10 carbon atoms. Specific examples thereof include vinyl, propenyl, butenyl, pentenyl, hexenyl, heptenyl, octenyl, nonenyl, decenyl and the like.

The alkynyl group may be linear or branched, and includes, for example, an alkynyl group having 2 to 20 carbon atoms, preferably 2 to 15 carbon atoms, and more preferably 2 to 10 carbon atoms. Specific examples thereof include ethynyl, propynyl, butynyl, pentynyl, hexynyl and the like.

The alkadienyl group may be linear, branched or cyclic, and includes, for example, an alkadienyl group having 4 or more carbon atoms, preferably 4 to 20 carbon atoms, more preferably 4 to 15 carbon atoms, and still more preferably 4 to 10 carbon atoms that has two double bonds in the chain of the above alkyl group. Specific examples thereof include 1,3-butadienyl, 2,3-dimethyl-1,3-butadienyl and the like.

The aryl group includes, for example, an aryl group having 6 to 20 carbon atoms, preferably 6 to 15 carbon atoms. Specific examples thereof include phenyl, naphthyl, anthryl, biphenyl, and the like.

The aralkyl group includes, for example, an aralkyl group having 7 to 20 carbon atoms, preferably 7 to 15 carbon atoms wherein at least one hydrogen atom of the above alkyl group is substituted with the above aryl group. Specific examples thereof include, for example, benzyl, 1-phenylethyl, 2-phenylethyl, 1-phenylpropyl, 3-naphthylpropyl and the like.

The substituted hydrocarbon group (hydrocarbon group having a substituent) includes the above hydrocarbon group of which at least one hydrogen atom is substituted with a substituent, for example, a substituted alkyl group, a substituted alkenyl group, a substituted alkynyl group, a substituted alkadienyl group, a substituted aryl group, a substituted aralkyl group and the like.

Specific examples of the substituted alkyl group among the substituted hydrocarbon groups include methoxymethyl, ethoxyethyl and the like. Specific examples of the substituted aryl group include tolyl (for example, 4-methylphenyl group), xylyl (for example, 3,5-dimethylphenyl group), 4-methoxy-3,5-dimethylphenyl, 4-methoxy-3,5-di-tert-butylphenyl and the like.

The optionally substituted heterocyclic group includes a heterocyclic group and a substituted heterocyclic group. The heterocyclic group includes an aliphatic heterocyclic group and an aromatic heterocyclic group.

The aliphatic heterocyclic group includes, for example, an aliphatic monoheterocyclic group, an aliphatic polyheterocyclic or fused heterocyclic group having 2 to 14 carbon atoms that contains at least 1, preferably 1 to 3 heteroatom(s) such as a nitrogen atom, an oxygen atom and/or a sulfur atom and has 3 to 8 members, preferably 5 or 6 members. Specific examples thereof include pyrrolidyl-2-one, piperidino, piperazinyl, morpholino, morpholinyl, tetrahydrofuryl, tetrahydropyranyl, thiolanyl and the like.

The aromatic heterocyclic group includes, for example, a 5- to 8-membered, preferably 5- or 6-membered monocyclic, polycyclic or fused hetero aryl group having 2 to 15 carbon atoms and contains at least 1, preferably 1 to 3 heteroatom(s) such as a nitrogen atom, an oxygen atom and/or a sulfur atom. Specific examples thereof include furyl, thienyl, pyridyl, pyrimidyl, pyrazyl, pyridazinyl, pyrazolyl, imidazolyl, oxazolyl, thiazolyl, benzofuryl, benzothienyl, quinolyl, isoquinolyl, quinoxalinyl, phthalazinyl, quinazolinyl, naphthyridinyl, cinnolinyl, benzoimidazolyl, benzooxazolyl, benzothiazolyl, acridinyl and the like.

The substituted heterocyclic group (heterocyclic group having a substituent) includes the above heterocyclic group of which at least one hydrogen atom is substituted with a substituent and examples thereof include a substituted aliphatic heterocyclic group and a substituted aromatic heterocyclic group.

The halogen atom includes fluorine, chlorine, bromine iodine and the like.

The halogenated hydrocarbon group includes the above hydrocarbon group of which at least one hydrogen atom is halogenated (for example, fluorinated, chlorinated, brominated and iodinated), that is, the above hydrocarbon group of which at least one hydrogen atom is substituted with the halogen atom. The halogenated hydrocarbon group includes, for example, a halogenated alkyl group, a halogenated aryl group, a halogenated aralkyl group and the like.

The halogenated alkyl group includes, for example, a halogenated alkyl group having 1 to 20 carbon atom(s). Specific example thereof includes chloromethyl, bromomethyl, chloroethyl, bromopropyl, fluoromethyl, fluoroethyl, fluoropropyl, fluorobutyl, fluoropentyl, fluorohexyl, fluoroheptyl, fluorooctyl, fluorononyl, fluorodecyl, difluoromethyl, difluoroethyl, fluorocyclohexyl, trifluoromethyl, 2,2,2-trifluoroethyl, 3,3,3-trifluoropropyl, pentafluoroethyl, 3,3,4,4,4-pentafluorobutyl, perfluoro-n-propyl, perfluoroisopropyl, perfluoro-n-butyl, perfluoroisobutyl, perfluoro-tert-butyl, perfluoro-sec-butyl, perfluoropentyl, perfluoroisopentyl, perfluoro-tert-pentyl, perfluoro-n-hexyl, perfluoroisohexyl, perfluoroheptyl, perfluorooctyl, perfluorononyl, perfluorodecyl, perfluorooctylethyl, perfluorocyclopropyl, perfluorocyclopentyl, perfluorocyclohexyl and the like. A halogenated alkyl group having 1 to 10 carbon atom(s) is preferable among the above halogenated alkyl groups.

The halogenated aryl group includes, for example, a halogenated aryl group having 6 to 20 carbon atoms. Specific example thereof includes 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-trifluoromethylphenyl, 3-trifluoromethylphenyl, 4-trifluoromethylphenyl, 2-trichloromethylphenyl, 3-trichloromethylphenyl, 4-trichloromethylphenyl, perfluorophenyl, perfluoronaphthyl, perfluoroanthryl, perfluorobiphenyl and the like. A halogenated aryl group having 6 to 15 carbon atoms is preferable among the above aryl groups.

The halogenated aralkyl group includes, for example, a halogenated aralkyl group having 7 to 20 carbon atoms. Specific example thereof includes 2-fluorobenzyl, 3-fluorobenzyl, 4-fluorobenzyl, 2-chlorobenzyl, 3-chlorobenzyl, 4-chlorobenzyl, 4-bromobenzyl, 4-iodobenzyl, 2-trifluoromethylbenzyl, 3-trifluoromethylbenzyl, 4-trifluoromethylbenzyl, 4-trichloromethylbenzyl, perfluorobenzyl and the like. A halogenated aralkyl group having 6 to 15 carbon atoms is preferable among the above halogenated aralkyl groups.

The optionally substituted alkoxy group includes an alkoxy group and a substituted alkoxy group.

The alkoxy group may be linear, branched or cyclic, and includes, for example, an alkoxy group having 1 to 20 carbon atom(s). Specific examples thereof include methoxy, ethoxy, n-propoxy, 2-propoxy, n-butoxy, 2-butoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, heptyloxy, octyloxy, nonyloxy, decyloxy, cyclohexyloxy and the like. Among the above alkoxy groups, an alkoxy group having 1 to 10 carbon atom(s) is preferable and an alkoxy group having 1 to 6 carbon atom(s) is more preferable.

The substituted alkoxy group (alkoxy group having a substituent) includes the above alkoxy group of which at least one hydrogen atom is substituted with a substituent.

The optionally substituted aryloxy group includes an aryloxy group and a substituted aryloxy group.

The aryloxy group includes, for example, an aryloxy group having 6 to 20 carbon atoms. Specific examples thereof include phenyloxy, naphthyloxy, anthryloxy and the like. Among the above aryloxy groups, an aryloxy group having 6 to 14 carbon atoms is preferable.

The substituted aryloxy group (aryloxy group having a substituent) includes the above aryloxy group of which at least one hydrogen atom is substituted with a substituent.

The optionally substituted aralkyloxy group includes an aralkyloxy group and a substituted aralkyloxy group.

The aralkyloxy group includes, for example, an aralkyloxy group having 7 to 20 carbon atoms. Specific examples thereof include benzyloxy, 1-phenylethoxy, 2-phenylethoxy, 1-phenylpropoxy, 2-phenylpropoxy, 3-phenylpropoxy, 1-phenylbutoxy, 2-phenylbutoxy, 3-phenylbutoxy, 4-phenylbutoxy, 1-phenylpentyloxy, 2-phenylpentyloxy, 3-phenylpentyloxy, 4-phenylpentyloxy, 5-phenylpentyloxy, 1-phenylhexyloxy, 2-phenylhexyloxy, 3-phenylhexyloxy, 4-phenylhexyloxy, 5-phenylhexyloxy, 6-phenylhexyloxy and the like. Among the above aralkyloxy groups, an aralkyloxy group having 7 to 12 carbon atoms is preferable.

The substituted aralkyloxy group (aralkyloxy group having a substituent) includes the above aralkyloxy group of which at least one hydrogen atom is substituted with a substituent.

The optionally substituted heteroaryloxy group includes a heteroaryloxy group and a substituted heteroaryloxy group.

The heteroaryloxy group includes, for example, a heteroaryloxy group having 2 to 20 carbon atoms, preferably 2 to 15 carbon atoms that contains at least 1, preferably 1 to 3 heteroatom(s) such as a nitrogen atom, an oxygen atom and a sulfur atom. Specific examples thereof include 2-pyridyloxy, 2-pyrazyloxy, 2-pyrimidyloxy, 2-quinolyloxy and the like.

The substituted heteroaryloxy group (heteroaryloxy group having a substituent) includes a heteroaryloxy group where at least one hydrogen atom of the above aralkyloxy group is substituted with a substituent.

The optionally substituted alkylthio group includes an alkylthio group and a substituted alkylthio group.

The alkylthio group may be linear, branched or cyclic, and includes, for example, an alkylthio group having 1 to 20 carbon atom(s). Specific examples thereof include methylthio, ethylthio, n-propiothio, 2-propiothio, n-butylthio, 2-butylthio, isobutylthio, tert-butylthio, pentylthio, hexylthio, cyclohexylthio and the like. Among the above alkylthio groups, an alkylthio group having 1 to 10 carbon atom(s) is preferable and an alkylthio group having 1 to 6 carbon atom(s) is more preferable.

The substituted alkylthio group (alkylthio group having a substituent) includes the above alkylthio group of which at least one hydrogen atom is substituted with a substituent.

The optionally substituted arylthio group includes an arylthio group and a substituted arylthio group.

The arylthio group includes, for example, an arylthio group having 6 to 20 carbon atoms. Specific examples thereof include phenylthio, naphthylthio, and the like. Among the above arylthio groups, an arylthio group having 6 to 14 carbon atoms is preferable.

The substituted arylthio group (arylthio group having a substituent) includes the above arylthio group of which at least one hydrogen atom is substituted with a substituent.

The optionally substituted aralkylthio group includes an aralkylthio group and a substituted aralkylthio group.

The aralkylthio group includes, for example, an aralkylthio group having 7 to 20 carbon atoms. Specific examples thereof include benzylthio, 2-phenethylthio, and the like. Among the above aralkylthio groups, an aralkylthio group having 7 to 12 carbon atoms is preferable.

The substituted aralkylthio group (aralkylthio group having a substituent) includes the above aralkylthio group of which at least one hydrogen atom is substituted with a substituent.

The optionally substituted heteroarylthio group includes a heteroarylthio group and a substituted heteroarylthio group.

The heteroarylthio group includes, for example, a heteroarylthio group having 2 to 20 carbon atoms, preferably 2 to 15 carbon atoms that contains at least 1, preferably 1 to 3 heteroatom(s) such as nitrogen atom, oxygen atom and sulfur atom and the like. Specific examples thereof include 4-pyridylthio, 2-benzimidazolylthio, 2-benzoxazolylthio, 2-benzthiazolylthio and the like.

The substituted heteroarylthio group (heteroarylthio group having a substituent) includes the above heteroarylthio group of which at least one hydrogen atom is substituted with a substituent.

The optionally substituted acyl group includes an acyl group and a substituted acyl group.

The acyl group may be linear, branched or cyclic and includes, for example, an acyl group having 1 to 20 carbon atom(s) that is derived from an acid such as a carboxylic acid, a sulfonic acid, a sulfinic acid, a phosphinic acid, a phosphonic acid and the like.

The acyl group derived from a carboxylic acid includes an acyl group derived from a carboxylic acid such as an aliphatic carboxylic acid, an aromatic carboxylic acid and the like and is represented by, for example, formula: —$COR^b$ [wherein, $R^b$ represents a hydrogen atom, an optionally substituted hydrocarbon group or an optionally substituted heterocyclic group (the optionally substituted hydrocarbon group and the optionally substituted heterocyclic may be the same as respective groups described above)]. Specific examples of the acyl group derived from the carboxylic acid include formyl, acetyl, propionyl, butyryl, pivaloyl, pentanoyl, hexanoyl, lauroyl, stearoyl, benzoyl, 1-naphthoyl, 2-naphthoyl and the like. Among the above acyl groups, an acyl group having 2 to 18 carbon atoms is preferable.

The acyl group derived from a sulfonic acid includes a sulfonyl group. The sulfonyl group includes, for example, a substituted sulfonyl group represented by formula: $R^c$—$SO_2$— [$R^c$ represents an optionally substituted hydrocarbon group or an optionally substituted heterocyclic group (the optionally substituted hydrocarbon group and the optionally substituted heterocyclic group may be the same as respective groups described above)]. Specific examples of the sulfonyl group include methanesulfonyl, trifluoromethanesulfonyl, benzenesulfonyl, p-toluenesulfonyl and the like.

The acyl group derived from a sulfinic acid includes a sulfinyl group. The sulfinyl group includes, for example, a substituted sulfinyl group represented by formula: $R^d$—SO— [$R^d$ represents an optionally substituted hydrocarbon group, an optionally substituted heterocyclic group, or a substituted amino group (the optionally substituted hydrocarbon group and the optionally substituted heterocyclic group may be the same as respective groups described above. The substituted amino group is described later)]. Specific examples of the sulfinyl group include methanesulfinyl, tert-butylsulfinyl, benzenesulfinyl and the like.

The acyl group derived from a phosphinic acid includes a phosphinyl group. The phosphinyl group includes, for example, a substituted phosphinyl group represented by formula: $(R^e)_2$—PO— [two of $R^e$s are the same or different and represent an optionally substituted hydrocarbon group (the optionally substituted hydrocarbon group may be the same as the optionally substituted hydrocarbon group described above)]. Specific examples of the phosphinyl group include dimethylphosphinyl, diphenylphosphinyl and the like.

The acyl group derived from a phosphonic acid includes a phosphonyl group. The phosphonyl group includes, for example, a substituted phosphinyl group represented by $(R^f O)_2$—PO— [two of $R^f$s are the same or different and represent an optionally substituted hydrocarbon group (the optionally substituted hydrocarbon group may be the same as the optionally substituted hydrocarbon group described above)]. Specific examples of the phosphonyl group include dimethylphosphonyl, diphenylphosphonyl and the like.

The substituted acyl group (acyl group having a substituent) includes the above acyl group of which at least one hydrogen atom is substituted with a substituent.

The optionally substituted acyloxy group includes an acyloxy group and a substituted acyloxy group.

The acyloxy group includes, for example, an acyloxy group having 2 to 20 carbon atoms derived from a carboxylic acid such as an aliphatic carboxylic acid and an aromatic carboxylic acid. Specific examples thereof include acetoxy, propionyloxy, butyryloxy, pivaloyloxy, pentanoyloxy, hexanoyloxy, lauroyloxy, stearoyloxy, benzoyloxy and the like. Among the above acyloxy groups, an acyloxy group having 2 to 18 carbon atoms is preferable.

The substituted acyloxy group (acyloxy group having a substituent) includes the above acyloxy group of which at least one hydrogen atom is substituted with a substituent.

The optionally substituted alkoxycarbonyl group includes an alkoxycarbonyl group and a substituted alkoxycarbonyl group.

The alkoxycarbonyl group may be linear, branched or cyclic, and includes, for example, an alkoxycarbonyl group having 2 to 20 carbon atoms. Specific examples thereof include methoxycarbonyl, ethoxycarbonyl, n-propoxycarbonyl, 2-propoxycarbonyl, n-butoxycarbonyl, tert-butoxycarbonyl, pentyloxycarbonyl, hexyloxycarbonyl, 2-ethylhexyloxycarbonyl, lauryloxycarbonyl, stearyloxycarbonyl, cyclohexyloxycarbonyl and the like.

The substituted alkoxycarbonyl group (alkoxycarbonyl group having a substituent) includes the above alkoxycarbonyl group of which at least one hydrogen atom is substituted with a substituent.

The optionally substituted aryloxycarbonyl group includes an aryloxycarbonyl group and a substituted aryloxycarbonyl group.

The aryloxycarbonyl group includes, for example, an aryloxycarbonyl group having 7 to 20 carbon atoms. Specific examples thereof include phenoxycarbonyl, naphthyloxycarbonyl and the like.

The substituted aryloxycarbonyl group (aryloxycarbonyl group having a substituent) includes the above aryloxycarbonyl group of which at least one hydrogen atom is substituted with a substituent.

The optionally substituted aralkyloxycarbonyl group includes an aralkyloxycarbonyl group and a substituted aralkyloxycarbonyl group.

The aralkyloxycarbonyl group includes, for example, an aralkyloxycarbonyl group having 8 to 20 carbon atoms. Specific examples thereof include benzyloxycarbonyl, phenethyloxycarbonyl, 9-fluorenylmethyloxycarbonyl and the like.

The substituted aralkyloxycarbonyl group (aralkyloxycarbonyl group having a substituent) includes the above aralkyloxycarbonyl group of which at least one hydrogen atom is substituted with a substituent.

The aminosulfonyl group includes, for example, an aminosulfonyl group represented by formula: $R^g$—$SO_2$— ($R^g$ represents an amino group or a substituted amino group). The substituted amino group represented by $R^g$ may be the same as the substituted amino group to be described later. Specific examples of the aminosulfonyl group include aminosulfonyl, dimethylaminosulfonyl, diethylaminosulfonyl, diphenylaminosulfonyl and the like.

The alkoxysulfonyl group includes, for example, an alkoxysulfonyl group represented by formula: $R^h$—$SO_2$— ($R^h$ represents an optionally substituted alkoxy group, an optionally substituted aryloxy group or an optionally substituted aralkyloxy group). The optionally substituted alkoxy group, the optionally substituted aryloxy group and the optionally substituted aralkyloxy group, which are represented by $R^h$, may be the same as the optionally substituted alkoxy group, the optionally substituted aryloxy group and the optionally substituted aralkyloxy group respectively, all of which are described later. Specific examples of the alkoxysulfonyl group include methoxysulfonyl, ethoxysulfonyl, phenoxysulfonyl, benzyloxysulfonyl and the like.

The substituted amino group includes a chained or cyclic amino group having 1 or 2 hydrogen atom(s) which is substituted with a substituent such as an amino protective group. The above amino protective group includes any group that is usually used as an amino protective group, for example, a group described as an amino protective group in "PROTECTIVE GROUPS IN ORGANIC SYNTHESIS THIRD EDITION (JOHN. WILEY & SONS INC. (1999))". Specific examples of the amino protective group include, for example, an optionally substituted hydrocarbon group such as an alkyl group, an aryl group and an aralkyl group, an optionally substituted acyl group, an optionally substituted alkoxycarbonyl group, an optionally substituted aryloxycarbonyl group, an optionally substituted aralkyloxycarbonyl group, a sulfonyl group and the like.

The optionally substituted hydrocarbon group, such as an alkyl group, an aryl group and an aralkyl group, the optionally substituted acyl group, the optionally substituted alkoxycarbonyl group, the optionally substituted aryloxycarbonyl group, the optionally substituted aralkyloxycarbonyl group and the sulfonyl group which are used as the above amino protective group are the same as the respective groups described above.

Specific example of the amino group substituted with the alkyl group, that is, an alkyl-substituted amino group includes, for example, monoalkylamino or dialkylamino group such as N-methylamino, N,N-dimethylamino, N,N-diethylamino, N,N-diisopropylamino, and N-cyclohexylamino; and the like.

Specific example of the amino group substituted with the aryl group, that is, an aryl-substituted amino group includes, for example, monoarylamino or diarylamino group such as N-phenyllamino, N,N-diphenyllamino, N-naphthylamino, and N-naphthyl-N-phenylamino; and the like.

Specific example of the amino group substituted with the aralkyl group, that is, an aralkyl-substituted amino group includes, for example, monoaralkylamino or diaralkylamino group such as N-benzylamino, and N,N-dibenzylamino; and the like.

Also, an amino group substituted with two substituents includes, for example, N-methyl-N-phenylamino, N-benzyl-N-methylamino and the like.

Specific examples of the amino group substituted with the acyl group, that is, an acylamino group include, for example, formylamino, acetylamino, propionylamino, pivaloylamino, pentanoylamino, hexanoylamino, benzoylamino and the like.

Specific examples of the amino group substituted with the alkoxycarbonyl group, that is, an alkoxycarbonylamino group include, for example, methoxycarbonylamino, ethoxycarbonylamino, n-propoxycarbonylamino, n-butoxycarbonylamino, tert-butoxycarbonylamino, pentyloxycarbonylamino, hexyloxycarbonylamino group and the like.

The amino group substituted with the aryloxycarbonyl group, that is, an aryloxycarbonylamino group includes, for example, an amino group of which one hydrogen atom is substituted with the above aryloxycarbonyl group. Specific examples thereof include, for example, phenoxycarbonylamino, naphthyloxycarbonylamino and the like.

Specific examples of the amino group substituted with the aralkyloxycarbonyl group, that is, an aralkyloxycarbonylamino group include, for example, benzyloxycarbonylamino, phenethyloxycarbonylamino and the like.

Specific examples of the amino group substituted with the sulfonyl group include, for example, —NHSO$_2$CH$_3$, —NHSO$_2$C$_6$H$_5$, —NHSO$_2$C$_6$H$_4$CH$_3$, —NHSO$_2$CF$_3$ and the like.

Specific examples of the cyclic amino group include a nitrogen-containing ring formed by bonding alkylene groups. The alkylene group may be linear or branched, and includes, for example, an alkylene group having 1 to 6 carbon atom(s). Specific examples thereof include methylene, ethylene, propylene, trimethylene, 2-methylpropylene, pentylene, 2,2-dimethylpropylene, 2-ethylpropylene and the like. The above alkylene group may contain an oxygen atom, a nitrogen atom, a carbonyl group and the like or a double bond at an end or at an arbitrary position of the alkylene chain.

The optionally substituted alkoxythiocarbonyl group includes an alkoxythiocarbonyl group and a substituted alkoxythiocarbonyl group.

The alkoxythiocarbonyl group may be linear, branched or cyclic and includes, for example, alkoxythiocarbonyl group having 2 to 20 carbon atoms. Specific examples thereof include methoxythiocarbonyl, ethoxythiocarbonyl, n-propoxythiocarbonyl, 2-propoxythiocarbonyl, n-butoxythiocarbonyl, tert-butoxythiocarbonyl, pentyloxythiocarbonyl, hexyloxythiocarbonyl, 2-ethylhexyloxythiocarbonyl, lauryloxythiocarbonyl, stearyloxythiocarbonyl, cyclohexyloxythiocarbonyl and the like.

The substituted alkoxythiocarbonyl group (alkoxythiocarbonyl group having a substituent) includes the above alkoxythiocarbonyl group of which at least one hydrogen atom is substituted with a substituent.

The optionally substituted aryloxythiocarbonyl group includes an aryloxythiocarbonyl group and a substituted aryloxythiocarbonyl group.

The aryloxythiocarbonyl group includes, for example, an aryloxythiocarbonyl group having 7 to 20 carbon atoms. Specific examples thereof include phenoxythiocarbonyl, naphthyloxythiocarbonyl and the like.

The substituted aryloxythiocarbonyl group (aryloxythiocarbonyl group having a substituent) includes the above aryloxythiocarbonyl group of which at least one hydrogen atom is substituted with a substituent.

The optionally substituted aralkyloxythiocarbonyl group includes an aralkyloxythiocarbonyl group and a substituted aralkyloxythiocarbonyl group.

The aralkyloxythiocarbonyl group includes, for example, aralkyloxythiocarbonyl group having 8 to 20 carbon atoms. Specific examples thereof include benzyloxythiocarbonyl, phenethyloxythiocarbonyl, 9-fluorenylmethyloxythiocarbonyl and the like.

The substituted aralkyloxythiocarbonyl group (aralkyloxythiocarbonyl group having a substituent) includes the above aralkyloxythiocarbonyl group of which at least one hydrogen atom is substituted with a substituent.

The optionally substituted alkylthiocarbonyl group includes an alkylthiocarbonyl group and a substituted alkylthiocarbonyl group.

The alkylthiocarbonyl group may be linear, branched or cyclic and includes, for example, alkylthiocarbonyl group having 2 to 20 carbon atoms. Specific examples thereof include methylthiocarbonyl, ethylthiocarbonyl, n-propylthiocarbonyl, 2-propylthiocarbonyl, n-butylthiocarbonyl, tert-butylthiocarbonyl, pentylthiocarbonyl, hexylthiocarbonyl, 2-ethylhexylthiocarbonyl, laurylthiocarbonyl, stearylthiocarbonyl, cyclohexylthiocarbonyl and the like.

The substituted alkylthiocarbonyl group (alkylthiocarbonyl group having a substituent) includes the above alkylthiocarbonyl group of which at least one hydrogen atom is substituted with a substituent.

The optionally substituted arylthiocarbonyl group includes an arylthiocarbonyl group and a substituted arylthiocarbonyl group.

The arylthiocarbonyl group includes, for example, an arylthiocarbonyl group having 7 to 20 carbon atoms. Specific examples thereof include phenylthiocarbonyl, naphthylthiocarbonyl and the like.

The substituted arylthiocarbonyl group (arylthiocarbonyl group having a substituent) includes the above arylthiocarbonyl group of which at least one hydrogen atom is substituted with a substituent.

The optionally substituted aralkylthiocarbonyl group includes an aralkylthiocarbonyl group and a substituted aralkylthiocarbonyl group.

The aralkylthiocarbonyl group includes, for example, aralkylthiocarbonyl group having 8 to 20 carbon atoms. Specific examples thereof include benzylthiocarbonyl, phenethylthiocarbonyl, 9-fluorenylmethylthiocarbonyl and the like.

The substituted aralkylthiocarbonyl group (aralkylthiocarbonyl group having a substituent) includes the above aralkylthiocarbonyl group of which at least one hydrogen atom is substituted with a substituent.

The optionally substituted carbamoyl group includes a carbamoyl group and a substituted carbamoyl group.

The substituted carbamoyl group includes, for example, a carbamoyl group wherein 1 or 2 hydrogen atom(s) of an amino group in the carbamoyl group are substituted with a substituent such as an optionally substituted hydrocarbon group. The optionally substituted hydrocarbon group may be the same as the optionally substituted hydrocarbon group described above. Specific examples of the substituted carbamoyl group include N-methylcarbamoyl, N,N-diethylcarbamoyl, N-phenylcarbamoyl and the like.

The substituted phosphino group includes, for example, a phosphino group wherein 1 or 2 hydrogen atom(s) are substituted with a substituent such as an optionally substituted hydrocarbon group. The optionally substituted hydrocarbon group may be the same as the optionally substituted hydrocarbon group described above. Specific examples of the substituted phosphino group include dimethylphosphino, diethylphosphino, diphenylphosphino, methylphenylphosphino and the like.

The substituted silyl group includes, for example, a tri-substituted silyl group wherein 3 hydrogen atoms of the silyl group are substituted with substituents such as the above optionally substituted hydrocarbon group and the above optionally substituted alkoxy group. Specific examples of the substituted silyl group include trimethylsilyl, triethylsilyl, tri(2-propyl)silyl, tert-butyldimethylsilyl, tert-butyldiphenylsilyl, triphenylsilyl, tert-butylmethoxyphenylsilyl, tert-butoxydiphenylsilyl and the like.

The substituted silyloxy group includes, for example, a silyloxy group having 1 to 18 carbon atom(s) which is substituted with 3 substituents wherein 1 to 3 hydrogen atom(s) of the silyloxy group are substituted with substituents such as the above optionally substituted hydrocarbon group and the above optionally substituted alkoxy group. Specific examples of the substituted silyloxy group include trimethylsilyloxy, triethylsilyloxy, tri(2-propyl)silyloxy, tert-butyldimethylsilyloxy, tert-butyldiphenylsilyloxy, triphenylsilyloxy, tert-butylmethoxyphenylsilyloxy, tert-butoxydiphenylsilyloxy and the like.

The group represented by $R^{41}$ in the formula (24) may be a metal atom such as an alkali metal atom. The above carboxy group and sulfo group may also be a salt of a metal atom such as an alkali metal atom. The alkali metal atom includes, for example, lithium, sodium, potassium, rubidium, caesium and the like.

When a ring is formed, for example, when a ring is formed by bonding the groups $R^{31}$ and $R^{32}$, $R^{31}$ and $R^{33}$, $R^{31}$ and $R^{34}$, $R^{32}$ and $R^{33}$, $R^{32}$ and $R^{34}$, $R^{33}$ and $R^{34}$, $R^{35}$ and $R^{36}$, $R^{38}$ and $R^{39}$, $R^{38}$ or $R^{39}$ and $R^{37}$, $R^{40}$ and $Q^{11}$, $R^{40}$ and $R^{41}$, $R^{41}$ and $Q^{11}$, $R^{42}$ and $Q^{12}$, $R^{44}$ and $Q^{12}$, $R^{42}$ and $R^{43}$, $R^{42}$ and $R^{44}$ or $R^{45}$, $R^{43}$ and $R^{44}$, $R^{43}$ and $R^{45}$, and $R^{44}$ and $R^{45}$, the ring includes, for example, a ring formed by combination of an optionally substituted alkylene group or an optionally substituted alkylenedioxy group. The formed ring may be monocyclic, polycyclic or fused-cyclic and example thereof includes, for example, 4- to 8-membered aliphatic ring and an aromatic ring.

The optionally substituted alkylene group includes an alkylene group and a substituted alkylene group.

The alkylene group may be linear or branched and includes, for example, an alkylene group having 1 to 6 carbon atom(s). Specific examples thereof include ethylene, propylene, trimethylene, 2-methylpropylene, 2,2-dimethylpropylene, 2-ethylpropylene and the like. The ring may have an oxygen atom, a sulfur atom, an imino group, a substituent imino group, a carbonyl group (C=O), a thiocarbonyl group (C=S) and the like in the carbon chain thereof. Specific examples of the formed ring include, for example, a cyclopentane ring, a cyclohexane ring, a lactone ring of, for example, 5 to 7 members, a lactam ring of, for example, 5 to 7 members, a cyclopentanone ring, a cyclohexanone ring and the like. Thus formed ring is preferably a ring wherein a carbon atom at the position subjected to asymmetric hydrogenation becomes an asymmetric carbon atom in homogeneous asymmetric hydrogenation. A substituent in the substituted imino group is the same as the substituent to be described later.

The substituted alkylene group (alkylene group having a substituent) includes, for example, the above alkylene group of which at least one hydrogen atom is substituted with a substituent.

The optionally substituted alkylenedioxy group includes an alkylenedioxy group and a substituted alkylenedioxy group.

The alkylenedioxy group includes, for example, alkylenedioxy group having 1 to 3 carbon atom(s). Specific examples thereof include methylenedioxy, ethylenedioxy, trimethylenedioxy, propylenedioxy and the like.

The substituted alkylenedioxy group (alkylenedioxy group having a substituent) includes the above alkylenedioxy group of which at least one hydrogen atom is substituted with a substituent. Specific examples thereof include difluoromethylenedioxy and the like.

The spacer includes an optionally substituted divalent organic group, such as an alkylene group, an arylene group and a heteroarylene group. The above divalent organic group may have at least one heteroatom or heteroatom group such as an oxygen atom, a carbonyl group, a sulfur atom, an imino group and a substituted imino group. A substituent in the substituted imino group is the same as a substituent to be described later.

The alkylene group includes, for example, an alkylene group having 1 to 10 carbon atom(s). Specific examples thereof include methylene, ethylene, trimethylene, propylene, tetramethylene, pentamethylene, hexamethylene, heptamethylene, octamethylene, nonamethylene, decamethylene and the like.

The arylene group includes, for example, an arylene group having 6 to 20 carbon atoms. Specific examples thereof include phenylene, biphenyldiyl, binaphthalenediyl, bisbenzodioxoldiyl and the like.

The heteroarylene group includes, for example, a 3- to 8-membered, preferably 5- or 6-membered monocyclic, polycyclic or fused-cyclic heteroarylene group having 2 to 20 carbon atoms and contains at least 1, preferably 1 to 3 heteroatom(s) such as a nitrogen atom, an oxygen atom and/or a sulfur atom. Specific examples thereof include bipyridinediyl, bisbenzothioldiyl, bisthioldiyl and the like.

The divalent organic group having a heteroatom or a heteroatom group includes, for example, —$CH_2$—O—$CH_2$—, —$C_6H_4$—O—$C_6H_4$— and the like.

These divalent organic groups may be substituted with a substituent which is described later.

The substituent includes, for example, an optionally substituted hydrocarbon group, an optionally substituted heterocyclic group, a halogen atom, a halogenated hydrocarbon group, an optionally substituted alkoxy, optionally substituted aryloxy group, an optionally substituted aralkyloxy group, an optionally substituted heteroaryloxy group, an optionally substituted alkylthio group, an optionally substituted arylthio group, an optionally substituted aralkylthio group, an optionally substituted heteroarylthio group, an optionally substituted acyl group, an optionally substituted acyloxy group, an optionally substituted alkoxycarbonyl group, an optionally substituted aryloxycarbonyl group, an optionally substituted aralkyloxycarbonyl group, an optionally substituted alkylenedioxy group, a nitro group, an amino group, a substituted amino group, a cyano group, a sulfo group, a substituted silyl group, a hydroxy group, a carboxy group, an optionally substituted alkoxythiocarbonyl group, an optionally substituted aryloxythiocarbonyl group, an optionally substituted aralkyloxythiocarbonyl group, an optionally substituted alkylthiocarbonyl group, an optionally substituted arylthiocarbonyl group, an optionally substituted aralkylthiocarbonyl group, an optionally substituted carbamoyl group, a substituted phosphino group, an aminosulfonyl group, an alkoxysulfonyl group, a oxo group and the like. These substituents may be the same as respective groups described above.

An optionally substituted alkylenedioxy group as the substituent is substituted with, for example, two adjacent hydrogen atoms in the aromatic ring of the above aryl group or aralkyl group. The optionally substituted alkylenedioxy group includes an alkylenedioxy group and a substituted alkylenedioxy group. The alkylenedioxy group includes, for example, an alkylenedioxy group having 1 to 3 carbon atom(s). Specific examples thereof include methylenedioxy, ethylenedioxy, trimethylenedioxy, propylenedioxy, and the like.

The substituted alkylenedioxy group (alkylenedioxy group having a substituent) includes the above alkylenedioxy group of which at least one hydrogen atom is substituted with the above substituent. Specific examples thereof include difluoromethylenedioxy and the like.

Specific examples of the alkenes include, for example, the compounds shown below:

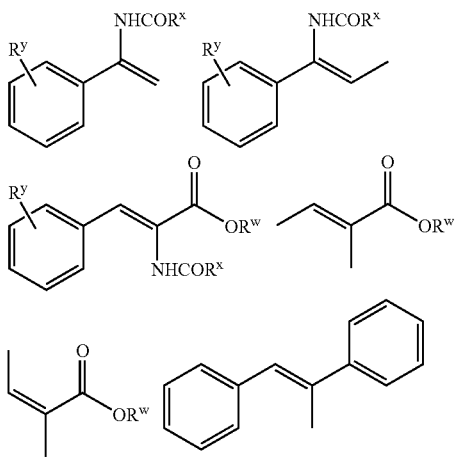

$R^w$: H, CH$_3$, C$_2$H$_5$, $^i$Pr, n-C$_4$H$_9$, Na, K, etc.
$R^x$: CH$_3$, C$_2$H$_5$, $^i$Pr, n-C$_4$H$_9$, etc.
$R^y$: H, 2-CH$_3$, 3-CH$_3$, 4-CH$_3$, 2-CH$_3$O, 3-CH$_3$O, 4-CH$_3$O,
2-$^t$Bu, 3-$^t$Bu, 4-$^t$Bu, 2-CN, 3-CN, 4-CN,
2-Cl, 3-Cl, 4-Cl, 2-Br, 3-Br, 4-Br, etc.

Specific examples of the ketones include, for example, methyl ethyl ketone, acetophenone, benzalacetone, 1-indanone, 3,4-dihydro-(2H)-naphthalenone ferrocenyl methyl ketone and, for example, the compounds shown below:

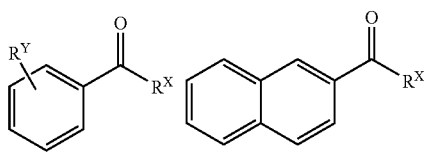

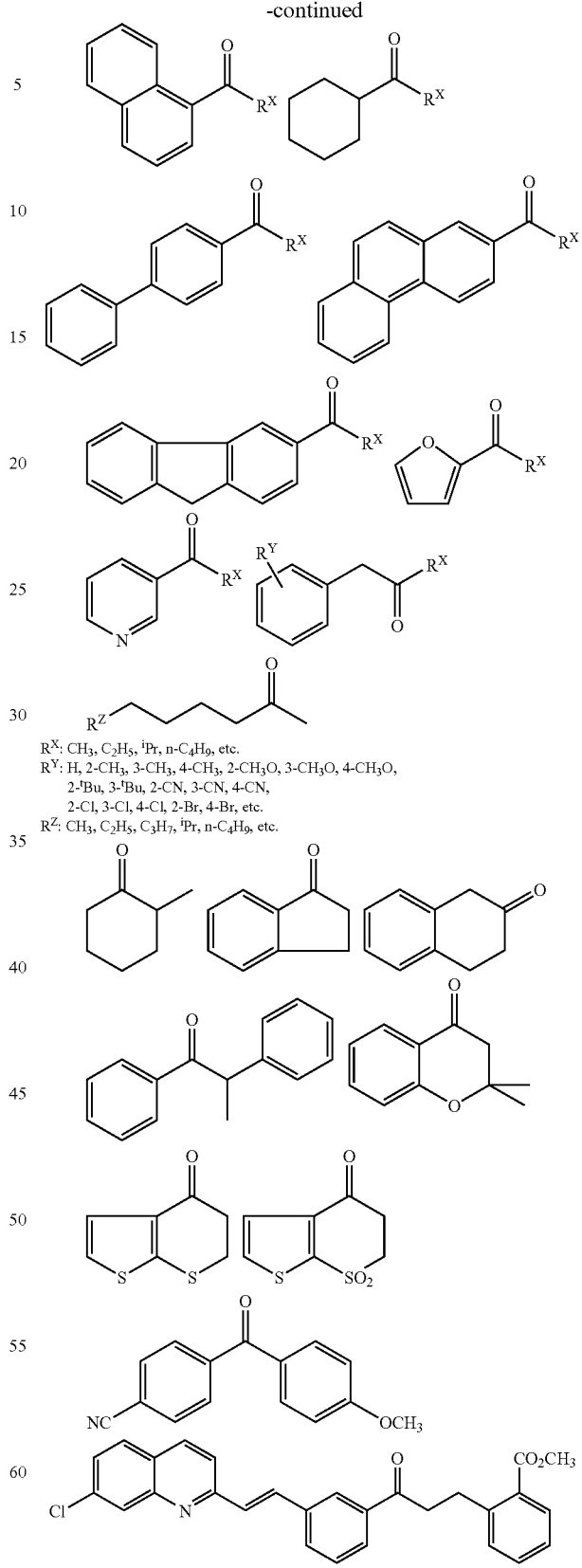

$R^x$: CH$_3$, C$_2$H$_5$, $^i$Pr, n-C$_4$H$_9$, etc.
$R^y$: H, 2-CH$_3$, 3-CH$_3$, 4-CH$_3$, 2-CH$_3$O, 3-CH$_3$O, 4-CH$_3$O,
2-$^t$Bu, 3-$^t$Bu, 2-CN, 3-CN, 4-CN,
2-Cl, 3-Cl, 4-Cl, 2-Br, 4-Br, etc.
$R^z$: CH$_3$, C$_2$H$_5$, C$_3$H$_7$, $^i$Pr, n-C$_4$H$_9$, etc.

Specific examples of the imines include, for example, the compounds shown below:

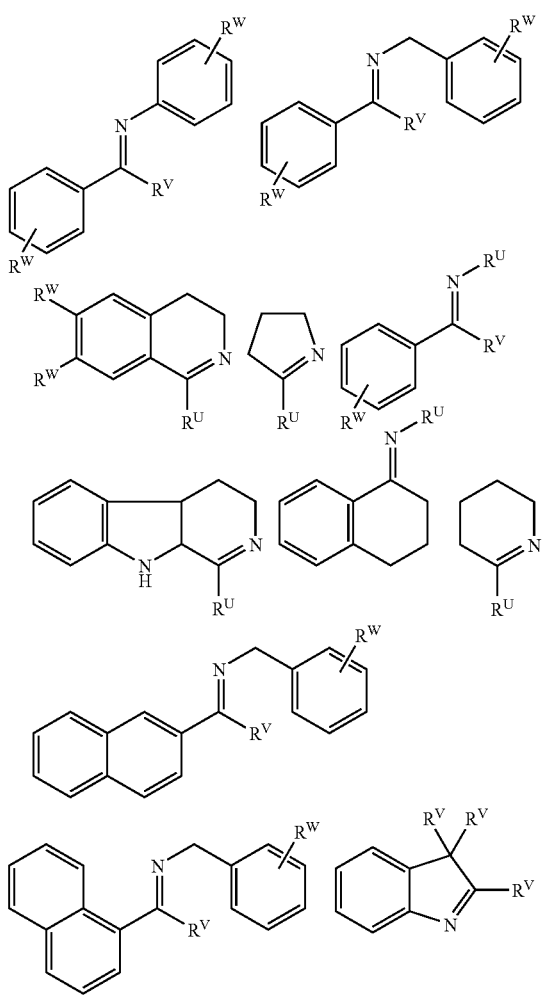

$R^U$: $CH_3$, $C_2H_5$, Pr, $^iPr$, Bu, $^tBu$, $C_6H_5$, $CH_2C_6H_5$, $C_6H_4CH_3$, $C_6H_4OCH_3$, OH, etc.
$R^V$: $CH_3$, $C_2H_5$, Pr, $^iPr$, Bu, $^tBu$, etc.
$R^W$: H, $CH_3$, $CH_3O$, $C_2H_5O$, Bu, $^tBu$, Cl, Br, $C_6H_5$, etc.

Specific examples of the ketocarboxylic acids include, for example, the compounds shown below:

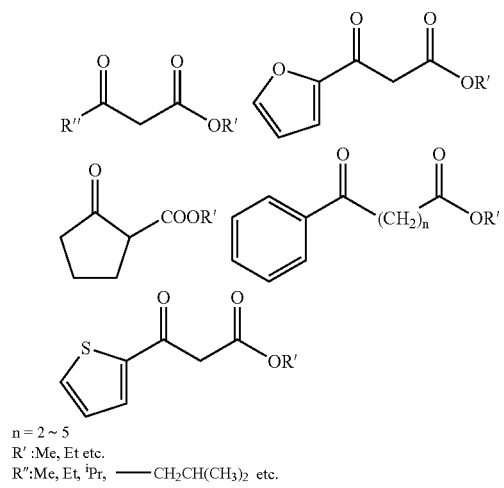

n = 2 ~ 5
R' : Me, Et etc.
R'': Me, Et, $^iPr$, —$CH_2CH(CH_3)_2$ etc.

Specific examples of the ketoalkenes include, for example, the compounds shown below:

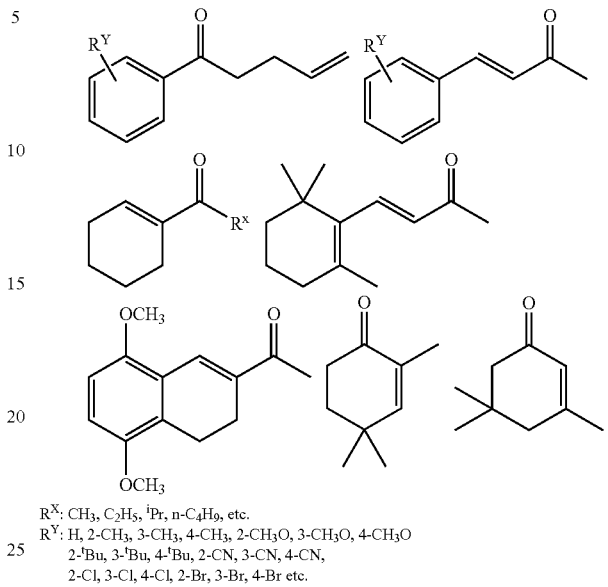

$R^X$: $CH_3$, $C_2H_5$, $^iPr$, n-$C_4H_9$, etc.
$R^Y$: H, 2-$CH_3$, 3-$CH_3$, 4-$CH_3$, 2-$CH_3O$, 3-$CH_3O$, 4-$CH_3O$
2-$^tBu$, 3-$^tBu$, 4-$^tBu$, 2-CN, 3-CN, 4-CN,
2-Cl, 3-Cl, 4-Cl, 2-Br, 3-Br, 4-Br etc.

The above unsaturated compound may have a chiral center in the molecule.

Preferably, the hydride of an unsaturated compound obtainable by the production method of the present invention is an optically active compound. In other words, hydrogenation in the present invention is preferably asymmetric hydrogenation. Therefore, the optically active compound preferably obtainable in the present invention is an optically active compound corresponding to each unsaturated compound. For example, the compounds obtainable in hydrogenation of alkenes are optically active alkanes; the compounds obtainable in asymmetric hydrogenation of ketones are optically active alcohols; the compounds obtainable in hydrogenation of imines are optically active amines; the compounds obtainable in hydrogenation of ketocarboxylic acids are optically active hydroxy esters; and the compounds obtainable in hydrogenation of ketoalkenes are hydroxyalkenes, hydroxyalkanes and/or ketoalkanes.

The optically active alkanes obtainable in asymmetric hydrogenation of alkenes include, for example, optically active alkanes represented by the following formula (31):

(31)

The optically active alcohols obtainable in asymmetric hydrogenation of ketones include, for example, optically active alcohols represented by the following formula (32):

(32)

The optically active amines obtainable in asymmetric hydrogenation of imines include, for example, optically active amines represented by the following formula (33):

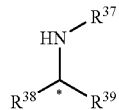
(33)

The optically active hydroxy esters obtainable in asymmetric hydrogenation of ketocarboxylic acids include, for example, optically active hydroxy esters represented by the following formula (34):

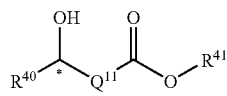
(34)

The optically active hydroxyalkenes, the optically active hydroxyalkanes and the optically active ketoalkanes obtainable in asymmetric hydrogenation of ketoalkenes are represented by, for example, the following formulae (35) to (37), respectively:

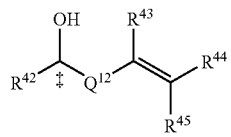
(35)

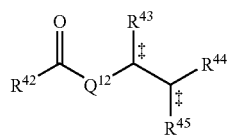
(36)

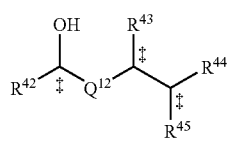
(37)

In the above formulae, the symbol * represents an asymmetric carbon atom and $R^{31}$ to $R^{45}$, $Q^{11}$ and $Q^{12}$ are the same as described above. However, some carbons may not become asymmetric carbon atom depending on the kinds of $R^{31}$ to $R^{45}$, for example, in the case where $R^{35}=R^{36}$ or in the case where either $R^{35}$ or $R^{36}$ is a hydrogen atom in the formula (32).

Specific examples of the optically active compound include a hydride obtainable from each unsaturated compound exemplified above (that is, a hydride of unsaturated compound).

The obtained optically active compound may be subjected to post-treatment such as purification and isolation and the like as needed, or may be subjected to post-treatment such as purification and isolation and the like as needed after protecting a functional group. The specific method for post-treatment is the same as described above.

Any pressure of hydrogen gas used as the hydrogen source is satisfactory as long as a hydrogen atmosphere is provided. The pressure of hydrogen gas may be 0.1 MPa or lower, but is appropriately selected usually in the range of 0.1 to 20 MPa, preferably 0.2 to 10 MPa considering economy and operability. High activity can be obtained even at economical 1 MPa or lower.

The hydrogen donor used as the hydrogen source includes, for example, formic acid or its salts, a combination of formic acid and a base, hydroquinone, cyclohexadiene, phosphorous acid and alcohols and the like. Among these, formic acid or its salts, a combination of formic acid and a base, and alcohols are especially preferable.

The above salts of formic acid include a metal salt of formic acid such as an alkaline metal salt of formic acid and an alkaline-earth metal salt of formic acid, an ammonium salt and a substituted amine salt and the like.

With regard to the combination of formic acid and a base, the formic acid may be present as a formate or a substantial formate in the reaction system.

The base to form the above metal salt of formic acid such as the alkaline metal salt of formic acid and the alkaline-earth metal salt of formic acid, the ammonium salt and the substituted amine salt and the bases present in the above combination of formic acid and a base include ammonium, an inorganic base, an organic base and the like.

The alkaline metal to form a salt by reacting with formic acid includes lithium, sodium, potassium, rubidium and caesium and the like; the alkaline-earth metal includes magnesium, calcium, strontium and barium; and the like.

The inorganic base includes, for example, an alkaline metal salt or an alkaline-earth metal salt such as potassium carbonate, potassium hydroxide, lithium hydroxide, sodium hydrogencarbonate, sodium carbonate, potassium hydrogencarbonate, sodium hydroxide, magnesium carbonate, calcium carbonate and the like; metal hydrides such as sodium hydride and the like; and the like.

The organic base includes, for example, alkaline metal alkoxides such as potassium methoxide, sodium methoxide, lithium methoxide, sodium ethoxide, potassium isopropoxide, lithium tert-butoxide, sodium tert-butoxide, and potassium tert-butoxide; acetates of an alkaline metal or an alkaline-earth metal such as sodium acetate, potassium acetate, magnesium acetate and calcium acetate; organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine and N-methylmorpholine and the like; organic metal compounds such as methylmagnesium bromide, ethylmagnesium bromide, propylmagnesium bromide, tert-butylmagnesium chloride, tert-butylmagnesium bromide, methyl lithium, ethyl lithium, propyl lithium, n-butyl lithium and tert-butyl lithium; a quaternary ammonium salt; and the like.

The alcohol as a hydrogen donor includes preferably a lower alcohol having a hydrogen atom at the a-position. Specific examples thereof include, for example, methanol, ethanol, n-propanol, isopropanol, n-butanol, sec-butanol and the like. Among these, isopropanol is preferable.

The amount of the hydrogen donor used is appropriately selected usually in the range of 0.1 to 100 equivalents, preferably 0.5 to 20 equivalents based on that of the unsaturated compound.

The asymmetric hydrogenation can be carried out in a solvent as needed. The solvent includes, for example, aromatic hydrocarbons such as benzene, toluene and xylene; aliphatic hydrocarbons such as pentane, hexane, heptane and octane; halogenated hydrocarbons such as dichloromethane, chloroform, carbon tetrachloride and dichloroethane; ethers such as diethyl ether, diisopropyl ether, tert-butyl methyl ether, cyclopentyl methyl ether, dimethoxyethane, tetrahydrofuran, dioxane, dioxolane and 2-methyltetrahydrofuran; alcohols such as methanol, ethanol, 2-propanol, n-butanol, tert-butanol and benzyl alcohol; polyhydric alcohols such as ethylene glycol, 1,2-propanediol, 1,3-propanediol and glycerin; amides such as N,N-dimethylformamide and N,N-dimethylacetoamide; ketones such as acetone and methyl isobutyl ketone; esters such as methyl acetate, ethyl acetate and butyl acetate; acetonitrile; N-methylpyrrolidone; dimethyl sulfoxide; water; and the like. These solvents may be used alone or in an appropriate combination of two or more thereof.

The amount of the solvent used is not specified because it depends on the kind and the solubility of the unsaturated compound used and economy. For example, when alcohols are used as a solvent, a range of a low concentration of 1% or lower to a solventless or close-to-solventless condition is allowable depending on the kind of the unsaturated compound used. The amount of the solvent used may be appropriately selected, for example, usually in the range of 0 to 200 times, preferably 0 to 40 times based on that of a reaction substrate.

The reaction temperature is not specified because it depends on the kind and the amount of the above catalyst used and the kind of the unsaturated compound used. However, it is appropriately selected usually in the range of −30 to 250° C., preferably 0 to 100° C. from the economical standpoint. A low temperature of −30 to 0° C. or a high temperature of 0 to 250° C. is feasible for the reaction.

The reaction time depends on the kind and the amount of the above catalyst used, the kind and the concentration of the unsaturated compound used as well as the reaction conditions such as reaction temperature and hydrogen pressure, but is appropriately selected usually in the range of 1 minute to 48 hours, preferably 10 minutes to 24 hours.

The asymmetric hydrogenation can be carried out either in a batch system or in a continuous system and in various types of reactors to be usually used in the art such as a flask, a reaction vessel and an autoclave.

The asymmetric hydrogenation can be carried out in the presence of an additive as needed. The additive includes an acid, a fluorine-containing alcohol, a base, a quaternary ammonium salt, a quaternary phosphonium salt, a halogen, a reducing agent and the like.

The acid includes an inorganic acid, an organic acid, a Lewis acid and the like.

The inorganic acid includes, for example, hydrochloric acid, hydrobromic acid, sulfuric acid, phosphoric acid, tetrafluoroboric acid, perchloric acid, periodic acid and the like.

The organic acid includes, for example, a carboxylic acid such as formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid and glycolic acid; a sulfonic acid such as methanesulfonic acid, benzenesulfonic acid, p-toluenesulfonic acid and trifluoromethanesulfonic acid; and the like.

The Lewis acid includes, for example, a halogenated aluminum such as aluminum chloride and aluminum bromide; a halogenated dialkylaluminum such as diethylaluminum chloride, diethylaluminum bromide and diisopropylaluminum chloride; a trialkoxyaluminum such as triethoxyaluminum, triisopropoxyaluminum and tri-tert-butoxyaluminum; a halogenated titanium such as titanium tetrachloride and the like; a tetraalkoxytitanium such as tetrapropoxytitanium and the like; a halogenated boron such as boron trifluoride, boron trichloride, boron tribromide and boron trifluoride diethyl ether complex; a halogenated zinc such as zinc chloride and zinc bromide; and the like.

These acids may be used alone or in an appropriate combination of two or more thereof.

The amount of the acid used is appropriately selected usually in the range of 0.0001 to 100 equivalents, preferably 0.001 to 10 equivalents based on that of the unsaturated compound used.

The fluorine-containing alcohol is preferably a fluorine-containing aliphatic alcohol. The fluorine-containing aliphatic alcohol includes, for example, a saturated or unsaturated fluorine-containing aliphatic alcohol of 2 to 10 carbon atoms. Specific examples thereof include 2,2,2-trifluoroethanol, 2,2-difluoroethanol, 3,3,3-trifluoropropanol, 2,2,3,3,3-pentafluoropropanol, 2,2,3,3-tetrafluoropropanol, 3,3,4,4,4-pentafluorobutanol, 4,4,5,5,5-pentafluoropentanol, 5,5,6,6,6-pentafluorohexanol, 3,3,4,4,5,5,6,6,6-nonafluorohexanol, 1,1,1,3,3,3-hexafluoro-2-propanol and the like. These fluorine-containing aliphatic alcohols may be used alone or in an appropriate combination of two or more thereof.

The amount of the fluorine-containing alcohol used is appropriately selected usually in the range of 0.01 to 100 equivalents, preferably 0.1 to 10 equivalents based on that of the unsaturated compound used.

The base includes an inorganic base, an organic base and the like. The inorganic base includes, for example, alkaline metal hydroxides such as lithium hydroxide, sodium hydroxide and potassium hydroxide; metal carbonates such as sodium carbonate, potassium carbonate, magnesium carbonate and calcium carbonate; metal hydrogencarbonates such as sodium hydrogencarbonate and potassium hydrogencarbonate; metal hydrides such as lithium hydride, sodium hydride and potassium hydride; ammonia; and the like. The organic base includes, for example, alkaline metal or alkaline-earth metal salts such as lithium methoxide, lithium ethoxide, lithium-tert-butoxide, sodium methoxide, sodium ethoxide, sodium-tert-butoxide, potassium methoxide, potassium ethoxide, potassium-tert-butoxide, potassium naphthalenide, sodium acetate, potassium acetate, magnesium acetate, calcium acetate, lithium diethylamide, lithium diisopropylamide, lithium bis(trimethylsilyl)amide, sodium bis(trimethylsilyl)amide, potassium bis(trimethylsilyl)amide, lithium diphenylphosphido, sodium diphenylphosphido and potassium diphenylphosphido; organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine and N-methylmorpholine; organic metal compounds such as methyllithium, ethyllithium, n-propyllithium, isopropyllithium, n-butyllithium, sec-butyllithium, tert-butyllithium, phenyllithium, methylmagnesium chloride, ethylmagnesium chloride, n-propylmagnesium chloride, isopropylmagnesium chloride, n-butylmagnesium chloride, sec-butylmagnesium chloride, tert-butylmagnesium chloride, phenylmagnesium chloride, methylmagnesium bromide, ethylmagnesium bromide, n-propylmagnesium bromide, isopropylmagnesium bromide, n-butylmagnesium bromide, sec-butylmagnesium bromide, tert-butylmagnesium bromide and phenylmagnesium bromide; and the like; and an optically active substance of the above diamine compound (optically active diamine compound) exemplified as a chiral ligand; and a racemate.

The amount of the base used is appropriately selected usually in the range of 0 to 100 equivalents, preferably 0 to 10 equivalents based on that of the unsaturated compound used.

The quaternary ammonium salt includes, for example, a quaternary ammonium salt having 4 to 24 carbon atoms, and specific example thereof includes tetrabutylammonium fluoride, tetrabutylammonium chloride, tetrabutylammonium bromide, tetrabutylammonium iodide, triethylbenzylammonium chloride, tetrabutylammonium triphenyldifluoro silicate and the like.

The amount of the quaternary ammonium salt used is appropriately selected usually in the range of 0 to 100 equivalents, preferably 0 to 10 equivalents based on that of the unsaturated compound used.

The quaternary phosphonium salt includes, for example, a quaternary phosphonium salt having 4 to 36 carbon atoms and specific example thereof includes tetraphenylphosphonium chloride, tetraphenylphosphonium bromide, tetraphenylphosphonium iodide, methyltriphenylphosphonium chloride, methyltriphenylphosphonium bromide, methyltriphenylphosphonium iodide and the like.

The amount of the quaternary phosphonium salt used is appropriately selected usually in the range of 0 to 100 equivalents, preferably 0 to 10 equivalents based on that of the unsaturated compound used.

The halogen includes bromine, iodine and the like.

The amount of the halogen used is appropriately selected usually in the range of 0 to 100 equivalents, preferably 0 to 10 equivalents based on that of the unsaturated compound used.

The reducing agent includes boron sodium hydride, lithium aluminum hydride, lithium diisobutylaluminum hydride and the like.

The amount of the reducing agent used is appropriately selected usually in the range of 0 to 100 equivalents, preferably 0 to 10 equivalents based on that of the unsaturated compound used.

The above additives may be used alone or in an appropriate combination of two or more thereof.

The optically active compound obtained by the production method of the present invention is useful as, for example, an intermediate of medicine and agrochemical, and a perfume.

The present invention is characterized in that an alkoxy group and the like are introduced into an optically active diphosphine compound having two methylenedioxybenzene groups at the 4- and 4'-positions thereof. The optically active diphosphine compound of the present invention is useful as a catalyst component having asymmetric catalytic activity for asymmetric hydrogenation of various unsaturated compounds.

The optically active diphosphine compound of the present invention can be easily and selectively subjected to halogenation and coupling reaction by means of substituting in advance an unnecessary reaction site for synthesis, and can be easily treated in reaction and purification steps by increasing lipid solubility, and thus an objective optically active diphosphine compound can be produced efficiently. Therefore, a hydride of the above unsaturated compound especially having optical activity that is useful as an intermediate of medicine and agrochemical and a perfume can be obtained not only in a high yield and high optical purity but also in improved operability and economy by the reaction catalyzed by a transition metal complex having the above optically active diphosphine compound as a ligand.

The transition metal complex having the above optically active diphosphine compound, especially said optically active diphosphine compound introduced a methoxy group is characterized by having brown-color. Therefore, the progress of reaction using the complex of the present invention can be more easily confirmed by sight compared with the conventional complex.

BEST MODE FOR CARRYING OUT THE INVENTION

The present invention will be more specifically described by way of the following examples, however, the invention is not limited thereto. The following instruments were used for measuring physical properties in the following examples.

NMR: DRX-500 (BRUKER JAPAN CO. LTD.)
$^1$H-NMR; 500.13 MHz
$^{31}$P-NMR; 202.46 MHz

Gas chromatography (GC): GLC Agilent 6850 Series
High-performance liquid chromatography (HPLC): Hitachi Ltd. LaCrom 7000

EXAMPLE 1

Synthesis of (+)-[4,4'-bis(7-methoxy-1,3-benzodioxol)]-5-diyl-diphenylphosphine ((+)-SEGPHOS-4-MeO)

(1) Synthesis of (7-methoxy-1,3-benzodioxol)-5-yl-diphenylphosphine oxide

To 0.27 g (11.1 mmol) of magnesium piece in a three-necked flask was added 2 mL of tetrahydrofuran (hereinafter, referred to as THF) after replacing with nitrogen. A mixed solution of 2.34 g of 5-bromo-7-methoxy-1,3-benzodioxol and 10 mL of THF was added dropwise to the resultant solution with stirring at 20° C. to 32° C. for 2 hours. After stirring further for 1.5 hours at room temperature, a mixed solution of 2.63 g of diphenylphosphonic chloride and 6 mL of THF was added dropwise to the resultant solution at 23° C. to 38° C. for 1 hour, followed by stirring at 40° C. for 2 hours. And then, the reaction mixture was poured slowly under cooling with ice to 11 mL of 1-N hydrochloric acid followed by stirring for 30 minutes. The reaction product was extracted 2 times with 20 mL of dichloromethane and then washed 2 times with a 15 mL of 2.5% aqueous solution of sodium hydrogencarbonate and then 2 times with 15 mL of water. The organic phase was dried over anhydrous magnesium sulfate. A solid obtained by evaporating off the solvent under reduced pressure was dissolved in 32 mL of ethyl acetate under heating and then recrystallized at 0° C. to give 2.65 g of the title compound.

$^1$H-NMR (CDCl$_3$): d 3.87(3H, s), 6.03(2H, s), 6.60(1H, dd, J=11.7, 1.3 Hz), 7.07(1H, dd, J=13.4, 1.2 Hz), 7.45-7.55 (6H, m), 7.56-7.71(4H, m).

(2) Synthesis of (4-iodo-7-methoxy-1,3-benzodioxol)-5-yl-diphenylphosphine oxide (2-1) Under the nitrogen stream, 0.83 g (8.17 mmol) of diisopropylamine was dissolved in 6 mL of THF. A solution (1.6 M) of 5.1 mL of n-butyllithium in n-hexane was added dropwise to the above solution at −10° C. for 20 minutes with stirring followed by stirring at the same temperature for 2.5 hours. A solution of 2.40 g (6.81 mmol) of (7-methoxy-1,3-benzodioxol)-5-yl-diphenylphosphine oxide in 48 mL of THF was added dropwise to thus obtained solution at −10° C. for 30 minutes followed by stirring at the same temperature for 30 minutes. And then, 1.73 g (6.81 mmol) of iodine was added to the obtained mixed solution and then heated to room temperature, followed by stirring further for 3 hours. The reaction mixture was added to 10 mL of 1N-hydrochloric acid under cooling with ice. The reaction product was extracted 2 times with 25 mL of dichloromethane and washed 2 times with 10 mL of 5% aqueous sodium hydrogencarbonate solution and then 2 times with 20 mL of water. The organic phase was dried over anhydrous magnesium sulfate. A solid obtained by evaporating off the solvent under reduced pressure was dissolved in 15 mL of ethyl acetate under heating and then recrystallized at 0° C. to give 0.63 g of the title compound.

$^1$H-NMR (CDCl$_3$): d 3.60(3H, s), 6.10(2H, s), 6.70(1H, d, J=14.3 Hz), 7.48-7.50(4H, m), 7.55-7.56(2H, m), 7.70-7.74 (4H, m).

(2-2) Under the nitrogen stream, 0.36 g (3.52 mmol) of diisopropylamine was dissolved in 8 mL of THF. A solution (1.6 M) of 2.0 mL of n-butyllithium in n-hexane was added dropwise to the above solution at −78° C. for 15 minutes with stirring, followed by stirring at −78° C. to −40° C. for 1.5 hours. A solution of 1.00 g (2.83 mmol) of (7-methoxy-1,3-benzodioxol)-5-yl-diphenylphosphine oxide obtained in the same manner as described in above (1) in 24 mL of THF was added dropwise to thus obtained solution at −78° C. to −75° C. for 20 minutes, followed by stirring at the same temperature for 30 minutes. And then, 0.79 g (3.12 mmol) of iodine was added to the obtained mixed solution at −78° C. to −75° C. for 3 hours and then heated to room temperature, followed by stirring further for 3 hours. The reaction mixture was added to 6 mL of 10% aqueous sodium thiosulfate solution under cooling with ice. The reaction product was extracted 2 times with 20 mL of ethyl acetate. The organic phase was washed 1 time with 5 mL of 1N-hydrochloric acid, 1 time with 5 mL of 1N-aqueous sodium hydrogencarbonate solution, and then 2 times with 5 mL of water, and was dried over anhydrous magnesium sulfate. A solid obtained by evaporating off the solvent under reduced pressure was dissolved in 6 mL of ethyl acetate under heating and then recrystallized at 0° C. to give 0.57 g of the title compound. The $^1$H-NMR spectra are compatible with the result of the above (2-1).

(3) Synthesis of (±)-[4,4'-bis(7-methoxy-1,3-benzodioxol)]-5-diyl-diphenylphosphine oxide To 1.6 g (3.34 mmol) of (4-iodo-7-methoxy-1,3-benzodioxol)-5-yl-diphenylphosphine oxide obtained in the same manner as described in above (2-1) in a three-necked flask was added 8 mL of dimethylformamide (hereinafter, referred to as DMF) after replacing with nitrogen. And then, 0.64 g (10.1 mmol) of copper powder was added to the resultant solution at 95° C. under heating and stirring, followed by stirring further for 4 hours at the same temperature. After cooled to room temperature, the reaction mixture was added to 20 mL of water and the mixture was filtered through celite. The reaction product was extracted 2 times with 20 mL of dichloromethane from the obtained filtrate, and the organic phase was dried over anhydrous magnesium sulfate. After evaporating off the solvent under reduced pressure, the residue was purified by column chromatography on silica gel to give 0.9 g of the title compound.

$^1$H-NMR (CDCl$_3$): d 3.68(6H, s), 5.28(2H, d, J=1.6 Hz), 5.71(2H, d, J=1.6 Hz), 6.47(2H, d, J=5.0 Hz), 7.26-7.37(6H, m), 7.41-7.46(6H, m), 7.59-7.63(4H, m), 7.71-7.75(4H, m).
$^{31}$P-NMR; (CDCl$_3$): d 30.4

(4) Preparative liquid chromatography of optically active (±)-[4,4'-bis(7-methoxy-1,3-benzodioxol)]-5-diyl-diphenylphosphine oxide 0.82 g of (±)-(4,4'-bis(7-methoxy-1,3-benzodioxol))-5-diyl-diphenylphosphine oxide (hereinafter, may be referred to as (±)-SEGPHOSO$_2$-4-MeO) was dissolved in 80 mL of 1,2-dichloroethane and preparatively isolated and purified under the following conditions of liquid chromatography to give 0.3 g of (+)-(4,4'-bis(7-methoxy-1,3-benzodioxol))-5-diyl-diphenylphosphine oxide (hereinafter, referred to as (+)-SEGPHOSO$_2$-4-MeO) having an optical purity of 99.2% ee.

Conditions of liquid chromatography: HPLC used: Waters 600E, column used: SUMICHIRAL OA-3100 (5 μm, F 20 mm×250 mm), eluent: hexane:1,2-dichloroethane:ethanol=40:20:40, flow rate: 5 mL/min, temperature: 25° C.

(5) Synthesis of (+)-[4,4'-bis(7-methoxy-1,3-benzodioxol)]-5-diyl-diphenylphosphine ((+)-SEGPHOS-4-MeO)

To 0.36 g (0.52 mmol) of (+)-SEGPHOSO$_2$-4-MeO obtained in above (4) in a three-necked flask was added 18 mL of toluene and 1.36 g (11.2 mmol) of dimethylaniline after replacing with nitrogen and then stirred at room temperature. And then, 1.38 g (10.2 mmol) of trichlorosilane was added to the mixed solution at room temperature, heated to 105° C. taking 2.5 hours and stirred at the same temperature for 4 hours. The reaction mixture was cooled with ice and added with 15 mL of 15% aqueous sodium hydroxide solution and stirred at room temperature for 30 minutes. After liquid separation, the reaction product in the aqueous layer was extracted 2 times with 20 mL of toluene and combined with the separated organic layer. The obtained organic layer was washed 2 times with 15 mL of 1-N hydrochloric acid and then 2 times with 20 mL of water, and dried over anhydrous magnesium sulfate. After evaporating off the solvent under reduced pressure, the residue was purified by column chromatography on silica gel to give 0.32 g of a white solid of the title compound (yield: 93%).

$^1$H-NMR (CDCl$_3$): d 3.68(6H, s), 5.28(2H, d, J=1.6 Hz), 5.71(2H, d, J=1.6 Hz), 6.47(2H, d, J=5.0 Hz), 7.26-7.37(6H, m), 7.41-7.46(6H, m), 7.59-7.63(4H, m), 7.71-7.75(4H, m).
$^{31}$P-NMR (CDCl$_3$): d −11.0

EXAMPLE 2

Preparation of [RuCl(p-cymene)((+)-SEGPHOS-4-MeO)]Cl

Into a 20 mL Schlenk flask was put 100 mg (0.15 mmol) of (+)-SEGPHOS-4-MeO obtained in Example 1 and added 4 mL of ethanol, 4 mL of dichloromethane and 43.5 mg of [RuCl$_2$(p-cymene)]$_2$ after replacing with nitrogen. And then, the reaction is carried out with stirring at 50° C. for 3 hours. After evaporating off the solvent under reduced pressure, the residue was dried under vacuum to give 140 mg of orange yellow-colored solid of the title compound.

$^{31}$P-NMR (CDCl$_3$): d 26.4(d, J=62.1 Hz), 41.5(d, J=62.1 Hz).

EXAMPLE 3

Preparation of [Me$_2$NH$_2$][{RuCl((+)-SEGPHOS-4-MeO)}$_2$(μ-Cl)$_3$]

After replacing with nitrogen, 4 mL of 1,4-dioxane was added to a mixture of 140 mg (0.15 mmol) of [RuCl(p-cymene)((+)-SEGPHOS-4-MeO)]Cl obtained in Example 2 and 13.9 mg of dimethylamine hydrochloride in a 30 mL Schlenk flask, and then the reaction is carried out with stirring at 115° C. for 16 hours. The excess dimethylamine hydrochloride was removed by filtration from the reaction mixture under nitrogen gas, and the solvent was removed by evaporation under reduced pressure from the filtrate. The residue was dried under vacuum to give 125 mg of brown-colored solid of the title compound.
$^{31}$P-NMR (CDCl$_3$): d 50.7(d, J=37.5 Hz), 51.5(d, J=38.9 Hz).

EXAMPLE 4

Asymmetric hydrogenation of ethyl 4-chloro-3-oxo-butyrate

Under a nitrogen atmosphere, 5.9 mg (6.1 mmol) of the [RuCl(p-cymene)((+)-SEGPHOS-4-MeO)]Cl obtained in the same manner as described in Example 2 was charged in stainless steel autoclave, and then 5 ml of THF, 5 ml of ethanol and 10.0 g (60.8 mmol) of ethyl 4-chloro-3-oxo-butyrate were added in stainless steel autoclave. The reaction was carried out with stirring for 4.5 hours at 100° C. under 1.0 MPa of hydrogen pressure. As the result of GLC measurement of the reaction mixture, the desired optically active ethyl 4-chloro-3-hydroxybutyrate was obtained with a conversion of 85.1% and an optical purity of 95.2% ee. The conversion was measured by an ordinary method using HP Innowax, and the optical purity was measured by an ordinary method using CHIRALCEL OJ.

EXAMPLE 5

Asymmetric hydrogenation of methyl 2-oxo-3-phenylpropionate

Under a nitrogen atmosphere, 5.0 mg (5.6 μmol) of [Me$_2$NH$_2$][{RuCl((+)-SEGPHOS-4-MeO)}$_2$(μ-Cl)$_3$] obtained in Example 3 was charged in stainless steel autoclave, and then 5 mL of methanol and 500 mg (2.8 mmol) of methyl 2-oxo-3-phenylpropionate were added in stainless steel autoclave. The reaction was carried out with stirring for 4.5 hours at 100° C. under 1.0 MPa of hydrogen pressure. As the result of GLC measurement of the reaction mixture, the desired optically active methyl 2-hydroxy-3-phenylpropionate was obtained with a conversion of 100% and an optical purity of 91.3% ee. The conversion was measured by an ordinary method using NEUTRA BOND-1, and the optical purity was measured by an ordinary method using CP CHIRASILDEX-CB.

EXAMPLE 6

Asymmetric hydrogenation of ethyl 2-oxo-4-phenylbutyrate

Under a nitrogen atmosphere, 4.3 mg (4.8 mmol) of [Me$_2$NH$_2$][{RuCl((+)-SEGPHOS-4-MeO)}$_2$(μ-Cl)$_3$] obtained in Example 3 was charged in stainless steel autoclave, and then 1.5 mL of ethanol and 500 mg (2.4 mmol) of ethyl 2-oxo-4-phenylbutyrate were added in stainless steel autoclave. The reaction was carried out with stirring under 5.0 MPa of hydrogen pressure at 50° C. for 17 hours. As the result of GLC measurement of the reaction mixture, the desired optically active ethyl 2-hydroxy-4-phenylbutyrate was obtained with a conversion of 100% and an optical purity of 79.7% ee. The conversion was measured by an ordinary method using NEUTRA BOND-1, and the optical purity was measured by an ordinary method using CP CHIRASILDEX-CB.

EXAMPLE 7

Asymmetric hydrogenation of Acetol

Under a nitrogen atmosphere, 6.0 mg (6.7 mmol) of [Me$_2$NH$_2$][{RuCl((+)-SEGPHOS-4-MeO)}$_2$(μ-Cl)$_3$] obtained in Example 3 was charged in stainless steel autoclave, and then 1.0 mL of methanol and 500 mg (6.7 mmol) of acetol were added in stainless steel autoclave. The reaction was carried out with stirring under 3.0 MPa of hydrogen pressure at 65° C. for 7 hours. As the result of GLC measurement of the reaction mixture, the desired optically active 1,2-propanediol was obtained with a conversion of 100% and an optical purity of 94.2% ee. The conversion was measured by an ordinary method using TC-FFAP, and the optical purity was measured by an ordinary method using CHIRALCEL OJ-H.

EXAMPLE 8

Asymmetric hydrogenation of ethyl 4-chloro-3-oxo-butyrate

Under a nitrogen atmosphere, 5.4 mg (6.1/μmol) of [Me$_2$NH$_2$][{RuCl((+)-SEGPHOS-4-MeO)}$_2$(μ-Cl)$_3$] obtained in Example 3 was charged in stainless steel autoclave, and then 4.0 mL of ethanol and 2.0 g (12.2 mmol) of ethyl 4-chloro-3-oxo-butyrate were added in stainless steel autoclave. The reaction was carried out with stirring under 3.0 MPa of hydrogen pressure at 90° C. for 4 hours. As the result of GLC measurement of the reaction mixture, the desired optically active ethyl 4-chloro-3-hydroxybutyrate was obtained with a conversion of 100% and an optical purity of 94.1% ee. The conversion was measured by an ordinary method using HP Innowax, and the optical purity was measured by an ordinary method using CHIRALCEL OJ-H.

INDUSTRIAL APPLICABILITY

The present invention provides a new diphosphine compound that is useful as a ligand of an asymmetric catalyst for asymmetric synthesis. The catalyst for asymmetric synthesis having the diphosphine compound of the present invention as a ligand is useful as a catalyst for producing an optically active compound that is useful as an intermediate of a medicine, an agrochemical and the like in a high yield and high optical purity. A diphosphine compound of the present invention, a complex using the compound, a catalyst using the complex and a method for producing an optically active compound using the catalyst have industrial applicability.

What is claimed is:

1. A diphosphine compound represented by the following formula (1):

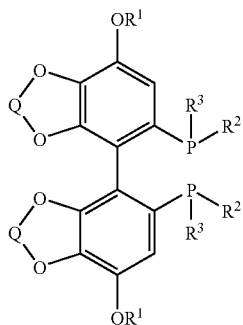

(1)

wherein, two $R^1$s are the same or different, and represent an optionally substituted hydrocarbon group or an optionally substituted heterocyclic group; two $R^2$s and $R^3$s each represent independently an optionally substituted hydrocarbon group or an optionally substituted heterocyclic group; and two Qs are the same or different, and represent a spacer.

2. The diphosphine compound according to claim 1, wherein the diphosphine compound represented by the formula (1) is an optically active diphosphine compound.

3. A diphenylphosphine oxide compound represented by the following formula (6)

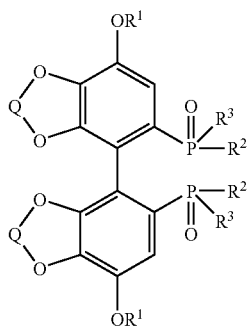

(6)

wherein, two $R^1$s are the same or different, and represent an optionally substituted hydrocarbon group or an optionally substituted heterocyclic group; two $R^2$s and $R^3$s each represent independently an optionally substituted hydrocarbon group or an optionally substituted heterocyclic group; and two Qs are the same or different, and represent a spacer.

4. The diphenylphosphine oxide compound according to claim 3, wherein the diphenylphosphine oxide compound represented by the formula (6) is an optically active diphenylphosphine oxide compound.

5. A chiral ligand, which comprises the optically active diphosphine compound described in claim 2.

6. A chiral catalyst, which comprises the optically active diphosphine compound described in claim 2.

7. A transition metal complex containing the diphosphine compound described in claim 1 or 2.

8. A transition metal complex obtained by the diphosphine compound described in claim 1 or 2 and a transition metal complex precursor.

9. The transition metal complex according to claim 7, wherein the transition metal complex is an optically active transition metal complex.

10. A chiral catalyst, which comprises the transition metal complex described in claim 9.

11. A chiral catalyst containing the diphosphine compound described in claim 2 and a transition metal complex precursor.

12. The chiral catalyst according to claim 10, wherein said catalyst is a catalyst for asymmetric synthesis.

13. The catalyst for asymmetric synthesis according to claim 12, wherein the catalyst for asymmetric synthesis is a catalyst for asymmetric reduction.

14. A method for producing an optically active compound, which comprises reacting a compound having a prochiral center in the presence of the catalyst described in claim 10.

15. A chiral catalyst, which comprises the optically active diphenyiphosphine oxide compound described in claim 4.

16. The transition metal complex according to claim 8, wherein the transition metal complex is an optically active transition metal complex.

17. A chiral catalyst, which comprises the transition metal complex described in claim 16.

18. The chiral catalyst according to claim 17, wherein said catalyst is a catalyst for asymmetric synthesis.

19. The chiral catalyst according to claim 11, wherein said catalyst is a catalyst for asymmetric synthesis.

20. The catalyst for asymmetric synthesis according to claim 18, wherein the catalyst for asymmetric synthesis is a catalyst for asymmetric reduction.

21. The catalyst for asymmetric synthesis according to claim 19, wherein the catalyst for asymmetric synthesis is a catalyst for asymmetric reduction.

22. A method for producing an optically active compound, which comprises reacting a compound having a prochiral center in the presence of the catalyst described in claim 17.

23. A method for producing an optically active compound, which comprises reacting a compound having a prochiral center in the presence of the catalyst described in claim 11.

24. The diphosphine compound according to claim 1, wherein $R^1$ is an alkyl group.

25. The diphenylphosphine oxide compound according to claim 3, wherein $R^1$ is an alkyl group.

* * * * *